(12) United States Patent
Swinnen et al.

(10) Patent No.: US 7,592,477 B2
(45) Date of Patent: Sep. 22, 2009

(54) SUBSTITUTED METHYLENE AMIDE DERIVATIVES AS MODULATORS OF PROTEIN TYROSINE PHOSPHATASES (PTPS)

(75) Inventors: Dominique Swinnen, Beaumont (FR); Agnes Bombrun, Monnetier-Mornex (FR); Jerome Gonzalez, Annemasse (FR); Patrick Gerber, Villars-sous-Yens (CH); Pierre-Andre Pittet, Gilly (CH)

(73) Assignee: Laboratoires Serono SA, Coinsins (CH)

( * ) Notice: Subject to any disclaimer, the term of this patent is extended or adjusted under 35 U.S.C. 154(b) by 478 days.

(21) Appl. No.: 10/501,344

(22) PCT Filed: Jan. 27, 2003

(86) PCT No.: PCT/EP03/00808

§ 371 (c)(1), (2), (4) Date: Jan. 26, 2005

(87) PCT Pub. No.: WO03/064376

PCT Pub. Date: Aug. 7, 2003

(65) Prior Publication Data

US 2005/0124656 A1 Jun. 9, 2005

(30) Foreign Application Priority Data

Jan. 29, 2002 (EP) .................................. 02100078
Apr. 25, 2002 (EP) .................................. 02100410

(51) Int. Cl.
C07C 229/00 (2006.01)
C07D 271/06 (2006.01)

(52) U.S. Cl. .......................................... 560/37; 548/131

(58) Field of Classification Search .................. 554/51, 554/54
See application file for complete search history.

(56) References Cited

U.S. PATENT DOCUMENTS 6,627,767 B2 * 9/2003 Liu et al. ....................... 560/19
2007/0185118 A1 * 8/2007 Hooft Van Huijsduijnen et al. ......................................................... 514/249

FOREIGN PATENT DOCUMENTS

| EP | 483 881 | 5/1992 |
|----|---------|--------|
| EP | 798 295 | 10/1997 |
| EP | 1 123 928 | 8/2001 |
| WO | 96/16940 | 6/1996 |
| WO | 00/23428 | 4/2000 |
| WO | 01/19830 | 3/2001 |
| WO | 02/18321 | 3/2002 |

OTHER PUBLICATIONS

Burrows et al J. Org. Chem. 1982, 47, 892-893.*

F. Zaragoza Dorwald, Side Reactions in Organic Synthesis: A Guide to Successful Synthetic Design 2005, Wiley-VCH Verlag GmbH and Co. KGaA, Wienheim.*
Gerald M. Reaven, et al., The American Journal of Medicine, vol. 60, pp. 80-88 1976.
Robert W. Stout, Metabolism, vol. 34, No. 12, suppl. 1, pp. 7-12 1985.
R.J. Jarrett, Diabetes/Metabolism Reviews, vol. 5, No. 7, pp. 547-558 1989.
Evanthia Diamanti-Kandarakis, et al., European Journal of Endocrinology, vol. 138, pp. 269-274 1998.
Dunaif, Endocrine Reviews, vol. 18, No. 6, pp. 774-800 1997.
Ralph A. Defronzo, et al., Diabetes Care, vol. 14, No. 3, pp. 173-194 1991.
Mounib Elchebly, et al., J. Mol. Med. vol. 78, pp. 473-482 Oct. 12, 2000.
Niels Peter Hundahl Møller, et al., Current Opinion in Drug Discovery & Development, vol. 3, No. 5, pp. 527-540 2000.
Lori D. Klaman, et al., Molecular and Cellular Biology, vol. 20, No. 15, pp. 5479-5489 2000.
Mary C. McGuire, et al., Diabetes, vol. 40, pp. 939-942 1991.
Joseph Meyerovitch, et al., J. Clin. Invest, vol. 84, pp. 976-983 1989.
Janet Sredy, et al., Metabolism, vol. 44, No. 8, pp. 1074-1081 1995.
Zhong-Yin Zhang, Current Opinion in Chemical Biology, vol. 5, pp. 416-423 2001.
Jeffrey D. Bjorge, et al. The Journal of Biological Chemistry, vol. 275, No. 52, pp. 41439-41446 Dec. 29, 2000.

(Continued)

*Primary Examiner*—Rita J Desai
*Assistant Examiner*—John Mabry
(74) *Attorney, Agent, or Firm*—Oblon, Spivak, McClelland, Maier & Neustadt, P.C.

(57) ABSTRACT

The present invention is related to substituted methylene amide derivatives of formula (I) and use thereof for the treatment and/or prevention of metabolic disorders mediated by insulin resistance or pyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). In particular, the present invention is related to the use of substituted methylene amide derivatives of formula (I) to modulate, notably to inhibit the activity of PTPs. Also the present invention relates to a method of treating diabetes type II, obesity and to regulate the appetite of mammals. The present invention is furthermore related to novel substituted methylene amide derivatives and method of preparation thereof. Formula (I).

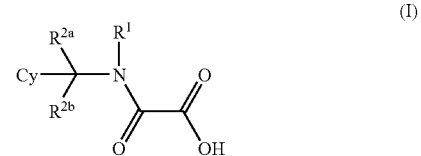

15 Claims, No Drawings

OTHER PUBLICATIONS

Pumima Pathre, et al., Journal of Neuroscience Research, vol. 63, p. 143-150 2001.

Lisa P. Shock, et al., Molecular Brain Research, vol. 28, pp. 110-116 1995.

Brian P. Kennedy, et al., Biochemical Pharmacology, vol. 60, pp. 877-883 2000.

Ralph E. Bowman, J. Chem. Soc., Perkin Trans, vol. 1, No. 10, pp. 2126-2133 1980.

Alan Cheng, et al., Developmental Cell, vol. 2, pp. 497-503 2002.

Janice M. Zabolotny, et al., Developmental Cell, vol. 2, pp. 489-495 2002.

* cited by examiner

SUBSTITUTED METHYLENE AMIDE DERIVATIVES AS MODULATORS OF PROTEIN TYROSINE PHOSPHATASES (PTPS)

FIELD OF THE INVENTION

The present invention is related to substituted methylene amide derivatives of formula (I), in particular for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). The compounds of this invention are particularly useful in the treatment of type II diabetes, obesity or the regulation of appetite.

Specifically, the present invention is related to substituted methylene amide derivatives for the modulation, notably the inhibition of the activity of PTPs, in particular of PTP1B.

BACKGROUND OF THE INVENTION

The prevalence of insulin resistance in glucose intolerant subjects is well known. Reaven et al (*American Journal of Medicine*, 60, 80 (1976)) used a continuous infusion of glucose and insulin (insulin/glucose clamp technique) and oral glucose tolerance tests to demonstrate that insulin resistance exists in a diverse group of non-obese, non-ketotic subjects. These subjects ranged from borderline glucose tolerant to overt, fasting hyperglycemia. The diabetic groups in these studies included both insulin dependent (IDDM) and non-insulin dependent (NIDDM) subjects.

Coincident with sustained insulin resistance is the more easily determined hyperinsulinemia, which may be measured by accurate determination of circulating plasma insulin concentration in the plasma of subjects. Hyperinsulinemia may be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia and insulin resistance with obesity and with ischemic diseases of the large blood vessels (e.g. atherosclerosis) has been well established by numerous experimental, clinical and epidemiological studies (Stout, *Metabolism*, 34, 7 (1985)). Statistically significant plasma insulin elevations at 1 and 2 hours after oral glucose load correlate with an increased risk of coronary heart disease.

Since most of these studies actually excluded diabetic subjects, data relating the risk of atherosclerotic diseases to the diabetic condition are not as numerous, but point in the same direction as for non-diabetic subjects. However, the incidence of atherosclerotic diseases in morbidity and mortality statistics in the diabetic population exceeds that of the nondiabetic population (Pyorala et al; Jarrett *Diabetes/Metabolism Reviews*, 5, 547 (1989)).

The association of hyperinsulinemia and insulin resistance with Polycystic Ovary Syndrome (PCOS) is also well acknowledged (Diamanti-Kandarakis et al.; Therapeutic effects of metformin on insulin resistance and hyperandrogenism in polycystic ovary syndrome; *European Journal of Endocrinology* 138, 269-274 (1998), Andrea Dunaif; Insulin Resistance and the Polycystic Ovary Syndrome: Mechanism and Implications for Pathogenesis; *Endocrine Reviews* 18(6), 774-800 (1997)).

The independent risk factors obesity and hypertension for atherosclerotic diseases are also associated with insulin resistance. Using a combination of insulin/glucose clamps, tracer glucose infusion and indirect calorimetry, it was demonstrated that the insulin resistance of essential hypertension is located in peripheral tissues principally muscle) and correlates directly with the severity of hypertension (DeFronzo and Ferrannini, *Diabetes Care*, 14, 173 (1991)). In hypertension of obese people, insulin resistance generates hyperinsulinemia, which is recruited as a mechanism to limit further weight gain via thermogenesis, but insulin also increases renal sodium re-absorption and stimulates the sympathetic nervous system in kidneys, heart, and vasculature, creating hypertension.

It is assumed that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (Mounib Elchebly, Alan Cheng, Michel L. Tremblay; Modulation of insulin signaling by protein tyrosine phosphatases; *J. Mol. Med.* 78, 473-482 (2000)).

Protein-tyrosine phosphatases (PTPs) play an important role in the regulation of phosphorylation of proteins and represent the counterparts of kinases. Among classical PTPs, there are two types: (i) non-receptor or intracellular PTPs and (ii) receptor-like PTPs. Most intracellular PTPs contain one catalytic domain only, whereas most receptor-like enzymes contain two. The catalytic domain consists of about 250 amino acids (Niels Peter Hundahl Moller et al. Protein tyrosine phosphatases (PTPs) as drug targets: Inhibitors of PTP-1B for the treatment of diabetes; *Current Opinion in Drug Discovery & Development* 3(5), 527-540 (2000)).

The interaction of insulin with its receptor leads to phosphorylation of certain tyrosine molecules within the receptor protein, thus activating the receptor kinase. PTPs dephosphorylate the activated insulin receptor, attenuating the tyrosine kinase activity. PTPs can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTP-alpha and SH-PTP2 (Lori Klaman et al.; Increased Energy Expenditure, Decreased Adiposity, and Tissue-specific insulin sensitivity in Protein-Tyrosine Phosphatase 1B-Deficient Mice; *Molecular and Cellular Biology*, 5479-5489 (2000)).

PTP1B is a member of the PTP family. This 50 kDa protein contains a conserved phosphatase domain at residues 30-278 and is localized to the cytoplasmic face of the endoplasmic reticulum by its C-terminal 35 residues. Its interactions with other proteins are mediated by proline-rich regions and SH2 compatible sequence. PTP1B is believed to act as a negative regulator in insulin signaling.

McGuire et al. (*Diabetes*, 40, 939 (1991)) demonstrated that non-diabetic glucose intolerant subjects possessed significantly elevated levels of PTP activity in muscle tissue vs. normal subjects, and that insulin infusion failed to suppress PTP activity as it did in insulin sensitive subjects.

Meyerovitch et al. (*J. Clinical Invest.*, 84, 976 (1989)) observed significantly increased PTP activity in the livers of two rodent models of IDDM, the genetically diabetic BB rat, and the STZ-induced diabetic rat. Sredy et al. (*Metabolism*, 44, 1074, (1995)) observed similar increased PTP activity in the livers of obese, diabetic ob/ob mice, which represent a typical rodent model of NIDDM.

Zhang et al (*Curr. Opin. Chem. Biol.*, 5(4), 416-23 (2001)) found that PTPs are also implicated in a wide variety of other disorders, including cancer. Bjorge, J. D. et al. (*J. Biol. Chem.*, 275(52), 41439-46 (2000)) indicates that PTP1B is the primary protein-tyrosine phosphatase capable of dephosphorylating c-Src in several human breast cancer cell lines and suggests a regulatory role for PTP1B in the control of c-Src kinase activity.

Pathre et al (*J. Neurosci. Res.*, 63(2), 143-150 (2001)) describes that PTP1B regulates neurite extension mediated by cell-cell and cell-matrix adhesion molecules. Further, Shock. L. P et al. (*Mol. Brain. Res.*, 28(1), 110-16 (1995)) demonstrates that a distinct overlapping set of PTPs is expressed in the developing brain and retinal Mueller glia, including 2 novel PTPs that may participate in neural cell communication.

The insulin receptor (IR) is a prototypical tyrosine kinase receptor whose ligand binding and dimerization results in auto-phosphorylation on multiple tyrosines. This is followed by the recruitment and phosphorylation of IRS1-4 (depending on the tissue) and PI3K. Although vanadium-containing compounds have been known since the 19$^{th}$ century to alleviate diabetes, it was understood only recently that these inhibitors stimulate the insulin signaling pathway by blocking PTP action. Evidence for the involvement of the IR (insulin receptor) and IRS-1 in this phenotype was that both proteins show increased tyrosine phosphorylation in the PTP1B-mutated mice. The available data strongly suggest that in particular PTP1B is a promising target for the development of drugs to treat diabetes and obesity (Brian P. Kennedy and Chidambaram Ramachandran; Protein Tyrosine Phosphatase-1B in Diabetes; *Biochemical Pharmacology, Vol.* 60, 877-883, (2000)).

A further protein involved in obesity is Leptin. Leptin is a peptide hormone that plays a central role in feeding and adiposity (*Leptin. Annu. Rev. Physiol.* 62 p. 413-437 (2000) by Ahima R. S. et al.). Recently, it has been suggested that PTP1B negatively regulates leptin signaling, and provide one mechanism by which it may regulate obesity. Further, it is known that pharmacological inhibitors of PTP1B hold promise as an alternative or a supplement to leptin in the treatment of obesity due to leptin resistance (*Developmental Cell.*, vol. 2, p. 497-503 (2002)).

Several small molecules have been proposed as inhibitors of PTPs, among others WO 02/18321.

SUMMARY OF THE INVENTION

The present invention relates to substituted methylene amide derivatives of formula (I)

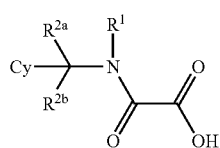

(I)

Such compounds are suitable for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). The compounds of this invention are inhibitors of PTPs.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"PTPs" are protein tyrosine phosphatases and include for instance PTP1B, TC-PTP, PTP-□, DEP-1, LAR, SHP-1, SHP-2, GLEPP-1, PTP-□, PTP-μ, VHR, hVH5, LMW-PTP, PTEN.

"$C_1$-$C_{12}$-alkyl" or "$C_1$-$C_{15}$-alkyl" refers to straight or branched monovalent alkyl groups having 1 to 12 or 1 to 15 carbon atoms. This term is exemplified by groups such as methyl, ethyl, n-propyl, isopropyl, n-butyl, isobutyl, tert-butyl, n-hexyl, n-octyl, n-nonyl, n-dodecyl, tridecyl, pentadecyl, n-pentyl and the like in straight or branched forms thereof.

"Aryl" refers to an unsaturated, aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_{12}$-alkyl aryl" refers to $C_1$-$C_{12}$-alkyl groups having an aryl substituent, including benzyl, phenethyl and the like.

"Heteroaryl" refers to a monocyclic heteromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl; 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_{12}$-alkyl heteroaryl" refers to $C_1$-$C_{12}$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH═CH$_2$), n-2-propenyl (allyl, —CH$_2$CH═CH$_2$) and the like.

"Alkynyl" refers to alkynyl groups having from 2 to 18 carbon atoms and having at least 1-2 sites of alkynyl unsaturation, e.g. ethynyl (—C≡CH), propargyl (—CH$_2$C≡CH), or —C≡CH—(C$_2$-C$_{16}$)alkyl.

"Acyl" refers to the group —C(O)R where R includes "$C_1$-$C_{12}$-alkyl", "aryl", "heteroaryl", "$C_1$-$C_{12}$-alkyl aryl" or "$C_1$-$C_{12}$-alkyl heteroaryl".

"Acyloxy" refers to the group —OC(O)R where R includes "$C_1$-$C_{12}$-alkyl", "aryl", "heteroaryl", "$C_1$-$C_{12}$-alkyl aryl" or "$C_1$-$C_{12}$-alkyl heteroaryl".

"Alkoxy" refers to the group —O—R where R includes "$C_1$-$C_{12}$-alkyl" or "aryl" or "heteroaryl" or "$C_1$-$C_{12}$-alkyl aryl" or "$C_1$-$C_{12}$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_{12}$-alkyl" or "aryl" or "heteroaryl" or "$C_1$-$C_{12}$-alkyl aryl" or "$C_1$-$C_{12}$-alkyl heteroaryl".

"Aminocarbonyl" refers to the group —C(O)NRR' where each R, R' includes independently hydrogen or $C_1$-$C_{12}$-alkyl or aryl or heteroaryl or "$C_1$-$C_{12}$-alkyl aryl" or "$C_1$-$C_{12}$-alkyl heteroaryl".

"Acylamino" refers to the group —NR(CO)R' where each R, R' is independently hydrogen or "$C_1$-$C_{12}$-alkyl" or "aryl" or "heteroaryl" or "$C_1$-$C_{12}$-alkyl aryl" or "$C_1$-$C_{12}$-alkyl heteroaryl".

"Halogen" refers to fluoro, chloro, bromo and iodo atoms.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Sulfonyl" refers to group "—$SO_2$—R" wherein R is selected from H, "aryl", "heteroaryl", "$C_1$-$C_{12}$-alkyl", "$C_1$-$C_{12}$-alkyl" substituted with halogens e.g. an —$SO_2$—$CF_3$ group, "$C_1$-$C_{12}$-alkyl aryl" or "$C_1$-$C_{12}$-alkyl heteroaryl".

"Sulfoxy" refers to a group "—S(O)—R" wherein R is selected from H, "$C_1$-$C_{12}$-alkyl", "$C_1$-$C_{12}$-alkyl" substituted with halogens e.g. an —SO—$CF_3$ group, "aryl", "heteroaryl", "$C_1$-$C_{12}$-alkyl aryl" or "$C_1$-$C_{12}$-alkyl heteroaryl".

"Thioalkoxy" refers to groups —S—R where R includes "$C_1$-$C_{12}$-alkyl" or "aryl" or "heteroaryl" or "$C_1$-$C_{12}$-alkyl aryl" or "$C_1$-$C_{12}$-alkyl heteroaryl". Preferred thioalkoxy groups include thiomethoxy, thioethoxy, and the like.

"Pharmaceutically acceptable salts or complexes" refers to salts or complexes of the below-specified compounds of formula (I). Examples of such salts include, but are not restricted, to base addition salts formed by reaction of compounds of formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, e.g. the corresponding esters of the substituted methylene amides of formula I, racemic products are usually obtained that do however also have a PTP inhibiting activity.

Said formula also comprises its tautomers, its geometrical isomers, its optically active forms as enantiomers, diastereoisomers and its racemate forms, as well as pharmaceutically acceptable salts thereof. Preferred pharmaceutically acceptable salts of the formula (I), are base addition salts formed by reaction of compounds of formula (I) with pharmaceutically acceptable bases like N-methyl-D-glucamine, tromethamine, sodium, potassium or calcium salts of carbonates, bicarbonates or hydroxides.

The substituted methylene amide derivatives according to the present invention are those of formula (I):

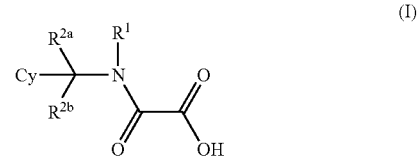

Formula (I) comprises also the geometrical isomers, the optically active forms, including enantiomers, diastereomers and its racemate forms, as well as pharmaceutically acceptable salts and pharmaceutically active derivatives thereof.

The substituents $R^1$, $R^{2a}$, $R^{2b}$ and Cy within Formula (I) are defined as follows:

$R^1$ is selected from the group consisting of substituted or unsubstituted ($C_1$-$C_{12}$)-alkyl, preferably substituted or unsubstituted ($C_1$-$C_6$)-alkyl, substituted or unsubstituted ($C_2$-$C_{12}$)-alkenyl, substituted or unsubstituted ($C_2$-$C_{12}$)-alkynyl, substituted or unsubstituted aryl, substituted or unsubstituted heteroaryl, substituted or unsubstituted (3-8-membered) cycloalkyl or heterocycloalkyl, substituted or unsubstituted ($C_1$-$C_{12}$)-alkyl-aryl or substituted or unsubstituted ($C_1$-$C_{12}$)-alkyl-heteroaryl, substituted or unsubstituted ($C_2$-$C_{12}$)-alkenyl-aryl or -heteroaryl, substituted or unsubstituted ($C_2$-$C_{12}$)-alkynyl-aryl or -heteroaryl.

In a preferred embodiment of the present invention, $R^1$ is A wherein A is a substituted or unsubstituted aryl, a substituted or unsubstituted heteroaryl, a substituted or unsubstituted (3-8 membered)heterocycloalkyl or (3-8 membered)cycloalkyl, in particular a substituted or unsubstituted phenyl.

In another preferred embodiment, A is a moiety of the formula —$CH_2$-A or —$CH_2$—$CH_2$-A, with A being a substituted or unsubstituted aryl, a substituted or unsubstituted heteroaryl, a substituted or unsubstituted (3-8-membered) heterocycloalkyl or a substituted or unsubstituted (3-8-membered)cycloalkyl. In particular, A may be a phenyl, pyridinyl, benzo-1,3-dioxolenyl, biphenyl, naphthyl, quinoxalinyl, thiazolyl, thienyl, furanyl or a piperidinyl group, being optionally substituted by 1 or 2 moieties selected from the group consisting of cyano, halogen, $NO_2$, $(C_1$-$C_6)$alkoxy, aryloxy or heteroaryloxy, $(C_1$-$C_6)$thioalkoxy, optionally halogenated $(C_1$-$C_6)$alkyl, $(C_2$-$C_6)$alkenyl, $(C_2$-$C_6)$alkynyl, aryl, heteroaryl, (3-8-membered)cycloalkyl or heterocycloalkyl, $(C_1$-$C_6)$alkyl aryl or heteroaryl, $(C_2$-$C_6)$alkenyl aryl or heteroaryl, $(C_2$-$C_6)$alkynyl aryl or heteroaryl, —$COR^3$, —$COOR^3$, —CO—$NR^3R^3$, —$NHCOR^3$ wherein $R^3$ is $(C_1$-$C_6)$alkyl or $(C_2$-$C_6)$alkenyl, —$SOR^3$, —$SO_2R^3$, —$SO_2NR^3R^{3'}$ with $R^3$, $R^{3'}$ being independently from each other selected from the group consisting of H, straight or branched $(C_1$-$C_6)$alkyl, $(C_2$-$C_6)$alkenyl, $(C_2$-$C_6)$alkynyl, aryl, heteroaryl, (3-8-membered)cycloalkyl or heterocycloalkyl.

$R^{2a}$ and $R^{2b}$ are each independently from each other selected from the group comprising or consisting of H or substituted or unsubstituted $(C_1$-$C_{12})$alkyl, preferably $R^{2a}$ and $R^{2b}$ are each H.

Cy is a substituted or unsubstituted aryl, a substituted or unsubstituted heteroaryl, a substituted or unsubstituted (3-8-membered)cycloalkyl or heterocycloalkyl.

Such aryl or heteroaryl include phenyl, naphthyl, phenantrenyl, pyrrolyl, furyl, thienyl, imidazolyl, pyridyl, oxazolyl, isoxazolyl, thiazolyl, isothiazolyl, pyrazolyl, 1,2,3-triazolyl, 1,2,4-triazolyl, 1,2,3-oxadiazolyl, benzo(1,2,5)oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, benzopyrimidinyl, benzofuryl, [2,3-dihydro]benzofuryl, isobenzofuryl, benzothienyl, benzotriazolyl, isobenzothienyl, indolyl; isoindolyl, 3H-indolyl, benzimidazolyl, benzothiazolyl, benzoxazolyl, pyridazinyl, pyrimidyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, xanthenyl, benzoquinolyl, oxolanyl, pyrolidinyl, pyrazolidinyl, 2H-benzo[d]1,3-dioxolenyl, indanyl, imidazolidinyl, 1,2,4-oxadiazolidinyl, 1,2,5-oxadiazolidinyl, 1,3,4-oxadiazolidinyl or isoxazolidinyl.

In particular, Cy is a substituted or unsubstituted thienyl or phenyl, e.g. a biphenyl group.

More specifically, Cy may be substituted or unsubstituted thienyl, substituted or unsubstituted phenyl which may be substituted by substituted or unsubstituted aryl or substituted or unsubstituted heteroaryl, e.g. an oxadiazole, or substituted or unsubstituted cycloalkyl moiety, or Cy is substituted or unsubstituted thienyl, substituted or unsubstituted phenyl which may be substituted by 1 or 2 moieties selected from the group consisting of NH—CO—$R^3$, —$SO_2$—$NR^3R^{3'}$ or —CO—$NR^3R^{3'}$ in which $R^3$, $R^{3'}$ are independently selected from H, substituted or unsubstituted $(C_1$-$C_{15})$alkyl, substituted or unsubstituted $(C_2$-$C_{12})$alkenyl, substituted or unsubstituted $(C_2$-$C_{12})$alkynyl, substituted or unsubstituted aryl, substituted or unsubstituted heteroaryl, substituted or unsubstituted (3-8-membered)cycloalkyl or substituted or unsubstituted heterocycloalkyl, substituted or unsubstituted $(C_1$-$C_{12})$alkyl aryl or heteroaryl, substituted or unsubstituted $(C_2$-$C_{12})$alkenyl-aryl or -heteroaryl, substituted or unsubstituted $(C_2$-$C_{12})$alkynyl-aryl or -heteroaryl.

According to one embodiment $R^{3'}$ is H and $R^3$ is selected from the group consisting of diphenyl-ethyl, dodecyl, octyl, 4-pentyl-benzyl, 4-phenoxy-phenethyl, ethyl-thiophen-2-yl, pentadecyl, tridecyl, hexyloxy-phenyl, (2-ethyl)-hexyl.

According to a further embodiment Cy is substituted or unsubstituted aryl, substituted or unsubstituted heteroaryl, substituted or unsubstituted (3-8-membered)-cycloalkyl or -heterocycloalkyl, being substituted by a substituted or unsubstituted $(C_2$-$C_{18})$alkynyl moiety.

According to a further embodiment Cy is substituted or unsubstituted phenyl, substituted or unsubstituted pyridinyl, substituted or unsubstituted naphthyl or substituted or unsubstituted benzofuranyl group, being substituted by B—$R^4$ wherein B is ethynyl group and $R^4$ is substituted or unsubstituted $(C_6$-$C_{16})$alkyl, substituted or unsubstituted (3-8 membered) cycloalkyl, substituted or unsubstituted $(C_1$-$C_{12})$ alkyl-(3-8 membered) cycloalkyl, substituted or unsubstituted phenyl or substituted or unsubstituted $(C_1$-$C_{12})$ alkyl phenyl. More particularly, Cy is phenyl being substituted by B—$R^4$ wherein B is ethynyl group and $R^4$ is substituted or unsubstituted $(C_6$-$C_{16})$alkyl.

According to a further embodiment $R^{2a}$ and $R^{2b}$ are each H, $R^1$ is —$CH_2$-A, or —$CH_2$—$CH_2$-A with A being phenyl or thienyl, optionally substituted by cyano, halogen, methoxy, hydroxy, phenoxy, —$NO_2$, trifluoromethyl while Cy is a thienyl, phenyl or biphenyl being substituted by —$SO_2R^3$, —CO—$NR^3R^{3'}$ in which $R^{3'}$ is H and $R^3$ is $(C_7$-$C_{12})$alkyl, particularly $(C_8$-$C_{12})$alkyl and more particularly a docecyl group.

Alternatively, $R^3$ is $(C_7$-$C_{15})$alkyl, particularly $(C_8$-$C_{15})$ alkyl and most preferred a dodecyl group.

More preferred compounds are those of formula (I')

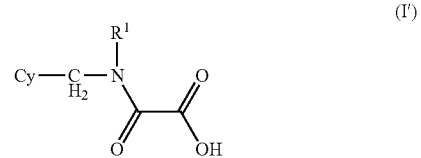

wherein
$R^1$ is selected from the group consisting of phenyl, benzyl, phenethyl, 1-methylbenzyl which may be substituted by $(C_1$-$C_6)$alkyl group or a cycloalkyl group;
Cy is a phenyl or a biphenyl group optionally substituted with —NH—CO—$R^3$, —CO—NH—$R^3$ or an oxadiazole group substituted with $R^3$ in which $R^3$ is $(C_2$-$C_{12})$alkyl, $(C_7$-$C_{15})$alkyl, particularly $(C_8$-$C_{15})$alkyl and more particularly a dodecyl group.

Some very few compounds falling into formula (I) are disclosed in the prior art. Said compounds are the following:
a) Compounds of formula (I), wherein Cy is an amidinonaphthyl moiety, $R^1$ is a phenyl group which is para-substituted by a —O-piperidine or —O-pyrrolidine moiety.

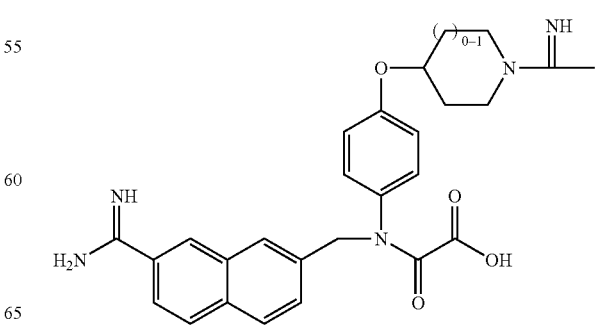

Such compounds are disclosed in WO 96/16940 (Yamanouchi Pharmaceutical Co.) and are said to have an antiplatelet aggregation effect. They purportedly inhibit activated blood coagulation factor X and are said to be useful as an antithrombotic agent.

b) A compound of formula (I), wherein Cy is a phenyl group, $R^{2a}$ and $R^{2b}$ are each H, $R^1$ is an indole moiety.

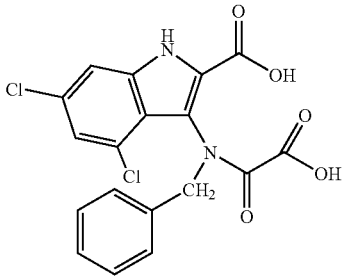

The above single compound is disclosed in EP483881 (Merrel Dow Pharmaceuticals) and is said to be useful for the treatment of neurodegenerative disease states.

c) A compound of formula (I), wherein Cy is a biphenyl group, $R^{2a}$ and $R^{2b}$ are each H, $R^1$ is a phenyl group ortho-substituted with a tert-butyl 5-aminoisoindoline-2-carboxylate.

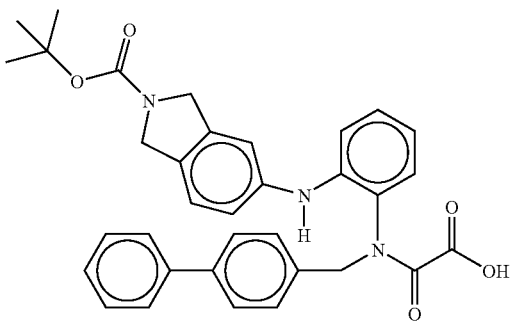

This single compound is mentioned in WO 00/23428 (Takeda Chemical Industries Ldt.) as an intermediate compound in the synthesis of 1,5-benzodiazepine compounds. No medical use has been associated with said compound.

d) A compound of formula (I), wherein Cy is a phenyl group, $R^{2a}$ and $R^{2b}$ are each H, $R^1$ is a 2,3,4-trihydronaphtalen-1-one.

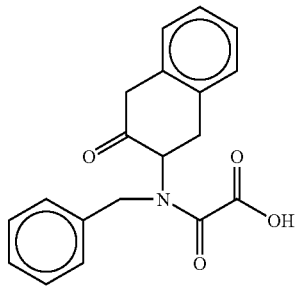

The above compound is disclosed in *J. Chem. Soc., Perkin Trans* 1(10), p. 2126-33 (1980) without any biologic activity or therapeutic application.

Intermediate compounds or prodrugs that may be transformed to give rise to the substituted methylene amide derivatives of formula (I) by hydrolysis are esters of the compounds of formulae (I-1) and (I-2) and include the following:

benzyl 4-({benzyl[ethoxy(oxo)acetyl]amino}methyl)benzoate
ethyl(benzyl {4-[(dodecylamino)carbonyl]benzyl}amino) (oxo)acetate
benzyl 4-({[ethoxy(oxo)acetyl][4-(trifluoromethyl)benzyl] amino}methyl)benzoate
ethyl oxo{{4-[(pentadecylamino)carbonyl]benzyl}[4-(trifluoromethyl)benzyl]-amino}acetate
ethyl{(4-{[dodecyl(methyl)amino]carbonyl}benzyl)[4-(trifluoromethyl)benzyl]amino}-(oxo)acetate
tert-butyl 4-{{4-[(benzyloxy)carbonyl]benzyl}[ethoxy(oxo) acetyl]amino}piperidine-1-carboxylate
tert-butyl 4-{{4-[(dodecylamino)carbonyl]benzyl}[ethoxy (oxo)acetyl]amino}piperidine-1-carboxylate
ethyl{{4-[(dodecylamino)carbonyl]benzyl}[4-(trifluoromethyl)benzyl]amino}(oxo)acetate
ethyl{{4-[(dodecylamino)carbonyl]benzyl}[3-(trifluoromethyl)benzyl]amino}(oxo)acetate
tert-butyl 4-({{4-[(dodecylamino)carbonyl]benzyl}[ethoxy (oxo)-acetyl]amino}-methyl)-piperidine-1-carboxylate
ethyl{{4-[(tert-butoxycarbonyl)amino]benzyl}[4-(trifluoromethyl)benzyl]amino}-(oxo)-acetate
ethyl{(4-aminobenzyl)[4-(trifluoromethyl)benzyl]amino} (oxo)acetate
ethyl oxo{[4-(tridecanoylamino)benzyl][4-(trifluoromethyl) benzyl]amino}acetate
ethyl[benzyl(4-{[4-(hexyloxy)benzoyl]amino}benzyl) amino](oxo)acetate
ethyl(benzyl{4-[(tert-butoxycarbonyl)amino] benzyl}amino)(oxo)acetate
ethyl[(4-aminobenzyl)(benzyl)amino](oxo)acetate
ethyl oxo{[4-(trifluoromethyl)benzyl][4-(undec-10-enoylamino)benzyl]amino}acetate
ethyl oxo{{4-[(9E)-tetradec-9-enoylamino]benzyl}[4-(trifluoromethyl)benzyl]amino}-acetate
ethyl{benzyl[4-(tridecanoylamino)benzyl]amino}(oxo)acetate
ethyl{{4[(2-hydroxydodecyl)amino]benzyl}[4-(trifluoromethyl)benzyl]amino}-(oxo)-acetate
ethyl oxo{[4-(trifluoromethyl)benzyl][4-(3-undecyl-1,2,4-oxadiazol-5-yl)benzyl]-amino}-acetate
ethyl{({5[(dodecylamino)sulfonyl]thien-2-yl}methyl)[4-(trifluoromethyl)benzyl]-amino}(oxo)acetate
tert-butyl 4-({{4-[(benzyloxy)carbonyl]benzyl}[ethoxy (oxo)acetyl]amino}-methyl)-piperidine-1-carboxylate
ethyl[{4-[(dodecylamino)carbonyl]benzyl}({1-[(4-methoxyphenyl)sulfonyl]piperidin-4-yl}methyl)amino](oxo)acetate
ethyl{{4-[(dodecylamino)carbonyl]benzyl}[1-(1-naphthyl) ethyl]amino}(oxo)acetate
ethyl(benzyl {3-[(dodecylamino)carbonyl]benzyl}amino) (oxo)acetate
ethyl[benzyl({5-[(dodecylamino)sulfonyl]thien-2-yl}methyl)amino](oxo)acetate
tert-butyl 4-({{4-[(dodecylamino)carbonyl]benzyl}[ethoxy (oxo)acetyl]amino}methyl) piperidine-1-carboxylate
ethyl[{4-[(dodecylamino)carbonyl]benzyl}(piperidin-4-ylmethyl)amino](oxo)acetate
ethyl[cyclopentyl({5-[(dodecylamino)sulfonyl]thien-2-yl}methyl)amino](oxo)acetate.

A further aspect of the present invention is the use of the compounds of formula (I) as medicament.

Preferred substituted methylene amide derivatives are those wherein $R^{2a}$ and $R^{2b}$ are each H, $R^1$ is —$CH_2$-A, with A being phenyl or thienyl, optionally substituted by cyano, halogen, methoxy, hydroxy, phenoxy, —$NO_2$, trifluoromethyl, Cy is a thienyl, phenyl or biphenyl being substituted by —$SO_2R^3$, —CO—$NR^3R^{3'}$ in which $R^{3'}$ is H and $R^3$ is ($C_7$-$C_{15}$)alkyl, particularly ($C_8$-$C_{15}$)alkyl and more particularly a dodecyl group.

Particularly preferred substituted methylene amide derivative are those wherein $R^{2a}$ and $R^{2b}$ are each H, $R^1$ is selected from the group consisting of phenyl, benzyl, phenethyl, 1-methylbenzyl which may be substituted by ($C_1$-$C_6$)alkyl group or a cycloalkyl group, Cy is a phenyl or a biphenyl group substituted with a moiety selected from the group consisting of —NH—CO—$R^3$, —CO—NH—$R^3$, or an oxadiazole group substituted with $R^3$, wherein $R^3$ is ($C_7$-$C_{15}$)alkyl, particularly ($C_8$-$C_{15}$)alkyl and more particularly a dodecyl group.

The compounds of formula (I) are useful in the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity or polycystic ovary syndrome (PCOS).

In one embodiment the compounds according to formula (I) are particularly useful in the treatment and/or prevention of diabetes type II, obesity and for the regulation of appetite in mammals.

The compounds according to formula (I) are suitable for the modulation of the activity of PTPs, in particular of PTP1B. It is therefore believed that the compounds of the present invention are therefore useful for the treatment and/or prevention of disorders which are mediated by PTPs, in particular of PTP1B. Said treatment involves the modulation— notably the down regulation or the inhibition—of PTPs, particularly of PTP1B.

A further aspect of the present invention is related to a pharmaceutical composition composition a comprising a methylene amide derivative according to Formula (I) and at least one further drug (in particular an anti-diabetes agent). In one embodiment the further diabetes agents are selected from the group comprising or consisting of insulin (or insulin mimicks), aldose reductase inhibitors, alpha-glucosidase inhibitors, sulfonyl urea agents, biguanides (e.g. metformin), thiazolidines (e.g. pioglitizone, rosiglitazone, cf. WO 02/100396) or PPARs agonists, or c-Jun Kinase or GSK-3 inhibitors.

Insulins useful with the method of the present invention include rapid acting insulins, intermediate acting insulins, long acting insulins and combination of intermediate and rapid acting insulins.

Aldose reductase inhibitors useful in the method of this invention include those known in the art. These include the non-limiting list of:

a) the spiro-isoquinoline-pyrrolidine tetrone compounds disclosed in U.S. Pat. No. 4,927,831 (Malamas), the contents of which are incorporated herein by reference, which includes ARI-509, also known as minalrestat or Spiro[isoquinoline-4(1H), 3'-pyrrolidine]-1,2',3,5'(2H)-tetrone, and analogs thereof, b) 2-[(4-bromo-2-fluorophenyl)methyl]-6-fluoro-(9CI);

c) the compounds of U.S. Pat. No. 4,439,617, the contents of which are incorporated herein by reference, which includes Tolrestat, also known as Glycine, N-[[6-methoxy-5-(trifluoromethyl)-1-naphtalenyl]thioxomethyl]-N-methyl-(9CI) or AY-27773 and analogs thereof;

d) Sorbinil (Registra No. 68367-52-2) also known as Spiro [4H-1-benzopyran-4,4'-imidazoline]-2',5'-dione, 6-fluoro-2,3-dihydro-, (4S)-(9CI) or CP 45634;

e) Methosorbinil;

f) Zopolrestat, which is 1-Phtalazineacetic acid, 3,44-dihydro-4-oxo-3-[[5-(trifluoromethyl)-2-benzothiazolyl]methyl]9CI) (Registry No. 110703-94-1);

g) Epalrestat, which is 3-Thiazolidineacetic acid, 5-[(2E)-2-methyl-3-phenyl-2-propenylidene]-4-oxo-2-thioxo-, (5Z)-(9CI) (Registry No. 82150-09-9);

h) Zenarestat (Registry No. 112733-40-6) or 3-[(4-bromo-2-fluorophenyl)-methyl]-7-chloro-3,4-dihydro-2,4-dioxo-1(2H)-quinazoline acetic acid;

i) Imirestat, also known as 2,7-difluorospiro(9H-fluorene-9, 4'-imidazolidine)-2',5'-dione;

j) Ponalrestat (Registry No. 72702-95-5), which is 1-Phtalazineacetic acid, 3-[(4-bromo-2-fluorophenyl)methyl]3,4-dihydro-4-oxo-(9CI) and also known as Statil or Statyl;

k) ONO-2235, which is 3-Thiazolidineacetic acid, 5-[(2E)-2-methyl-3-phenyl-2-propenylidene-4-oxo-2-thioxo-, (5Z) (9CI);

l) GP-1447, which is {3-[(4,5,7-trifluorobenzothiazol-2-yl) methyl]-5-methylphenylacetic acid};

m) CT-112, which is 5-(3-ethoxy-4-pentyloxyphenyl)-2,4-thiazolidinedione;

n) BAL-ARI 8, which is Glycine, N[(7-fluoro-9-oxo-9H-xanthen-2-yl)sulfonyl]-N-methyl-)9CI), Reg. No. 124066-40-6));

o) AD-5467, which is 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI);

p) ZD5522, which is (3',5'-dimethyl-4'-nitromethylsulfonyl-2-(2-tolyl)acetanilide);

q) 3,4-dihydro-2,8-diisopropyl-3-thioxo-2H-1,4-benzoxazine-4-acetic acid;

r) 1-[(3-bromo-2-benzofuranyl)sulfonyl]-2,4-imidazolidinedione (M-16209), s) NZ-314, which is 1-Imidazolidineacetic acid, 3-[(3-nitrophenyl)methyl]-2,4,5-trioxo-9(CI) (Registry No. 128043-99-2), t) 1-phtalazineacetic acid, 3,4-dihydro-4-oxo-3-[(5-trifluoromethyl)-2-benzothiazolyl]-methyl];

u) M-79175, which is Spiro[4H-1-benzopyran-4,4'-imidazolidine]-2',5'-dione; 6-fluoro-2,3-dihydro-2-methyl-, (2R, 4S)-(9CI);

v) SPR-210, which is 2H-1,4-Benzothiazine-2-acetic acid, 3,4-dihydro-3-oxo-4-[(4,5,7-trifluoro-2-benzothiazolyl) methyl]-(9CI);

w) Spiro[pyrrolidine-3,6'(5'H)-pyrrolo[1,2,3-de][1,4]benzoxazine]-2,5,5'-trione, 8'-chloro-2'-3'-dihydro-(9CI)(also known as AND 138 or 8-chloro-2',3'-dihydrospiro[pyrolizine-3,6'(5H)-pyrrolo-[1,2,3-de]-[1,4]benzoxazine]2,5,5'-trione);

x) 6-fluoro-2,3-dihydro-2',5'-dioxo-(2S-cis)-spiro[4H-1-benzopyran-4,4'-imidazolidine]-2-carboxamide (also known as SNK-860);

or a pharmaceutically acceptable salt form of one or more of these compounds.

Among the more preferred aldose reductase inhibitors of this invention are minalrestat, Tolrestat, Sorbinil, Methosorbinil, Zopolrestat, Epalrestat, Zenarestat, Imirestat and Ponalrestat or the pharmaceutically acceptable salt forms thereof.

The alpha-glucosidase inhibitors useful for the method of the present invention include miglitol or acarbose, or the pharmaceutically acceptable salt form thereof.

Sulfonylurea agents useful with the method of the present invention include glipizide, Glyburide (Glibenclamide) Clorpropamide, Tolbutamide, Tolazamide and Glimepiride, or the pharmaceutically acceptable salt forms thereof.

Preferably, said supplementary pharmaceutically active agent is selected from the group consisting of a rapid acting insulin, an intermediate acting insulin, a long acting insulin, a combination of intermediate and rapid acting insulins, Inalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, or SNK-860, Miglitol, Acarbose, Glipizide, Glyburide, Chlorpropamide, Tolbutamide, Tolazamide, or Glimepriride.

Still a further object of the invention is a process for preparing substituted methylene amide derivatives according to formula I.

The substituted methylene amide derivatives of the present invention may be prepared from readily available starting materials using the below general methods and procedures. It will be appreciated that where typical or preferred experimental conditions (i.e. reaction temperatures, time, moles of reagents, solvents, etc.) are given, other experimental conditions may also be used, unless otherwise stated. Optimum reaction conditions may vary with the particular reactants or solvents used, but such conditions can be determined by one skilled in the art by routine optimisation procedures.

By the following set out general methods and procedures compounds of formula (Ia) are, obtained.

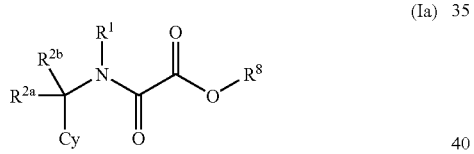

(Ia)

The substituents of (Ia) are as above defined and $R^1$ is H, $(C_1$-$C_6)$alkyl or (3-8 membered) cycloalkyl group.

Generally, substituted methylene amide derivatives according to the general formula (I) may be obtained by several processes, using both solution-phase and solid-phase chemistry protocols. Depending on the nature of Cy, $R^1$, $R^{2a}$, $R^{2b}$ and $R^8$, some processes will be preferred to others, this choice of the most suitable process being assumed by the practitioner skilled in the art.

Preparation using Solution Phase:

Generally, substituted methylene amide derivative of formula (I) may be obtained by the initial synthesis of the esters (Ia) and their subsequent hydrolysis to give rise to the substituted methylene amide derivative of the general formula (I).

a) Carboxamide and Sulfonamide Substituted Methylene Amide Derivatives of Formula (I)

In the following the general preparation of carboxamide and sulfonamide substituted methylene amide derivatives of formula (I), wherein $R^1$, $R^{2a}$, $R^{2b}$ and Cy are as above-defined, shall be illustrated (see Scheme A below).

Substituted methylene amide derivatives of formula (I) may be prepared by coupling the corresponding carboxylic acid derivatives ($LG_2$—CO—CO—$R^8$), wherein $LG_2$ is a suitable leaving group—including Cl, N-hydroxy succinimide or benzotriazol-1-yl—and the primary or secondary amine Cy-$CR^{2a}R^{2b}$—$NHR^1$. Preparation of said amide derivatives is performed using conditions and methods well known to those skilled in the art to prepare an amide bond from an amine and a carboxylic acid or carboxylic acid derivative (e.g. acid chloride), with standard coupling agents, such as e.g. DIC, EDC, TBTU, DECP, DCC, PyBOP®, Isobutyl chloroformate or others in the presence or not of bases such as TEA, DIEA, NMM in a suitable solvent such as DCM, THF or DMF. Substituted methylene amides of formula (Ia) are then submitted to hydrolysis using hydroxide (e.g. NaOH) and leading to the desired compounds of Formula (I).

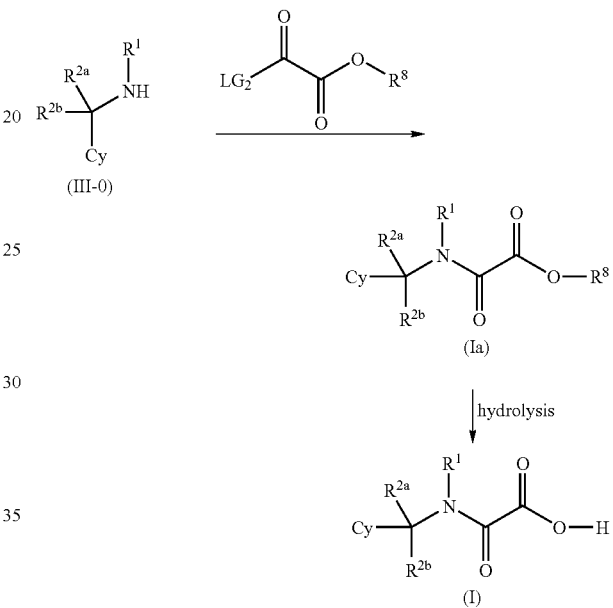

Scheme A

General preparation according to the invention also includes compounds of Formula (I) in which Cy is particularly substituted by either —CO—$NR^3R^{3'}$, —NH—CO—$R^3$ or —$SO_2$—$R^3R^{3'}$ such as described in the schemes below, wherein $R^3$ and $R^{3'}$ are as above-defined, and where chemical transformations of compounds of formula (Ia), also allow the obtention of compounds of formula (I).

b) Carboxamide and Sulfonamide Substituted Methylene Amide Derivatives of Formula (I-1)

In the following the general preparation of carboxamide and sulfonamide substituted methylene amide derivatives of formula (I-1)—i.e. compounds of formula (I), wherein Cy is as above defined and is substituted by either —CO—$NR^3R^{3'}$ (X=—CO—) or —$SO_2$—$NR^3R^{3'}$ (X=—$SO_2$—)—shall be illustrated (see Scheme 1 below).

Substituted methylene amide derivatives of formula (I-1), wherein Cy is substituted with —CO—$NR^3R^3$ may be prepared from the corresponding carboxylic derivatives (II-1), wherein $LG_1$ is a suitable leaving group—including OH, Cl, O-alkyl or O-alkylaryl and from a primary or secondary amine —$NHR^3R^{3'}$, wherein $R^3$, $R^{3'}$ is independently from each other selected from the group consisting of H, $(C_1$-$C_{15})$ alkyl, $(C_2$-$C_{12})$alkenyl, $(C_2$-$C_{12})$alkynyl, aryl, heteroaryl, (3-8-membered)cycloalkyl or heterocycloalkyl, $(C_1$-$C_{12})$ alkyl aryl or heteroaryl, $(C_2$-$C_{12})$alkenyl-aryl or -heteroaryl, $(C_2$-$C_{12})$alkynyl-aryl or -heteroaryl. A general protocol for such preparation is given below in the Examples (see Method A), using conditions and methods well known to those skilled in the art to prepare an amide bond from an amine and a carboxylic acid or carboxylic acid derivative (e.g. acid chloride), with standard coupling agents, such as e.g. DIC, EDC, TBTU, DECP, DCC, PyBOP®, Isobutyl chloroformate or others in the presence or not of bases such as TEA, DIEA, NMM in a suitable solvent such as DCM, THF or DMF.

Substituted methylene amides of formula (I-1), wherein Cy is substituted with —SO$_2$—NR$^3$R$^{3'}$ (X=—SO$_2$—) may also be prepared from the corresponding sulfonic acid derivatives (II-1), wherein LG$_1$ is a leaving group such as e.g. OH, Cl, O-Alkylaryl or O-Alkyl, and a primary or secondary amine NHR$^3$R$^{3'}$ (see Scheme 1; Method A).

According to a further process, the substituted methylene amides of formula (I-1), wherein Cy is substituted with —CO—NR$^3$R$^{3'}$ or —SO$_2$NR$^3$R$^{3'}$ (X=—CO— or —SO$_2$—) may be prepared from the corresponding amines (III-1) by coupling with the ester LG$_2$-CO—CO—OR$^8$ wherein R$^8$ is an alkyl group and LG$_2$ is a leaving group such as for example Cl, N-hydroxy succinimide, or benzotriazol-1-yl, such as above-described in Scheme 1 (Method B).

Compounds (III-1), wherein P is H or any protecting groups such as Boc or Fmoc, may be prepared by addition of the corresponding carboxylic or sulfonic acid derivatives (III-1') (X=—CO—, X=—SO$_2$— respectively), whereby LG$_1$ is a leaving group such as e.g. OH, Cl or O-alkyl, with primary

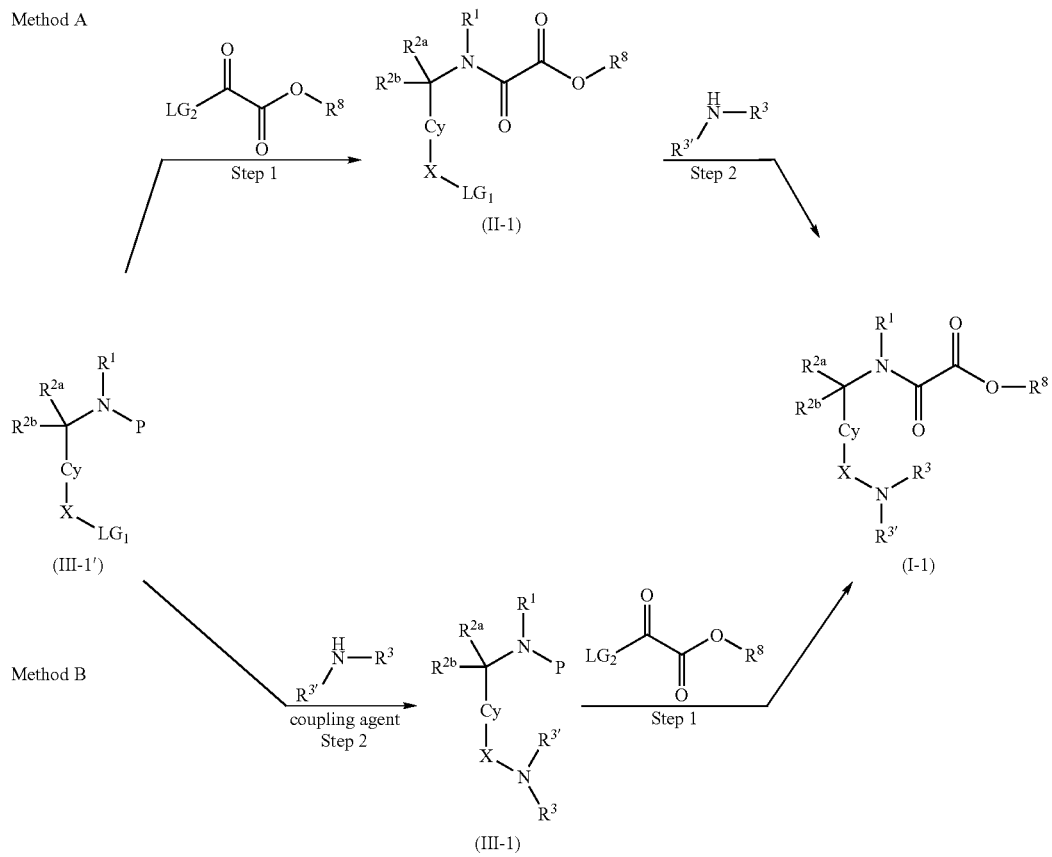

Scheme 1

The carboxylic acid and sulfonic acid derivatives (II-1) (wherein X=—CO— or —SO$_2$—) may be obtained from the corresponding amine (III-1'), wherein P=H, by coupling with the ester as set out in Step 1. Thereby, LG$_2$ is a leaving group (e.g. Cl, N-hydroxy succinimide, benzotriazol-1-yl).

Said amines (III-1') in which P is H, may be obtained by deprotection of their corresponding protected form, wherein P is a protecting group such as e.g. Boc or Fmoc. For all the protection, deprotection methods, see Philip J. Kocienski, in "Protecting Groups", Georg Thieme Verlag Stuttgart, N.Y., 1994 and, Theodora W. Greene and Peter G. M. Wuts in "Protective Groups in Organic Synthesis", 3$^{rd}$ edition, John Wiley & Sons Inc., 1999 (N.Y.).

or secondary amines NHR$^3$R$^{3'}$ following solution-phase chemistry protocols such as described in the Examples and shown in Scheme 1 (Method B).

c) Substituted Methylene Amide Derivatives of Formula (I-2)

According to a further process, substituted methylene amide derivatives of formula (I-2), i.e. substituted methylene amide derivatives of formula (I), wherein Cy is substituted with —NR$^3$COR$^{3'}$ and R$^3$ and R$^3$ are as above-defined, may be prepared from the corresponding amine (II-2), wherein P' is H, and LG$_1$-CO—R$^{3'}$ (XI) (X=—CO—) following the protocols described in the Examples and shown in Scheme 2 (Method C). LG$_1$ is a suitable leaving group such as e.g. Cl, OH or O-alkyl.

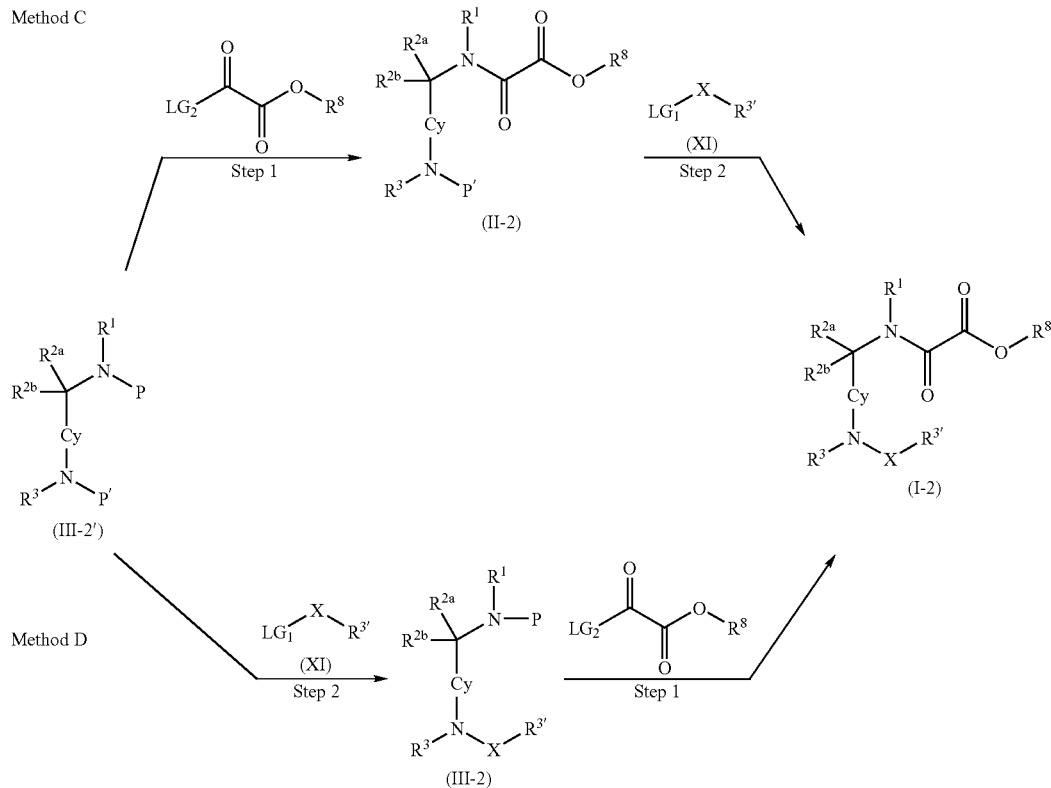

Scheme 2

The amines of formula (II-2) wherein P' is H, may be obtained by deprotection of their corresponding protected form, wherein P' is a protecting group such as e.g. Boc or Fmoc.

The amines of formula (II-2) wherein P' is H or any protecting groups such as Boc or Fmoc, may be obtained from the corresponding amine (III-2'), wherein P is H, by coupling with the ester as set out in Step 1. Thereby, $LG_2$ is a leaving group (e.g. Cl, N-hydroxy succinimide, benzotriazol-1-yl).

Said amines (III-2'), wherein P is H, may be obtained by deprotection of their corresponding protected form, wherein P is a protecting group such as e.g. Boc or Fmoc.

According to one embodiment, substituted methylene amide derivatives of formula (I-2), wherein Cy is as above-defined, may be substituted with —$NR^3COR^{3'}$ and may be prepared from the corresponding amines (III-2), wherein P is H, by coupling with the ester $LG_2$-CO—$COOR^8$, wherein $R^8$ is ($C_1$-$C_6$)alkyl, preferably ethyl or methyl, and $LG_2$ is a leaving group as above described (see Scheme 2 (Method D)).

Amines (III-2), wherein P is H, can be obtained by deprotection of their corresponding protected form, wherein P is a protecting group such as e.g. Boc or Fmoc.

Compounds (III-2), wherein P is H or any protecting groups such as Boc or Fmoc, are prepared by addition of the corresponding amines (III-2'), wherein P' is H, with derivatives of formula $LG_1$-CO—$R^{3'}$ (IX) (X=—CO—), whereby $LG_1$ is a suitable leaving group such as e.g. Cl, OH or O-alkyl following protocols described in the Examples and as shown above in Method D.

Compounds of formula (I-2) wherein X is different from the carbonyl functionality may be prepared by replacing compounds of formula (XI) with those containing the appropriate functional groups, e.g. sulfonyl chlorides, isocyanates, isothiocyanates, chloroformates, substituted alkyl halides, epoxides or others to yield sulfonamide, urea, thiourea, carbamate, substituted alkyl derivatives, substituted α, β-aminoalcohols, or others, respectively.

d) Preparation of the Precursor Compounds of Formula (I-3)

According to another process, substituted methylene amide derivatives of formula (I-3), i.e. substituted methylene amide derivatives of formula (I), wherein Cy is substituted with an oxadiazole (as an example for a heteroaryl) and $R^3$ is as above-defined, may be prepared from the corresponding acid derivative of formula (II-1), wherein $LG_1$ is a suitable leaving group such as e.g. Cl, OH or O-alkyl and imide oxime of formula (X) following protocols such as described in the Examples and shown in Scheme 3 (Method E). Thus, the starting acid derivatives of formula (II-1) are reacted with imide oxime of formula (X) using standard coupling agents, such as DIC, EDC, TBTU, DECP, DCC, PyBOP®, Isobutyl chloroformate or others in a suitable solvent such as DCM, followed by exposure to base, such as pyridine, to promote the cyclization yielding oxadiazole of formula (I-3).

According to an alternative process, the substituted methylene amides of formula (I-3) may be prepared from the corresponding amines (III-3) by coupling with the ester $LG_2$-CO—CO—$OR^8$ wherein $R^8$ is an alkyl or cycloalkyl group and $LG_2$ is a leaving group such as for example Cl, N-hydroxy succinimide, or benzotriazol-1-yl, such as described in Scheme 3 (Method F).

Compounds (III-3), wherein P is H, may be obtained by deprotection of their corresponding protected form, wherein P is a protecting group such as e.g. Boc or Fmoc.

Compounds (III-3), wherein P is H or any protecting groups such as Boc or Fmoc, may be prepared from their precursor of formula (III-3') and amide oxime of formula (X) following protocols such as described in the Examples and shown in Scheme 3 (Method F).

According to a further process, the substituted methylene amides of formula (I-4) may be prepared from the corresponding amines (III-4) by coupling with the ester $LG_2$-CO—CO—$OR^8$ wherein $R^8$ is an alkyl group and $LG_2$ is a leaving group such as Cl, N-hydroxy succinimide or benzotriazol-1-yl, such as described in Scheme 4 (Method H).

Compounds (III-4), wherein P is H, may be obtained by deprotection of their corresponding protected form, wherein P is a protecting group (e.g. Boc or Fmoc).

Compounds (III-4), wherein P is H or any protecting groups (e.g. Boc or Fmoc), may be prepared from their precursor of formula (III-4') and an alkyne of formula (XII) following protocols such as described in the Examples and shown in Scheme 4 (Method H).

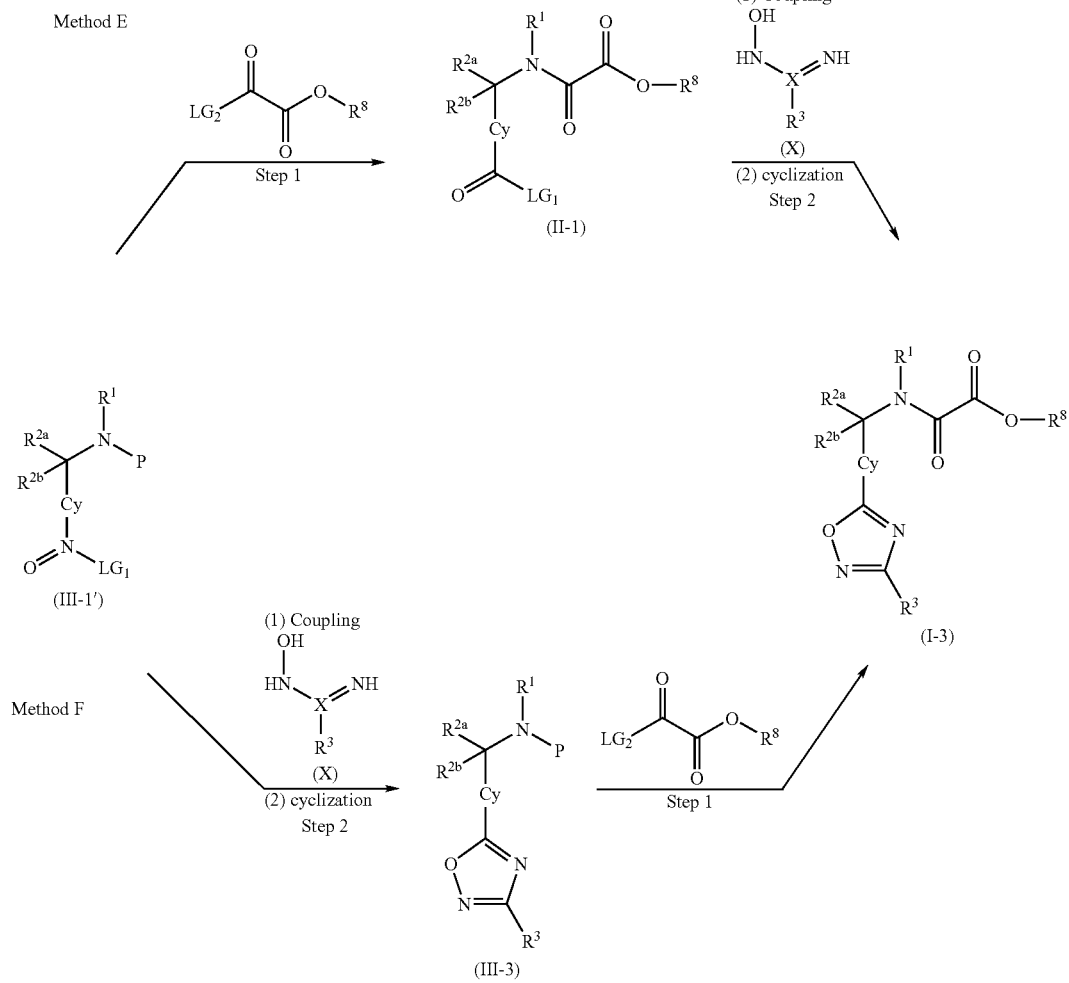

e) Preparation of the Precursor Compounds of Formula (I-4)

According to another process, substituted methylene amide derivatives of formula (I-4), i.e. substituted methylene amide derivatives of formula (I), wherein Cy is substituted with X, and X is halogen atom (e.g. Br, I, Cl) or a suitable leaving group such as —$OSO_2CF_3$, and may be prepared from the corresponding acid derivative of formula (I-4), following protocols such as described in the Examples and shown in Scheme 4 (Method G).

Thus, derivatives of formula (II-4) can be reacted with a substituted alkyne of formula (XII) in the presence or not of additives, such as copper (1) salts in conjunction with palladium catalysts, (e.g. palladium tetrakis(triphenylphosphine), and amines (e.g. triethylamine). Preferred conditions imply use of copper(I) bromide, palladium tetrakis(triphenylphosphine) in triethylamine e.g. 90° C.

Scheme 4

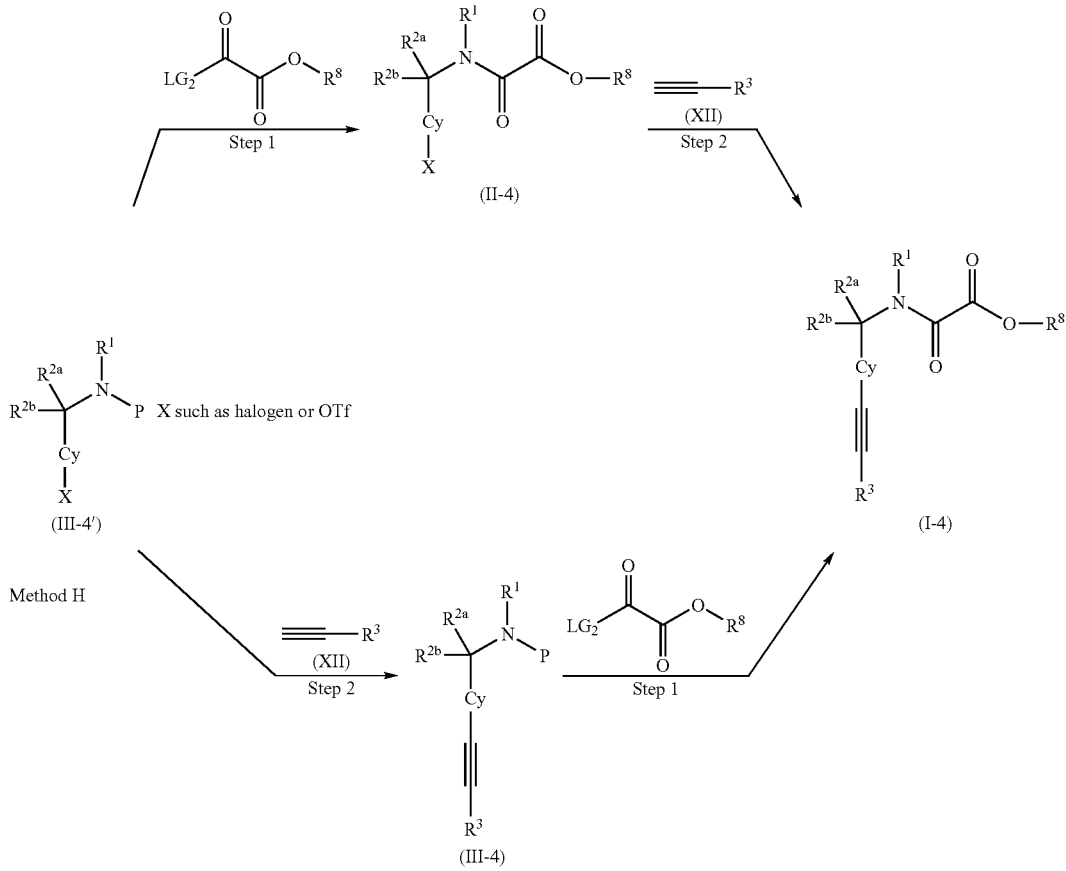

f) Preparation of the Precursor Compounds of Formula (III)

The precursor compounds of formulae (III), (including III-1', III-1, III-2', III-2, III-3, III-4, or III-4'), mentioned in Schemes 1, 2, 3 and 4, wherein Cy may be substituted with a moiety Q, like a substituted or unsubstituted aryl or substituted or unsubstituted heteroaryl, e.g. an oxadiazole, a substituted or unsubstituted cycloalkyl moiety, or —CO—NR$^3$R$^{3'}$, —COOR$^3$, —NP'R$^3$, —NR$^3$COR$^{3'}$, —CO-LG$_1$, —SO$_2$-LG$_1$, —SO$_2$NR$^3$R$^{3'}$, —C≡C—R$^3$ wherein R$^3$ and R$^{3'}$ may be independently from each other, substituted or unsubstituted (C$_1$-C$_{15}$)alkyl or X wherein X is as defined in e), may be prepared from the corresponding precursors of formulae (VII), (VIII) or (IX), using a variety of synthetic strategies for which some examples are indicated in the below Scheme 5.

Compounds of formula (III)—wherein R$^{2b}$ is H—may for instance be prepared by alkylation of the amines (IV)—wherein R$^1$ is as above-defined and wherein P is H or a suitable protecting group such as e.g. Boc or Fmoc—with the carbonyl derivatives (IX), wherein R$^{2a}$ is as above defined. The reaction (see Scheme 5, Method I) may be performed in the presence of a suitable reducing agent including NaBH(OAc)$_3$, NaBH$_3$CN, NaBH$_4$ or hydrogen and an appropriate catalyst such as Pd/C or PtO$_2$.

Alternatively, compounds of formula (III) may be prepared by alkylation of amines of formula (IV) with the derivatives of formula (VIII), wherein LG is a suitable leaving group including Cl, Br, I, OH, OMs, OTs (see Method J). R$^{2b}$ and R$^{2b}$ are as above-defined.

Also, compounds of formula (III) may be prepared by alkylation of amines of formula (VII), with the alkylating agents of formula (VI) wherein LG is the above-mentioned leaving group (Scheme 5, Method K).

Still a further alternative is set out in Scheme 5, Method L. This embodiment illustrates the preparation of compounds of formula (III) by alkylation of the amines of formula (VII) with carbonyl derivatives (V)—wherein A is as above-defined—in the presence of a reducing agent such as e.g. NaBH(OAc)$_3$, NaBH$_3$CN, NaBH$_4$ or hydrogen with an appropriate catalyst such, as e.g. Pd/C or PtO$_2$, in order to provide compounds of formula (III), wherein R$^1$ is —CH—R$^5$-A in which R$^5$ is selected from the group consisting of (C$_1$-C$_{12}$)allyl, preferably (C$_1$-C$_6$)alkyl, (C$_2$-C$_{12}$)alkenyl, (C$_2$-C$_{12}$)alkynyl, aryl, heteroaryl, (3-8-membered)cycloalkyl or heterocycloalkyl, (C$_1$-C$_{12}$)alkyl-aryl or (C$_1$-C$_{12}$)alkyl-heteroaryl, (C$_2$-C$_{12}$)alkenyl-aryl or -heteroaryl, (C$_2$-C$_{12}$)alkynyl-aryl or -heteroaryl.

Scheme 5

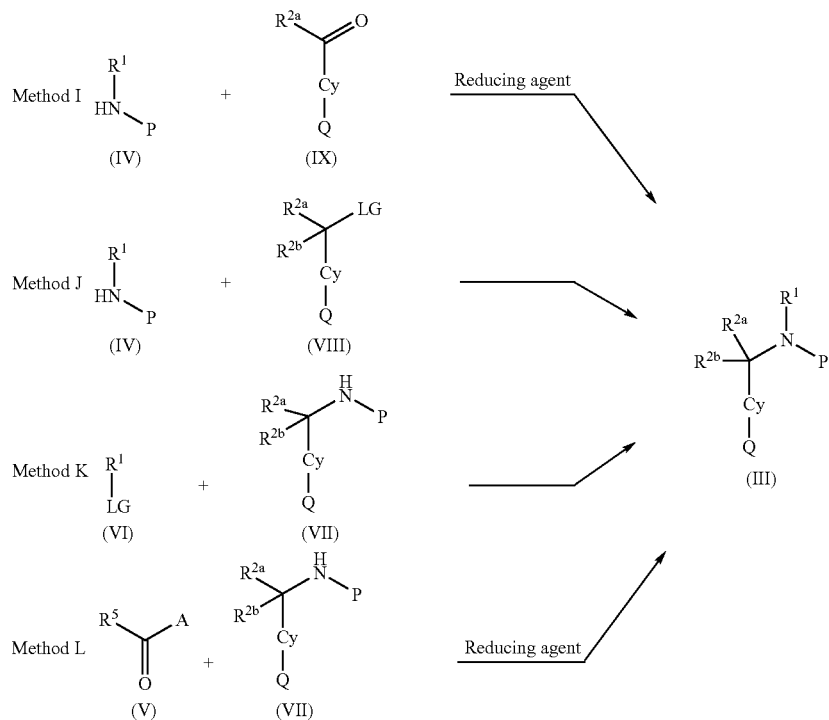

The precursor compounds of formulae (IV), (V), (VI), (VIII), (VIII) or (IX) are either commercially available or readily accessible from commercial starting materials such as those selected from:
(dl)-trans-2-benzyloxycyclopentylamine, 1-(1-naphthyl) ethylamine, 1,2,3,4-tetrahydro-1-naphthylamine, 1,2-dodecylene oxide, 1-aminoindane, 1-deoxy-1-(methylamino)glucitol, 2-amino-2-hydroxymethyl-1,3-propanediol, 2-(2,4,6-trimethyl-phenyl)-ethylamine, 2-(3-chlorophenyl)ethylamine, 2-(3-methoxyphenyl) ethylamine, 2-(4-biphenyl)ethylamine, 2-(4-methoxyphenyl)ethylamine, 2,2-diphenylethylamine, 2-amino-1-methoxypropane, 2-fluorobenzaldehyde, 2-formylthiazole, 2-morpholino-1,3-thiazole-5-carbaldehyde, 2-phenoxyphenethylamine, 2-phenylglycine ethyl ester hydrochloride, 2-pyridinecarboxaldehyde, 2-quinoxaloyl chloride, 2-thiophenecarboxaldehyde, 3-(benzyloxy) aniline, 3-(trifluoromethyl)benzaldehyde, 3,3-diphenylpropylamine, 3,5-dichlorobenzylamine, 3-aminophenyl trifluoromethyl sulfone, 3-carboxybenzaldehyde, 3-chlorobenzaldehyde, 3-cyanobenzaldehyde, 3-hydroxybenzaldehyde, 3-iodobenzoyl chloride, 3-nitrobenzaldehyde, 3-phenylbenzyl amine hydrobromide, 3-phenylpropylamine, 3-pyridinecarboxaldehyde, 3-thiophenecarboxaldehyde, 4-(1,2,3-thiadiazol-4-yl), benzylamine hydrochloride, 4-(aminomethyl)-1-N-Boc-aniline, 4-(dimethylamino)phenyl isocyanate, 4-(methyl-sulfonyl) benzaldehyde, 4-(trifluoromethyl)benzylamine, 4-amino-1-benzylpiperidine, 4-benzamidobenzylamine, 4-bromoaniline, 4-chloromethylbenzoyl chloride, 4-chlorobenzaldehyde, 4-cyanobenzaldehyde, 4-dimethylaminobenzaldehyde, 4-formyl-benzoic acid, 4-formyl-benzoic acid benzyl ester, 4-hydroxybenzaldehyde, 4-methoxybenzene-sulfonyl chloride, 4-nitrobenzaldehyde, 4-n-pentylbenzylamine hydrochloride, 4-pentylbenzylamine hydrochloride, 4-phenoxyaniline, 4-phenoxybenzaldehyde, 4-phenoxybenzylamine, 4-phenoxyphenethylamine, 4-phenylbutylamine, 4-pyridinecarboxaldehyde, 4-tolyl boronic acid, 5-formyl-2-thiophenecarboxylic acid, 6-(trifluoromethyl)pyridine-3-carboxaldehyde, aniline, benzaldehyde, benzoylperoxide, benzylamine, chloro-oxo-acetic acid ethyl ester, cis-delta 9-trans-tetradecenoyl chloride, cyclohexyl isocyanate, cyclohexyl isocyanate, cyclopentanone, dl-3-amino-3-phenylpropionic acid, dl-alpha-methyl-benzylamine, dodecylamine, Fmoc-(3-aminomethyl)-benzoic acid, Fmoc-(4-aminomethyl)-benzoic acid, hexanoyl chloride, isopropylamine, lithium hydroxide monohydrate, 1-phenylglycine t-butyl ester, methyl 4-formylbenzoate, N-bromo-succinimide, octylamine, p-anisaldehyde, pentadecylamine, piperonal, piperonylamine, sodium cyanoborohydride, sodium triacetoxyborohydride, tetrabutylammonium iodide, tetradec-9-enoyl chloride, tetrakis-triphenylphosphine palladium(0), thiophene-2-ethylamine, trans-2-phenylcyclopropylamine hydrochloride, trans-3-(trifluoromethyl)cinnamoyl chloride, tridecanoic acid, tridecanoyl chloride.

A preferred process for preparing compounds of formula (III) is set out in the above Scheme 5, Method I. Therein, the reductive amination of carbonyl compounds of formula (IX) wherein Q is —COO—Bn is performed with amines of formula (IV) and a reducing agent such as $NaBH(OAc)_3$ in a suitable solvent such as DCE or THF. The process thus affords the amine of formula (III), wherein Q is C(O)OBn.

According to the methods described in Scheme 1 (Method A), the resulting amine (III) is coupled with an ester $LG_2$-CO—COO—$R^8$, wherein $R^8$ is a ($C_1$-$C_6$)alkyl or cycloalkyl, preferably ethyl or methyl, and $LG_2$ is a leaving group such as e.g. Cl, in the presence of a base such as DIEA in an aprotic solvent (such as e.g. DCM or THF), thus affording substituted methylene amide derivatives of formula (II-1). Subsequent benzyl deprotection using standard $H_2$/Pd methods and followed by the coupling of the resulting acid, wherein X is CO and $LG_1$ is —OBn, with amines —NHR$^3$R$^{3'}$, with using standard carbodiimide—or standard mixed anhydride—mediated methods affords the desired compounds of formula (I-1), wherein R$^8$ is ethyl or methyl (see Scheme 1). The latter compounds may be hydrolysed to yield compounds of formula (Ia) of this invention, wherein R$^8$ is H, by their treatment with hydroxide such as e.g. NaOH in an appropriate protic solvent (such as e.g. EtOH), followed by acidification of the reaction mixture.

According to a further preferred process of preparing compounds of formula (Ia), carbonyl derivatives of formula (IX) (see Scheme 5), wherein Q is —CONR$^3$R$^{3'}$ may be prepared from their commercially available or readily accessible from commercial starting materials precursor in which Q is —COOH and amines HNR$^3$R$^3$ using standard carbodiimide- or standard mixed anhydride-mediated methods. The reductive amination of the carbonyl derivatives of formula (IX) wherein Q is —CONR$^3$R$^{3'}$ with amines of formula (IV) and a reducing agent such as NaBH(OAc)$_3$ in a suitable solvent such as DCE or THF affords the amine of formula (III) wherein Q is —CONR$^3$R$^{3'}$, following the methods described in Method I, Scheme 5. The resulting amine (III) is coupled with the ester $LG_2$-CO—COO—R$^8$, wherein R$^8$ is a ($C_1$-$C_6$) alkyl or cycloalkyl, preferably ethyl or methyl, and $LG_2$ is a leaving group such as e.g. Cl, in the presence of a base such as DIEA in an aprotic solvent (such as e.g. DCM or THF) affording the ester (I-1). The latter compounds may be hydrolysed to compounds of formula (Ia) of this invention, wherein R$^8$ is H, by their treatment with hydroxide such as e.g. NaOH in an appropriate protic solvent (such as e.g. EtOH), followed by acidification of the reaction mixture.

Basic salts of the compounds of formula (I) are prepared in a conventional manner as is known by a person skilled in the art. In particular the N-Me-D-glucamine and the tromethamine (i.e. 2-amino-2-(hydroxymethyl)-1,3-propanediol) salts of this invention provide water-soluble derivatives and improved bioavailability.

The methods of preparation of the substituted methylene amides of formula (I) of this invention according to the above protocols have the specific advantage of being convenient and economic in the sense that they involve only a few steps.

g) Preparation using Solid-Phase and/or Mixed Solid/Solution Phase:

According to yet another general approach, substituted methylene amides according to the general formula (Ia), wherein the substituents R$^1$, R$^{2a}$, R$^{2b}$ and Cy are as above defined, may be prepared by solid-phase and/or mixed solid/solution-phase synthesis protocols such as those described in the examples and shown in Schemes 1, 2, 3, 4, 5 and 6 above using well known technical approaches (such as IRORI®). It will be appreciated by the practitioner skilled in the art that basically the same conditions, methods and reagents as above described in Schemes 1, 2, 3 and 4 for the solution-phase synthesis of compounds of formula (Ia) could be applied to the solid-phase and/or mixed solid-/solution-phase synthesis of said compounds. In the context of such a solid-phase and/or mixed solid-solution-phase synthesis protocol, R$^3$ is as above-defined. Cleavage from the resin is effected under acidic conditions, affording the corresponding substituted methylene amide derivatives of formula (Ia). It is to be understood that further to the resin types mentioned in the Examples such as e.g. Sasrin aldehyde resins, other suitable reagents, notably resins, known to a person skilled in the art could be employed for the solid-phase synthesis of compounds of general formula (Ia).

The filled circles in the below Scheme 6 illustrate the resin beads to which the compounds are linked during the solid phase synthesis.

In one particularly preferred process, resin-bound amines of formula NHR$^3$R$^6$ (D), wherein R$^6$ represents any suitable resin (Scheme 6) and R$^3$ is above-defined in the description, are prepared from commercially available per se or readily accessible from resins such as e.g. Sasrin aldehyde or bromo-Wang resins and amines, using standard reductive amination or alkylation conditions well known to the practitioner skilled in the art. The resin-bound to amines NHR$^3$R$^6$ (D) may then be acylated with compounds of formula (VIII-1') wherein X is —CO— and $LG_1$ is Cl in the presence of base such as e.g. DIEA, in suitable solvent such as NMP or DCM; or X may also be is —SO$_2$— and $LG_1$ is Cl using standard conditions involving a base such as DIEA in an aprotic solvent such as DCM or THF affording compounds of formula (VIII-1) (Scheme 6, Method N).

According to the methods outlined in Scheme 5 (Method 3), the displacement of the leaving group LG from the latter resin-bound intermediates (VIII-1) by their reaction with amines NHPR$^1$ (IV) in the presence of iodide such as TBAI or NaI in a suitable solvent such as e.g. NMP at suitable temperature such as 80° C. can afford resin-bound compounds of Formula (III-1). Finally, this compounds is coupled with the ester $LG_2$-CO—COO—R$^8$, wherein R$^8$ is preferably ethyl or methyl and $LG_2$ is a leaving group such as e.g. Cl, in the presence of a base such as DIEA in an aprotic solvent (such as e.g. DCM or THF) affording the resin-bound ester (I-1). The latter compounds can be hydrolysed to compounds of formula (Ia) of this invention, wherein R$^8$ is H, by their treatment with hydroxide such as e.g. NaOH in an appropriate solvent (such as e.g. THF). Cleavage from the resin is performed under acidic conditions (such as e.g. a DCM solution containing 20% TFA), affording the corresponding desired substituted methylene amide derivatives of Formula (Ia).

Scheme 6

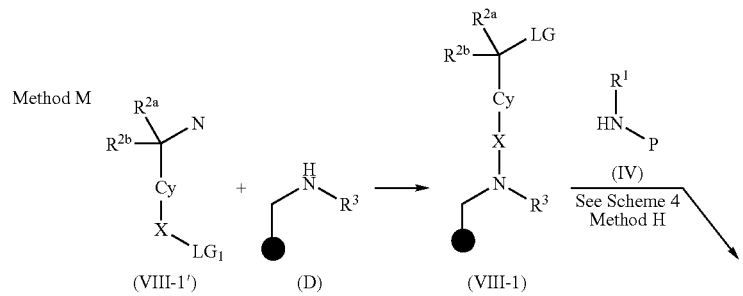

-continued

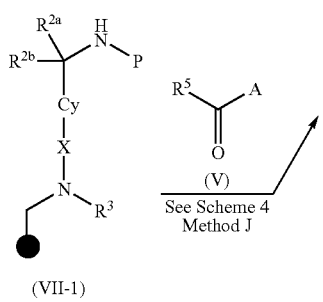

(III-1)

Method N

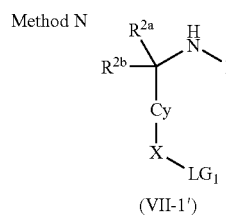 + 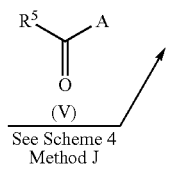 → 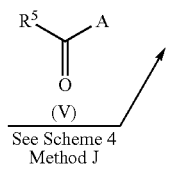 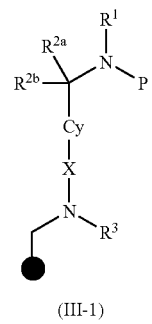

(VII-1')   (D)   (VII-1)   See Scheme 4 Method J

In one other preferred synthetic approach Method N), the resin-bound amines of formula $NHR^6R^3$ (D), wherein $R^6$ represents a suitable resin (Scheme 6) can be acylated with compounds of formula (VII-1'), wherein X is —CO—, $LG_1$ is OH, $R^1$, $R^{2a}$, $R^{2b}$, $R^3$ and $R^5$ are as above-defined and P is a protecting group such as Fmoc or Pht, using standard conditions involving a coupling reagent such as e.g. PyBOP®, in a suitable solvent such as NMP or DCM affording resin-bound compounds of formula (VII-1). The same resin-bound amines of formula $NHR^6R^3$ can be sulfonylated with compounds of formula (VII-1'), wherein X is —$SO_2$—, $LG_1$ is Cl and P is a protecting group such as Fmoc or Pht, using standard conditions involving a base such as DIEA affording resin-bound compounds of formula (VII-1). These latter intermediates can be deprotected following standard conditions and then alkylated following the methods outlined in Scheme 5 (Method H) to afford the compounds of formula (III-1). Finally, these compounds are converted to the desired substituted methylene amides of formula (Ia), following the methods described above.

When employed as pharmaceuticals, substituted methylene amide derivatives of the present invention are typically administered in the form of a pharmaceutical composition. Hence, pharmaceutical compositions comprising a compound of formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, substituted methylene amide derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the substituted methylene amide derivative according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, substituted methylene amide derivatives of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences, 17th* Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The following abbreviations are hereinafter used in the accompanying examples: min (minute), h (hour), g (gram), mg (milligram), mmol (millimole), m.p. (melting point), eq (equivalents), mL (milliliter), µL (microliters), mL (milliliters), APCI (Atmospheric pressure chemical ionization), ESI (Electro-spray ionization), L (liters), AcOEt (Ethyl acetate), Boc (tert-Butoxycarbonyl), $CH_3CN$ (Acetonitrile), DBU (Diazabicyclo [5.4.0]undec-7-ene), DCC (Dicyclohexyl carbodiimide), DCE (Dichloroethane), DIEA (Diisopropylethylamine), Fmoc (9-Fluorenylmethoxycarbonyl), $CDCl_3$ (deuterated chloroform), c-Hex (Cyclohexanes), DCM (Dichloromethane), DIC (Diisopropyl carbodiimide), DMAP (4-Dimethylaminopyridine), DMF (Dimethylformamide), DMSO (Dimethylsulfoxide), DMSO-$d_6$ (Deuterated dimethylsul-foxide), EDC (1-(3-Dimethyl-amino-propyl)-3-ethyl-carbodiimide), EtOAc (Ethyl acetate), $Et_2O$ (Diethyl ether), EtOH (Ethanol), HOBt (1-Hydroxybenzotriazole), $K_2CO_3$ (Potassium carbonate), MeOH (Methanol), $CD_3OD$ (Deuterated methanol), $MgSO_4$ (Magnesium sulfate), NaH (Sodium hydride), $NaHCO_3$ (Sodium bicarbonate), $NaBH_3CN$ (Sodium cyanoborohydride), $NaBH_4$ (Sodium borohydride), $NaBH(OAc)_3$ (Sodium triacetoxyborohydride), NMM (N-methyl-morpholine), NMP (N-Methylpyrrolidone), nBuLi (n-Butyl-lithium), $Pd(PPh_3)_4$ (Tetrakis triphenylphosphine palladium), PetEther (Petroleum ether), Pht (Phtalimide), PyBOP® (Bentotriazole-1-yl-oxy-tris-pyrrolidino-phosphonium hexafluorophosphate), rt (room temperature), SPE (solid phase extraction), TEA (Triethylamine), TFA (Trifluoro-acetic acid), THE (Tetrahydrofuran), TBTU (2-(1-H-benzotriazole-1-yl)-1,1,3,3-tetramethyluromium tetrafluoroborate).

The HPLC, MS and NMR data provided in the examples described below were obtained as followed. HPLC: Waters Symmetry $C_8$ column 50 mm×4.6 mm; UV detection at 254 nm; flow: 2 mL/min; Conditions A: 8 min gradient from 0.1% TFA in $H_2O$ to 0.07% TFA in $CH_3CN$; Conditions B: 10 min gradient from 0.1% TFA in $H_2O$ to 0.07% TFA in $CH_3CN$. The semi-preparative reverse-phase HPLC was obtained as followed: Supelcosil ABZ+Plus column (25 cm×21.2 mm, 12 µm); UV detection at 254 nm and 220 nm; flow 20 mL/min; Condition C: 10 min gradient from 30% $CH_3CN$ in 0.1% TFA in $CH_3CN$ to 100% $CH_3CN$ followed by 5 min elution at 100% $CH_3CN$. The MS data provided in the examples described below were obtained as followed: Mass spectrum: PE sciex API 150 EX (APCI or ESI) or LC/MS Waters ZMD (ESI). The NMR data provided in the examples described below were obtained as followed: $^1$H-NMR: Bruker DPX-300 MHz.

EXAMPLES

Example 1

(benzyl{4-[(dodecylamino)carbonyl]benzyl}amino) (oxo)acetic acid

Step a) Formation of the Secondary Amine of Formula (III) Following the Method I (See Scheme 5), e.g. 4-(benzylamino-methyl)-benzoic acid benzyl ester To a solution of 4-formyl-benzoic acid benzyl ester (5.00 g, 20.81 mmol) (compound described in *Bioorg. Med. Chem.;* 5; 9; 1873-82 (1997)) and benzyl amine (2.453 g, 22.89 mmol) in DCE (150 mL) was added at once $NaBH(OAc)_3$ (6.175 g, 29.14 mmol) and the resulting mixture was stirred overnight at rt. 30 mL of a saturated aqueous solution of $NaHCO_3$ were added to the reaction mixture, the aqueous layer was separated and extracted with DCM (3×200 mL). The combined organic layers were dried over $MgSO_4$, filtered and concentrated to afford a yellowish oil. This crude product was purified by column chromatography over silica gel (AcOEt/c-Hex 4/1 to 1/1 in about 1 h) to give the title compound as a colorless oil (4.780 g, 69%). $^1$H NMR ($CDCl_3$, 300 MHz) δ 7.95 (m, 2H), 7.37-7.16 (m, 12H), 5.27 (s, 2H), 3.77 (s, 2H), 3.70 (s, 2H). M$^+$(ESI): 332.2. HPLC (Condition B), Rt: 4.26 min (HPLC purity: 98.5%).

Step b) Formation of the Oxamic Ester of Formula (II-1) Following the Method A (See Scheme 1), e.g. 4-[(benzyl-ethoxyoxalyl-amino)-methyl]-benzoic acid benzyl ester To a solution of 4-(benzylamino-methyl)-benzoic acid benzyl ester (4.50 g, 13.58 mmol) and TEA (2.748 g, 27.16 mmol) in anhydrous THF (100 mL) at 0° C. under inert atmosphere, was added dropwise the chloro-oxo-acetic acid ethyl ester (2.781 g, 20.37 mmol) diluted in THF (10 mL). The reaction mixture was stirred at 0° C. for 2 h. The solvent was evaporated and 100 mL of DCM were added. 20 mL of a saturated aqueous solution of $NaHCO_3$ were added and the aqueous layer was separated and extracted with DCM (3×50 mL). The combined organic layers were dried over $MgSO_4$, filtered and concentrated to afford a yellowish oil. This crude product was purified by column chromatography over silica gel (AcOEt/c-Hex 4/1 to 2/1 in about 1 h) to give the title compound as a colorless oil (5.810 g, 99%). $^1$H NMR ($CDCl_3$, 300 MHz) δ 7.95 (m, 2H), 7.37-7.11 (m, 12H), 5.30 (s, 2H), 4.44 (m, 2H), 4.31-4.22 (m, 4H), 1.22 (t, J=7.5 Hz, 3H). M$^+$(APCI): 432.0. HPLC (Condition B), Rt: 7.2 min (HPLC purity: 99.4%).

Step c) Formation of the Oxamic Ester of Formula (II-1), e.g. 4-[(benzyl-ethoxyoxalyl-amino)-methyl]-benzoic acid H$_2$ (1 atm) was bubbled slowly trough a suspension of 10% Pd/C (300 mg) in EtOH (50 mL) for 15 min at rt. To this suspension was then added a solution of 4-[(benzyl-ethoxyoxalyl-amino)-methyl]-benzoic acid benzyl ester (5.500 g, 12.75 mmol) diluted in 15 mL of EtOH. The resulting reaction mixture was stirred under H$_2$ (1 atm) for 5 h at rt. The reaction mixture was filtered over a pad of celite to remove the catalyst. The solvent was evaporated to afford the title compound as a colorless oil used in the next steps without further purification (4.217 g, 97%). $^1$H NMR (CDCl$_3$, 300 MHz) δ 8.07 (m, 2H), 7.37-7.11 (m, 7H), 4.51 (m, 2H), 4.39-4.30 (m, 4H), 1.27 (m, 3H). M$^-$(APCI): 340.0; M$^+$(APCI): 342.0. HPLC (Condition A), Rt: 4.31 min (HPLC purity: 99.1%).

Step d) Formation of the Oxamic Ester of Formula (I-1) Following the Method A (See Scheme 1), e.g. ethyl(benzyl{4-[(dodecylamino)carbonyl]benzyl}amino)(oxo)acetate, using 1-ethyl-3-(3-dimethylaminopropyl)carbodiimide hydrochloride To a solution of 4-[(benzyl-ethoxyoxalyl-amino)-methyl]-benzoic acid (1500 mg, 4.39 mmol) in anhydrous THF (15 mL) at RT was added EDC (1.261 g, 6.58 mmol) and dodecylamine (1.018 g, 5.49 mmol) under inert atmosphere. The resulting mixture was stirred overnight at rt. The solvent was evaporated and the residue dissolved in DCM (30 mL) and washed with a 1N aqueous solution of HCl (2 mL). The combined organic layers were dried over MgSO$_4$, filtered and concentrated to afford a colorless oil. This crude product was purified by column chromatography over silica gel (AcOEt/c-Hex 3/1 to 1/1 in about 15 min) to give the title compound as a colorless oil (500 mg, 22%). $^1$H NMR (CDCl$_3$, 300 MHz) δ 7.75 (m, 2H), 7.37-7.26 (m, 7H), 6.09 (br s, 1H), 4.5 (m, 2H), 4.36-4.30 (m, 4H), 3.45 (m, 2H), 1.62 (m, 3H), 1.36-1.27 (m, 20H), 0.88 (m, 3H). M$^-$(ESI): 507.2. HPLC (Condition A), Rt: 6.98 min (HPLC purity: 99.9%).

Step e) Formation of the Oxamic Acid of Formula (I), e.g. (benzyl{4-[(dodecylamino)-carbonyl]benzyl}amino)(oxo)acetic acid To a solution of ethyl(benzyl{4-[(dodecylamino)carbonyl]benzyl}amino)(oxo)acetate (690 mg, 1.36 mmol) in EtOH (4 mL) was added a 1N aqueous solution of NaOH (1.36 mL, 1.36 mmol) and the resulting reaction mixture was stirred at rt for 2 h. The solvents were evaporated and the residue dissolved in EtOAc (20 mL) and washed with a 1N aqueous solution of HCl (5 mL). The aqueous layer was separated and washed with EtOAc (2×10 mL). The combined organic layers were dried over MgSO$_4$, filtered and concentrated to afford the title compound as a white solid (603 mg, 93%). $^1$H NMR (CD$_3$OD, 300 MHz) δ 7.80 (m, 2H), 7.45-7.28 (m, 6H), 7.22 (m, 1H), 4.54 (s, 2H), 4.50 (s, 2H), 3.38 (t, J=6.5 Hz), 1.64 (m, 2H), 1.38-1.21 (m, 18H), 0.88 (t, 3H, J=6.6 Hz). M$^-$(ESI): 479.2 HPLC (Condition A), Rt: 6.01 min (HPLC purity: 98.6%). Analysis calculated for C$_{29}$H$_{40}$N$_2$O$_4$: C, 72.47; H, 8.39; N, 5.83%. Found: C, 72.30; H, 8.36; N, 5.79%.

Example 2

(benzyl{4-[(dodecylamino carbonyl]benzyl}amino)(oxo)acetic acid, tromethamine (i.e. 2-amino-2-hydroxymethyl)-1,3-propanediol) salt A mixture of (benzyl{4-[(dodecylamino)carbonyl]benzyl}amino)(oxo)acetic acid (1.842 g, 3.83 mmol), tris(hydroxymethyl)amino methane (0.464 g, 3.83 mmol) and EtOH (38 mL) were heated until a homogeneous solution was obtained. The solvent was removed in vacuum and the residue was dissolved in a 9/1 mixture of H$_2$O/EtOH. The resulting solution was then lyophilized to afford the title compound as a fluffy white powder (2.299 g, 99%). M$^-$(LC/MS(ESI)): 479.5; M$^+$(LC/MS(ESI)): 481.3. HPLC (Condition A), Rt: 6.0 min (HPLC purity: 98.6%). Analysis calculated for C$_{29}$H$_{40}$N$_2$O$_4$·C$_4$H$_{11}$NO$_3$: C, 65.86; H, 8.54; N, 6.98%. Found: C, 65.10; H, 8.78; N, 6.90%.

Example 3

(benzyl{4-[(dodecylamino)carbonyl]benzyl}amino)(oxo)acetic acid, N-methyl-D-glucamine (i.e. 1-deoxy-1-(methylamino glucitol) salt The same procedure as employed in the preparation of Example 2 but using N-methyl-D-glucamine gave the title compound as a white solid (89%). M$^-$(LC/MS(ESI)): 479.3; M$^+$(LC/MS(ESI)): 481.3. HPLC (Condition A), Rt: 6.1 min (HPLC purity: 99.25%).
Analysis calculated for C$_{29}$H$_{40}$N$_2$O$_4$·C$_7$H$_{17}$NO$_5$■1.2H$_2$O: C, 61.99; H, 8.24; N, 6.02%. Found: C, 61.84; H, 8.60; N, 5.99%.

Example 4 oxo{{4-[(pentadecylamino)carbonyl]benzyl}[4-(trifluoromethyl)benzyl]amino}acetic acid Step a) Formation of benzyl 4-({[4-(trifluoromethyl)benzyl]amino}methyl)benzoate The same procedure as employed in the preparation of Example 1 (step a) but using 4-trifluoromethyl-benzylamine gave the title compound as a yellow oil (74%).
M$^+$(LC/MS(ESI)): 400.3. HPLC (Condition A), Rt: 3.76 min (HPLC purity 97.6%).

Step b) Formation of benzyl 4-({[ethoxy(oxo)acetyl][4-(trifluoromethyl)benzyl]amino}methyl)benzoate The same procedure as employed in the preparation of Example 1 (step b) but using the benzyl 4-({[4-(trifluoromethyl)benzyl]amino}methyl)benzoate gave the title compound as a colorless oil (95%). $^1$H NMR (CDCl$_3$, 300 MHz) δ 7.95 (t, 2H, J=8.3 Hz), 7.48 (m, 2H), 7.37-7.13 (m, 9H), 5.25 (br s, 2H), 4.41 (br s, 2H), 4.27-4.18 (m, 4H), 1.20 (t, 3H, J=7.0 Hz). M$^-$(LC/MS(ESI)): 498.1; M$^+$(LC/MS(ESI)): 500.3. HPLC (Condition A), Rt: 6.14 min (HPLC purity: 98.9%).

Step c) Formation of 4-({[ethoxy(oxo)acetyl][4-(trifluoromethyl)benzyl]amino}methyl)-benzoic acid The same procedure as employed in the preparation of Example 1 (step c) but using benzyl 4-({[ethoxy(oxo)acetyl][4-(trifluoromethyl)benzyl]amino}methyl)benzoate gave the title compound as a colorless foam (84%). M$^-$(LC/MS(ESI)): 408.2; M$^+$(LC/MS(ESI)): 410.1. HPLC (Condition A), Rt: 4.43 min (HPLC purity: 98.9%).

Step d) Formation of ethyl oxo{{4-[(pentadecylamino)carbonyl]benzyl}[4-(trifluoro methyl)benzyl]amino}acetate The same procedure as employed in the preparation of Example 1 (step d) but using 4-({[ethoxy(oxo)acetyl][4-(trifluoromethyl)benzyl]amino}methyl)benzoic acid gave the title compound as a white solid (78%). M⁻(ESI): 617.2. HPLC (Condition A), Rt: 7.54 min (HPLC purity: 97.7%).

Step e) Formation of the oxo{{4-[(pentadecylamino) carbonyl]benzyl}[4-(trifluoromethyl) benzyl] amino}acetic acid The same procedure as employed in the preparation of Example 1 (step e) but using the ethyl oxo{{4-[(pentadecylamino)carbonyl]benzyl}[4-(trifluoromethyl)benzyl] amino}-acetate gave the title compound as a colorless foam (84%). ¹H NMR (CD₃OD, 300 MHz) δ 7.77 (m, 2H), 7.58 (m, 3H), 7.44 (d, 1H, J=8.3 Hz), 7.38 (d, 1H, J=8.3 Hz), 7.30 (d, 1H, J=8.3 Hz), 4.56-4.50 (m, 4H), 3.37 (t, 2H, J=7.2 Hz), 1.64 (m, 2H), 1.30 (m, 24H), 0.91 (t, 3H, J=6.6 Hz). M⁻(LC/MS (ESI)): 589.1; M⁺(LC/MS(ESI)): 591.1. HPLC (Condition A), Rt: 7.25 min (HPLC purity: 98.1%).

Example 5

(benzyl{4-[(pentadecylamino)carbonyl] benzyl}amino)(oxo)acetic acid

Step a) Formation of the secondary amine of formula (III) following the Method I (See Scheme 5), e.g. 4-(benzylamino-methyl)-benzoic acid benzyl ester To a solution of 4-formyl-benzoic acid benzyl ester (5.00 g, 20.81 mmol) and benzyl amine (2.453 g, 22.89 mmol) in DCE (150 mL) was added at once NaBH(OAc)₃ (6.175 g, 29.14 mmol) and the resulting mixture was stirred overnight at rt. 30 mL of a saturated aqueous solution of NaHCO₃ were added to the reaction mixture, the aqueous layer was separated and washed with DCM (3×200 mL). The combined organic layers were dried over MgSO₄, filtered and concentrated to afford a yellowish oil. This crude product was purified by column chromatography over silica gel (AcOEt/c-Hex 4/1 to 1/1 in about 1 h) to give the title compound as a colorless oil (4.780 g, 69%). ¹H NMR (CDCl₃, 300 MHz) δ 7.95 (m, 2H), 7.37-7.16 (m, 12H), 5.27 (s, 2H), 3.77 (s, 2H), 3.70 (s, 2H) M⁺(ESI): 332.2. HPLC (Condition B), Rt: 4.26 min (HPLC purity: 98.5%).

Step b) Formation of the Oxamic Ester of Formula (II-1) Following the Method A (See Scheme 1), e.g. of the 4-[(benzyl-ethoxyoxalyl-amino)-methyl]-benzoic acid benzyl ester To a solution of 4-(benzylamino-methyl)-benzoic acid benzyl ester (4.50 g, 13.58 mmol) and TEA (2.748 g, 27.16 mmol) in anhydrous THF (100 mL) at 0° C. under inert atmosphere, was added dropwise the chloro-oxo-acetic acid ethyl ester (2.781 g, 20.37 mmol). The reaction mixture was stirred at 0° C. for 2 h. Most of the solvents were evaporated and 100 mL of DCM were added. 20 mL of a saturated aqueous solution of NaHCO₃ were added to the reaction mixture, the aqueous layer was separated and extracted with DCM (3×50 mL). The combined organic layers were dried over MgSO₄, filtered and concentrated to afford a yellowish oil. This crude product was purified by column chromatography over silica gel (AcOEt/c-Hex 4/1 to 2/1 in about 1 h) to give 4-[(benzyl-ethoxyoxalyl-amino)-methyl]-benzoic acid benzyl ester as a colorless oil (5.810 g, 99%). ¹H NMR (CDCl₃, 300 MHz) δ 7.95 (m, 2H), 7.37-7.11 (m, 12H), 5.30 (s, 2H), 4.44 (m, 2H), 4.31-4.22 (m, 4H), 1.22 (m, 3H). M⁺(APCI): 432.0. HPLC (Condition B), Rt: 7.2 min (HPLC purity: 99.4).

Step c) Formation of the of the Oxamic Ester of formula (II-1), e.g. 4-[(benzyl-ethoxyoxalyl-amino)-methyl]-benzoic acid H₂ (1 atm) was bubbled slowly trough a suspension of 10% Pd/C (300 mg) in EtOH (50 mL) for 15 min at rt. To this suspension was then added a solution of 4-[(benzyl-ethoxyoxalyl-amino) -methyl]-benzoic acid benzyl ester (5.500 g, 12.75 mmol) diluted in 15 mL of EtOH. The resulting reaction mixture was stirred under 1 atm H₂ for 5 h at rt. The reaction mixture was filtered over a pad of celite to remove the catalyst. EtOH was evaporated to afford the title compound as a colorless oil used in the next steps without further purification (4.217 g, 97%). ¹H NMR (CDCl₃, 300 MHz) δ 8.07 (m, 2H), 7.37-7.11 (m, 7H), 4.51 (m, 2H), 4.39-4.30 (m, 4H), 1.27 (m, 3H). M⁻(APCI): 340.0; M⁺(APCI): 342.0. HPLC (Condition A), Rt: 4.31 min (HPLC purity: 99.1%).

Step d) Formation of the Oxamic Ester of Formula (I-1) Following the Method A (See Scheme 1), e.g. ethyl(benzyl{4-[(pentadecylamino)carbonyl] benzyl}amino)(oxo)acetate, using supported cyclohexylcarbodiimide To a solution of 4-[(benzyl-ethoxyoxalyl-amino)methyl]-benzoic acid (102 mg, 0.3 mmol) and pentadecylamine (39.9 mg, 0.2 mmol) in DCM (2 mL), the N-cyclohexylcarbodiimide, N-methyl polystyrene HL (Novabiochem, 355 mg, 0.6 mmol, loading: 1.69 mmol/g) was added at once the and the resulting reaction mixture was stirred overnight at rt. The resin was filtered and the solvents were evaporated under vacuum to afford a colorless oil. This crude product was purified by column chromatography over silica gel (EtOAc) to give the title compound as a colorless oil (39 mg, 35%). ¹H NMR (CDCl₃, 300 MHz) δ 7.75 (m, 2H), 7.37-7.26 (m, 7H), 6.13 (br s, 1H), 4.5 (m, 2H), 4.36-4.30 (m, 4H), 3.45 (m, 2H), 1.62 (m, 2H), 1.36-1.27 (m, 26H), 0.88 (t, J=8.0 Hz, 3H). M⁻(APCI): 549.1; M⁺(APCI): 551.4 HPLC (Condition A), Rt: 7.46 min (HPLC purity: 98.2%).

Step e) Formation of the Oxamic Acid of Formula (I-1), e.g. (benzyl{4-[(pentadecylamino)-carbonyl] benzyl}amino)(oxo)acetic acid To a solution of ethyl(benzyl{4-[(pentadecylamino)carbonyl]benzyl}amino)(oxo)acetate (28.0 mg, 0.051 mmol) in EtOH (1 mL) was added NaOH (14.9 mg, 0.37 mmol) dissolved in H₂O (0.37 mL) and the resulting reaction mixture was stirred at rt for 2 h. The solvents were evaporated then EtOAc (5 mL) and a 1N aqueous solution of HCl (1 mL) were added to the residue. The aqueous layer was separated and extracted with EtOAc (2×5 mL). The combined organic layers were dried over MgSO₄, filtered and concentrated to afford a white solid (27.5 mg, 96%). ¹H NMR (CD₃OD, 300 MHz) δ 7.70 (m, 2H), 7.37 (d, 1H, J=8.3 Hz), 7.30-7.10 (m, 6H), 4.39 (m, 4H), 3.26 (t, 2H, J=7.0 Hz), 1.54 (m, 2H), 1.26 (m, 24H), 0.90 (t, J=7.5 Hz, 3H). M⁻(APCI): 521.6. HPLC (Condition A), Rt: 6.96 min (HPLC purity: 98.4%).

Example 6

(benzyl{4-[(tridecylamino)carbonyl]benzyl}amino) (oxo)acetic acid

Step a) Formation of ethyl(benzyl{4-[(tridecylamino)carbonyl]benzyl}amino)(oxo) acetate The same procedure as employed in the preparation of Example 5, step d, but using tridecylamine gave the title compound as a colorless oil (40%). M⁻(APCI): 523.2; M⁺(APCI): 521.2. HPLC (Condition A), Rt: 7.06 min (HPLC purity: 99.2%).

Step b) Formation of (benzyl{4-[(tridecylamino) carbonyl]benzyl}amino)(oxo)acetic acid The same procedure as employed in the preparation of Example 5, step e, but using the ethyl(benzyl{4-[(tridecylamino)carbonyl]benzyl}amino)(oxo)acetate gave the title compound as a white solid (94%). $^1$H NMR (CD$_3$OD, 300 MHz) δ 7.73 (m, 2H), 7.40 (m, 1H), 7.29-7.16 (m, 6H), 4.45-4.36 (m, 4H), 3.34 (t, 2H, J=7.2 Hz), 1.57 (m, 2H), 1.30-1.23 (m, 20H), 0.84 (t, 3H, J=6.6 Hz). M⁻(APCI): 493.2. HPLC (Condition A), Rt: 6.47 min (HPLC purity: 99.6%).

Example 7

[benzyl(4-{dodecyl(methyl)amino]carbonyl}benzyl) amino](oxo)acetic acid

Step a) Formation of ethyl(benzyl{4-[(tridecylamino)carbonyl]benzyl}amino)(oxo)acetate The same procedure as employed in the preparation of Example 5, step d, but using dodecyl-methyl-amine gave the title compound as a colorless oil (54%). HPLC (Condition A), Rt: 7.13 min (HPLC purity: 92.5%).

Step b) Formation of [benzyl(4-{[dodecyl(methyl) amino)carbonyl}benzyl)amino](oxoacetic acid The same procedure as employed in the preparation of Example 5, step e, but using the ethyl(benzyl{4[(tridecylamino)carbonyl]benzyl}amino)(oxo)acetate gave the title compound as a colorless oil (86%). $^1$H NMR (CD$_3$OD, 300 MHz) δ 7.46 (m, 1H), 7.38-7.24 (m, 8H), 4.51-4.43 (m, 4H), 3.54 (m, 1H), 3.30 (m, 1H), 3.07 (s, 1.5H), 2.95 (d, 1.5H, J=4.1 Hz), 1.69-1.58 (2m, 2H), 1.40-1.18 (m, 18H), 0.89 (m, 3H). M⁻(LC/MS(ESI)): 493.5; M⁺(LC/MS(ESI)): 495.8. HPLC (Condition A), Rt: 6.47 min (HPLC purity: 99.9%).

Example 8

{(4-{[dodecyl(methyl)amino]carbonyl}benzyl)[4-(trifluoromethyl)benzyl]amino}(oxo)acetic acid Step a) Formation of ethyl{(4-{[dodecyl(methyl) amino]carbonyl}benzyl)[4-(trifluoromethyl)benzyl] amino}(oxo)acetate The same procedure as employed in the preparation of Example 5, step d, but using 4-({[ethoxy(oxo)acetyl][4-(trifluoromethyl)benzyl]amino}methyl)benzoic acid and dodecyl-methyl-amine gave the title compound as a colorless oil (56%). HPLC (Condition A), Rt: 7.41 min (HPLC purity: 82%).

Step b) Formation of {(4-{[dodecyl(methyl)amino] carbonyl}benzyl)[4-(trifluoromethyl)-benzyl]amino} (oxo)acetic acid The same procedure as employed in the preparation of Example 5, step e, but using the ethyl{(4{[dodecyl(methyl) amino]carbonyl}benzyl)[4-(trifluoromethyl)benzyl] amino}-(oxo)acetate gave the title compound as a colorless oil (68%). $^1$H NMR (CD$_3$OD, 300 MHz) δ 7.7-7.52 (m, 3H), 7.50-7.30 (m, 5H), 4.62-4.5 (m, 3.5H), 3.85 (m, 0.5H), 3.54 (m, 1H), 3.30 (m, 1H), 3.07 (s, 1.5H), 2.95 (m, 1.5H), 1.72-1.52 (2m, 2H), 1.50-1.10 (m, 18l), 0.95 (m, 3H). M⁻(LC/MS (ESI)): 562.1; M⁺(LC/MS(ESI)): 563.8. HPLC (Condition A), Rt: 6.81 min (HPLC purity: 90.5%).

Example 9

([1-(tert-butoxycarbonyl)-4-piperidinyl]{4-[(dodecylamino)carbonyl]benzyl}amino)(oxo)acetic acid Step a) Formation of tert-butyl 4-({4-[(benzyloxy) carbonyl]benzyl}amino)piperidine-1-carboxylate The same procedure as employed in the preparation of Example 5, step a, but using 1-Boc-4-amino-piperidine gave the title compound as a colorless oil (83%). M⁺(LC/MS (ESI)): 425.5. HPLC (Condition A), Rt: 3.52 min (HPLC purity: 97.8%).

Step b) Formation of tert-butyl 4-{{4-[(benzyloxy) carbonyl]benzyl}[ethoxy(oxo)acetyl] amino}piperidine-1-carboxylate The same procedure as employed in the preparation of Example 5, step b, but starting from tert-butyl 4-({4-[(benzyloxy)carbonyl]benzyl}amino)piperidine-1-carboxylate gave the title compound as a yellow foam (99%). M⁻(APCI): 523.4. HPLC (Condition A), Rt: 5.7 min (HPLC purity: 98.4%).

Step c) Formation of 4-({[1-(tert-butoxycarbonyl) piperidin-4-yl][ethoxy(oxo)acetyl]-amino}methyl) benzoic acid The same procedure as employed in the preparation of Example 5, step c, but starting from tert-butyl 4-{{4-[(benzyloxy)carbonyl]benzyl}[ethoxy(oxo)acetyl] amino}piperidine-1-carboxylate gave the title compound as a white foam (99%). HPLC (Condition A), Rt: 4.1 min (HPLC purity 95.7%).

Step d) Formation of tert-butyl 4-{{4-[(dodecylamino)carbonyl]benzyl}[ethoxy(oxo)-acetyl] amino}piperidine-1-carboxylate The same procedure as employed in the preparation of Example 5, step d, but starting from 4-({[1-(tert-butoxycarbonyl)piperidin-4-yl][ethoxy(oxo)acetyl]amino}methyl) benzoic acid gave the title compound as a colorless oil (25%). M⁻(LC/MS(ESI)): 600.8; M⁺(LC/MS(ESI)): 602.5. HPLC (Condition A), Rt: 6.75 min (HPLC purity: 99.1%).

Step e) Formation of ([1-(tert-butoxycarbonyl)-4-piperidinyl]{4-[(dodecylamino)carbonyl] benzyl}amino)(oxo)acetic acid The same procedure as employed in the preparation of Example 5, step e, but starting from tert-butyl 4-{{4-[(dodecylamino)carbonyl]benzyl}[ethoxy(oxo)acetyl] amino}piperidine-1-carboxylate gave the title compound as a yellow oil (55%). $^1$H NMR (CD$_3$OD, 300 MHz) δ 7.79 (m, 2H), 7.47 (d, 0.5H, 3=8.3 Hz), 7.24 (d, 1.5H, J=8.3 Hz), 4.64 (m, 2H), 4.08 (m, 2H), 3.90 (m, 1H), 3.40 (t, 2H, J=7.2 Hz), 2.73 (m, 2H), 1.64 (m, 1H), 1.50 (m, 5H), 1.35-1.13 (m, 28H), 0.91 (t, J=7.9 Hz, 3H). M⁻(LC/MS(ESI)): 572.8; M⁺(LC/MS (ESI)): 574.5 HPLC (Condition A), Rt: 6.18 min (HPLC purity: 99.2%).

Example 10

{{4-[(dodecylamino)carbonyl]benzyl}[4-(trifluoromethyl)benzyl]amino}(oxo)acetic acid

Step a) Formation of the amide of formula (IX) wherein Q is —CONR$^3$R$^{3'}$, e.g. N-dodecyl-4-formyl-benzamide, using isobutyl chloroformate To a solution of 4-formyl-benzoic acid (22.5 g, 149.9 mmol) and 4-methyl morpholine (18.2 g, 180.0 mmol) in anhydrous THF (200 mL) at −15° C. was added dropwise isobutyl chloroformate (22.5 g, 165.0 mmol) under inert atmosphere. After 15 min, dodecylamine (30.56 g, 164.9 mmol) was added at once, and the resulting mixture was stirred 3 h at rt. The solvent was evaporated in vacuum, and the resulting residue dissolved in DCM (200 mL) and washed with a 0.1N aqueous solution of HCl (3×30), with brine (1×30 mL). The combined organic layers were dried over MgSO4, filtered and concentrated to afford a white powder (45 g). This crude product was purified by column chromatography over silica gel (EtOAc/c-Hex 4/1 to 1/1 in about 1 h) to give the title compound as a fluffy white solid (38 g, 80%). $^1$H NMR (CDCl$_3$, 300 MHz) δ 10.06 (s, 1H), 7.76 (m, 4H), 6.18 (m, 1H), 3.44 (q, 2H, J=13 Hz, J=7.2 Hz), 1.61 (m, 2H), 1.4 to 1.2 (m, 18H), 0.86 (t, 3H, J=7.0 Hz). M$^-$(LC/MS(ESI)): 316.3; M$^+$(LC/MS(ESI)): 318.3. HPLC (Condition A), Rt: 5.9 min (HPLC purity: 98.7%).

Step b) Formation of the secondary amine of formula (III) following the Method I (See Scheme 5), e.g. N-dodecyl-4-[(4-trifluoromethyl-benzylamino)-methyl]-benzamide To a solution of N-dodecyl-4-formyl-benzamide (3 g, 9.45 mmol) and 4-trifluoromethyl-benzylamine (1.82 g, 10.4 mmol) in DCE (25 mL) was added at once NaBH(OAc)$_3$ (2.80 g, 13.23 mmol) and the resulting mixture was stirred overnight at rt. 5 mL of a saturated aqueous solution of NaHCO$_3$ were added to the reaction mixture, the aqueous layer was separated and washed with DCM (3×20 mL). The combined organic layers were dried over MgSO$_4$, filtered and concentrated to afford a yellowish oil. This crude product was purified by column chromatography over silica gel (EtOAc/c-Hex 15/85 to 75/25 in about 1 h) to give the title compound as a white solid (2.66 g, 59%). $^1$H NMR (CDCl$_3$, 300 MHz) δ 7.76 (d, 2H, J=8.3 Hz), 7.61 (d, 2H, 8.1 Hz), 7.49 (d, 2H, J=8.1 Hz), 7.40 (d, 2H, J=8.2 Hz), 6.12 (br s, 1H), 3.86 (s, 4H), 3.43 (q, 2H, J=13.0 Hz, J=7.0 Hz), 1.63 (m, 2H), 1.6 to 1.2 (br s, 18H), 0.86 (t, 3H, J=7.0 Hz). M$^-$(LC/MS(ESI)): 475.32; M$^+$(LC/MS(ESI)): 477.4 HPLC (Condition A), Rt: 4.97 min (HPLC purity: 95.1%).

Step c) Formation of the Oxamic Ester of formula (II-1) following the Method A (See Scheme 1), e.g. ethyl{{4-[(dodecylamino)carbonyl]benzyl}[4-(trifluoromethyl)benzyl]-amino}-(oxo)acetate To a solution of N-dodecyl-4-[(4-trifluoromethyl-benzylamino)-methyl]-benzamide (2.60 g, 5.46 mmol) and TEA (1.104 g, 10.91 mmol) in anhydrous THF (20 mL) at 0° C. under inert atmosphere, was added dropwise the chloro-oxoacetic acid ethyl ester (1.117 g, 8.18 mmol). The reaction mixture was stirred at 0° C. for 1.25 h. The solvents were evaporated and 50 mL of DCM were added. 20 mL of H$_2$O were added to the reaction mixture, the aqueous layer was separated and extracted with DCM (3×50 mL). The combined organic layers were dried over MgSO$_4$, filtered and concentrated. This crude product was purified by column chromatography over silica gel (AcOEt/c-Hex ⅓ to ½ on about 1 h) to give the title compound as a yellow solid (2.770 g, 88%). $^1$H NMR (CDCl$_3$, 300 MHz) δ 7.73 (m, 2H), 7.60 (m, 2H), 7.37-7.23 (m, 4H), 6.09 (br s, 1H), 4.5 (s, 2H), 4.37-4.32 (m, 4H), 3.43 (m, 2H), 1.60 (m, 2H), 1.36-1.20 (m, 21H), 0.86 (m, 3H). M$^-$(LC/MS(ESI)): 575.5; M$^+$(LC/MS(ESI)): 577.4. HPLC (Condition A), Rt: 6.84 min (HPLC purity: 99.2%).

Step d) Formation of the Oxamic Acid of Formula (I), e.g. {{4-(dodecylamino)carbonyl]-benzyl}[4-(trifluoromethyl)benzyl]amino}(oxo)acetic acid The same procedure as employed in the preparation of Example 1, step e, but starting from ethyl{{4-[(dodecylamino)carbonyl]benzyl}[4-(trifluoromethyl)benzyl]amino}(oxo)acetate gave the title compound as a white powder (83%). $^1$H NMR (CD$_3$OD, 300 MHz) δ 7.79 (m, 2H), 7.65 (m, 2H), 7.51 (d, 1H, J=8.1 Hz), 7.41 (m, 2H), 7.30 (d, 1H, J=8.1 Hz), 4.6 (m, 4H), 3.33 (t, 2H, J=7.1 Hz), 1.62 (m, 2H), 1.37-1.31 (m, 18H), 0.88 (t, 3H, J=6.5 Hz). M$^-$(LC/MS (ESI)): 547.3; M$^+$(LC/MS(ESI)): 549.5. HPLC (Condition A), Rt: 6.34 min (HPLC purity: 99.2%). Analysis calculated for C$_{30}$H$_{39}$F$_3$N$_2$O$_4$: C, 65.68; H, 7.16; N, 5.11%. Found: C, 65.65; H, 7.18; N, 5.08%.

Example 11

{{4-[(dodecylamino)carbonyl]benzyl}[4-(trifluoromethyl)benzyl]amino}(oxo)acetic acid, N-methyl-D-glucamine (i.e. 1-deoxy-1-(methylamino)glucitol) salt The same procedure as employed in the preparation of Example 2 but using N-methyl-D-glucamine and {{4-(dodecylamino)carbonyl]benzyl}[4-(trifluoromethyl)benzyl]amino}(oxo)acetic acid gave the title compound as a white powder (81%). M$^-$(LC/MS(ESI)): 548.1; M$^+$(LC/MS(ESI)): 550.2. HPLC (Condition A), Rt: 6.3 min (HPLC purity: 99%). Analysis calculated for C$_{30}$H$_{39}$F$_3$N$_2$O$_4$·C$_7$H$_{17}$NO$_5$■1.1H$_2$O: C, 58.19; H, 7.39; N, 5.50%. Found: C, 58.09; H, 7.66; N, 5.45%.

Example 12

{{4-[(dodecylamino)carbonyl]benzyl}[3-(trifluoromethyl)benzyl]amino}-(oxo)acetic acid

Step a) Formation of N-dodecyl-4-({[3-(trifluoromethyl)benzyl]amino}methyl)benzamide The same procedure as employed in the preparation of Example 10, step b, but starting from 3-trifluoromethyl-benzylamine gave the title compound as a colorless oil (55%). $^1$H NMR (DMSO-d$_6$, 300 MHz) δ 8.38 (t, 1H, J=5.5 Hz), 7.78 (d, 2H, J=8.2 Hz), 7.71 (s, 1H), 7.65-7.51 (m, 3H), 7.41 (d, 2H, J=8.1 Hz), 3.75 (s, 2H), 3.72 (s, 2H), 3.38-3.28 (m, 2H), 1.50 (m, 2H), 1.23 (br s, 18H), 0.84 (t, 3H, J=8.0 Hz). M$^+$(LC/MS (ESI)): 477.5. HPLC (Condition A), Rt: 4.90 min (HPLC purity: 95.3%).

Step b) Formation of ethyl{{4-[(dodecylamino)carbonyl]benzyl}[3-(trifluoromethyl) benzyl]amino}(oxo)acetate The same procedure as employed in the preparation of Example 10, step c, but starting from N-dodecyl-4-({[3-(trifluoromethyl)benzyl]amino}methyl)benzamide gave the title compound as a colorless oil (97%). M$^+$(LC/MS(ESI)): 577.6. HPLC (Condition A), Rt: 6.98 min (HPLC purity: 97.4%).

Step c) Formation of {{4-[(dodecylamino)carbonyl]benzyl}[3-(trifluoromethyl)benzyl]amino}(oxo)acetic acid The same procedure as employed in the preparation of Example 10, step d, but starting from ethyl{{4-[(dodecylamino)carbonyl]benzyl}[3-(trifluoromethyl)benzyl]amino}(oxo)acetate gave the title compound as a colorless oil (82%). $^1$H NMR (DMSO-d$_6$, 300 MHz) δ 7.85-7.55 (m, 6H), 7.35 (d, 1H, J=8.2 Hz), 7.23 (d, 1H, J=8.2 Hz), 4.55 (d, J=6.0 Hz, 2H), 4.50 (d, J=12.4 Hz, 2H), 3.22 (t, J=7.4 Hz, 2H), 1.58-1.39 (m, 2H), 1.37-1.11 (m, 18H), 0.85 (t, J=6.7 Hz, 3H). M$^-$(LC/MS(ESI)): 547.4; M$^+$(LC/MS(ESI)): 549.4. HPLC (Condition A), Rt: 6.69 min (HPLC purity: 97.9%).

Example 13

{{4-[(dodecylamino)carbonyl]benzyl}[3-(trifluoromethyl)benzyl]amino}-(oxo)acetic acid, N-methyl-D-glucamine (i.e. 1-deoxy-1-(methylamino glucitol) salt The same procedure as employed in the preparation of Example 2 but using N-methyl-D-glucamine and {{4-[(dodecylamino)carbonyl]benzyl}[3-(trifluoromethyl)benzyl]amino}(oxo)acetic acid gave the title compound as a white fluffy powder (82%). M$^-$(LC/MS(ESI)): 547.4; M$^+$(LC/MS(ESI)): 549.4. HPLC (Condition A), Rt: 6.69 min (HPLC purity: 99.1%). Analysis calculated for C$_{30}$H$_{39}$F$_3$N$_2$O$_4$·C$_7$H$_{17}$NO$_5$: C 59.74; H 7.59; N 5.65%. Found: C 59.13; H 7.90; N 5.57%.

Example 14

({[1-(tert-butoxycarbonyl)-4-piperidinyl]methyl}{4-[(dodecylamino carbonyl]benzyl}amino)(oxo)acetic acid Step a) Formation of tert-butyl 4-[({4-[(dodecylamino)carbonyl]benzyl}amino)methyl]piperidine-1-carboxylate The same procedure as employed in the preparation of Example 10, step b, but starting from 4-(aminomethyl)-1-N-Boc-piperidine gave the title compound as a colorless oil (31%). M$^-$(ESI): 514.2. HPLC (Condition B), Rt: 6.2 min (HPLC purity: 96.2%).

Step b) Formation of tert-butyl 4-({{4-[(dodecylamino)carbonyl]benzyl}[ethoxy(oxo) acetyl]amino}methyl)piperidine-1-carboxylate The same procedure as employed in the preparation of Example 10, step c, but starting from tert-butyl 4-[({4-[(dodecylamino)carbonyl]benzyl}amino)methyl]piperidine-1-carboxylate gave the title compound as a colorless oil (81%). $^1$H NMR (CDCl3, 300 MHz) δ 7.75 (m, 2H), 7.30 (m, 2H), 6.25 (br s, 1H), 4.49-4.30 (m, 2H), 4.40-4.20 (m, 2H), 4.05 (br s, 2H), 3.42 (m, 2H), 3.20-3.05 (m, 2H), 2.60 (m, 2H), 1.9-1.7 (m, 1H), 1.55 (m, 4H), 1.40-1.0 (m, 31H), 0.86 (m, 3H). M$^-$(APCI): 614.2; M$^+$(APCI): 616.4. HPLC (Condition B), Rt: 8.8 min (HPLC purity: 97.8%).

Step c) Formation of ({[1-(tert-butoxycarbonyl)-4-piperidinyl]methyl}{4-[(dodecylamino)carbonyl]benzyl}amino)(oxo)acetic acid The same procedure as employed in the preparation of Example 10, step d, but starting from tert-butyl 4-({{4-[(dodecylamino)carbonyl]benzyl}[ethoxy(oxo)acetyl]amino}-methyl)piperidine-1-carboxylate gave the title compound as a colorless oil (97%). $^1$H NMR (CDCl$_3$, 300 MHz) δ 7.72 (m, 2H), 7.26 (m, 2H), 6.21 (m, 1H), 4.84 (br s, 1H), 4.69 (br s, 1H), 4.10 (m, 2H), 3.45 (m, 3H), 3.20 (m, 1H), 2.63 (m, 2H), 1.85 (m, 1H), 1.61 (m, 4H), 1.45-1.05 (m, 30H), 0.88 (t, J=8.0 Hz, 3H). M$^-$(APCI): 586.2. HPLC (Condition A), Rt: 8.15 min (HPLC purity: 91.6%).

Example 15 oxo{[4-(tridecanoylamino)benzyl][4-(trifluoromethyl)benzyl]amino}acetic acid

Step a) Formation of the Secondary Amine of Formula (III) Following the Method I (See Scheme 5), e.g. tert-butyl 4-({[4-(trifluoromethyl)benzyl]amino}methyl)phenylcarbamate To a solution of 4-(aminomethyl)-1-N-Boc-aniline (1.778 g, 8.0 mmol) and 4-trifluoromethyl-benzaldehyde (1.156 g, 6.64 mmol) in DCE (50 mL) was added at once NaBH(OAc)$_3$ (2.374 g, 11.20 mmol) and the resulting mixture was stirred overnight at rt. 15 mL of a saturated aqueous solution of NaHCO$_3$ were added to the reaction mixture, the aqueous layer was separated and washed with DCM (3×200 mL). The combined organic layers were dried over MgSO$_4$, filtered and concentrated. The crude product was purified by column chromatography over silica gel (AcOEt/c-Hex 1/1 then 7/3) to give the title compound as a colorless oil (2.688 g, 88%). $^1$H NMR (DMSO-d$_6$, 300 MHz) δ 9.3 (s, 1H), 7.66 (d, 2H, J=8.0 Hz), 7.56 (d, 2H, J=8.0 Hz), 7.37 (d, 2H, J=8.5 Hz), 7.20 (d, 2H, J=8.5 Hz), 3.73 (s, 2H), 3.59 (s, 2H), 1.47 (s, 9H). M$^-$(LC/MS(ESI)): 379.2; M$^+$(LC/MS(ESI)): 381.4. HPLC (Condition A), Rt: 3.38 min (HPLC purity: 99.1%).

Step b) Formation of the Oxamic Ester of Formula (II-2) Following the Method C (See Scheme 2), e.g. ethyl{{4-[(tert-butoxycarbonyl)amino]benzyl}[4-(trifluoromethyl-)benzyl]amino}-(oxo)acetate To a solution tert-butyl 4-({[4-(trifluoromethyl)benzyl]amino}methyl)phenylcarbamate (2.69 g, 7.07 mmol) and DIEA (1.83 g, 14.13 mmol) in anhydrous DCM (30 mL) at 0° C. under inert atmosphere, was added dropwise the chloro-oxo-acetic acid ethyl ester (1.06 g, 7.77 mmol). The reaction mixture was stirred 3 h at 0° C., then 1 h at rt. A 1 N aqueous solution of HCl (5 mL) was added and the mixture was extracted with DCM (3×30 mL). The combined organic layers were washed with water (3×20 mL), dried over MgSO$_4$, filtered and concentrated to afford a yellowish oil. This crude product was purified by column chromatography over silica gel (AcOEt/c-Hex 1/4) to give the title compound as a colorless oil (2.980 g, 88%). M$^-$(LC/MS(ESI)): 479.3. HPLC (Condition A), Rt: 5.65 min (HPLC purity: 99.9%).

Step c) Deprotection of the Oxamic Ester of Formula (II-2) (See Scheme 2), Formation of e.g. ethyl{(4-aminobenzyl)[4-(trifluoromethyl)benzyl]amino}(oxo)acetate To a solution of ethyl{{4-[(tert-butoxycarbonyl)amino]benzyl}[4-(trifluoromethyl)-benzyl]amino}(oxo)acetate (2.980 g, 6.2 mmol) in DCM (40 mL) was added TFA (10 mL) and the resulting reaction mixture was stirred for 4 h at rt. The solvents were evaporated under vacuum to afford an orange oil. This crude product was dissolved in Et$_2$O, washed with a saturated aqueous solution of NaHCO$_3$, water (2×20 mL) and brine (1×20 mL). The combined organic layers were dried over MgSO$_4$, filtered and concentrated to afford a orange oil (2.245 g, 95%). $^1$H NMR (CDCl$_3$, 300 MHz) δ 7.59 (m, 2H), 7.33 (m, 2H), 7.01 (m, 2H), 6.65 (m, 2H), 4.49 (s, 1H), 4.40-4.28 (m, 4H), 4.20 (s, 1H), 1.38-1.26 (m, 3H) M$^-$(LC/MS(ESI)): 379.1. HPLC (Condition A), Rt: 3.3 min (HPLC purity: 92.4%).

Step d) Formation of the Oxamic Ester of Formula (I-2) Following the Method C (See Scheme 2), e.g. ethyl oxo{[4-(tridecanoylamino)benzyl][4-(trifluoromethyl)benzyl]amino}acetate To a cold (0° C.) solution of ethyl{(4-aminobenzyl)[4-(trifluoromethyl)benzyl]amino}-(oxo)acetate (800 mg, 2.10 mmol) and DIEA (326 mg, 2.52 mmol) in DCM (10.0 mL) was added tridecanoyl chloride (539 mg, 2.31 mmol) under inert atmosphere. The resulting reaction mixture was stirred 1 h at 0° C. then 3.5 h at rt. A 1 N aqueous solution of HCl (2 mL) was added and the mixture was extracted with DCM (3×30 mL). The combined organic layers were washed with water (3×20 mL), dried over MgSO$_4$, filtered and concentrated to afford a colorless oil. This crude product was purified by column chromatography over silica gel (AcOEt/c-Hex 1/4) to give the title compound as a colorless oil (1.067 g, 88%). $^1$H NMR (CDCl$_3$, 300 MHz) δ 7.59 (m, 2H), 7.50 (m, 2H), 7.38 (d, 2H, J=8.1 Hz), 7.29 (d, 2H, J=8.0 Hz), 7.18 (m, 2H), 4.47 (m, 2H), 4.37-4.28 (m, 4H), 2.34 (t, 2H, J=7.5 Hz), 1.71 (m, 2H), 1.38-1.26 (m, 21H), 0.87 (t, J=8.1 Hz, 3H) M$^-$(LC/MS(ESI)): 575.2; M$^+$(LC/MS(ESI)): 577.0. HPLC (Condition A), Rt: 7.1 min (HPLC purity: 98.2%).

Step e) Formation of the Oxamic Ester of Formula (I-2), e.g. oxo{[4-(tridecanoylamino)-benzyl][4-(trifluoromethyl)benzyl]amino}acetic acid The same procedure as employed in the preparation of Example 1, step e, but starting from ethyl oxo{[4-(tridecanoylamino)benzyl][4-(trifluoromethyl)benzyl]amino}acetate gave the title compound as a white powder (99%). $^1$H NMR (CD$_3$OD, 300 MHz) δ 7.65-7.12 (m, 8H), 4.54 (s, 2H), 4.45 (s, 2H), 2.34 (t, J=6.9 Hz, 2H), 1.69-1.63 (m, 2H), 1.40-1.22 (m, 18H), 0.87 (t, J=8.6 Hz, 3H). M$^-$(LC/MS(ESI)): 547.5; M$^+$(LC/MS(ESI)): 549.3. HPLC (Condition A), Rt: 6.56 min (HPLC purity: 99.6%). Analysis calculated for C$_{30}$H$_{39}$F$_3$N$_2$O$_4$·C$_7$H$_{17}$NO$_5$: C, 59.74; H, 7.59; N, 5.65%. Found: C, 59.54; H, 7.68; N, 5.53%.

Example 16 oxo{[4-(tridecanoylamino)benzyl][4-(trifluoromethyl)benzyl]amino}acetic acid, N-methyl-D-glucamine (i.e. 1-deoxy-1-(methylamino)glucitol) salt The same procedure as employed in the preparation of Example 2 but using N-methyl-D-glucamine and oxo{[4-(tridecanoylamino)benzyl][4-(trifluoromethyl)benzyl]amino}acetic acid gave the title compound as a white powder (83%). M$^-$(LC/MS(ESI)): 547.5; M$^+$(LC/MS(ESI)): 549.3. HPLC (Condition A), Rt: 6.56 min (HPLC purity: 99.6%). Analysis calculated for C$_{30}$H$_{39}$F$_3$N$_2$O$_4$·C$_7$H$_{17}$NO$_5$: C, 59.74; H, 7.59; N, 5.65%. Found: C, 59.54; H, 7.68; N, 5.53%.

Example 17

[benzyl(4-{[4-(hexyloxy)benzoyl]amino}benzyl)amino](oxo)acetic acid

Step a) Formation of tert-butyl 4-[(enzylamino)methyl]phenylcarbamate

The same procedure as employed in the preparation of Example 15, step a but using 4-(aminomethyl)-1-N-Boc-aniline and benzaldehyde gave the title compound as a white solid (61%). M$^+$(ESI): 313.2. HPLC (Condition A), Rt: 2.89 min (HPLC purity: 99.4%).

Step b) Formation of ethyl(benzyl{4-[(tert-butoxycarbonyl)amino]benzyl}amino)(oxo)-acetate The same procedure as employed in the preparation of Example 15, step b but using tert-butyl 4-[(benzylamino)methyl]phenylcarbamate gave the title compound as a brown foam (89%). M$^-$(APCI): 411.0; M$^+$(APCI): 413.2. HPLC (Condition A), Rt: 5.32 min (HPLC purity: 98.1%).

Step c) Formation of ethyl[(4-aminobenzyl)(benzyl)amino](oxo)acetate

The same procedure as employed in the preparation of Example 15, step c but using ethyl (benzyl{4-[(tert-butoxycarbonyl)amino]benzyl}amino)(oxo)acetate gave the title compound as a brown oil (99.9%). HPLC (Condition A), Rt: 2.69 min (HPLC purity: 91.5%).

Step d) Formation of ethyl[benzyl(4-{[4-(hexyloxy)benzoyl]amino}benzyl)amino]-(oxo)acetate The same procedure as employed in the preparation of Example 15, step d but using 4-hexyloxy-benzoyl chloride and ethyl[(4-aminobenzyl)(benzyl)amino](oxo)acetate gave the title compound as a colorless oil (58%). M$^-$(ESI): 515.2. HPLC (Condition A), Rt: 6.0 min (HPLC purity: 94.9%).

Step e) Formation of [benzyl(4-{[4-(hexyloxy)benzoyl]amino}benzyl)amino](oxo)acetic acid The same procedure as employed in the preparation of Example 15, step e using ethyl[benzyl(4-{[4-(hexyloxy)benzoyl]amino}benzyl)amino](oxo)acetate gave the title compound as a white gum (99.9%). $^1$H NMR (CD$_3$OD, 300 MHz) δ 7.93 (d, 2H, J=8.3 Hz), 7.67 (m, 2H), 7.38-7.25 (m, 7H), 7.02 (d, 2H, J=9.0 Hz), 4.43 (m, 4H), 4.06 (t, 2H, J=6.4 Hz), 1.81 (m, 2H), 1.50 (m, 2H), 1.38 (m, 4H), 0.88 (t, J=7.9 Hz, 3H). M$^-$(LC/MS(ESI)): 487.4; M$^+$(LC/MS(ESI)): 489.4. HPLC (Condition A), Rt: 5.42 min (HPLC purity: 96.4%).

Example 18 oxo{[4-(trifluoromethyl)benzyl][4-(10-undecenoylamino)benzyl]amino}-acetic acid

Step a) Formation of ethyl oxo{[4-(trifluoromethyl)benzyl][4-(undec-10-enoylamino)-benzyl]amino}acetate The same procedure as employed in the preparation of Example 15, step d using ethyl{(4-aminobenzyl)[4-(trifluoromethyl)benzyl]amino}(oxo)acetate and undec-10-enoyl chloride gave the title compound as a colorless oil (71%). HPLC (Condition A), Rt: 6.7 min (HPLC purity: 99%).

Step b) Formation of oxo{[4-(trifluoromethyl)benzyl][4-(10-undecenoylamino)benzyl]amino}acetic acid The same procedure as employed in the preparation of Example 15, step e using ethyl oxo{[4-(trifluoromethyl)benzyl][4-(undec-10-enoylamino)benzyl]amino}acetate gave the title compound as a colorless oil (89%). $^1$H NMR (CDCl$_3$, 300 MHz) δ 10.2 (s, 1H), 8.03 (d, 1H, J=8.0 Hz), 7.61-7.51 (m, 3H), 7.50-7.44 (t, 1H, J=9.0 Hz), 7.38 (d, 1H, J=7.9 Hz), 7.29 (d, 1H, J=7.1 Hz), 7.17 (d, 1H, J=7.7 Hz), 7.11 (d, 1H, J=7.7 Hz), 5.84-5.75 (m, 1H), 5.02-4.91 (m, 2H), 4.58-4.44 (m, 4H), 2.38 (m, 2H), 2.06 (m, 2H), 1.7 (br s, 2H), 1.29 (br s, 10H). M⁻(LC/MS(ESI)): 516.9; M⁺(LC/MS(ESI)): 519.2. HPLC (Condition A), Rt: 5.7 min (HPLC purity: 99.4%).

Example 19 oxo{{4-[(9E)-9-tetradecenoylamino]benzyl}[4-(trifluoromethyl)benzyl]amino}acetic acid

Step a) Formation of ethyl oxo{{4-[(9E)-tetradec-9-enoylamino]benzyl}[4-(trifluoromethyl)benzyl]amino}acetate The same procedure as employed in the preparation of Example 15, step d using ethyl{(4-aminobenzyl)[4-(trifluoromethyl)benzyl]amino}(oxo)acetate and tetradec-9-enoyl chloride gave the title compound as a colorless oil (81%). M⁻(LC/MS(ESI)): 588.0. HPLC (Condition A), Rt: 7.3 min (HPLC purity: 96.9%).

Step b) Formation of oxo{{4-[(9E)-9-tetradecenoylamino]benzyl}[4-(trifluoromethyl)-benzyl]amino}acetic acid The same procedure as employed in the preparation of Example 15, step e using ethyl oxo{{4-[(9E)-tetradec-9-enoylamino]benzyl}[4-(trifluoromethyl)benzyl]amino}acetate gave the title compound as a colorless oil (94%). $^1$H NMR (CD$_3$OD, 300 MHz) δ 7.58-7.00 (m, 8H), 5.30-5.19 (m, 2H), 4.45 (s, 2H), 4.37 (s, 2H), 2.26 (t, 2H, J=7.3 Hz), 1.98-1.88 (m, 4H), 1.66-1.53 (m, 2H), 1.32-1.16 (m, 12H), 0.80 (t, 3H). M⁻(LC/MS(ESI)): 559.7; M⁺(LC/MS/(ESI)): 561.2. HPLC (Condition A), Rt: 6.72 min (HPLC purity: 98.9%).

Example 20 oxo{{4-[(9E)-9-tetradecenoylamino]benzyl}[4-(trifluoromethyl)benzyl]-amino}acetic acid, N-methyl-D-glucamine (i.e. 1-deoxy-1-(methylamino)glucitol) salt The same procedure as employed in the preparation of Example 2 but using N-methyl-D-glucamine and oxo{{4-[(9E)-9-tetradecenoylamino]benzyl}[4-(trifluoromethyl)benzyl]amino}acetic acid gave the title compound as a white fluffy powder (93.8%). M⁻(LC/MS(ESI)): 559.7; M⁺(LC/MS(ESI)): 561.2. HPLC (Condition A), Rt: 6.72 min (HPLC purity: 98.9%). Analysis calculated for C$_{31}$H$_{39}$F$_3$N$_2$O$_4$·C$_7$H$_{17}$NO$_5$: C, 60.38; H, 7.47; N, 5.56%. Found: C, 60.19; H, 7.70; N, 5.36%.

Example 21

{benzyl[4-(tridecanoylamino)benzyl]amino}(oxo)acetic acid

Step a) Formation of ethyl{benzyl[4-(tridecanoylamino)benzyl]amino}(oxo)acetate The same procedure as employed in the preparation of Example 5, step d using ethyl[(4-aminobenzyl)(benzyl)amino](oxo)acetate and tridecanoic acid gave the title compound as a colorless oil (39%). M⁻(ESI): 507.2. HPLC (Condition A), Rt: 7 min (HPLC purity-91.3%).

Step b) Formation of oxo{{4-[(9E)-9-tetradecenoylamino]benzyl}[4-(trifluoromethyl)-benzyl]amino}acetic acid The same procedure as employed in the preparation of Example 15, step e using ethyl{benzyl[4-(tridecanoylamino)benzyl]amino}(oxo)acetate gave the title compound as a white gum (99%). $^1$H NMR (CD$_3$OD, 300 MHz) δ 7.54 (m, 2H), 7.38-7.15 (m, 7H), 4.43 (m, 4H), 2.38 (t, 2H, J=7.3 Hz), 1.69 (m, 2H), 1.27 (m, 18H), 0.90 (t, J=8.0 Hz, 31). M⁻(ESI): 479.2. HPLC (Condition A), Rt: 6.19 min (HPLC purity: 94.9%).

Example 22

{{4-[(2-hydroxydodecyl)amino]benzyl}[4-(trifluoromethyl)benzyl]amino}(oxo)acetic acid

Step a) Formation of ethyl{{4-[(2-hydroxydodecyl)amino]benzyl}[4-(trifluoromethyl)-benzyl]amino}(oxo)acetate To a solution of ethyl{(4-aminobenzyl)[4-(trifluoromethyl)benzyl]amino}(oxo)acetate (38 mg, 0.10 mmol) and 1,2-dodecylene oxide (22 mg, 0.12 mmol) in 1.0 mL CH$_3$CN were added at once magnesium perchlorate (27 mg, 0.12 mmol) under inert atmosphere. The reaction mixture was stirred 24 at rt. 2 mL of H$_2$O were added and the resulting mixture was extracted with EtOAc (2×5 mL), dried over MgSO$_4$, filtered and the solvents were evaporated under vacuum to give a slightly yellow oil (61 mg).

Purification on SiO$_2$ (AcOEt/c-Hex) gave the title compound as a colorless oil (15.3 mg, 27%). $^1$H NMR (CDCl$_3$, 300 MHz) δ 7.61-7.46 (m, 2H), 7.36-7.21 (m, 2H), 7.05-6.88 (m, 2H), 6.61-6.47 (m, 2H), 4.43 (s, 1H), 4.38-4.17 (m, 4H), 4.14 (s, 1H), 3.17 (br s, 1H), 3.25-3.13 (m, 1H), 3.01-2.81 (m, 1H), 1.55-1.05 (m, 23H), 0.81 (t, J=7.9 Hz, 3H). M⁺(LC/MS (ESI)): 565.4. HPLC (Condition A), Rt: 5.96 min (HPLC purity: 94.8%).

Step b) Formation of {{4-[(2-hydroxydodecyl)amino]benzyl}[4-(trifluoromethyl)benzyl]amino}(oxo)acetic acid The same procedure as employed in the preparation of Example 1, step e using ethyl{{4-[(2-hydroxydodecyl)amino]benzyl}[4-(trifluoromethyl)benzyl]amino}(oxo)acetate gave the title compound as a yellow solid (90%). $^1$H NMR (CD$_3$OD, 300 MHz) δ 7.57 (m, 2H), 7.46 (m, 1H), 7.33 (m, 1H), 7.18 (d, 1H, J=7.5 Hz), 7.10 (d, 1H, J=7.2 Hz), 6.83 (m, 2H), 4.69 (b rs, 1H), 4.48 (br s, 2H), 4.38 (s, 1H), 3.72 (br s, 1H), 3.25-3.15 (m, 1H), 3.13-2.98 (m, 1H), 1.47 (br s, 2H), 1.26 (br s, 16H), 0.86 (br s, 3H). M⁻(LC/MS(ESI)): 535.0; M⁺(LC/MS(ESI)): 537.1. HPLC (Condition A), Rt: 5.11 min (HPLC purity: 88.5%).

Example 23 oxo{[4-(trifluoromethyl)benzyl][4-(3-undecyl-1,2,4-oxadiazol-5-yl)benzyl]amino}acetic acid

Step a) Formation of N-hydroxydodecanimidamide

To a solution of undecyl cyanide (1.810 g, 9.98 mmol) in EtOH (20 mL) was added a 50% aqueous solution of hydroxylamine (1 mL) and the resulting reaction mixture was stirred at 70° C. for 48 h. The solvents were evaporated and the resulting white solid was dissolved in EtOAc (100 mL) and washed with H$_2$O (2×20 mL), dried over MgSO$_4$, filtered and the solvents evaporated under vacuum to give the title compound as a white solid (2.001 g, 94%). $^1$H NMR (CDCl$_3$, 300 MHz) δ 6.21-4.99 (br s, 1H), 4.49 (br s, 2H), 2.07 (t, J=7.6 Hz, 2H), 1.55-1.40 (m, 2H), 1.34-1.09 (m, 16H), 0.81 (t, J=7.0 Hz, 3H)

Step b) Formation of benzyl 4-({(tert-butoxycarbonyl)[4-(trifluoromethyl)benzyl]amino}methyl)benzoate To a solution of benzyl 4-({[4-(trifluoromethyl)benzyl]amino}methyl)benzoate (3.60 g, 9.01 mmol) and triethylamine (1.094 g, 10.82 mmol) in DCM (50 mL) was added the di-tert-butyl dicarbonate (2.164 g, 9.91 mmol) and the resulting reaction mixture was stirred at rt for 5 h. H$_2$O was added (10 mL) and the mixture extracted with DCM (3×50 mL). The combined organic layers were washed with a 1 N aqueous solution of HCl (10 mL), a saturated aqueous solution of NaHCO$_3$, water (2×20 mL) and brine (1×20 mL). The combined organic layers were dried over MgSO$_4$, filtered and concentrated to afford a colorless oil. This crude product was purified by column chromatography over silica gel (AcOEt/c-Hex 5/95) to give the title compound as a colorless oil (4.303 g, 96%). $^1$H NMR (CDCl$_3$, 300 MHz) δ 8.12 (d, J=8.1 Hz, 2H), 7.67 (d, J=8.1 Hz, 2H), 7.60-7.22 (m, 9H), 5.46 (s, 2H), 4.57 (s, 2H), 4.58 (s, 2H), 1.56 (s, 9H). HPLC (Condition A), Rt: 6.55 min (HPLC purity: 99.7%).

Step c) Formation of 4-({(tert-butoxycarbonyl)[4-(trifluoromethyl)benzyl]amino}methyl)-benzoic acid H$_2$ (1 atm) was bubbled slowly trough a suspension of 10% Pd/C (917 mg) in EtOH (25 mL) for 15 min at rt. To this suspension was then added a solution of benzyl 4-({(tert-butoxycarbonyl)[4-(trifluoromethyl)benzyl]amino}methyl)benzoate (4.303 g, 8.61 mmol) diluted in EtOH (5 mL). The resulting reaction mixture was stirred under 1 atm H$_2$ for 4.5 h at rt. The reaction mixture was filtered over a pad of celite to remove the catalyst. EtOH was evaporated to afford the title compound as a colorless oil used in the next steps without further purification (3.520 g, 99%). $^1$H NMR (CDCl$_3$, 300 MHz) δ 8.11 (d, J=8.1 Hz, 2H), 7.62 (d, J=8.1 Hz, 2H), 7.45-7.21 (m, 4H), 5.54 (s, 2H), 4.45 (s, 2H), 1.50 (s, 9H). HPLC (Condition A), Rt: 5.42 min (HPLC purity: 96.1%).

Step d) Formation of tert-butyl 4-{[(dodecanimidoylamino)oxy]carbonyl}benzyl[4-(trifluoromethyl)benzyl]carbamate To a solution of 4-({(tert-butoxycarbonyl)[4-(trifluoromethyl)benzyl]amino}methyl)-benzoic acid (102 mg, 0.25 mmol), N-hydroxydodecanimidamide (70 mg, 0.33 mmol) and DMAP (3 mg, 0.03 mmol) in anhydrous DCM (15 mL) was added EDC (62 mg, 0.33 mmol) and the resulting reaction mixture was stirred at RT for 14 h. Evaporation of the solvents gave an oil. This crude product was purified by column chromatography over silica gel (AcOEt/c-Hex 80/20) to give the title compound as a colorless oil (36 mg, 24%). $^1$H NMR (CDCl$_3$, 300 MHz) δ 8.01 (d, J=8.1 Hz, 2H), 7.60 (d, J=8.1 Hz, 2H), 7.40-7.20 (m, 4H), 4.88 (br s, 2H), 4.51 (s, 2H), 4.42 (s, 2H), 2.36 (t, J=8.2 Hz, 2H), 1.75-1.59 (m, 2H), 1.49 (s, 9H), 1.45-1.16 (m, 16H), 0.89 (t, J=7.0 Hz, 3H). HPLC (Condition A), Rt: 5.42 min (HPLC purity: 96.1%).

Step e) Formation of tert-butyl 4-(trifluoromethyl)benzyl[4-(3-undecyl-1,2,4-oxadiazol-5-yl)benzyl]carbamate A solution of tert-butyl 4-{[(dodecanimidoylamino)oxy]carbonyl}benzyl[4-(trifluoromethyl)benzyl]carbamate in pyridine was stirred under inert atmosphere at 120° C. for 4 h. The resulting brown solution was evaporated (under high vacuum) and the resulting oil was purified by column chromatography over silica gel (AcOEt/c-Hex 20/80) to give the title compound as a colorless oil (50 mg, 71%). $^1$H NMR (CDCl$_3$, 300 MHz) δ 8.00 (d, J=8.1 Hz, 2H), 7.51 (d, J=8.1 Hz, 2H), 7.35-7.14 (m, 4H), 4.43 (s, 2H), 4.35 (s, 2H), 2.71 (t, J=7.5 Hz, 2H), 1.80-1.65 (m, 2H), 1.41 (s, 9H), 1.36-1.12 (m, 16H), 0.89 (t, J=7.0 Hz, 3H).

Step f) Formation of N-[4-(trifluoromethyl)benzyl]-N-[4-(3-undecyl-1,2,4-oxadiazol-5-yl)benzyl]amine hydrochloride To a cold (0° C.) solution of tert-butyl 4-(trifluoromethyl)benzyl[4-(3-undecyl-1,2,4-oxadiazol-5-yl)benzyl]carbamate (43 mg, 0.07 mmol) in DCM (3 mL) was added a solution of HCl (4N in dioxane, 3 mL) and the resulting reaction mixture was stirred 3 h at 0° C., then 14 h at rt. Evaporation of the solvent gave the title compound as a white powder used in the next steps without further purification (29 mg, 99%). M$^-$(APCI): 486.0; M$^+$(APCI): 488.2 HPLC (Condition A), Rt: 5.4 min (HPLC purity: 82%).

Step g) Formation of ethyl oxo{[4-(trifluoromethyl)benzyl][4-(3-undecyl-1,2,4-oxadiazol-5-yl)benzyl]amino}acetate To a cold (0° C.) solution of N-[4-(trifluoromethyl)benzyl]-N-[4-(3-undecyl-1,2,4-oxadiazol-5-yl)benzyl]amine hydrochloride (45 mg, 0.09 mmol) and DIEA (24 mg, 0.19 mmol) in anhydrous DCM (1 mL) was added dropwise the chloro-oxo-acetic acid ethyl ester (24 mg, 0.19 mmol). The reaction mixture was stirred at 0° C. for 3 h. Evaporation of the solvents under vacuum gave an orange oil. This crude product was purified by column chromatography over silica gel (AcOEt/c-Hex 1/9) to give the title compound as a colorless oil (38 mg, 75%). $^1$H NMR (CDCl$_3$, 300 MHz) δ 8.10 (d, J=8.3 Hz, 1H), 8.02 (d, J=8.3 Hz, 1H), 7.56 (d, J=8.2 Hz, 1H), 7.53 (d, J=8.2 Hz, 1H), 7.39-7.21 (m, 4H), 4.50 (s, 2H), 4.37 (s, 2H), 4.29 (dq, J1=7.1 Hz, J2=2.3 Hz, 2H), 2.72 (t, J=7.4 Hz, 2H), 1.85-1.65 (m, 2H), 1.41-1.05 (m, 19H), 0.89 (t, J=7.0 Hz, 3H). HPLC (Condition A), Rt: 7.5 min (HPLC purity: 88.8%).

Step h) Formation of oxo{[4-(trifluoromethyl)benzyl][4-(3-undecyl-1,2,4-oxadiazol-5-yl)benzyl]amino}acetic acid The same procedure as employed in the preparation of Example 1, step e using ethyl oxo{[4-(trifluoromethyl)benzyl][4-(3-undecyl-1,2,4-oxadiazol-5-yl)benzyl]amino}acetate gave the title compound as a white powder (89%). $^1$H NMR (CDCl$_3$, 300 MHz) δ 8.10-7.99 (m, 2H), 7.61-7.50 (m, 2H), 7.32 (d, J=8.6 Hz, 2H), 7.27 (d, J=7.9 Hz, 2H), 4.98 (s, 2H), 4.58 (s, 2H), 2.74 (t, J=8.0 Hz, 2H), 1.81-1.66 (m, 2H), 1.42-1.04 (m, 16H), 0.81 (t, J=6.7 Hz, 3H). M$^-$(APCI): 558.4. HPLC (Condition A), Rt: 7.4 min (HPLC purity: 98.6%).

Example 24

{({5-[(dodecylamino)sulfonyl]-2-thienyl}methyl)[4-(trifluoromethyl)-benzyl]amino}(oxo)acetic acid Step a) Formation of 2-(thien-2-ylmethyl)-1H-isoindole-1,3(2H)-dione A solution of thiophene-2-methylamine (4.203 g, 37.13 mmol) and of phtalic anhydride (5.00 g, 33.76 mmol) in toluene (100 mL) was stirred and heated at reflux for 3 h to remove the formed water by azeotropic distillation (Dean-Stark). The solvent was then evaporated under vacuum. The residue was dissolved in DCM (100 mL), washed with water (3×30 mL), dried over MgSO$_4$, filtered and concentrated to afford the title compound as a white solid (7.78 g, 95%). $^1$H NMR (CDCl$_3$, 300 MHz) δ 7.84 (d, 1H. J=5.4 Hz), 7.83 (d, 1H. J=5.4 Hz), 7.69 (d, 1H, J=5.4 Hz), 7.68 (d, 1H, J=5.4 Hz), 7.20 (d, 0.5H, J=5.2 Hz), 7.19 (d, 0.5H, J=5.2 Hz), 7.14 (m, 1H), 6.92 (d, 0.5H, J=5.1 Hz), 6.91 (d, 0.5H, J=5.1 Hz), 5.01 (s, 2H). HPLC (Condition A), Rt: 4.11 min (HPLC purity: 99.2%).

Step b) Formation of 5-[(1,3-dioxo-1,3-dihydro-2H-isoindol-2-yl)methyl]thiophene-2-sulfonyl chloride To a cold (−78° C.) solution of 2-(thien-2-ylmethyl)-1H-isoindole-1,3(2H)-dione (6.78 g, 27.87 mmol) in DCM (56 mL) was added dropwise (in about 10 min) chlorosulfonic acid (16.237 g, 139.3 mmol, 9.33 mL, d: 1.74) diluted in DCM (9.3 mL). The reaction mixture was stirred 2 h at −78° C., then 1 h at −40° C. and overnight at rt. The resulting brown solution was poured on ice. The mixture was extracted with DCM (3×200 mL), and the combined organic layers were washed with water (3×200 mL), dried over MgSO$_4$, filtered and concentrated to afford a yellowish oil. This crude product was purified by column chromatography over silica gel (AcOEt/c-Hex 1/4 to 1/3 to 1/2 in about 1 h) to give the title compound as a white solid (6.42 g, 67%). $^1$H NMR (CDCl$_3$, 300 MHz) δ 7.89 (d, 1H. J=5.5 Hz), 7.87 (d, 1H. J=5.5 Hz), 7.76 (d, 1H, J=5.5 Hz), 7.75 (d, 1H, J=5.5 Hz), 7.71 (d, 1H, J=4.0 Hz), 7.18 (d, 1H, J=4.0 Hz), 5.05 (s, 2H). HPLC (Condition A), Rt: 4.6 min (HPLC purity: 94.8%).

Step c) Formation of 5-[(1,3-dioxo-1,3-dihydro-2H-isoindol-2-yl)methyl]-N-dodecylthiophene-2-sulfonamide To a solution of 5-[(1,3-dioxo-1,3-dihydro-2H-isoindol-2-yl)methyl]thiophene-2-sulfonyl chloride (2.00 g, 5.85 mmol), DIEA (1.134 g, 8.78 mmol) in DCM (20 mL) was added dodecyl amine (1.41 g, 7.61 mmol) at rt and the reaction mixture was stirred for 2 h at rt. A 1 M aqueous solution of HCl (10 mL) was added and the aqueous layers were extracted with DCM (2×30 mL). The combined organic layers were dried over MgSO$_4$, filtered and concentrated to afford a yellowish oil. This crude product was purified by column chromatography over silica gel (AcOEt/c-Hex 1/4 to 4/1 in about 0.5 h) to give the title compound as a white solid (2.10 g, 73%). $^1$H NMR (CD$_3$OD, 300 MHz) δ 7.91 (m, 2H), 7.85 (m, 2H), 7.43 (d, 1H, J=3.7 Hz), 7.17 (d, 1H, J=3.7 Hz), 5.05 (s, 2H), 2.90 (t, 2H, J=6.9 Hz), 1.50-1.38 (m, 2H), 1.35-1.16 (m, 18H), 0.86 (t, J=7.9 Hz, 3H) M$^-$(LC/MS): 489.3; M$^+$(LC/MS): 491.2. HPLC (Condition A), Rt: 6.64 min (HPLC purity: 95.9%).

Step d) Deprotection of 5-[(1,3-dioxo-1,3-dihydro-2H-isoindol-2-yl)methyl]-N-dodecylthiophene-2-sulfonamide; formation of 5-(aminomethyl)-N-dodecylthiophene-2-sulfonamide To a solution of 5-[(1,3-dioxo-1,3-dihydro-2H-isoindol-2-yl)methyl]-N-dodecylthiophene-2-sulfonamide (2.069 g, 4.22 mmol) in EtOH (20 mL) was added hydrazine hydrate (0.614 mL, 633 mg, d: 1.030, 12.65 mmol). The resulting reaction mixture was stirred at reflux for 3 h and then cooled down to rt. The white precipitate was removed by filtration and the solvents were evaporated under vacuum. The residue was dissolved in DCM (20 mL) and the precipitate removed by filtration. The collected solvents were concentrated to afford of a colorless oil which turns solid on standing (1.5 g, 99%). $^1$H NMR (DMSO-d$_6$, 300 MHz) δ 7.37 (m, 1H), 6.94 (m, 1H), 3.91 (s, 2H), 2.78 (m, 21), 1.95-1.65 (m, 20H), 0.86 (t, J=7.6 Hz, 3H). M$^-$(LC/MS (ESI)): 359.2; M$^+$(LC/MS (ESI)): 361.2, HPLC (Condition A), Rt: 4.5 min (HPLC purity: 95%).

Step e) Formation of N-dodecyl-5-({[4-(trifluoromethyl)benzyl]amino}methyl)thiophene-2-sulfonamide To a solution of 5-(aminomethyl)-N-dodecylthiophene-2-sulfonamide (797 mg, 2.21 mmol) and 4-trifluoromethylbenzaldehyde (350 mg, 2.01 mmol) in DCE (50 mL) was added at once NaBH(OAc)$_3$ (596 mg, 2.81 mmol) and the resulting mixture was stirred overnight at rt. 30 mL of a saturated aqueous solution of NaHCO$_3$ were added to the reaction mixture, the aqueous layer was separated and washed with DCM (3×200 mL). The combined organic layers were dried over MgSO$_4$, filtered and concentrated to afford a yellowish oil. This crude product was purified by column chromatography over silica gel (AcOEt/c-Hex 1/4 to 1/2 in about 1 h) to give the title compound as a colorless oil (675 mg, 64%). $^1$H NMR (CDCl$_3$, 300 MHz) δ 7.60 (m, 2H), 7.46 (m, 2H), 7.37 (d, 0.7H, J=8.0 Hz), 6.88 (d, 1H, J=3.8 Hz), 4.00 (s, 2H), 3.90 (s, 2H), 3.02 (m, 2H), 1.85-1.55 (m, 2H), 1.5 (m, 2H), 1.22 (s, 18H), 0.87 (t, 3H, 6.6 Hz). M$^-$(LC/MS (ESI)): 517.2; M$^+$(LC/MS (ESI)): 519.2 HPLC (Condition A), Rt: 5.27 min (HPLC purity: 97.2%).

Step f) Formation of ethyl{({5-[(dodecylamino)sulfonyl]thien-2-yl}methyl)[4-(trifluoromethyl)benzyl]amino}(oxo)acetate The same procedure as employed in the preparation of Example 1, step b but using N-dodecyl-5-({[4-(trifluoromethyl)benzyl]amino}methyl)thiophene-2-sulfonamide gave the title compound as a colorless oil (360 g, 45%).

$^1$H NMR (CDCl$_3$, 300 MHz) δ 7.66 (t, 2H, J=9.0 Hz), 7.42 (m, 2H), 7.37 (d, 0.7H, J=8.0 Hz), 6.87 (d, 0.3H, J=3.8 Hz), 6.86 (d, 0.7H, J=3.8 Hz), 4.60 (m, 2H), 4.52 (m, 2H), 4.36 (m, 2H), 3.02 (m, 2H), 1.50 (m, 3H), 1.40-1.20 (m, 21H), 0.86 (t, 3H, 6.6 Hz) M$^-$(APCI): 617.2; M$^+$(APCI): 619.2

HPLC (Condition A), Rt: 7.1 min (HPLC purity: 99.9%).

Step g) Formation of {({5-[(dodecylamino)sulfonyl]-2-thienyl}methyl)[4-(trifluoromethyl)-benzyl]amino}(oxo)acetic acid The same procedure as employed in the preparation of Example 1, step e but using ethyl{({5-[(dodecylamino)sulfonyl]thien-2-yl}methyl)[4-(trifluoromethyl)benzyl]amino}(oxo)-acetate gave the title compound as a colorless foam (96%). $^1$H NMR (CD$_3$OD, 300 MHz) δ 7.61 (m, 2H), 7.52 (m, 1H), 7.40 (m, 1H), 7.32 (m, 1H), 7.08 (m, 0.5H), 6.85 (m, 0.5H), 4.71 (m, 4H), 2.88 (m, 2H), 1.46 (m, 2H), 1.27 (m, 18H), 0.87 (t, J=8.1 Hz, 3H). M$^-$(LC/MS(ESI)): 589.1; M$^+$(LC/MS(ESI)): 591.3. HPLC (Condition A), Rt: 6.58 min (HPLC purity: 99.9%).

Example 25

{({5-[(dodecylamino)sulfonyl]-2-thienyl}methyl)[4-(trifluoromethyl)benzyl]-amino}(oxo)acetic acid, N-methyl-D-glucamine (i.e. 1-deoxy-1-(methylamino)glucitol) salt The same procedure as employed in the preparation of Example 2 but using N-methyl-D-glucamine and {({5-[(dodecylamino)sulfonyl]-2-thienyl}methyl)[4-(trifluoromethyl)-benzyl]amino}(oxo)acetic acid gave the title compound as a white powder (92%). M⁻(LC/MS(ESI)): 589.1; M⁺(LC/MS(ESI)): 591.3. HPLC (Condition A), Rt: 6.58 min (HPLC purity: 99.9%). Analysis calculated for $C_{27}H_{37}F_3N_2O_5S_2 \cdot C_7H_{17}NO_5$: C, 51.96; H, 6.93; N, 5.35%. Found: C, 51.54; H, 6.96; N, 5.26%.

Example 26

[{4-[(dodecylamino)carbonyl]benzyl}({1-[(4-methoxyphenyl)sulfonyl]-4-piperidinyl}methyl)amino](oxo)acetic acid Step a) Formation of tert-butyl 4-[({4-[(dodecylamino)carbonyl]benzyl}amino)methyl]-piperidine-1-carboxylate The same procedure as employed in the preparation of Example 10, step b, but starting from 4-(aminomethyl)-1-N-Boc-piperidine gave the title compound as a colorless oil (74%). ¹H NMR (DMSO-d₆, 300 MHz) δ 8.36 (t, 1H, J=5.6 Hz), 7.76 (d, 2H, 3=8.2 Hz), 7.37 (d, 2H, J=7.9 Hz), 3.90 (m, 2H), 3.71 (s, 2H), 3.22 (m, 2H), 2.66 (m, 2H), 2.33 (d, 2H, J=6.4 Hz), 1.67 (m, 2H), 1.49 (m, 3H), 1.37 (s, 9H), 1.23 (br s, 18H), 1.02-0.80 (m, 5H) M⁻(LC/MS(ESI)): 514.4; M⁺(LC/MS(ESI)): 516.7. HPLC (Condition A), Rt: 4.77 min (HPLC purity: 97.8%).

Step b) Formation of tert-butyl 4-({{4-[(dodecylamino)carbonyl]benzyl}[ethoxy(oxo)-acetyl]amino}methyl)piperidine-1-carboxylate The same procedure as employed in the preparation of Example 10, step c, but tert-butyl 4-[({4-[(dodecylamino)carbonyl]benzyl}amino)methyl]piperidine-1-carboxylate gave the title compound as a colorless oil (97%). M⁻(LC/MS(ESI)): 614.2; M⁺(LC/MS(ESI)): 616.3. HPLC (Condition A), Rt: 6.86 min (HPLC purity: 98.6%).

Step c) Formation of ethyl[{4-[(dodecylamino)carbonyl]benzyl}(piperidin-4-ylmethyl)-amino](oxo)acetate hydrochloride To a cold (0° C.) solution of tert-butyl 4-({{4-[(dodecylamino)carbonyl]benzyl}[ethoxy(oxo)acetyl]amino}methyl)piperidine-1-carboxylate (3.84 g, 6.24 mmol) in DCM (25 mL) was added a 4 N solution of HCl in dioxane (31.1 mL) and the resulting reaction mixture was stirred 4 h at 0° C. Evaporation of the solvents gave a white amorphous solid (73%). ¹H NMR (DMDO-d₆, 300 MHz) δ 9.03 (m, 0.5H), 8.70 (m, 0.5H), 8.50 (m, 1H), 7.85 (m, 2H), 7.33 (m, 2H), 4.56 (d, 2H, J=8.9 Hz), 4.40-4.20 (m, 2H), 3.35-3.10 (m, 7H), 2.80 (m, 2H), 1.70 (m, 2H), 1.52 (m, 2H), 1.43-1.15 (m, 21H), 0.86 (m, 3H). M⁻(LC/MS(ESI)): 514.4; M⁺(LC/MS(ESI)): 516.4. HPLC (Condition A), Rt: 4.68 min (HPLC purity: 99.4%).

Step d) Formation of ethyl[{4-[(dodecylamino)carbonyl]benzyl}({1-[(4-methoxyphenyl)-sulfonyl]piperidin-4-yl}methyl)amino](oxo)acetate To a solution of ethyl[{4-[(dodecylamino)carbonyl]benzyl}(piperidin-4-ylmethyl)amino](oxo)acetate hydrochloride (900 mg, 1.63 mmol), DIAE (527 mg, 4.07 mmol) and DMAP (20 mg, 0.16 mmol) in anhydrous THF (50 mL) was added 4-methoxybenzene-sulfonyl chloride (404 mg, 1.96 mmol) dissolved in THF (2.0 mL). The reaction mixture was stirred 14 h at rt. The solvent was evaporated and the resulting residue was dissolved in DCM (100 mL), washed with water (20 mL) and the aqueous layer was extracted with DCM (3×50 mL). The combined organic layers were dried over MgSO₄, filtered and evaporated under vacuum. The crude product was purified by column chromatography over silica gel (AcOEt/c-Hex 1/4 to 1/1 in about 1 h) to give the title compound as a white foam (992 mg, 89%). ¹H NMR (CDCl₃, 300 MHz) δ 7.76 (d, 2H, J=8.3 Hz), 7.69 (d, 2H, J=9.2 Hz), 7.27 (t, 2H, J=7.9 Hz), 7.07 (m, 2H), 6.12 (m, 1H), 4.60 (s, 1H), 4.48 (s, 1H), 3.89 (s, 3H), 3.76 (m, 2H), 3.13 (d, 1H, J=6.8 Hz), 3.07 (d, 1H, J=7.0 Hz), 2.32-2.12 (m, 2H), 1.80-1.55 (m, 6H), 1.45-1.20 (m, 24H), 0.89 (t, 3H, J=7.9 Hz). M⁻(APCI): 684.4. HPLC (Condition A), Rt: 6.84 min (HPLC purity: 99.7%).

Step e) Formation of [{4-[(dodecylamino)carbonyl]benzyl}({1-[(4-methoxyphenyl)sulfonyl]-4-piperidinyl}methyl)amino](oxo)acetic acid The same procedure as employed in the preparation of Example 1, step e but using ethyl [{4-[(dodecylamino)carbonyl]benzyl}({1-[(4-methoxyphenyl)sulfonyl]piperidin-4-yl}methyl)amino](oxo)acetate gave the title compound as a white powder (94%). ¹H NMR (CD₃OD, 300 MHz) δ 7.76 (m, 2H), 7.66 (m, 1H), 7.38 (d, 1H, J=8.3 Hz), 7.32 (d, 1H, J=7.9 Hz), 7.08 (m, 2H), 4.60 (m, 2H), 3.87 (s, 3H), 3.66 (m, 2H), 3.55 (m, 1H), 3.36 (t, 2H, J=7.1 Hz), 3.16 (m, 2H), 2.17 (m, 2H), 1.61 (m, 5H), 1.35-1.18 (m, 21H), 0.87 (t, 3H, J=8.0 Hz). M⁻(LC/MS(ESI)): 656.2; M⁺(LC/MS(ESI)): 658.3. HPLC (Condition A), Rt: 6.04 min (HPLC purity: 99.9%).

Example 27

[{4-[(dodecylamino)carbonyl]benzyl}({1-[(4-methoxyphenyl)sulfonyl]-4-piperidinyl}methyl)amino](oxo)acetic acid, N-methyl-D-glucamine (i.e. 1-deoxy-1-(methylamino)glucitol) salt The same procedure as employed in the preparation of Example 2 but using N-methyl-D-glucamine and [{4-[(dodecylamino)carbonyl]benzyl}({1-[(4-methoxyphenyl)sulfonyl]-4-piperidinyl}methyl)amino](oxo)acetic acid gave the title compound as white pellets (94.1%). M⁻(LC/MS(ESI)): 656.2; M⁺(LC/MS(ESI)): 658.3. HPLC (Condition A), Rt: 6.04 min (HPLC purity: 99.9%). Analysis calculated for $C_{35}H_{51}N_3O_7S \cdot C_7H_{17}NO_5$: C, 59.13; H, 8.03; N, 6.57%. Found: C, 58.73; H, 8.10; N, 6.57%.

Example 28

{{4-[(dodecylamino)carbonyl]benzyl}[1-(1-naphthyl)ethyl]amino}-(oxo)acetic acid

Step a) Formation of the Resin-bound Amines of Formula (D) (See Scheme 5), e.g. the Resin-bound dodecylamine The resin PS-MB-CHO HL (Argonaut Technologies Inc., 30 mg, 1.42 mmol/g, 0.0426 mmol, 100-200 mesh) was swelled in 1% HAc in DCE/TMOF (80/20) (1.0 mL) for 15 min at rt. Dodecylamine (24 mg, 0.128 mmol) and sodium triacetoxyborohydride (27 mg, 0.128 mmol) were added and the reaction mixture was shaken at rt for 14 h. The resin was washed successively with THF (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with Et₂O (1×10 min). The resin was then dried under vacuum to afford the resin-bound dodecylamine which was used directly in the next step.

Step b) Formation of the Resin-bound Amides of Formula (VIII-1) (See Scheme 5, Method K), e.g. resin-bound 4-chloromethyl-N-dodecyl-benzamide The resin-bound dodecylamine (described in step a, 0.0426 mmol) was swelled in DCM (1.0 mL) for 15 min at rt. DIEA (28 mg, 0.213 mmol) and 4-chloromethylbenzoyl chloride (40 mg, 0.213 mmol) were added and the reaction mixture was shaken at 0° C. for 2 h then 14 h at rt. The resin was washed successively with THF (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with $Et_2O$ (1×10 min). The resin was then dried under vacuum to afford the resin-bound 4-chloromethyl-N-dodecyl-benzamide which was used directly in the next step.

Step c) Formation of the Resin-bound Secondary Amines of Formula (III-1) (See Scheme 5), e.g. Resin-bound N-dodecyl-4-({[1-(1-naphthyl)ethyl]amino}methyl)benzamide The resin-bound 4-chloromethyl-N-dodecyl-benzamide (described in step b, 0.0426 mmol) was swelled in NMP (0.25 mL) for 15 min at rt. DIEA (33 mg, 0.256 mmol), tetrabutylammonium iodide (94.4 mg, 0.256 mmol) and 1-naphthalen-1-yl-ethylamine (44 mg, 0.256 mmol) dissolved in NMP (0.75 mL) were added and the reaction mixture was shaken 14 h at 80° C. The resin was washed successively with THF (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with $Et_2O$ (1×10 min). The resin was then dried under vacuum to afford the resin-bound N-dodecyl-4-({[1-(1-naphthyl)ethyl]amino}-methyl)benzamide which was used directly in the next step.

Step d) Formation of the Resin-bound Oxamic Ester of Formula (I-1) (See Scheme 1), e.g. Resin-bound ethyl{{4-[(dodecylamino)carbonyl]benzyl}[1-(1-naphthyl)ethyl]amino}(oxo)acetate The resin-bound N-dodecyl-4-({[1-(1-naphthyl)ethyl]amino}methyl)benzamide (described in step c, 0.0426 mmol) was swelled in DCM (1.0 mL) for 15 min at 0° C. DIEA (28 mg, 0.213 mmol) and chloro-oxo-acetic acid ethyl ester (29 mg, 0.213 mmol) were added and the reaction mixture was shaken 3 h at 0° C. then 14 h at rt. The resin was washed successively with THF (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with $Et_2O$ (1×10 min). The resin was then dried under vacuum to afford the resin-bound ethyl{{4-[(dodecylamino)carbonyl]benzyl}[1-(1-naphthyl)ethyl]amino}-(oxo)acetate which was used directly in the next step.

Step e) Formation of the Resin-bound Oxamic Acid of Formula (I-1) (See Scheme 1), e.g. Resin-bound {{4-[(dodecylamino)carbonyl]benzyl}[1-(1-naphthyl)ethyl]amino}(oxo)acetic acid The resin-bound ethyl{{4-[(dodecylamino)carbonyl]benzyl}[1-(1-naphthyl)ethyl]amino}-(oxo)acetate (described in step d, 0.0426 mmol) was swelled in THF (0.300 mL) for 15 min at rt. Lithium hydroxide monohydrate (36 mg, 0.852 mmol) diluted in $H_2O$ (0.060 mL) was added and the resulting reaction mixture was shaken 14 h at rt. The resin was washed successively with THF (1×15 min), $H_2O$ (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with $Et_2O$ (1×10 min). The resin was then dried under vacuum to afford the resin-bound {{4-[(dodecylamino)carbonyl]benzyl}[1-(1-naphthyl)-ethyl]amino}(oxo)acetic acid which was used directly in the next step.

Step f) Cleavage of the Resin-bound Oxamic Acid of Formula (I-1); Formation of the Oxamic Acid of Formula (I1) (See Scheme 1), e.g. {{4-[(dodecylamino)carbonyl]benzyl}[1-(1-naphthyl)ethyl]amino}(oxo)acetic acid The resin-bound {{4-[(dodecylamino)carbonyl]benzyl}[1-(1-naphthyl)ethyl]amino}(oxo)-acetic acid (described in step e, 0.0426 mmol) was poured in TFA/DCM 20/80 (2 mL) for 1 h at rt. The resin was filtered and the solvents were evaporated under vacuum to afford a colorless oil. The crude product was purified on a SPE column (Sorbent $NH_2$, Isolute® 1 g, 0.71 mmol/g) as follows: the column was equilibrated with DCM (2×10 mL) and the crude product (diluted in 1 mL DCM) was poured onto the column. The column was washed with DCM (2×5 mL) then with dioxane (2×5 mL) and the title compounds was finally eluted with a 2 N HCl in dioxane (2×2 mL). Evaporation of the HCl-containing fractions under vacuum gave the title compound as a colorless oil (6.5 mg). $M^-$(LC/MS(ESI)): 543.0; $M^+$(LC/MS(ESI)): 545.8. HPLC (Condition A), Rt: 6.67 min (HPLC purity: 99.1%).

Example 29

[{4-[(dodecylamino)carbonyl]benzyl}(2-carboxy-1-phenylethyl)amino](oxo)acetic acid The same procedure as employed in the preparation of Example 28 but using 2-phenylglycine ethyl ester hydrochloride in step c gave the title compound as a white powder (15 mg). $M^-$(LC/MS(ESI)): 523.1; $M^+$(LC/MS(ESI)): 525.9. HPLC (Condition A), Rt: 5.57 min (HPLC purity: 95.7%).

Example 30

[{4-[(dodecylamino)carbonyl]benzyl}(2-methoxy-1-methylethyl)amino](oxo)acetic acid The same procedure as employed in the preparation of Example 28 but using 2-amino-1-methoxypropane in step c gave the title compound as a colorless oil (3.7 mg). $M^-$(LC/MS(ESI)): 461.3; $M^+$(LC/MS(ESI)): 463.3. HPLC (Condition A), Rt: 5.9 min (HPLC purity: 98.1%).

Example 31

(4-bromo {4-[(dodecylamino)carbonyl]benzyl}anilino)(oxo)acetic acid

The same procedure as employed in the preparation of Example 28 but using 4-bromoaniline in step c gave the title compound as a colorless oil (2 mg). $M^+$(LC/MS(ESI)): 548.3. HPLC (Condition A), Rt: 6.44 min (HPLC purity: 90.5%).

Example 32

({4-[(dodecylamino)carbonyl]benzyl}anilino)(oxo)acetic acid

The same procedure as employed in the preparation of Example 28 but using aniline in step c gave the title compound as a colorless oil (3.1 mg). M⁻(LC/MS(ESI)): 465.1; M⁺(LC/MS(ESI)): 467.2. HPLC (Condition A), Rt: 6.1 min (HPLC purity: 91.9%).

Example 33

([2-(3-chlorophenyl)ethyl]{4-[(dodecylamino)carbonyl]benzyl}amino)(oxo)acetic acid The same procedure as employed in the preparation of Example 28 but using 2-(3-chlorophenyl)ethylamine in step c gave the title compound as a colorless oil (5 mg). M⁻(LC/MS(ESI)): 527.1; M⁺(LC/MS(ESI)): 530.6. HPLC (Condition A), Rt: 6.66 min (HPLC purity: 96.1%).

Example 34

{{4-[(dodecylamino)carbonyl]benzyl}[2-(3-methoxyphenyl)ethyl]amino}(oxo)acetic acid The same procedure as employed in the preparation of Example 28 but using 2-(3-methoxyphenyl)ethylamine in step c gave the title compound as a yellow oil (8.9 mg).
M⁻(LC/MS(ESI)): 523.1; M⁺(LC/MS(ESI)): 525.3. HPLC (Condition A), Rt: 6.35 min (HPLC purity: 97.2%).

Example 35

{{4-[(dodecylamino)carbonyl]benzyl}[((d,l)-trans-2-phenylcyclopropyl]amino}(oxo)acetic acid The same procedure as employed in the preparation of Example 28 but using (d,l)-trans-2-phenylcyclopropylamine hydrochloride in step c gave the title compound as a colorless oil (5.5 mg). M⁻(LC/MS(ESI)): 505.3; M⁺(LC/MS(ESI)): 507.2. HPLC (Condition A), Rt: 6.42 min (HPLC purity: 80.0%).

Example 36

([(d,l)-trans-2-(benzyloxy)cyclopentyl]{4-[(dodecylamino)carbonyl]benzyl}amino)(oxo)acetic acid The same procedure as employed in the preparation of Example 28 but using (d,l)-2-benzyloxycyclopentylamine in step c gave the title compound as a yellow oil (12.3 mg). M⁻(LC/MS(ESI)): 563.3; M⁺(LC/MS(ESI)): 565.4. HPLC (Condition A), Rt: 6.68 min (HPLC purity: 97.7%).

Example 37

({4-[(dodecylamino)carbonyl]benzyl}-4-phenoxyanilino)(oxo)acetic acid

The same procedure as employed in the preparation of Example 28 but using 4-phenoxyaniline in step c gave the title compound as a yellow oil (11.2 mg). M⁻(LC/MS(ESI)): 557.7; M⁺LC/MS(ESI)): 559.4. HPLC (Condition A), Rt: 6.64 min (HPLC purity: 94.3%).

Example 38

[{4-[(dodecylamino)carbonyl]benzyl}(1,2,3,4-tetrahydro-1-naphthalenyl)amino](oxo)acetic acid The same procedure as employed in the preparation of Example 28 but using 1,2,3,4-tetrahydro-1-naphthylamine in step c gave the title compound as a colorless oil (11.6 mg). M⁻(LC/MS(ESI)): 519.0; M⁺(LC/MS(ESI)): 521.0. HPLC (Condition A), Rt: 6.62 min (HPLC purity: 81.1%).

Example 39

((1-benzyl-4-piperidinyl){4-[(dodecylamino)carbonyl]benzyl}amino)(oxo)-acetic acid The same procedure as employed in the preparation of Example 28 but using 4-amino-1-benzylpiperidine in step c gave the title compound as a white powder (4.3 mg). M⁻(LC/MS(ESI)): 562.0; M⁺(LC/MS(ESI)): 564.7. HPLC (Condition A), Rt: 4.69 min (HPLC purity: 68.8%).

Example 40

{{4-[(dodecylamino)carbonyl]benzyl}[2-(4-phenoxyphenyl)ethyl]amino}(oxo)acetic acid The same procedure as employed in the preparation of Example 28 but using 4-phenoxyphenethylamine in step c gave the title compound as a colorless oil (4 mg). M⁻(LC/MS(ESI)): 585.6; M⁺(LC/MS(ESI)): 587.3. HPLC (Condition A), Rt: 6.91 min (HPLC purity: 97.1%).

Example 41

{{4-[(dodecylamino)carbonyl]benzyl}[2-(2-phenoxyphenyl)ethyl]amino}(oxo)acetic acid The same procedure as employed in the preparation of Example 28 but using 2-phenoxyphenethylamine in step c gave the title compound as a colorless oil (4.7 mg). M⁻(LC/MS(ESI)): 584.9; M⁺(LC/MS(ESI)): 586.9. HPLC (Condition A), Rt: 6.93 min (HPLC purity: 97.9%).

Example 42

((2-[1,1'-biphenyl]-4-ylethyl){4-[(dodecylamino)carbonyl]benzyl}-amino)(oxo)acetic acid The same procedure as employed in the preparation of Example 28 but using 2-(4-biphenyl)ethylamine in step c gave the title compound as a colorless oil (3.9 mg). M⁻(LC/MS(ESI)): 569.1; M⁺(LC/MS(ESI)): 571.2. HPLC (Condition A), Rt: 6.92 min (HPLC purity: 96.5%).

Example 43

(([1,1'-biphenyl]-3-ylmethyl){4-[(dodecylamino)carbonyl]benzyl}-amino)(oxo)acetic acid The same procedure as employed in the preparation of Example 28 but using 3-phenylbenzyl amine in step c gave the title compound as a colorless oil (6.2 mg). M⁻(LC/MS (ESI)): 555.7; M+(LC/MS(ESI)): 557.0. HPLC (Condition A), Rt: 6.54 min (HPLC purity: 81%).

Example 44

(3-(benzyloxy){4-[(dodecylamino)carbonyl] benzyl}anilino)(oxo)acetic acid

The same procedure as employed in the preparation of Example 28 but using 3-(benzyloxy)aniline in step c gave the title compound as a yellow oil (10.3 mg). M−(LC/MS(ESI)): 571.0; M+(LC/MS(ESI)): 573.4. HPLC (Condition A), Rt: 6.35 min (HPLC purity: 94.5%).

Example 45

([4-(benzoylamino)benzyl]{4-[(dodecylamino)carbonyl]benzyl}amino)(oxo)acetic acid The same procedure as employed in the preparation of Example 28 but using 4-benzamidobenzylamine in step c gave the title compound as a yellow oil (1.8 mg). M−(LC/MS (ESI)): 598.8; M+(LC/MS(ESI)): 600.1. HPLC (Condition A), Rt: 5.93 min (HPLC purity: 55.1%).

Example 46

N-(carboxycarbonyl)-N-{4-[(dodecylamino)carbonyl]benzyl}-3-phenyl-beta-alanine

The same procedure as employed in the preparation of Example 28 but using dl-3-amino-3-phenylpropionic acid in step c gave the title compound as a white powder (7.5 mg). M−(LC/MS(ESI)): 537.7; M+(LC/MS(ESI)): 539.0. HPLC (Condition A), Rt: 5.57 min (HPLC purity: 57.3%).

Example 47

{{4-[(dodecylamino)carbonyl]benzyl}[4-(1,2,3-thiadiazol-4-yl)benzyl]-amino}(oxo)acetic acid The same procedure as employed in the preparation of Example 28 but using 4-(1,2,3-thiadiazol-4-yl)benzylamine hydrochloride in step c gave the title compound as a brown powder (7.4 mg). M−(LC/MS(ESI)): 562.9; M+(LC/MS (ESI)): 565.7. HPLC (Condition A), Rt: 6.02 min (HPLC purity: 94.2%).

Example 48

[{4-[(dodecylamino)carbonyl]benzyl}(4-pentylbenzyl)amino](oxo)acetic acid

The same procedure as employed in the preparation of Example 28 but using 4-pentylbenzylamine hydrochloride in step c gave the title compound as a colorless oil (9.3 mg). M−(LC/MS(ESI)): 549.0; M+(LC/MS(ESI)): 551.1. HPLC (Condition A), Rt: 7.04 min (HPLC purity: 97.1%).

Example 49

[{4-[(dodecylamino)carbonyl]benzyl}(1-phenylethyl)amino](oxo)acetic acid

The same procedure as employed in the preparation of Example 28 but using d,l-□-methylbenzylamine in step c gave the title compound as a white powder (14.6 mg). M−(LC/MS(ESI)): 493.1; M+(LC/MS(ESI)): 495.0. HPLC (Condition A), Rt: 6.11 min (HPLC purity: 92.1%).

Example 50

(benzyl{3-[(dodecylamino)carbonyl]benzyl}amino)(oxo)acetic acid

Step a) Formation of the Resin-bound Amines of Formula (D) (See Scheme 5), e.g. the Resin-bound Dodecylamine The same procedure as employed in the preparation of Example 28, step a, gave the title compound.

Step b) Formation of the Resin-bound Protected Amines of Formula (VII-1) (See Scheme 5), e.g. the Resin-bound 9H-fluoren-9-ylmethyl 3-[(dodecylamino)carbonyl]benzylcarbamate The resin-bound dodecylamine (described in step a, 0.0426 mmol) was swelled in NMP (0.25 mL) for 15 min at rt. DIEA (44 mg, 0.340 mmol), Fmoc-(3-aminomethyl)-benzoic acid (64 mg, 0.170 mmol) and PyBOP® (89 mg, 0.170 mmol) were dissolved in NMP (0.75 mL) and shaken for 15 min at rt. The solution was added to the resin and the resulting reaction mixture was shaken 14 h at rt. The resin was washed successively with NMP (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with Et₂O (1×10 min). The resin was then dried under vacuum to afford the title compound which was used directly in the next step.

Step c) Fmoc-deprotection of the Resin-bound Protected Amines of Formula (VII-1) (See Scheme 5); e.g. Formation the Resin-bound 3-(aminomethyl)-N-dodecylbenzamide The resin-bound 9H-fluoren-9-ylmethyl 3-[(dodecylamino)carbonyl]benzylcarbamate (described in step b, 0.0426 mmol) was treated with a 20% solution (v/v) of piperidine in DMF (4 mL, 1×5 min, then again 2×15 min with a fresh solution of piperidine in DMF). The resin was washed successively with DMF (1×15 min), MeOH (1×15 min), MeOH (3×10 min), DMF (3×10 min), MeOH (1×5 min), THF (3×10 min), MeOH (1×5 min), DCM (3×10 min) and with Et₂O (1×10 min). The resin was then dried under vacuum to afford the title compound which was used directly in the next step.

Step d) Formation of the Resin-bound Secondary Amines of Formula (III-1) (See Scheme 5, Method L), e.g. Resin-bound 3-[(benzylamino)methyl]-N-dodecylbenzamide The resin-bound 3-(aminomethyl)-N-dodecylbenzamide (described in step c, 0.0426 mmol) was swelled in THF/TMOF 80/20 (1.0 mL) for 15 min at rt. Benzaldehyde (45 mg, 0.426 mmol) was added and the mixture was shaken 14 h at rt. The resin was washed with 10% TMOF in anhydrous THF (2×15 min, then 2×60 min), then with anhydrous THF (1×30 min). The resin was then poured in anhydrous THF (1.0 mL) and sodium triacetoxyborohydride (27 mg, 0.128 mmol) was added and the mixture was shaken 14 h at rt. The resin was washed successively with THF (1×15 min), MeOH (1×15 min), MeOH (3×10 min), DMF (3×10 min), MeOH (1×5 min), THF (3×10 min), MeOH (1×5 min), DCM (3×10 min) and with Et$_2$O (1×10 min). The resin was then dried under vacuum to afford the title compound which was used directly in the next step.

Step e) Formation of the Resin-bound Oxamic Ester of formula (I-1) (See Scheme 1), e.g. Resin-bound ethyl(benzyl{3-[(dodecylamino)carbonyl]benzyl}amino)(oxo)acetate The same procedure as employed in the preparation of Example 28, step d, but using the resin-bound 3-[(benzylamino)methyl]-N-dodecylbenzamide (described in step d, 0.0426 mmol) gave the title compound which was used directly in the next step.

Step f) Formation of the Resin-bound Oxamic Acid of Formula (I-1) (See Scheme 1), e.g. Resin-bound (benzyl{3-[(dodecylamino)carbonyl]benzyl}amino) (oxo)acetic acid The same procedure as employed in the preparation of Example 28, step e, but using the resin-bound ethyl(benzyl {3-[(dodecylamino)carbonyl]benzyl}amino)(oxo)acetate (described in step e, 0.0426 mmol) gave the title compound which was used directly in the next step.

Step g) Cleavage of the Resin-bound Oxamic Acid of Formula (I-1); Formation of the Oxamic Acid of Formula (I) (See Scheme 1), e.g. (benzyl{3-[(dodecylamino)carbonyl]benzyl}amino)-(oxo)acetic acid The same procedure as employed in the preparation of Example 28, step f, but using the resin-bound (benzyl{3-[(dodecylamino)carbonyl]benzyl}amino)(oxo)acetic acid (described in step f, 0.0426 mmol) gave the title compound as a yellow oil (15.5 mg). $^1$H NMR (CD$_3$OD, 300 MHz) δ 7.70-7.08 (m, 9H), 4.43 (s, 2H), 4.41 (s, 2H), 3.34-3.20 (m, 2H), 1.61-1.45 (m, 2H), 1.37-1.10 (m, 18H), 0.80 (t, J=8.6 Hz, 3H). M$^-$(LC/MS(ESI)): 479.4; M$^+$(LC/MS(ESI)): 481.2. HPLC (Condition A), Rt: 6.28 min (HPLC purity: 80.3%).

Example 51

{{3-[(dodecylamino)carbonyl]benzyl}[4-(methylsulfonyl)benzyl]amino}-(oxo)acetic acid The same procedure as employed in the preparation of Example 50 using dodecylamine in step a, Fmoc-(3-aminomethyl)-benzoic acid in step b and 4-(methylsulfonyl)benzaldehyde in step d gave the title compound as a yellow oil (16.2 mg). $^1$H NMR (CD$_3$OD, 300 MHz) δ 8.00-7.25 (m, 8H), 4.61-4.46 (m, 4H), 3.32-3.23 (m, 2H), 3.01 (s, 3H), 1.60-1.45 (m, 2H), 1.36-1.12 (m, 18H), 0.80 (t, J=8.7 Hz, 3H). M$^-$(LC/MS(ESI)): 557.0; M$^+$(LC/MS(ESI)): 559.1. HPLC (Condition A), Rt: 5.71 min (HPLC purity: 86.5%).

Example 52

((3-cyanobenzyl){3-[(dodecylamino)carbonyl]benzyl}amino)(oxo)acetic acid

The same procedure as employed in the preparation of Example 50 using dodecylamine in step a, Fmoc-(3-aminomethyl)-benzoic acid in step b and 3-cyanobenzaldehyde in step d gave the title compound. M$^+$(LC/MS(ESI)): 506.6

Example 53

{{3-[(dodecylamino)carbonyl]benzyl}[4-(trifluoromethyl)benzyl]amino}-(oxo)acetic acid The same procedure as employed in the preparation of Example 50 using dodecylamine in step a, Fmoc-(3-aminomethyl)-benzoic acid in step b and 4-(trifluoromethyl)benzaldehyde in step d gave the title compound. M$^+$(LC/MS(ESI)): 548.9

Example 54

[(4-chlorobenzyl)(3-{[(4-pentylbenzyl)amino]carbonyl}benzyl)-amino](oxo)-acetic acid The same procedure as employed in the preparation of Example 50 using 4-n-pentylbenzyl amine hydrochloride in step a, Fmoc-(3-aminomethyl)-benzoic acid in step b and 4-chloro-benzaldehyde in step d gave the title compound. M$^+$(LC/MS(ESI)): 507.7

Example 55 oxo{[4-({[2-(2-thienyl)ethyl]amino}carbonyl)benzyl][4-(trifluoromethyl)-benzyl]amino}acetic acid The same procedure as employed in the preparation of Example 50 using thiophene-2-ethylamine in step a, Fmoc-(4-aminomethyl)-benzoic acid in step b and 4-(trifluoromethyl)benzaldehyde in step d gave the title compound. M$^+$(LC/MS(ESI)): 491.6

Example 56

{benzyl[(3'-{[(2,2-diphenylethyl)amino]carbonyl}[1,1'-biphenyl]-4-yl)-methyl]amino}(oxo)acetic acid Step a) Formation of tert-butyl-3-bromo benzoate To a mixture of 3-bromo benzoic acid (10 g, 0.5 mol), silver carbonate (276 g, 1 mol) and dry molecular sieves (100 g) taken in dry CH$_2$Cl$_2$ (2 L), tert-butylbromide (115 mL, 1 mol) was added dropwise at 0° C. and the reaction mixture was stirred overnight at RT. The solid was filtered and washed with dichloromethane. Organic layer was washed with 10% aqueous solution of NaHCO$_3$ (2×500 mL), water (2×500 mL), brine and dried. The solvent was removed under vacuum to give tert-butyl-3-bromobenzoate (70 g, 57%).

Step b) Formation of tert-butyl-3-(4-tolyl)bromobenzoate

To a mixture of tert-butyl-3-bromobenzoate (65 g, 0.25 mol), 4-tolyl boronic acid (41.3 g, 0.30 mol) and sodium carbonate (150 g) in a mixture of toluene (500 mL) and water (50 mL), tetrakis-triphenylphosphine palladium(0) (14.5 g, 0.05 mol) was added and the reaction mixture was refluxed overnight. Cooled to RT, toluene layer was separated. The organic layer was washed with water, brine, dried. The solvent was removed under vacuum to give tert-butyl-3-(4-tolyl) benzoate (62 g, 90%).

Step c) Formation of 4-(3-tert-butoxy carbonyl phenyl)benzyl bromide

To a solution of tert-Butyl-3-(4-tolyl)benzoate (60 g, 0.22 mol) in CCl$_4$ (800 mL) were added NBS (47.8 g, 0.268 mol)

and benzoylperoxide (10 g) and the reaction mixture was refluxed overnight. Cooled to RT and filtered. The filtrate was concentrated to give 4-(3-tert-butoxy carbonyl phenyl)benzyl bromide (65 g, 84%).

Step d) Formation of 4-(3-carboxyphenyl)benzylamine hydrochloride

Ammonia gas was passed through a cooled solution of 4-(3-tert-butoxycarbonylphenyl) benzyl bromide (65 g, 0.18 mol) in methanol (2 L) for 6 h. Then the reaction mixture was stirred at RT overnight. Methanol was removed under vacuum. To the residue 6N aqueous solution of HCl (200 mL) was added and stirred overnight. Concentrated completely to get 4-(3-carboxyphenyl)benzylamine as a hydrochloride salt (20 g, 41%).

Step e) Formation of N-Fmoc-4-(3-carboxyphenyl)benzylamine

A solution of 4-(3-carboxyphenyl)benzylamine hydrochloride (20 g, 0.075 mol) in 10% $Na_2CO_3$ (350 mL) and dioxane (100 mL) was cooled to 0° C. with stirring. A solution of Fmoc-OSu (30.7 g, 0.091 mol) in dioxane (100 mL) was added in one portion and the reaction mixture was stirred at RT for 3 h. Acidified with 1.5 N aqueous solution of HCl and extracted with EtOAc (3×400 mL). The organic layer was washed with water (3×500 mL), brine dried over $Na_2SO_4$ and concentrated, purification by column chromatography using dichloromethane/methanol (9:1) to give N-Fmoc-4-(3-carboxyphenyl)benzylamine (16 g). This was further purified by recrystallization from THF/PetEther gave the title pure product (8 g).

Step f) Formation of {benzyl[(3'-{[(2,2-diphenyl-ethyl)amino]carbonyl}[1,1'-biphenyl]-4-yl)methlyl]amino}(oxo)acetic acid The same procedure as employed in the preparation of Example 50 using 2,2-diphenyl-ethylamine in step a, N-Fmoc-4-(3-carboxyphenyl)benzylamine in step b and benzaldehyde in step d gave the title compound. $M^+$(LC/MS(ESI)): 569.5

Example 57

{(3-cyanobenzyl)[(3'-{[(2,2-diphenylethyl)amino]carbonyl}[1,1'-biphenyl]-4-yl)methyl]amino}(oxo)acetic acid The same procedure as employed in the preparation of Example 50 using 2,2-diphenyl-ethylamine in step a, N-Fmoc-4-(3-carboxyphenyl)benzylamine in step b and 3-cyano-benzaldehyde in step d gave the title compound. $M^+$(LC/MS(ESI)): 594.4

Example 58

{(4-chlorobenzoyl)[(3'-{[(2,2-diphenylethyl)amino]carbonyl}[1,1'-biphenyl]-4-yl)methyl]amino}(oxo)acetic acid The same procedure as employed in the preparation of Example 50 using 2,2-diphenyl-ethylamine in step a, N-Fmoc-4-(3-carboxyphenyl)benzylamine in step b and 4-chlorobenzaldehyde in step d gave the title compound. $M^+$(LC/MS(ESI)): 605.3

Example 59

{[(3'-{[(2,2-diphenylethyl)amino]carbonyl}[1,1'-biphenyl]-4-yl)methyl][4-(trifluoromethyl)benzyl]amino}(oxo)acetic acid The same procedure as employed in the preparation of Example 50 using 2,2-diphenylethylamine in step a, N-Fmoc-4-(3-carboxyphenyl)benzylamine in step b and 4-(trifluoromethyl)benzaldehyde in step d gave the title compound. $M^+$(LC/MS(ESI)): 637.4

Example 60

((3-cyanobenzyl){[3'-({[2-(4-phenoxyphenyl)ethyl]amino}carbonyl)[1,1'-biphenyl]-4-yl]methyl}amino)(oxo)acetic acid The same procedure as employed in the preparation of Example 50 using 4-phenoxy-phenethylamine in step a, N-Fmoc-4-(3-carboxyphenyl)benzylamine in step b and 3-cyanobenzaldehyde in step d gave the title compound. $M^+$(LC/MS(ESI)): 610.4

Example 61 oxo{{[3'-({[2-(4-phenoxyphenyl)ethyl]amino}carbonyl)[1,1'-biphenyl]-4-yl]methyl}[4-(trifluoromethyl)benzyl]amino}acetic acid The same procedure as employed in the preparation of Example 50 using 4-phenoxy-phenethylamine in step a, N-Fmoc-4-(3-carboxyphenyl)benzylamine in step b and 4-(trifluoromethyl)benzaldehyde in step d gave the title compound. $M^+$(LC/MS(ESI)): 653.4

Example 62

[(3-cyanobenzyl)({3'-[(octylamino)carbonyl][1,1'-biphenyl]-4-yl}methyl)-amino](oxo)acetic acid The same procedure as employed in the preparation of Example 50 using octylamine in step a, N-Fmoc-4-(3-carboxyphenyl)benzylamine in step b and 3-cyanobenzaldehyde in step d gave the title compound. $M^+$(LC/MS(ESI)): 526.4

Example 63

[(4-chlorobenzyl)({3'-[(octylamino)carbonyl][1,1'-biphenyl]-4-yl}methyl)-amino](oxo)acetic acid The same procedure as employed in the preparation of Example 50 using octylamine in step a, N-Fmoc-4-(3-carboxyphenyl)benzylamine in step b and 4-chlorobenzaldehyde in step d gave the title compound. $M^+$(LC/MS(ESI)): 537.4

Example 64

{({3'-[(octylamino)carbonyl][1,1'-biphenyl]-4-yl}methyl)[4-(trifluoromethyl)-benzyl]amino}(oxo)acetic acid The same procedure as employed in the preparation of Example 50 using octylamine in step a, N-Fmoc-4-(3-carboxyphenyl)benzylamine in step b and 4-(trifluoromethyl)-benzaldehyde in step d gave the title compound. $M^+$(LC/MS(ESI)): 569.4

Example 65

{(3-cyanobenzyl)[(3'-{[(3-phenylpropyl)amino]carbonyl}[1,1'-biphenyl]-4-yl)methyl]amino}(oxo)acetic acid The same procedure as employed in the preparation of Example 50 using 3-phenylpropyl-amine in step a, N-Fmoc-4-(3-carboxyphenyl)benzylamine in step b and 3-cyanobenzaldehyde in step d gave the title compound. M$^+$(LC/MS (ESI)): 532.4

Example 66

[3-cyanobenzyl)({3'-[(dodecylamino)carbonyl][1,1'-biphenyl]-4-yl}methyl)amino](oxo)acetic acid The same procedure as employed in the preparation of Example 50 using dodecylamine in step a, N-Fmoc-4-(3-carboxyphenyl)benzylamine in step b and 3-cyanobenzaldehyde in step d gave the title compound. M$^+$(LC/MS(ESI)): 582.5

Example 67

[(4-chlorobenzyl)({3'-[(dodecylamino)carbonyl][1,1'-biphenyl]-4-yl}methyl)-amino](oxo)acetic acid The same procedure as employed in the preparation of Example 50 using dodecylamine in step a, N-Fmoc-4-(3-carboxyphenyl)benzylamine in step b and 4-chlorobenzaldehyde in step d gave the title compound. M$^+$(LC/MS(ESI)): 592.5

Example 68

{({3'-[(dodecylamino)carbonyl][1,1'-biphenyl]-4-yl}methyl)[4-(trifluoromethyl)benzyl]amino}(oxo)acetic acid The same procedure as employed in the preparation of Example 50 using dodecylamine in step a, N-Fmoc-4-(3-carboxyphenyl)benzylamine in step b and 4-(trifluoromethyl)benzaldehyde in step d gave the title compound. M$^+$(LC/MS(ESI)): 625.5

Example 69

{benzyl[(3'-{[(4-pentylbenzyl)amino]carbonyl}[1,1'-biphenyl]-4-yl)methyl]-amino}(oxo)acetic acid The same procedure as employed in the preparation of Example 50 using 4-n-pentylbenzyl-amine hydrochloride in step a, N-Fmoc-4-(3-carboxyphenyl)benzylamine in step b and benzaldehyde in step d gave the title compound. M$^+$(LC/MS(ESI)): 549.5

Example 70

{(3-cyanobenzyl)[(3'-{[(4-pentylbenzyl)amino]carbonyl}[1,1'-biphenyl]-4-yl)methyl]amino}(oxo)acetic acid The same procedure as employed in the preparation of Example 50 using 4-n-pentylbenzylamine hydrochloride in step a, N-Fmoc-4-(3-carboxyphenyl)benzylamine in step b and 3-cyanobenzaldehyde in step d gave the title compound. M$^+$(LC/MS(ESI)): 574.5

Example 71

{(4-chlorobenzyl)[(3'-{[(4-pentylbenzyl)amino]carbonyl}[1,1'-biphenyl]-4-yl)methyl]amino}(oxo)acetic acid The same procedure as employed in the preparation of Example 50 using 4-n-pentylbenzyl-amine hydrochloride in step a, N-Fmoc-4-(3-carboxyphenyl)benzylamine in step b and 4-chlorobenzaldehyde in step d gave the title compound. M$^+$(LC/MS(ESI)): 584.3

Example 72 oxo{[(3'-{[(4-pentylbenzyl)amino]carbonyl}[1,1'-biphenyl]-4-yl)methyl][4-(trifluoromethyl)benzyl]amino}acetic acid The same procedure as employed in the preparation of Example 50 using 4-n-pentylbenzylamine hydrochloride in step a, N-Fmoc-4-(3-carboxyphenyl)benzylamine in step b and 4-(trifluoromethyl)benzaldehyde in step d gave the title compound. M$^+$(LC/MS(ESI)): 617.5

Example 73 oxo{[(3'-{[(4-phenylbutyl)amino]carbonyl}[1,1'-biphenyl]-4-yl)methyl][4-(trifluoromethyl)benzyl]amino}acetic acid The same procedure as employed in the preparation of Example 50 using 4-phenylbutylamine in step a, N-Fmoc-4-(3-carboxyphenyl)benzylamine in step b and 4-(trifluoromethyl)benzaldehyde in step d gave the title compound. M$^+$(LC/MS(ESI)): 589.5

Example 74

{(3-cyanobenzyl)[(3-{[(2-mesitylethyl)amino]carbonyl}[1,1'-biphenyl]-4-yl)methyl]amino}(oxo)acetic acid The same procedure as employed in the preparation of Example 50 using 2-(2,4,6-trimethyl-phenyl)-ethylamine in step a, N-Fmoc-4-(3-carboxyphenyl)benzylamine in step b and 3-cyanobenzaldehyde in step d gave the title compound. M$^+$(LC/MS(ESI)): 560.5

Example 75

{(4-chlorobenzyl)[(3'-{[(2-mesitylethyl)amino]carbonyl}[1,1'-biphenyl]-4-yl)methyl]amino}(oxo)acetic acid The same procedure as employed in the preparation of Example 50 using 2-(2,4,6-trimethyl-phenyl)-ethylamine in step a, N-Fmoc-4-(3-carboxyphenyl)benzylamine in step b and 4-chlorobenzaldehyde in step d gave the title compound. M$^+$(LC/MS(ESI)): 570.4

Example 76

{[(3'-{[(2-mesitylethyl)amino]carbonyl}[1,1'-biphenyl]-yl)methyl][4-(trifluoromethyl)benzyl]amino}(oxo)acetic acid The same procedure as employed in the preparation of Example 50 using 2-(2,4,6-trimethyl-phenyl)-ethylamine in step a, N-Fmoc-4-(3-carboxyphenyl)benzylamine in step b and 4-(trifluoromethyl)benzaldehyde in step d gave the title compound. M⁺(LC/MS(ESI)): 603.5

Example 77

((4-chlorobenzyl){[3'-({[2-(4-methoxyphenyl)ethyl]amino}carbonyl)[1,1'-biphenyl]-4-yl]methyl}amino)(oxo)acetic acid The same procedure as employed in the preparation of Example 50 using 2-(4-methoxyphenyl)ethylamine in step a, N-Fmoc-4-(3-carboxyphenyl)benzylamine in step b and 4-chlorobenzaldehyde in step d gave the title compound. M⁺(LC/MS(ESI)): 558.3

Example 78

[{4-[(dodecylamino)carbonyl]benzyl}(4-methoxybenzyl)amino](oxo)acetic acid

The same procedure as employed in the preparation of Example 50 using dodecylamine in step a, Fmoc-(4-aminomethyl)-benzoic acid in step b and p-anisaldehyde in step d gave the title compound as a yellow oil (20.2 mg). M⁻(LC/MS(ESI)): 509.2; M⁺(LC/MS(ESI)): 511.3. HPLC (Condition A), Rt: 6.19 min (HPLC purity: 80.2%).

Example 79

{{4-[(dodecylamino)carbonyl]benzyl}[4-(methylsulfonyl)benzyl]amino}-(oxo)acetic acid The same procedure as employed in the preparation of Example 50 using dodecylamine in step a, Fmoc-(4-aminomethyl)-benzoic acid in step b and 4-(methylsulfonyl)benzaldehyde in step d gave the title compound as a yellow oil (21.7 mg). M⁻(LC/MS(ESI)): 557.2; M⁺(LC/MS(ESI)): 559.1. HPLC (Condition A), Rt: 5.71 min (HPLC purity: 92.3%).

Example 80

[{3-[(dodecylamino)carbonyl]benzyl}(4-methoxybenzyl)amino](oxo)acetic acid

The same procedure as employed in the preparation of Example 50 using dodecylamine in step a, Fmoc-(3-aminomethyl)-benzoic acid in step b and p-anisaldehyde in step d gave the title compound as a yellow oil (18.3 mg). M⁻(LC/MS(ESI)): 509.4; M⁺(LC/MS(ESI)): 511.2. HPLC (Condition A), Rt: 6.22 min (HPLC purity: 76.1%).

Example 81

{{3-[(dodecylamino)carbonyl]benzyl}[3-(trifluoromethyl)benzyl]amino}-(oxo)acetic acid The same procedure as employed in the preparation of Example 50 using dodecylamine in step a, Fmoc-(3-aminomethyl)-benzoic acid in step b and 3-(trifluoromethyl)benzaldehyde in step d gave the title compound as a yellow oil (19.4 mg). M⁻(LC/MS(ESI)): 547.2; M⁺(LC/MS(ESI)): 549.3. HPLC (Condition A), Rt: 6.58 min (HPLC purity: 91%).

Example 82

({4-[(dodecylamino)carbonyl]benzyl}{[6-(trifluoromethyl)-3-pyridinyl]-methyl}amino)(oxo)acetic acid The same procedure as employed in the preparation of Example 50 using dodecylamine in step a, Fmoc-(3-aminomethyl)-benzoic acid in step b and 6-(trifluoromethyl)pyridine-3-carboxaldehyde in step d gave the title compound as a pale yellow oil (33 mg). M⁻(LC/MS(ESI)): 548.3; M⁺(LC/MS(ESI)): 550.4. HPLC (Condition A), Rt: 6.03 min (HPLC purity: 83.5%).

Example 83

4-[((carboxycarbonyl){3-[(dodecylamino)carbonyl]benzyl}amino)-methyl]-benzoic acid The same procedure as employed in the preparation of Example 50 using dodecylamine in step a, Fmoc-(3-aminomethyl)-benzoic acid in step b and methyl 4-formylbenzoate in step d gave the title compound as a white solid (33 mg). M⁻(LC/MS(ESI)): 523.8; M⁺(LC/MS(ESI)): 525.3. HPLC (Condition A), Rt: 5.45 min (HPLC purity: 92.6%).

Example 84

({3-[(dodecylamino)carbonyl]benzyl}{4-[hydroxy(oxido)amino]-benzyl}-amino)(oxo)acetic acid The same procedure as employed in the preparation of Example 50 using dodecylamine in step a, Fmoc-(3-aminomethyl)-benzoic acid in step b and 4-nitrobenzaldehyde in step d gave the title compound as an orange oil (28 mg). M⁻(LC/MS(ESI)): 524.2; M⁺(LC/MS(ESI)): 526.4. HPLC (Condition A), Rt: 6.14 min (HPLC purity: 64.5%).

Example 85

[{3-[(dodecylamino)carbonyl]benzyl}(2-fluorobenzyl)amino](oxo)acetic acid

The same procedure as employed in the preparation of Example 50 using dodecylamine in step a, Fmoc-(3-aminomethyl)-benzoic acid in step b and 2-fluorobenzaldehyde in step d gave the title compound as a yellow solid (26 mg). M⁻(LC/MS(ESI)): 497.3; M⁺(LC/MS(ESI)): 499.4. HPLC (Condition A), Rt: 6.19 min (HPLC purity: 78%).

Example 86

[{3-[(dodecylamino)carbonyl]benzyl}(2-pyridinylmethyl)amino](oxo)acetic acid

The same procedure as employed in the preparation of Example 50 using dodecylamine in step a, Fmoc-(3-aminomethyl)-benzoic acid in step b and 2-pyridinecarboxaldehyde in step d gave the title compound as a brown oil (29 mg). M⁻(LC/MS(ESI)): 480.3; M⁺(LC/MS(ESI)): 482.4. HPLC (Condition A), Rt: 4.67 min (HPLC purity: 89%).

Example 87

[{3-[(dodecylamino)carbonyl]benzyl}(3-thienylmethyl)amino](oxo)acetic acid

The same procedure as employed in the preparation of Example 50 using dodecylamine in step a, Fmoc-(3-aminomethyl)-benzoic acid in step b and 3-thiophenecarboxaldehyde in step d gave the title compound as an orange oil (24 mg). M⁻(LC/MS(ESI)): 485.2; M⁺(LC/MS(ESI)): 487.4. HPLC (Condition A), Rt: 6.13 min (HPLC purity: 64%).

Example 88

[{3-[(dodecylamino)carbonyl]benzyl}(4-hydroxybenzyl)amino](oxo)acetic acid

The same procedure as employed in the preparation of Example 50 using dodecylamine in step a, Fmoc-(3-aminomethyl)-benzoic acid in step b and 4-hydroxybenzaldehyde in step d gave the title compound as an orange oil (29 mg). M⁻(LC/MS(ESI)): 495.3; M⁺(LC/MS(ESI)): 497.3. HPLC (Condition A), Rt: 5.55 min (HPLC purity: 81.1%).

Example 89

[{3-[(dodecylamino)carbonyl]benzyl}(4-phenoxybenzyl)amino](oxo)acetic acid

The same procedure as employed in the preparation of Example 50 using dodecylamine in step a, Fmoc-(3-aminomethyl)-benzoic acid in step b and 4-phenoxybenzaldehyde in step d gave the title compound as a yellow oil (30 mg). M⁻(LC/MS(ESI)): 571.5; M⁺(LC/MS(ESI)): 573.3. HPLC (Condition A), Rt: 6.68 min (HPLC purity: 77.3%).

Example 90

({3-[(dodecylamino)carbonyl]benzyl}{[6-(trifluoromethyl)-3-pyridinyl]methyl}amino)(oxo)acetic acid The same procedure as employed in the preparation of Example 50 using dodecylamine in step a, Fmoc-(3-aminomethyl)-benzoic acid in step b and 6-(trifluoromethyl)pyridine-3-carboxaldehyde in step d gave the title compound as a pale yellow oil (32 mg). M⁺(LC/MS(ESI)): 550.5. HPLC (Condition A), Rt: 6.19 min (HPLC purity: 79.8%).

Example 91

3-[((carboxycarbonyl){3-[(dodecylamino)carbonyl]benzyl}amino)methyl]-benzoic acid The same procedure as employed in the preparation of Example 50 using dodecylamine in step a, Fmoc-(3-aminomethyl)-benzoic acid in step b and 3-carboxybenzaldehyde in step d gave the title compound as a pale yellow oil (33 mg). M⁺(LC/MS(ESI)): 525.3 HPLC (Condition A), Rt: 5.53 min (HPLC purity: 76%).

Example 92

5-[((carboxycarbonyl){3-[(dodecylamino)carbonyl]benzyl}amino)methyl]-2-thiophenecarboxylic acid The same procedure as employed in the preparation of Example 50 using dodecylamine in step a, Fmoc-(3-aminomethyl)-benzoic acid in step b and 5-formyl-2-thiophenecarboxylic acid in step d gave the title compound as a pale yellow oil (31 mg). M⁻(LC/MS(ESI)): 529.2; M⁺(LC/MS(ESI)): 531.2. HPLC (Condition A), Rt: 5.32 min (HPLC purity: 54%).

Example 93

({4-[(dodecylamino)carbonyl]benzyl}{4-[hydroxy(oxido)amino]benzyl}-amino)(oxo)acetic acid The same procedure as employed in the preparation of Example 50 using dodecylamine in step a, Fmoc-(4-aminomethyl)-benzoic acid in step b and 4-nitrobenzaldehyde in step d gave the title compound as a brown oil (28 mg). M⁻(LC/MS(ESI)): 524.2; M⁺(LC/MS(ESI)): 526.3. HPLC (Condition A), Rt: 6 min (HPLC purity: 58.5%).

Example 94

((1,3-benzodioxol-5-ylmethyl){4-[(dodecylamino)carbonyl]-benzyl}amino)-(oxo)acetic acid The same procedure as employed in the preparation of Example 50 using dodecylamine in step a, Fmoc-(4-aminomethyl)-benzoic acid in step b and piperonal in step d gave the title compound as an orange oil (27 mg). M⁻(LC/MS(ESI)): 523.2; M⁺(LC/MS(ESI)): 526.4 HPLC (Condition A), Rt: 6.08 min (HPLC purity: 59.8%).

Example 95

[{4-[(dodecylamino)carbonyl]benzyl}(2-fluorobenzyl)amino](oxo)acetic acid

The same procedure as employed in the preparation of Example 50 using dodecylamine in step a, Fmoc-(4-aminomethyl)-benzoic acid in step b and 2-fluorobenzaldehyde in step d gave the title compound as a yellow solid (30 mg). M⁻(LC/MS(ESI)): 497.3; M⁺(LC/MS(ESI)): 499.5. HPLC (Condition A), Rt: 6.2 min (HPLC purity: 79.1%).

Example 96

[{4-[(dodecylamino carbonyl]benzyl}(4-phenoxybenzyl)amino](oxo)acetic acid

The same procedure as employed in the preparation of Example 50 using dodecylamine in step a, Fmoc-(4-aminomethyl)-benzoic acid in step b and 4-phenoxybenzaldehyde in step d gave the title compound as a pale yellow oil (28 mg). M⁻(LC/MS(ESI)): 571.2; M⁺(LC/MS(ESI)): 573.4. HPLC (Condition A), Rt: 6.67 min (HPLC purity: 64.5%).

Example 97

4-[((carboxycarbonyl){4-[(dodecylamino)carbonyl]benzyl}amino)-methyl]-benzoic acid The same procedure as employed in the preparation of Example 50 using dodecylamine in step a, Fmoc-(4-aminomethyl)-benzoic acid in step b and methyl 4-formylbenzoate in step d gave the title compound as a white solid (28 mg). M⁻(LC/MS(ESI)): 523.2; M⁺(LC/MS(ESI)): 525.2. HPLC (Condition A), Rt: 5.49 min (HPLC purity: 62.9%).

Example 98

5-[((carboxycarbonyl){4-[(dodecylamino)carbonyl]benzyl}amino)methyl]-2-thiophenecarboxylic acid The same procedure as employed in the preparation of Example 50 using dodecylamine in step a, Fmoc-(4-aminomethyl)-benzoic acid in step b and 5-formyl-2-thiophenecarboxylic acid in step d gave the title compound as a pale yellow oil (28 mg). M⁻(LC/MS(ESI)): 529.2; M⁺(LC/MS(ESI)): 531.7. HPLC (Condition A), Rt: 5.37 min (HPLC purity: 58%).

Example 99

[{3-[(dodecylamino)carbonyl]benzyl}(2-thienylmethyl)amino](oxo)acetic acid

The same procedure as employed in the preparation of Example 50 using dodecylamine in step a, Fmoc-(3-aminomethyl)-benzoic acid in step b and 2-thiophenecarboxaldehyde in step d gave the title compound as a colorless oil (6.8 mg).

M⁻(LC/MS(ESI)): 485.4; M⁺(LC/MS(ESI)): 487.3. HPLC (Condition A), Rt: 6.11 min (HPLC purity: 97.6%).

Example 100

[{4-[(dodecylamino)carbonyl]benzyl}(isopropyl)amino](oxo)acetic acid

The same procedure as employed in the preparation of Example 50 using dodecylamine in step a, 4-chloromethylbenzoyl chloride in step b and isopropylamine in step d gave the title compound as a pale yellow oil (21 mg). M⁻(LC/MS(ESI)): 431.3; M⁺(LC/MS(ESI)): 433.3 HPLC (Condition A), Rt: 4.12 min (HPLC purity: 85.5%).

Example 101

((3,5-dichlorobenzyl){4-[(dodecylamino)carbonyl]benzyl}amino)(oxo)acetic acid

The same procedure as employed in the preparation of Example 50 using dodecylamine in step a, 4-chloromethylbenzoyl chloride in step b and 3,5-dichlorobenzylamine in step d gave the title compound as a pale yellow oil (24 mg). M⁻(LC/MS(ESI)): 547.2; M⁺(LC/MS(ESI)): 551.1. HPLC (Condition A), Rt: 6.61 min (HPLC purity: 82%).

Example 102

[(3,5-dichlorobenzyl)(4-{[(3,3-diphenylpropyl)amino]carbonyl}-benzyl)amino](oxo)acetic acid The same procedure as employed in the preparation of Example 50 using 3,3-diphenylpropylamine in step a, 4-chloromethylbenzoyl chloride in step b and 3,5-dichlorobenzylamine in step d gave the title compound as a pale yellow oil (22 mg). M⁻(LC/MS(ESI)): 573.0; M⁺(LC/MS(ESI)): 575.0. HPLC (Condition A), Rt: 5.13 min (HPLC purity: 81.2%).

Example 103

[(4-{[(2-[1,1'-biphenyl]-4-ylethyl)amino]carbonyl}benzyl)(3,5-dichlorobenzyl)amino](oxo)acetic acid The same procedure as employed in the preparation of Example 50 using 2-(4-biphenyl)ethylamine in step a, 4-chloromethylbenzoyl chloride in step b and 3,5-dichlorobenzylamine in step d gave the title compound as a pale yellow oil (21 mg). M⁻(LC/MS(ESI)): 559.6. HPLC (Condition A), Rt: 5.06 min (HPLC purity: 79.7%).

Example 104

[(1,3-benzodioxol-5-ylmethyl)(4-{[(2-[1,1'-biphenyl]-4-ylethyl)amino]-carbonyl}benzyl)amino](oxo)acetic acid The same procedure as employed in the preparation of Example 50 using 2-(4-biphenyl)-ethylamine in step a, 4-chloromethylbenzoyl chloride in step b and piperonylamine in step d gave the title compound as a pale yellow oil (23 mg). M⁻(LC/MS(ESI)): 535.1; M⁺(LC/MS(ESI)): 537.0. HPLC (Condition A), Rt: 4.46 min (HPLC purity: 79.1%).

Example 105

(2,3-dihydro-1H-inden-1-yl{4-[(dodecylamino)carbonyl]benzyl}-amino)-(oxo)acetic acid The same procedure as employed in the preparation of Example 50 using dodecylamine in step a, 4-chloromethylbenzoyl chloride in step b and 1-aminoindane in step d gave the title compound as a pale yellow oil (23 mg). M⁻(LC/MS(ESI)): 505.2; M⁺(LC/MS(ESI)): 507.7 HPLC (Condition A), Rt: 6.28 min (HPLC purity: 67.9%).

Example 106

{2,3-dihydro-1H-inden-1-yl[4-({[2-(4-phenoxyphenyl)ethyl]amino}-carbonyl)benzyl]amino}(oxo)acetic acid The same procedure as employed in the preparation of Example 50 using 4-phenoxyphenethylamine in step a, 4-chloromethylbenzoyl chloride in step b and 1-aminoindane in step d gave the title compound as a pale yellow oil (21 mg). M⁻(LC/MS(ESI)): 533.3; M⁺(LC/MS(ESI)): 535.0. HPLC (Condition A), Rt: 4.67 min (HPLC purity: 67.3%).

Example 107

[{4-[(dodecylamino)carbonyl]benzyl}(4-pyridinylmethyl)amino](oxo)acetic acid

The same procedure as employed in the preparation of Example 50 using dodecylamine in step a, Fmoc-(4-aminomethyl)-benzoic acid in step b and 4-pyridinecarboxaldehyde in step d gave a crude product which was purified by reverse phase HPLC chromatography (Condition C) affording the title compound as a white solid (5 mg). M⁻(LC/MS(ESI)): 480.3; M⁺(LC/MS(ESI)): 482.3. HPLC (Condition A), Rt: 4.35 min (HPLC purity: 93.7%).

Example 108

([4-(dimethylamino)benzyl]{4-[(dodecylamino)carbonyl]benzyl}amino)-(oxo)acetic acid The same procedure as employed in the preparation of Example 50 using dodecylamine in step a, Fmoc-(4-aminomethyl)-benzoic acid in step b and 4-dimethylaminobenzaldehyde in step d gave a crude product which was purified by reverse phase HPLC chromatography (Condition C) affording the title compound as a brown oil (2 mg). M⁻(LC/MS(ESI)): 522.3; M⁺(LC/MS(ESI)): 524.6. HPLC (Condition A), Rt: 4.57 min (HPLC purity: 80.5%).

Example 109

[{4-[(dodecylamino)carbonyl]benzyl}(3-pyridinylmethyl)amino](oxo)acetic acid

The same procedure as employed in the preparation of Example 50 using dodecylamine in step a, Fmoc-(4-aminomethyl)-benzoic acid in step b and 3-pyridinecarboxaldehyde in step d gave a crude product which was purified by reverse phase HPLC chromatography (Condition C) affording the title compound as a white solid (6 mg). M⁻(LC/MS(ESI)): 480.3; M⁺(LC/MS(ESI)): 482.5. HPLC (Condition A), Rt: 4.41 min (HPLC purity: 86.8%).

Example 110

((4-cyanobenzyl){4-[(dodecylamino)carbonyl]benzyl}amino)(oxo)acetic acid

The same procedure as employed in the preparation of Example 50 using dodecylamine in step a, Fmoc-(4-aminomethyl)-benzoic acid in step b and 4-cyanobenzaldehyde in step d gave a crude product which was purified by reverse phase HPLC chromatography (Condition C) affording the title compound as a yellow oil (6 mg). M⁻(LC/MS(ESI)): 504.4; M⁺(LC/MS(ESI)): 506.2. HPLC (Condition A), Rt: 5.85 min (HPLC purity: 87.3%).

Example 111

[{4-[(dodecylamino)carbonyl]benzyl}(1,3-thiazol-2-ylmethyl)amino](oxo)-acetic acid The same procedure as employed in the preparation of Example 50 using dodecylamine in step a, Fmoc-(4-aminomethyl)-benzoic acid in step b and 2-formylthiazole in step d gave a crude product which was purified by reverse phase HPLC chromatography (Condition C) affording the title compound as a yellow oil (4 mg). M⁻(APCI): 486.2; M⁺(APCI): 488.2 HPLC (Condition A), Rt: 5.48 min (HPLC purity: 85.4%).

Example 112

({4-[(dodecylamino)carbonyl]benzyl}{[2-(4-morpholinyl)-1,3-thiazol-5-yl]methyl}amino)(oxo)acetic acid The same procedure as employed in the preparation of Example 50 using dodecylamine in step a, Fmoc-(4-aminomethyl)-benzoic acid in step b and 2-morpholino-1,3-thiazole-5-carbaldehyde in step d gave a crude product which was purified by reverse phase HPLC chromatography (Condition C) affording the title compound as an orange oil (5 mg). M⁻(LC/MS(ESI)): 571.3; M⁺(LC/MS(ESI)): 573.4. HPLC (Condition A), Rt: 4.62 min (HPLC purity: 97.7%).

Example 113

[{3-[(dodecylamino)carbonyl]benzyl}(4 pyridinylmethyl)amino](oxo)acetic acid

The same procedure as employed in the preparation of Example 50 using dodecylamine in step a, Fmoc-(3-aminomethyl)-benzoic acid in step b and 4-pyridinecarboxaldehyde in step d gave a crude product which was purified by reverse phase HPLC chromatography (Condition C) affording the title compound as an orange oil (5 mg). M⁻(LC/MS(ESI)): 480.5; M⁺(LC/MS(ESI)): 482.3. HPLC (Condition A), Rt: 4.34 min (HPLC purity: 89.7%).

Example 114

[{3-[(dodecylamino)carbonyl]benzyl}(3-pyridinylmethyl)amino](oxo)acetic acid

The same procedure as employed in the preparation of Example 50 using dodecylamine in step a, Fmoc-(3-aminomethyl)-benzoic acid in step b and 3-pyridinecarboxaldehyde in step d gave a crude product which was purified by reverse phase HPLC chromatography (Condition C) affording the title compound as a yellow oil (7 mg). M⁻(LC/MS(ESI)): 480.4; M⁺(LC/MS(ESI)): 482.3. HPLC (Condition A), Rt: 4.36 min (HPLC purity: 89.7%).

Example 115

[{3-[(dodecylamino)carbonyl]benzyl}(3-hydroxybenzyl)amino](oxo)acetic acid

The same procedure as employed in the preparation of Example 50 using dodecylamine in step a, Fmoc-(3-aminomethyl)-benzoic acid in step b and 3-hydroxybenzaldehyde in step d gave a crude product which was purified by reverse phase HPLC chromatography (Condition C) affording the title compound as a yellow oil (4 mg). M⁻(LC/MS(ESI)): 495.4; M⁺(LC/MS(ESI)): 497.3. HPLC (Condition A), Rt: 5.58 min (HPLC purity: 82.5%).

Example 116

((4-cyanobenzyl){3-[(dodecylamino)carbonyl]benzyl}amino)(oxo)acetic acid

The same procedure as employed in the preparation of Example 50 using dodecylamine in step a, Fmoc-(3-aminomethyl)-benzoic acid in step b and 4-cyanobenzaldehyde in step d gave a crude product which was purified by reverse phase HPLC chromatography (Condition C) affording the title compound as an orange oil (5 mg). M⁻(LC/MS(ESI)): 504.3; M⁺(LC/MS(ESI)): 506.3. HPLC (Condition A), Rt: 5.86 min (HPLC purity: 97.5%).

Example 117

[{3-[(dodecylamino)carbonyl]benzyl}(1,3-thiazol-2-ylmethyl)amino](oxo)acetic acid The same procedure as employed in the preparation of Example 50 using dodecylamine in step a, Fmoc-(3-aminomethyl)-benzoic acid in step b and 2-formylthiazole in step d gave a crude product which was purified by reverse phase HPLC chromatography (Condition C) affording the title compound as a red oil (4 mg). M⁻(LC/MS(ESI)): 486; M⁺(LC/MS(ESI)): 488.5. HPLC (Condition A), Rt: 5.49 min (HPLC purity: 68.3%).

Example 118

({3-[(dodecylamino)carbonyl]benzyl}{[2-(4-morpholinyl)-1,3-thiazol-5-yl]methyl}amino)(oxo)acetic acid The same procedure as employed in the preparation of Example 50 using dodecylamine in step a, Fmoc-(3-aminomethyl)-benzoic acid in step b and 2-morpholino-1,3-thiazole-5-carbaldehyde in step d gave a crude product which was purified by reverse phase HPLC chromatography (Condition C) affording the title compound as an orange oil (4 mg). M⁻(LC/MS(ESI)): 571.4; M⁺(LC/MS(ESI)): 573.0. HPLC (Condition A), Rt: 4.59 min (HPLC purity: 96.3%).

Example 119

((1,3-benzodioxol-5-ylmethyl){3-[(dodecylamino)carbonyl]benzyl}amino)-(oxo)acetic acid The same procedure as employed in the preparation of Example 50 using dodecylamine in step a, Fmoc-(3-aminomethyl)-benzoic acid in step b and piperonal in step d gave a crude product which was purified by reverse phase HPLC chromatography (Condition C) affording the title compound as a white solid (6.3 mg). M⁻(LC/MS(ESI)): 523.3; M⁺(LC/MS(ESI)): 525.4. HPLC (Condition A), Rt: 6.07 min (HPLC purity: 97.4%).

Example 120

[{4-[(dodecylamino)carbonyl]benzyl}(2-thienylmethyl)amino](oxo)acetic acid

The same procedure as employed in the preparation of Example 50 using dodecylamine in step a, Fmoc-(4-aminomethyl)-benzoic acid in step b and 2-thiophenecarboxaldehyde in step d gave a crude product which was purified by reverse phase HPLC chromatography (Condition C) affording the title compound as a white powder (2.4 mg). M⁻(LC/MS (ESI)): 485.2; M⁺(LC/MS(ESI)): 487.4. HPLC (Condition A), Rt: 5.9 min (HPLC purity: 90.4%).

Example 121

[{4-[(dodecylamino)carbonyl]benzyl}(2-pyridinylmethyl)amino](oxo)acetic acid

The same procedure as employed in the preparation of Example 50 using dodecylamine in step a, Fmoc-(4-aminomethyl)-benzoic acid in step b and 2-pyridinecarboxaldehyde in step d gave a crude product which was purified by reverse phase HPLC chromatography (Condition C) affording the title compound as a white powder (5.0 mg). M⁻(LC/MS (ESI)): 480.5; M⁺(LC/MS(ESI)): 482.4. HPLC (Condition A), Rt: 4.66 min (HPLC purity: 96.3%).

Example 122

[{4-[(dodecylamino)carbonyl]benzyl}(3-thienylmethyl)amino](oxo)acetic acid

The same procedure as employed in the preparation of Example 50 using dodecylamine in step a, Fmoc-(4-aminomethyl)-benzoic acid in step b and 3-thiophenecarboxaldehyde in step d gave a crude product which was purified by reverse phase HPLC chromatography (Condition C) affording the title compound as a white powder (2.6 mg). M⁻(LC/MS (ESI)): 485.4; M⁺(LC/MS(ESI)): 487.4. HPLC (Condition A), Rt: 5.9 min (HPLC purity: 95%).

Example 123

[{4-[(dodecylamino)carbonyl]benzyl}(4-hydroxybenzyl)amino](oxo)acetic acid

The same procedure as employed in the preparation of Example 50 using dodecylamine in step a, Fmoc-(4-aminomethyl)-benzoic acid in step b and 4-hydroxybenzaldehyde in step d gave a crude product which was purified by reverse phase HPLC chromatography (Condition C) affording the title compound as a white powder (3.3 mg). M⁻(LC/MS (ESI)): 495.4; M⁺(LC/MS(ESI)): 497.3. HPLC (Condition A), Rt: 5.47 min (HPLC purity: 95.3%).

Example 124

3-[(((carboxycarbonyl){4-[(dodecylamino)carbonyl]benzyl}amino)-methyl]benzoic acid The same procedure as employed in the preparation of Example 50 using dodecylamine in step a, Fmoc-(4-aminomethyl)-benzoic acid in step b and 3-carboxybenzaldehyde in step d gave a crude product which was purified by reverse phase HPLC chromatography (Condition C) affording the title compound as a colorless oil (5.7 mg). M⁻(LC/MS(ESI)): 523.2; M⁺(LC/MS(ESI)): 525.4. HPLC (Condition A), Rt: 5.43 min (HPLC purity: 95.5%).

Example 125

[benzyl({5-[(dodecylamino)sulfonyl]-2-thienyl}methyl)amino](oxo)acetic acid

Step a) Formation of the Resin-Bound Amines of Formula (D) (See Scheme 5), e.g. the Resin-Bound Dodecylamine The same procedure as employed in the preparation of Example 28, step a, gave the title compound which was used directly in the next step.

Step b) Formation of the Resin-Bound Protected Amines of Formula (VII-1) (See Scheme 5, Method L), e.g. the Resin-Bound 5-[(1,3-dioxo-1,3-dihydro-2H-isoindol-2-yl)methyl]-N-dodecyl-thiophene-2-sulfonamide The resin-bound dodecylamine (described in step a, 0.0426 mmol) was swelled in DCM (1.0 mL) for 15 min at rt. DIEA (33 mg, 0.256 mmol) and 5-[(1,3-dioxo-1,3-dihydro-2H-isoindol-2-yl)methyl]thiophene-2-sulfonyl chloride (44 mg, 0.128 mmol) were added and the resulting reaction mixture was shaken 14 h at rt. The resin was washed successively with NMP (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with Et₂O (1×10 min). The resin was then dried under vacuum to afford the title compound which was used directly in the next step.

Step c) Phtalimide-Deprotection of the Resin-Bound Protected Amines of Formula (VII-1) (See Scheme 5); e.g. Formation of the Resin-Bound 5-(aminomethyl)-N-dodecylthiophene-2-sulfonamide The resin-bound 5-[(1,3-dioxo-1,3-dihydro-2H-isoindol-2-yl)methyl]-N-dodecylthiophene-2-sulfonamide (described in step b, 0.0426 mmol) was treated with a 60% solution (v/v) hydrazine monohydrate in DMF (1.15 mL) and shaken 14 h at rt. The resin was washed successively with DMF (1×15 min), MeOH (1×15 min), MeOH (3×10 min), DMF (3×10 min), MeOH (1×5 min), THF (3×10 min), MeOH (1×5 min), DCM (3×10 min) and with Et₂O (1×10 min). The resin was then dried under vacuum to afford the title compound which was used directly in the next step.

Step d) Formation of the Resin-Bound Secondary Amines of Formula (III-1) (See Scheme 5, Method L), e.g. the Resin-Bound 5-[(benzylamino)methyl]-N-dodecylthiophene-2-sulfonamide The same procedure as employed in the preparation of Example 50, step d, using benzaldehyde and the resin-bound 5-(aminomethyl)-N-dodecylthiophene-2-sulfonamide (described in step c, 0.0426 mmol) gave the title compound which was used directly in the next step.

Step e) Formation of the Resin-Bound Oxamic Ester of Formula (I-1) (See Scheme 1), e.g. Resin-Bound ethyl[benzyl({5-[(dodecylamino)sulfonyl]thien-2-yl}methyl)amino]-(oxo)acetate The same procedure as employed in the preparation of Example 28, step d, but using the resin-bound 5-[(benzylamino)methyl]-N-dodecylthiophene-2-sulfonamide (described in step d, 0.0426 mmol) gave the title compound which was used directly in the next step.

Step f) Formation of the Resin-Bound Oxamic Acid of Formula (I-1) (See Scheme 1), e.g. Resin-Bound [benzyl({5-[(dodecylamino)sulfonyl]-2-thienyl}methyl)amino](oxo)acetic acid The same procedure as employed in the preparation of Example 28, step e, but using the resin-bound ethyl[benzyl ({5-[(dodecylamino)sulfonyl]thien-2-yl}methyl)amino] (oxo)-acetate (described in step e, 0.0426 mmol) gave the title compound which was used directly in the next step.

Step g) Cleavage of the Resin-Bound Oxamic Acid of Formula (I-1); Formation of the Oxamic Acid of Formula (I) (See Scheme 1), e.g. [benzyl({5-[(dodecylamino)sulfonyl]-2-thienyl}-methyl)amino](oxo) acetic acid The same procedure as employed in the preparation of Example 28, step f, but using the resin-bound [benzyl({5-[(dodecylamino)sulfonyl]-2-thienyl}methyl)amino](oxo) acetic acid (described in step f, 0.0426 mmol) gave the title compound as a white gum (20 mg). M$^-$(LC/MS(ESI)): 521.2; M$^+$(LC/MS(ESI)): 523.0. HPLC (Condition A), Rt: 6.17 min (HPLC purity: 86.2%).

Example 126

[cyclopentyl({5-[(dodecylamino)sulfonyl]-2-thienyl}methyl)amino](oxo)acetic acid Step a) Formation of the Resin-Bound 5-[(cyclopentylamino)methyl]-N-dodecylthiophene-2-sulfonamide The resin-bound 5-(aminomethyl)-N-dodecylthiophene-2-sulfonamide (example 125, step c, 0.23 mmol) was swelled in a 1% HAc in DMF mixture for 15 min at rt Cyclopentanone (97 mg, 1.15 mmol) and sodium cyanoborohydride (144 mg, 2.3 mmol) were then added and the reaction mixture shaken 14 h at rt. The resin was washed successively with DMF (1×15 min), MeOH (1×15 min), THF (1×15 min), MeOH (3×10 min), DMF (3×10 min), MeOH (1×5 min), THF (3×10 min), MeOH (1×5 min), DCM (3×10 min) and with Et$_2$O (1×10 min). The resin was then dried under vacuum to afford the title compound which was used directly in the next step.

Step b) Formation of the Resin-Bound ethyl[cyclopentyl({5-[(dodecylamino)sulfonyl]thien-2-yl}methyl)amino](oxo)acetate The same procedure as employed in the preparation of Example 28, step d but using resin-bound 5-[(cyclopentylamino)methyl]-N-dodecylthiophene-2-sulfonamide gave the title compound which was used directly in the next step.

Step c) Cleavage of the Resin-Bound ethyl[cyclopentyl({5-[(dodecylamino)sulfonyl]thien-2-yl}methyl) amino](oxo)acetate; formation of the ethyl[cyclopentyl({5-[(dodecylamino)sulfonyl]thien-2-yl}methyl) amino](oxo)acetate The same procedure as employed in the preparation of Example 28, step f but using resin-bound ethyl[cyclopentyl ({5-[(dodecylamino)sulfonyl]thien-2-yl}methyl)amino] (oxo)acetate gave a yellow oil. This crude product was purified by column chromatography over silica gel to give the title compound (11 mg, 10%). M$^-$(LC/MS(ESI)): 527.2; M$^+$(LC/MS(ESI)): 529.4. HPLC (Condition A), Rt: 6.94 min (HPLC purity: 91.0%).

Step d) Formation of [cyclopentyl({5-[(dodecylamino)sulfonyl]-2-thienyl}methyl)amino](oxo)acetic acid The same procedure as employed in the preparation of Example 1, step e but using ethyl[cyclopentyl({5-[(dodecylamino)sulfonyl]thien-2-yl}methyl)amino](oxo)acetate gave the title compound as a colorless foam (96%). $^1$H NMR (CD$_3$OD, 300 MHz) δ 7.25 (m, 1H), 7.0 (m, 1H), 4.64 (s, 1H), 4.30 (m, 1H), 2.76 (t, 2H, J=7.3 Hz), 1.81 (m, 2H), 1.79-1.41 (m, 8H), 1.29 (m, 19H), 0.91 (t, 3H, J=6.8 Hz). M$^-$(LC/MS (ESI)): 499.2; M$^+$(LC/MS(ESI)): 501.2. HPLC (Condition A), Rt: 6.09 min (HPLC purity: 78.7%).

Example 127

(({5-[(dodecylamino)sulfonyl]-2-thienyl}methyl){3-[hydroxy(oxido)-amino]benzyl}amino)(oxo)acetic acid The same procedure as employed in the preparation of Example 125 using dodecylamine in step a and 3-nitrobenzaldehyde in step d gave the title compound as an orange oil (29 mg). M$^-$(LC/MS(ESI)): 566.3; M$^+$(LC/MS(ESI)): 568.2. HPLC (Condition A), Rt: 6.23 min (HPLC purity: 61.7%).

Example 128

[({5-[(dodecylamino)sulfonyl]-2-thienyl}methyl)(4-methoxybenzyl)amino]-(oxo)acetic acid The same procedure as employed in the preparation of Example 125 using dodecylamine in step a and p-anisaldehyde in step d gave the title compound as a yellow oil (27 mg). M$^-$(LC/MS(ESI)): 551.2; M$^+$(LC/MS(ESI)): 553.4. HPLC (Condition A), Rt: 6.26 min (HPLC purity: 73.3%).

Example 129

[({5-[(dodecylamino)sulfonyl]-2-thienyl}methyl)(2-fluorobenzyl)amino]-(oxo)acetic acid The same procedure as employed in the preparation of Example 125 using dodecylamine in step a and 2-fluorobenzaldehyde in step d gave the title compound as a yellow solid (28 mg). M$^-$(LC/MS(ESI)): 539.1; M$^+$(LC/MS(ESI)): 541.2. HPLC (Condition A), Rt: 6.33 min (HPLC purity: 70%).

Example 130

{({5-[(dodecylamino)sulfonyl]-2-thienyl}methyl)[4-(methylsulfonyl)-benzyl]amino}(oxo)acetic acid The same procedure as employed in the preparation of Example 125 using dodecylamine in step a and 4-(methylsulfonyl)benzaldehyde in step d gave the title compound as a yellow oil (36 mg). M$^-$(LC/MS(ESI)): 599.2; M$^+$(LC/MS (ESI)): 601.3. HPLC (Condition A), Rt: 5.81 min (HPLC purity: 69.4%).

Example 131

[({5-[(dodecylamino)sulfonyl]-2-thienyl}methyl)(4-phenoxybenzyl)amino](oxo)acetic acid The same procedure as employed in the preparation of Example 125 using dodecylamine in step a and 4-phenoxybenzaldehyde in step d gave the title compound as a yellow oil (33 mg). M$^-$(LC/MS(ESI)): 613.2; M$^+$(LC/MS(ESI)): 615.0. HPLC (Condition A), Rt: 6.78 min (HPLC purity: 68.5%).

Example 132

4-{[(carboxycarbonyl)({5-[(dodecylamino)sulfonyl]-2-thienyl}methyl)-amino]methyl}benzoic acid The same procedure as employed in the preparation of Example 125 using dodecylamine in step a and methyl 4-formylbenzoate in step d gave the title compound as a yellow oil (5 mg). M⁻(LC/MS(ESI)): 565.3; M⁺(LC/MS (ESI)): 567.3. HPLC (Condition A), Rt: 5.43 min (HPLC purity: 99.9%).

Example 133

((({5-[(dodecylamino sulfonyl]-2-thienyl}methyl){[6-(trifluoromethyl)-3-pyridinyl]methyl}amino)(oxo) acetic acid The same procedure as employed in the preparation of Example 125 using dodecylamine in step a and 6-(trifluoromethyl)pyridine-3-carboxaldehyde in step d gave the title compound as an orange oil (30 mg). M⁻(LC/MS(ESI)): 590.3; M⁺(LC/MS(ESI)): 592.2. HPLC (Condition A), Rt: 6.25 min (HPLC purity: 61.7%).

Example 134

{({5-[(dodecylamino)sulfonyl]-2-thienyl}methyl)[3-(trifluoromethyl)- benzyl]amino}(oxo)acetic acid The same procedure as employed in the preparation of Example 125 using dodecylamine in step a and 3-(trifluoromethyl)benzaldehyde in step d gave the title compound as a yellow oil (19 mg). M⁻(LC/MS(ESI)): 589.3; M⁺(LC/MS (ESI)): 591.3. HPLC (Condition A), Rt: 6.43 min (HPLC purity: 81.5%).

Example 135

[(3-chlorobenzyl)({5-[(dodecylamino)sulfonyl]-2-thienyl}methyl)amino]-(oxo)acetic acid The same procedure as employed in the preparation of Example 125 using dodecylamine in step a and 3-chlorobenzaldehyde in step d gave the title compound as a yellow oil (21 mg). M⁻(LC/MS(ESI)): 556; M⁺(LC/MS(ESI)): 558. HPLC (Condition A), Rt: 6.32 min (HPLC purity: 81.9%).

Example 136

{[(5-{[(3,3-diphenylpropyl)amino]sulfonyl}-2-thienyl)methyl][3-(trifluoromethyl)benzyl]amino}(oxo) acetic acid The same procedure as employed in the preparation of Example 125 using 3,3-diphenylpropylamine in step a and 3-(trifluoromethyl)benzaldehyde in step d gave the title compound as a yellow oil (17 mg). M⁻(LC/MS(ESI)): 615.3; M⁺(LC/MS(ESI)): 617.3. HPLC (Condition A), Rt: 5.12 min (HPLC purity: 75.7%).

Example 137

{(3-chlorobenzyl)[(5-{[(3,3-diphenylpropyl)amino] sulfonyl}-2-thienyl)-methyl]amino}(oxo)acetic acid The same procedure as employed in the preparation of Example 125 using 3,3-diphenylpropylamine in step a and 3-chlorobenzaldehyde in step d gave the title compound as a yellow oil (15 mg). M⁻(LC/MS(ESI)): 582.5; M⁺(LC/MS (ESI)): 585.1. HPLC (Condition A), Rt: 5.01 min (HPLC purity: 72.1%).

Example 138 oxo{{[5-({[2-(4-phenoxyphenol)ethyl] amino}sulfonyl)-2-thienyl]methyl}[3-(trifluoromethyl)benzyl]amino}acetic acid The same procedure as employed in the preparation of Example 125 using 4-phenoxyphenethylamine in step a and 3-(trifluoromethyl)benzaldehyde in step d gave the title compound as a yellow oil (22 mg). M⁻(LC/MS(ESI)): 617.0; M⁺(LC/MS(ESI)): 619.0. HPLC (Condition A), Rt: 5.15 min (HPLC purity: 77.1%).

Example 139

((3-chlorobenzyl){[5-({[2-(4-phenoxyphenyl)ethyl] amino}sulfonyl)-2-thienyl]methyl}amino)(oxo)acetic acid The same procedure as employed in the preparation of Example 125 using 4-phenoxyphenethylamine in step a and 3-chlorobenzaldehyde in step d gave the title compound as a yellow oil (20 mg). M⁻(LC/MS(ESI)): 584; M⁺(LC/MS (ESI)): 586. HPLC (Condition A), Rt: 5.0 min (HPLC purity: 79%).

Example 140

{[(5-{[(2-[1,1'-biphenyl]-4-ylethyl)amino]sulfonyl}-2-thienyl)methyl][3-(trifluoromethyl)benzyl]amino} (oxo)acetic acid The same procedure as employed in the preparation of Example 125 using 2-(4-biphenyl)-ethylamine in step a and 3-(trifluoromethyl)benzaldehyde in step d gave the title compound as a yellow oil (20 mg). M⁻(LC/MS(ESI)): 601.2; M⁺(LC/MS(ESI)): 603.0. HPLC (Condition A), Rt: 5.13 min (HPLC purity: 71.4%).

Example 141

((({1-[(cyclohexylamino)carbonyl]-4-piperidinyl}methyl){4-[(dodecylamino)carbonyl] benzyl}amino)(oxo)acetic acid Step a) Formation of tert-butyl 4-[({4-[(benzyloxy) carbonyl]benzyl}amino)methyl]-piperidine-1-carboxylate The same procedure as employed in the preparation of Example 1, step a but using 4-(aminomethyl)-1-Boc-piperidine gave the title compound as a white solid (8.045 g, 63%). ¹H NMR(CDCl₃, 300 MHz) δ 8.02 (d, 2H, J=8.3 Hz), 7.45-7.30 (m, 7H), 5.35 (s, 2H), 4.10 (m, 2H), 3.83 (s, 2H), 2.67 (t, 2H, J=12.3 Hz), 2.48 (d, 2H, J=6.5 Hz), 1.70 (d, 2H, J=13.4 Hz), 1.59 (m, 1H), 1.43 (s, 9H), 1.16-1.02 (m, 2H). M⁺(LC/MS (ESI)): 439.6. HPLC (Condition A), Rt: 3.66 min (HPLC purity: 91.9%).

Step b) Formation of tert-butyl 4-({{4-[(benzyloxy) carbonyl]benzyl}[ethoxy(oxo)acetyl]-amino}methyl) piperidine-1-carboxylate The same procedure as employed in the preparation of Example 1, step b but using tert-butyl 4-[({4-[(benzyloxy) carbonyl]benzyl}amino)methyl]piperidine-1-carboxylate gave the title compound as a yellow foam (8.50 g, 87%). $^1$H NMR (CDCl$_3$, 300 MHz) δ 8.05 (m, 2H), 7.46-7.29 (m, 7H), 5.35 (br s, 2H), 4.67 (s, 1H), 4.52 (s, 1H), 4.39-4.25 (m, 2H), 4.10 (m, 2H), 3.08 (d, 1H, J=7.1 Hz), 2.61 (m, 2H), 1.90-1.65 (m, 1H), 1.57 (m, 2H), 1.43 (s, 9H), 1.36 (t, 2H, J=7.1 Hz), 1.20-1.02 (m, 2H). M$^-$(LC/MS (ESI)): 537.8; M$^+$(LC/MS (ESI)): 539.5. HPLC (Condition A), Rt: 5.68 min (HPLC purity: 98.4%).

Step c) Deprotection of tert-butyl 4-({{4-[(benzy-loxy)carbonyl]benzyl}-[ethoxy(oxo) acetyl] amino}methyl)piperidine-1-carboxylate; formation of 4-({{[1-(tert-butoxycarbonyl)piperidin-4-yl]me-thyl}[ethoxy(oxo)acetyl]-amino}methyl)benzoic acid The same procedure as employed in the preparation of Example 1, step c but using tert-butyl 4-({{4-[(benzyloxy) carbonyl]benzyl}[ethoxy(oxo)acetyl]amino}methyl)piperi-dine-1-carboxylate gave the title compound as a white foam (6.80 g, 96%). $^1$H NMR (CDCl$_3$, 300 MHz) δ 8.10 (m, 2H), 7.37 (m, 2H), 4.70 (s, 1H), 4.55 (s, 1H), 4.40-4.20 (m, 2H), 4.09 (m, 2H), 3.40-3.10 (m, 2H), 3.62 (m, 2H), 1.90-1.68 (m, 1H), 1.59 (m, 2H), 1.43 (s, 9H), 1.30-1.00 (m, 5H). M$^-$(APCI): 447.0. HPLC (Condition A), Rt: 4.31 min (HPLC purity: 98.4%).

Step d) Formation of 4-{[[ethoxy(oxo)acetyl](piperi-din-4-ylmethyl)amino]methyl}benzoic acid To a solution of 4-({{[1-(tert-butoxycarbonyl)piperidin-4-yl]methyl}[ethoxy(oxo)acetyl]-amino}methyl)benzoic acid (5.80 g, 12.93 mmol) in DCM (150 mL) was added TFA (9.90 mL) and the resulting reaction mixture was stirred at rt for 3 h, evaporated under vacuum to give the title compound as a pink oil (7.93 g, 99.9%). $^1$H NMR (DMSO-d$_6$, 300 MHz) δ 8.7 (m, 1H), 8.39 (m, 1H), 7.96 (d, 1H, J=8.3 Hz), 7.94 (d, 1H, J=8.3 Hz), 7.39 (d, 1H, J=8.3 Hz), 7.37 (d, 1H, J=8.3 Hz), 4.64 (s, 1H), 4.58 (s, 1H), 4.33 (q, 0.9H, J=7.2 Hz), 4.23 (q, 1.1H, J=7.2 Hz), 3.33-3.22 (m, 2H), 3.18 (d, 1H, J=7.6 Hz), 3.10 (d, 1H, J=7.2 Hz), 2.90-2.69 (m, 2H), 1.98 (m, 1H), 1.40-1.21 (m, 3H), 1.16 (t, 2H, J=7.1 Hz). HPLC (Condition A), Rt: 1.87 min (HPLC purity 98.9%).

Step e) Formation of 4-{[[ethoxy(oxo)acetyl]({1-[(9H-fluoren-9-ylmethoxy)carbonyl]piperidin-4-yl}methyl)amino]methyl}benzoic acid To a solution of 4-{[[ethoxy(oxo)acetyl](piperidin-4-ylm-ethyl)amino]methyl}benzoic acid (7.650 g, 16.54 mmol) in dioxane/H$_2$O (1/1) (120 mL) was added Fmoc-OSu (6.697 g, 19.85 mmol) and a 1 M aqueous solution of NaHCO$_3$ (10 mL). The resulting reaction mixture was stirred for 1.25 h, then concentrated under vacuum. The oily residue dissolved in DCM (120 mL) was washed with a 1 N aqueous solution until pH 1, dried over MgSO$_4$, filtered and the solvents were evaporated under vacuum. This crude product was purified by column chromatography over silica gel (AcOEt/c-Hex 1/4 to 1/1 in about 1 h) to give the title compound as a white powder (3.755 g, 40%). $^1$H NMR (CDCl$_3$, 300 MHz) δ 8.1 (m, 2H), 7.75 (d, 2H, J=7.6 Hz), 7.55 (d, 2H, J=7.2 Hz), 7.38 (m, 4H), 7.29 (t, 2H, J=7.3 Hz), 4.70 (s, 1H), 4.56 (s, 1H), 4.45-4.07 (m, 7H), 3.0 (m, 2H), 2.45 (m, 2H), 1.7-1.5 (m, 1H), 1.40 (m, 2H), 1.38 (t, 1H, J=7.0 Hz), 1.31-1.21 (m, 3H), 1.0-0.8 (m, 2H). M$^-$(LC/MS (ESI)): 569.4; M$^+$(LC/MS (ESI)): 571.8. HPLC (Condition A), Rt: 4.83 min (HPLC purity: 99.3%).

Step f) Formation of the Resin-Bound Dodecylamine

The same procedure as employed in the preparation of Example 28, step a, gave the title compound which was used directly in the next step.

Step g) Formation of the Resin-Bound 9H-fluoren-9-ylmethyl 4-({{4-[(dodecylamino) carbonyl]benzyl} [ethoxy(oxo)acetyl]amino}methyl)piperidine-1-car-boxylate The same procedure as employed in the preparation of Example 50, step b using 4-{[[ethoxy(oxo)acetyl]({1-[(9H-fluoren-9-ylmethoxy)carbonyl]piperidin-4-yl}methyl)-amino]methyl}benzoic acid and the resin-bound dodecy-lamine gave the title compound.

Step h) Formation of the Resin-Bound ethyl[{4-[(dodecylamino)carbonyl]benzyl}(piperidin-4-ylm-ethyl)amino](oxo)acetate The same procedure as employed in the preparation of Example 50, step c using the resin-bound 9H-fluoren-9-ylm-ethyl 4-({{4-[(dodecylamino)carbonyl]benzyl}[ethoxy (oxo)-acetyl]amino}methyl)piperidine-1-carboxylate gave the title compound which was used directly in the next step.

Step i) Formation of the Resin-Bound ethyl(({1-[(cyclohexylamino)carbonyl]piperidin-4-yl}methyl) {4-[(dodecylamino)carbonyl]benzyl}amino)(oxo) acetate The resin-bound ethyl[{4-[(dodecylamino)carbonyl]ben-zyl}(piperidin-4-ylmethyl)amino]-(oxo)acetate (described in step h, 0.0426 mmol) was swelled in THF (0.5 mL) for 15 min at rt. Cyclohexyl isocyanate (18 mg, 0.143 mmol) dis-solved in THF (0.9 mL) and TEA (29 mg, 0.282 mmol) was added and the reaction mixture was shaken 14 h at rt. The resin was washed successively with THF (1×0.15 min), MeOH (1×15 min), THF (1×15 min), MeOH (3×10 min), DMF (3×10 min), MeOH (1×5 min), THF (3×10 min), MeOH (1×5 min), DCM (3×10 min) and with Et$_2$O (1×10 min). The resin was then dried under vacuum to afford the title com-pound which was used directly in the next step.

Step j) Formation of the Resin-Bound ((({J-[(cyclo-hexylamino)carbonyl]-4-piperidinyl}-methyl){4-[(dodecylamino)carbonyl]benzyl}amino)(oxo)acetic acid The same procedure as employed in the preparation of Example 28, step e, but using the resin-bound ethyl(({1-[(cyclohexylamino)carbonyl]piperidin-4-yl}methyl){4-[(dodecylamino)carbonyl]benzyl}amino)(oxo)acetate (de-scribed in step i, 0.0426 mmol) gave the title compound which was used directly in the next step.

Step k) Formation of the (({1-[(cyclohexylamino) carbonyl]-4-piperidinyl}methyl){4-[(dodecylamino) carbonyl]benzyl}amino)(oxo)acetic acid The same procedure as employed in the preparation of Example 28, step f, but using the resin-bound (({1-[(cyclo-hexylamino)carbonyl]-4-piperidinyl}methyl){4-[(dodecy-lamino)carbonyl]benzyl}amino)(oxo)acetic acid (described in step j, 0.0426 mmol) gave the title compound as a white solid (23 mg). M$^-$(ESI): 611.4; M$^+$(ESI): 613.4. HPLC (Con-dition A), Rt: 5.9 min (HPLC purity: 93.1%).

Example 142

([(1-{[4-(dimethylamino)anilino]carbonyl}-4-piperidinyl)methyl]{4-[(dodecylamino)carbonyl]benzyl}amino)(oxo)acetic acid The same procedure as employed in the preparation of Example 141 using dodecylamine in step f and 4-(dimethylamino)phenyl isocyanate in step i gave the title compound as a brown oil (17 mg). M$^+$(ESI): 648.2; M$^+$(ESI): 650.4. HPLC (Condition A), Rt: 4.49 min (HPLC purity: 95.9%).

Example 143

{{4-[(dodecylamino)carbonyl]benzyl}[(1-hexanoyl-4-piperidinyl)-methyl]amino}(oxo)acetic acid The same procedure as employed in the preparation of Example 141 using dodecylamine in step f and hexanoyl chloride in step i gave the title compound as a yellow oil (17 mg). M$^-$(ESI): 584.4; M$^+$(ESI): 586.4. HPLC (Condition A), Rt: 6.06 min (HPLC purity: 83.3%).

Example 144

({4-[(dodecylamino)carbonyl]benzyl}{[1-(3-iodobenzoyl)-4-piperidinyl]-methyl}amino)(oxo)acetic acid The same procedure as employed in the preparation of Example 141 using dodecylamine in step f and 3-iodobenzoyl chloride in step i gave the title compound as a brown solid (14 mg). M$^-$(ESI): 716.2. HPLC (Condition A), Rt: 6.12 min (HPLC purity: 90.8%).

Example 145

{{4-[(dodecylamino)carbonyl]benzyl}[(1-{(2E)-3-[3-(trifluoromethyl)-phenyl]-2-propenoyl}-4-piperidinyl)methyl]amino}(oxo)acetic acid The same procedure as employed in the preparation of Example 141 using, dodecylamine in step f and trans-3-(trifluoromethyl)cinnamoyl chloride in step i gave the title compound as a white foam (19 mg). M$^-$(ESI): 684.2; M$^+$(ESI): 686.4. HPLC (Condition A), Rt: 6.28 min (HPLC purity: 95%).

Example 146

({4-[(dodecylamino)carbonyl]benzyl}{[1-(2-guinoxalinylcarbonyl)-4-piperidinyl]methyl}amino)(oxo)acetic acid The same procedure as employed in the preparation of Example 141 using dodecylamine in step f and 2-quinoxaloyl chloride in step i gave the title compound as a brown oil (18 mg). M$^-$(ESI): 642.4. HPLC (Condition A), Rt: 5.74 min (HPLC purity: 88.1%).

Example 147

[({1-[(4-methoxyphenyl)sulfonyl]-4-piperidinyl}methyl)(4-{[(4-phenoxybenzyl)amino]carbonyl}benzyl)amino](oxo)acetic acid The same procedure as employed in the preparation of Example 141 using 4-phenoxybenzylamine in step f and 4-methoxybenzenesulfonyl chloride in step i gave the title compound as a brown foam (33 mg). M$^-$(LC/MS(ESI)): 670.8; M$^+$(LC/MS(ESI)): 672.0. HPLC (Condition A), Rt: 4.67 min (HPLC purity: 92.6%).

Example 148

[{[1-(3-iodobenzoyl)-4-piperidinyl]methyl}(4-{[(4-phenoxybenzyl)-amino]carbonyl}benzyl)amino](oxo)acetic acid The same procedure as employed in the preparation of Example 141 using 4-phenoxybenzyl-amine in step f and 3-iodobenzoyl chloride in step i gave the title compound as a brown oil (35 mg). M$^-$(LC/MS(ESI)): 730.7; M$^+$(LC/MS(ESI)): 732.4. HPLC (Condition A), Rt: 4.68 min (HPLC purity: 90.9%).

Example 149 oxo{(4-{[(4-phenoxybenzyl)amino]carbonyl}benzyl)[(1-{(2E)-3-[3-(trifluoromethyl)phenyl]-2-propenoyl}-4-piperidinyl)methyl]amino}acetic acid The same procedure as employed in the preparation of Example 141 using phenoxybenzylamine in step f and trans-3-(trifluoromethyl)cinnamoyl chloride in step i gave the title compound as a brown foam (33 mg). M$^-$(LC/MS(ESI)): 698; M$^+$(LC/MS(ESI)): 700.0. HPLC (Condition A), Rt: 4.95 min (HPLC purity: 89.3%).

Example 150

{{4-[(dodecylamino)carbonyl]phenyl}[2-(methoxycarbonyl)benzyl]-amino}(oxo)acetic acid Step a) Preparation of N-dodecyl-4-nitrobenzamide At 0° C., to a solution of 4-nitro-benzoyl chloride (12.664 g, 68.25 mmol) and DIEA (9.7 g, 75.05 mmol) in anhydrous DCM (200 mL) was added dropwise a solution of dodecylamine (12.650 g, 68.25 mmol in 50 mL of DCM). The reaction mixture was stirred at 0° C. for 30 min, then 1.5 h at rt. The solvents were evaporated and the residue dissolved in boiling AcOEt, washed with water, a 10% aqueous solution of HCl, water, dried over MgSO$_4$ and filtered. The solvents were evaporated to give a yellow solid (23.02 g). This residue was washed twice with diethylether (50 mL) to give after evaporation of the solvent the title compound as a pale yellow powder (20.31 g, 89%). $^1$H NMR (DMSO-d$_6$, 300 MHz) δ 8.77 (t, 1H, J=5.5 Hz), 8.30 (d, 2H, J=9.0 Hz), 8.04 (d, 2H, J=9.0 Hz), 3.25 (q, 2H, J=6.3 Hz), 1.43-1.58 (m, 2H), 1.12-1.35 (m, 18H), 0.83 (t, 3H, J=6.7 Hz). HPLC (Condition A), Rt: 6.55 min (HPLC purity: 93.2%).

Step b) Preparation of 4-amino-N-dodecylbenzamide

The same procedure as employed in the preparation of Example 1 (step c) using N-dodecyl-4-nitrobenzamide and hydrogen at a pressure of 20 bar at 50° C. gave the title compound (98%). $^1$H NMR (DMSO-d$_6$, 300 MHz) δ 7.93 (t, 1H, J=5.6 Hz), 7.53 (d, 2H, J=8.7 Hz), 6.50 (d, 2H, J=8.7 Hz), 8.30 (s, 2H), 3.16 (m, 2H), 1.36-1.52 (m, 2H), 1.12-1.33 (m, 18H), 0.83 (t, 3H, J=6.7 Hz). HPLC (Condition A), Rt: 4.87 min (HPLC purity 99.7%).

Step c) Preparation of methyl 2-[({4-[(dodecylamino)carbonyl]phenyl}amino)methyl]-benzoate To a solution of 4-amino-N-dodecylbenzamide (0.304 g, 1.0 mmol), acetic acid (0.060 g, 1.0 mmol) and methyl 2-formylbenzoate (0.164 g, 1.0 mmol) in ethanol (2 mL) was added at once NaBH$_3$CN (0.075 g, 1.20 mmol). The resulting mixture was stirred overnight at rt. A saturated solution of NaHCO$_3$ (10 mL) was added to the reaction mixture, the aqueous layer was separated and extracted with DCM. The combined organic layers were dried over MgSO$_4$, filtered and concentrated to give a colorless oil. This crude product was purified by column chromatography over silica gel to give the title compound as a colorless oil (0.212 g, 47%). M$^+$(LC/MS (ESI)): 453.6. HPLC (Condition A), Rt: 6.64 min (HPLC purity: 100%).

Step d) Preparation of methyl 2-({{4-[(dodecylamino)carbonyl]phenyl}[ethoxy(oxo)acetyl]amino}methyl)benzoate The same procedure as employed for the preparation of Example 1 (step b) using methyl 2-[({4-[(dodecylamino)carbonyl]phenyl}amino)methyl]benzoate amine gave the title compound as a yellow oil (74%). M$^+$(LC/MS(ESI)): 553.3; M$^-$(LC/MS(ESI)): 552.0. HPLC (Condition A), Rt: 6.77 min (HPLC purity: 98.9%).

Step e) Preparation of {{4-[(dodecylamino)carbonyl]phenyl}[2-(methoxycarbonyl)benzyl]-amino}(oxo)acetic acid The same procedure as employed in the preparation of Example 1 (step e) using methyl 2-({{4-[(dodecylamino)carbonyl]phenyl}[ethoxy(oxo)acetyl]amino}methyl)benzoate gave the title compound as a colorless oil (91%). M$^-$(LC/MS(ESI)): 527.0; M$^+$(LC/MS(ESI)): 529.0. HPLC (Condition A), Rt: 6.50 min (HPLC purity: 84.2%).

Example 151

[[4-({[2-(1,1'-biphenyl-4-yl)ethyl]amino}carbonyl)-2-bromobenzyl](4-iodobenzyl)amino](oxo)acetic acid

Step a) Preparation of methyl-3-bromo-4-methylbenzoate

A mixture of 3-bromo-4-methylbenzoic acid (40 g, 0.186 mol) and SOCl$_2$ (88 g, 0.74 mol) in methanol (600 mL) was refluxed for 12 h. The solvent was distilled off and the crude residue was diluted with ethyl acetate (50 mL). The ethyl acetate layer was washed with 10% NaHCO$_3$ solution, water, brine and dried. The solvent was removed under vacuum to give methyl-3-bromo-4-methylbenzoate (40 g, 95%) as a solid.

Step b) Preparation of 2-bromo-4-methoxycarbonyl benzylbromide

A mixture of methyl-3-bromo-4-methylbenzoate (40 g, 0.17 mol), NBS (34 g, 0.19 mol) and benzoylperoxide (4.0 g) in CCl$_4$ (500 mL) was refluxed for 6 h. The reaction mixture was cooled and filtered off the solid. The filtrate was concentrated under vacuum to give 2-bromo-4-methoxycarbonyl-benzyl bromide (50 g, 93%) as a solid.

Step c) Preparation of 3-Bromo-4-aminomethylbenzamide

A mixture of 2-bromo-4-methoxycarbonyl benzylbromide (50 g, 0.162 mol), methanol (500 mL) and liquid ammonia (2.5 L) was stirred at −10° C. for 24 h. The reaction mixture was concentrated under vacuum and the residue was diluted with water (750 mL). The solid precipitate obtained was filtered and dried under vacuum to give 3-bromo-4-aminomethyl benzamide (35 g, 94%).

Step d) Preparation of 2-Bromo-4-carboxybenzylamine

A mixture of 3-bromo-4-aminomethylbenzamide (35 g, 0.15 mol), methanol (250 mL) and 20% NaOH solution (185 mL) was refluxed for 30 h. The reaction mixture was concentrated, acidified with an aqueous solution of HCl (6N) to give a solid precipitate.

The solid was filtered, washed with water and dried under vacuum to give 2-bromo-4-carboxybenzylamine (26 g, 74%).

Step e) Preparation of N-(Fmoc)-2-Bromo-4-carboxybenzylamine

To a solution of 2-bromo-4-carboxybenzylamine (20 g, 0.086 mol) in dioxane (250 mL), was added an aqueous solution of Na$_2$CO$_3$ (10%, 350 mL) with stirring. The reaction mixture was cooled to 10° C., added Fmoc-OSu (32 g, 0.096 mol) in portions and allowed to stir at RT for 8 h. The solid precipitate was filtered off and washed with diethyl ether (2×200 mL). The solid was acidified with 3N HCl and filtered under suction. The crude solid was recrystalised from methanol/diethyl ether to give N-(Fmoc)-2-bromo-4-carboxybenzylamine (26 g, 67%) as a solid.

Step f) Preparation of N-(Fmoc)-2-bromo-4-(chlorocarbonyl)benzylcarbamate

Oxalyl chloride (635 mg, 5.0 mmol) was added dropwise to a suspension of 2-bromo-4-carboxybenzylamine (452 mg, 1.0 mmol) in DCM. A catalytic amount of DMF was added and then stirred overnight at ambient temperatures. The solvent was then removed in vacuo to give the title compound.

Step g) Preparation of [[4-({[2-(1,1'-biphenyl-4-yl)ethyl]amino}carbonyl)-2-bromobenzyl]-(4-iodobenzyl)amino](oxo)acetic acid The same procedure as employed in the preparation of Example 50 using 2-(4-biphenyl)ethylamine in step a, N-(Fmoc)-2-bromo-4-(chlorocarbonyl)benzylcarbamate and DIEA in step b and 4-iodo-benzaldehyde in step d gave the title compound. M$^+$(LC/MS(ESI)): 697.2

Example 152

[(2-bromo-4-{[(4-pentylbenzyl)amino]carbonyl}benzyl)(4-iodobenzyl)amino](oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 4-iodo-benzaldehyde in step d gave the title compound. M$^+$(LC/MS(ESI)): 677.2

Example 153

[{2-bromo-4-[(dodecylamino)carbonyl]benzyl}(4-iodobenzyl)amino](oxo)acetic acid

The same procedure as employed in the preparation of Example 50 using dodecylamine in step a, N-(Fmoc)-2-bromo-4-(chlorocarbonyl)benzylcarbamate (Example 151) and DIEA in step b and 4-iodo-benzaldehyde in step d gave the title compound. $M^+$(LC/MS(ESI)): 685.2

Example 154

[(2,6-dibromo-4-{[(4-pentylbenzyl)amino]carbonyl}benzyl)(4-iodobenzyl)amino](oxo)acetic acid

Step a) Preparation of methyl-3,5-dibromo-4-bromomethyl benzoate

A mixture of methyl-3,5-dibromo-4-methylbenzoate (50 g, 0.16 mol), NBS (31.7 g, 0.17 mol) and benzoyl peroxide (5.0 g) in $CCl_4$ (500 mL) was refluxed for 4 h under the illumination of a 200 W bulb. The reaction mixture was cooled and filtered off the solid. The filtrate was concentrated under vacuum to give methyl-3,5-dibromo-4-bromomethyl benzoate (62 g, 98%) as a solid.

Step b) Preparation of 3,5-dibromo-4-aminomethylbenzamide

To a solution of methyl-3,5-dibromo-4-bromomethyl benzoate (50 g, 0.129 mol) in methanol (750 mL) at 40° C. was collected ammonia (approximately 1 L) by passing ammonia gas. After stirring the reaction mixture at −40° C. for 24 h, excess ammonia was removed by passing $N_2$ gas at ambient temperature. The reaction mixture was then concentrated and residue was diluted with water (1 L). The solid precipitate was filtered off and dried under suction. The solid was further dried under vacuum to give 3,5-dibromo-4-aminomethyl benzamide (40 g, 98%).

Step c) Preparation of 2,6-dibromo-4-carboxy benzylamine

A mixture of 3,5-dibromo-4-aminomethyl benzamide (40 g, 0.129 mol), methanol (500 mL) and an aqueous solution of NaOH (10%, 310 mL) was refluxed for 20 h. The reaction mixture was concentrated to 150 mL and cooled to 0° C. The solid precipitate obtained was filtered, washed with diethyl ether (500 mL). The solid obtained was acidified with an aqueous solution of HCl (1.5 N, 100 mL) to pH=6 to give solid precipitate. The solid was filtered, washed with water and dried under vacuum to give 2,6-dibromo-4-carboxy benzylamine (35 g, 87%) as a solid.

Step d) Preparation of N-(Fmoc)-2,6-dibromo-4-carboxybenzylamine

To a solution of 2,6-dibromo-4-carboxybenzylamine (20 g, 0.064 mol) in dioxane (500 mL), was added an aqueous solution of $Na_2CO_3$ (10%, 410 mL) with stirring. After stirring at 26° C. for 15 min was added Fmoc-OSu (30.5 g, 0.09 mol) in portions for 2 h and allowed to stir at ambient temperature for 24 h. The solid precipitate was filtered off and washed with diethyl ether (3×200 mL), followed by methanol (3×200 mL). The solid salt was acidified with an aqueous solution of HCl (3 N, 100 mL) to pH=2. The precipitate was filtered under suction and dried. The crude solid was recrystalised from methanol/diethyl ether to give N-(Fmoc)-2,6-dibromo-4-carboxybenzylamine (30 g, 87%) as a solid.

Step e) Preparation of [(2,6-dibromo-4-{[(4-pentylbenzyl)amino]carbonyl}benzyl)(4-iodobenzyl)amino](oxo)acetic acid The same procedure as employed in the preparation of Example 50 using 4-pentylbenzylamine in step a, N-(Fmoc)-2,6-dibromo-4-carboxybenzylamine in step b and 4-iodobenzaldehyde in step d gave the title compound. $M^+$(LC/MS(ESI)): 757.2

Example 155

((4-iodobenzyl){[4'-({[2-(4-phenoxyphenyl)ethyl]amino}carbonyl)-1,1'-biphenyl-4-yl]methyl}amino)(oxo)acetic acid

Step a) Preparation of tert-butyl-4-bromo benzoate

A mixture of 4-bromobenzoic acid (100 g, 0.5 mol), trifluoromethane sulphonic acid (2.6 mL, 0.03 mol) and isobutylene (1.5 L) in dichloromethane (1.5 L) was stirred at RT in a closed autoclave for 5 days. The organic layer was washed with an aqueous solution of $NaHCO_3$ (10%), water, brine, dried and concentrated to give tert-butyl-4-bromobenzoate (90 g, 71%).

Step b) Preparation of tert-butyl-4-(4-tolyl)benzoate

To a mixture of tert-butyl-4-bromobenzoate (40 g, 0.15 mol), 4-tolylboronic acid (23.3 g, 0.17 mol) and sodium carbonate (150 g) in toluene (350 mL) and water (350 mL) was added tetrakis(triphenylphosphine)palladium(0) (8.7 g, 0.007 mol) and the reaction mixture was refluxed for 10 h under nitrogen atmosphere. The organic layer was separated, washed with water, dried and concentrated to give tert-butyl-4-(4-tolyl)benzoate (32 g, 77%).

Step c) Preparation of 4-(4-tert-butoxycarbonylphenyl)benzyl bromide

To a solution of tert-butyl-4-(4-tolyl)benzoate (32 g, 0.12 mol) in carbontetrachloride (500 mL) was added N-bromo-succinimide (23.3 g, 0.13 mol) and benzoyl peroxide (4.0 g). The reaction mixture was refluxed for 10 h. After cooling to RT, the reaction mixture was filtered. The filtrate was concentrated and the crude was recrystallised from petEther to give 4-(4-tert-butoxycarbonylphenyl)benzylbromide (26 g, 69%).

Step d) Preparation of 4-(4-Carboxyphenyl)benzylamine hydrochloride

To a solution of 4-(4-tert-Butoxycarbonyl)benzylbromide (25 g, 0.071 mol) in methanol (2 L), cooled to −20° C. was passed through the reaction mixture ammonia for 5 h. The reaction mixture was stirred at RT for 30 h. Methanol was removed under vacuum. To the residue an aqueous solution of HCl (6N, 200 mL) was added and stirred at RT overnight. The solvents were evaporated under vacuum and the resulting residue was washed with diethyl ether to give 4-(4-carboxyphenyl)benzylamine hydrochloride (10 g, 53%).

Step e) Preparation of N-Fmoc-4-(4-carboxyphenyl)benzylamine 4-(4-Carboxyphenyl)benzylamine hydrochloride (10 g, 0.038 mol) was taken in a mixture of 10% $Na_2CO_3$ (100 mL) and dioxane (25 mL). To this a solution of Fmoc-OSu (15.4 g, 0.045 mol) in dioxane (50 mL) was added at 10° C. and the reaction was stirred at RT for 4 h. Solvent was removed under reduced pressure and the residue was acidified with an aqueous solution of HCl (1.5 N), extracted with EtOAc and the crude was recrystallised from EtOAc to give N-Fmoc-4-(4-carboxyphenyl)benzylamine (8.5 g, 45%).

Step f) Preparation of ((4-iodobenzyl){[4'-({[2-(4-phenoxyphenyl)ethyl]amino}carbonyl)-1,1'-biphenyl-4-yl]methyl}amino)(oxo)acetic acid The same procedure as employed in the preparation of Example 50 using 4-phenoxyphenethylamine in step a, N-Fmoc-4-(4-carboxyphenyl)benzylamine in step b and 4-iodo-benzaldehyde in step d gave the title compound. $M^+$(LC/MS(ESI)): 711.3

Example 156

{[2-bromo-4-({[2-(4-phenoxyphenyl)ethyl]amino}carbonyl)benzyl][(4'-fluoro-1,1'-biphenyl-3-yl)methyl]amino}(oxo)acetic acid The same procedure as employed in the preparation of Example 50 using 4-phenoxyphenethylamine in step a, N-(Fmoc)-2-bromo-4-(chlorocarbonyl)benzylcarbamate (Example 151) and DIEA in step b and 3-(4-fluorophenyl)benzaldehyde in step d gave the title compound. $M^+$(LC/MS(ESI)): 681.3

Example 157

{[4-({[2-(1,1'-biphenyl-4-yl)ethyl]amino}carbonyl)-2-bromobenzyl][(4'-fluoro-1,1'-biphenyl-3-yl)methyl]amino}(oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and 3-(4-fluorophenyl)benzaldehyde in step d gave the title compound. $M^+$(LC/MS(ESI)): 665.3

Example 158

{(2-bromo-4-{[(4-pentylbenzyl)amino]carbonyl}benzyl)[(4'-fluoro-1,1'-biphenyl-3-yl)methyl]amino}(oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 3-(4-fluorophenyl)benzaldehyde in step d gave the title compound. $M^+$(LC/MS(ESI)): 645.3

Example 159

{[2,6-dibromo-4-({[2-(4-phenoxyphenyl)ethyl]amino}carbonyl)benzyl][4'-fluoro-1,1'-biphenyl-3-yl)methyl]amino}(oxo)acetic acid The same procedure as employed in the preparation of Example 50 using 4-phenoxyphenethylamine in step a, N-(Fmoc)-2,6-dibromo-4-carboxybenzylamine (Example 154) in step b and 3-(4-fluorophenyl)benzaldehyde in step d gave the title compound. $M^+$(LC/MS(ESI)): 761.3

Example 160

{[4-({[2-(1,1'-biphenyl-4-yl)ethyl]amino}carbonyl)-2,6-dibromobenzyl][(4'-fluoro-1,1'-biphenyl-3-yl)methyl]amino}(oxo)acetic acid The same procedure as employed in the preparation of Example 50 using 2-(4-biphenyl)ethylamine in step a, N-(Fmoc)-2,6-dibromo-4-carboxybenzylamine (Example 154) in step b and 3-(4-fluorophenyl)benzaldehyde in step d gave the title compound. $M^+$(LC/MS(ESI)): 745.2

Example 161

{(2,6-dibromo-4-{[(4-pentylbenzyl)amino]carbonyl}benzyl)[(4'-fluoro-1,1'-biphenyl-3-yl)methyl]amino}(oxo)acetic acid The same procedure as employed in the preparation of Example 50 using 4-pentylbenzylamine in step a, N-(Fmoc)-2,6-dibromo-4-carboxybenzylamine (Example 154) in step b and 3-(4-fluorophenyl)benzaldehyde in step d gave the title compound.
$M^+$(LC/MS(ESI)): 725.3

Example 162

{{2,6-dibromo-4-[(dodecylamino)carbonyl]benzyl}[(4'-fluoro-1,1'-biphenyl-3-yl)methyl]amino}(oxo)acetic acid The same procedure as employed in the preparation of Example 50 using dodecylamine in step a, N-(Fmoc)-2,6-dibromo-4-carboxybenzylamine (Example 154) in step b and 3-(4-fluorophenyl)benzaldehyde in step d gave the title compound. $M^+$(LC/MS(ESI)): 733.3

Example 163

([(4'-fluoro-1,1'-biphenyl-3-yl)methyl]{[4'-({[2-(4-phenoxyphenyl)ethyl]-amino}carbonyl)-1,1'-biphenyl-4-yl]methyl}amino)(oxo)acetic acid The same procedure as employed in the preparation of Example 50 using 4-phenoxyphenethylamine in step a, N-Fmoc-4-(4-carboxyphenyl)benzylamine (Example 155) in step b and 4'-fluoro-biphenyl-3-carbaldehyde in step d gave the title compound. $M^+$(LC/MS(ESI)): 679.4

Example 164

{({4'-[(dodecylamino)carbonyl]-1,1'-biphenyl-4-yl}methyl)[(4'-fluoro-1,1'-biphenyl-3-yl)methyl]amino}(oxo)acetic acid The same procedure as employed in the preparation of Example 50 using dodecylamine in step a, N-Fmoc-4-(4-carboxyphenyl)benzylamine Example 155) in step b and 4'-fluoro-biphenyl-3-carbaldehyde in step d gave the title compound. $M^+$(LC/MS(ESI)): 651.5

Example 165

{(2-bromo-4-{[(4-pentylbenzyl)amino]carbonyl}benzyl)[2-(trifluoromethoxy)benzyl]amino}(oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 2-(trifluoromethoxy)benzaldehyde in step d gave the title compound. M+(LC/MS(ESI)): 635.3

Example 166

{(2,6-dibromo-4-{[(4-pentylbenzyl)amino]carbonyl}benzyl)[2-(trifluoromethoxy)benzyl]amino}(oxo)acetic acid The same procedure as employed in the preparation of Example 50 using 4-pentylbenzylamine in step a, N-(Fmoc)-2,6-dibromo-4-carboxybenzylamine (Example 154) in step b and 2-(trifluoromethoxy)benzaldehyde in step d gave the title compound. M+(LC/MS(ESI)): 713.3

Example 167 oxo{{[4'-({[2-(4-phenoxyphenyl)ethyl]amino}carbonyl)-1,1'-biphenyl-4-yl]methyl}[2-(trifluoromethoxy)benzyl]amino}acetic acid The same procedure as employed in the preparation of Example 50 using 4-phenoxyphenethylamine in step a, N-Fmoc-4-(4-carboxyphenyl)benzylamine (Example 155) in step b and 2-(trifluoromethoxy)benzaldehyde in step d gave the title compound. M+(LC/MS(ESI)): 669.3

Example 168

{({4'-[(dodecylamino)carbonyl]-1,1'-biphenyl-4-yl}methyl)[2-(trifluoromethoxy)benzyl]amino}(oxo)acetic acid The same procedure as employed in the preparation of Example 50 using dodecylamine in step a, N-Fmoc-4-(4-carboxyphenyl)benzylamine (Example 155) in step b and 2-(trifluoromethoxy)benzaldehyde in step d gave the title compound. M+(LC/MS(ESI)): 641.3

Example 169

[[2-bromo-4-({[2-(4-phenoxyphenyl)ethyl]amino}carbonyl)benzyl](3-phenoxybenzyl)amino](oxo)acetic acid The same procedure as employed in the preparation of Example 50 using 4-phenoxyphenethylamine in step a, N-(Fmoc)-2-bromo-4-(chlorocarbonyl)benzylcarbamate (Example 151) and DIEA in step b and 3-phenoxy-benzaldehyde in step d gave the title compound. M+(LC/MS(ESI)): 679.3

Example 170

[[4-({[2-(1,1'-biphenyl-4-yl)ethyl]amino}carbonyl)-2-bromobenzyl](3-phenoxybenzyl)amino](oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and 3-phenoxy-benzaldehyde in step d gave the title compound. M+(LC/MS(ESI)): 663.3

Example 171

[(2-bromo-4-{[(4-pentylbenzyl)amino]carbonyl}benzyl)(3-phenoxybenzyl)amino](oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 3-phenoxy-benzaldehyde in step d gave the title compound. M+(LC/MS(ESI)): 643.3

Example 172

[[2,6-dibromo-4-({[2-(4-phenoxyphenyl)ethyl]amino}carbonyl)benzyl](3-phenoxybenzyl)amino](oxo)acetic acid The same procedure as employed in the preparation of Example 50 using 4-phenoxyphenethylamine in step a, N-(Fmoc)-2,6-dibromo-4-carboxybenzylamine (Example 154) in step b and 3-phenoxy-benzaldehyde in step d gave the title compound. M+(LC/MS(ESI)): 759.2

Example 173

[[4-({[2-(1,1'-biphenyl-4-yl)ethyl]amino}carbonyl)-2,6-dibromobenzyl](3-phenoxybenzyl)amino](oxo)acetic acid The same procedure as employed in the preparation of Example 50 using 2-(4-biphenyl)ethylamine in step a, N-(Fmoc)-2,6-dibromo-4-carboxybenzylamine (Example 154) in step b and 3-phenoxy-benzaldehyde in step d gave the title compound. M+(LC/MS(ESI)): 743.3

Example 174

[(2,6-dibromo-4-{[(4-pentylbenzyl)amino]carbonyl}benzyl)(3-phenoxybenzyl)amino](oxo)acetic acid The same procedure as employed in the preparation of Example 50 using 4-pentylbenzylamine in step a, N-(Fmoc)-2,6-dibromo-4-carboxybenzylamine (Example 154) in step b and 3-phenoxy-benzaldehyde in step d gave the title compound. M+(LC/MS(ESI)): 723.3

Example 175

[{2,6-dibromo-4-[(dodecylamino)carbonyl]benzyl}(3-phenoxybenzyl)-amino](oxo)acetic acid The same procedure as employed in the preparation of Example 50 using dodecylamine in step a, N-(Fmoc)-2,6-dibromo-4-carboxybenzylamine (Example 154) in step b and 3-phenoxy-benzaldehyde in step d gave the title compound. M+(LC/MS(ESI)): 731.3

Example 176 oxo((3-phenoxybenzyl){[4'-({[2-(4-phenoxyphenyl)ethyl]amino}carbonyl)-1,1'-biphenyl-4-yl]methyl}amino)acetic acid The same procedure as employed in the preparation of Example 50 using 4-phenoxyphenethylamine in step a, N-Fmoc-4-(4-carboxyphenyl)benzylamine (Example 155) in step b and 3-phenoxy-benzaldehyde in step d gave the title compound. M+(LC/MS(ESI)): 677.4

Example 177 oxo[[(4'-{[(4-pentylbenzyl)amino]carbonyl}-1,1'-biphenyl-4-yl)methyl](3-phenoxybenzyl)amino]acetic acid The same procedure as employed in the preparation of Example 50 using 4-pentylbenzylamine in step a, N-Fmoc- 4-(4-carboxyphenyl)benzylamine (Example 155) in step b and 3-phenoxy-benzaldehyde in step d gave the title compound. M+(LC/MS(ESI)): 641.5

Example 178

[({4'-[(dodecylamino)carbonyl]1,1'-biphenyl-4-yl}methyl)(3-phenoxybenzyl)amino](oxo)acetic acid The same procedure as employed in the preparation of Example 50 using dodecylamine in step a, N-Fmoc-4-(4-carboxyphenyl)benzylamine (Example 155) in step b and 3-phenoxy-benzaldehyde in step d gave the title compound. M+(LC/MS(ESI)): 649.4

Example 179

[[2-bromo-4-({[2-(4-phenoxyphenyl)ethyl]amino}carbonyl)benzyl](2-iodobenzyl)amino](oxo)acetic acid The same procedure as employed in the preparation of Example 50 using 4-phenoxyphenethylamine in step a, N-(Fmoc)-2-bromo-4-(chlorocarbonyl)benzylcarbamate (Example 151) and DIEA in step b and 2-iodo-benzaldehyde in step d gave the title compound. M+(LC/MS(ESI)): 713.0

Example 180

[[4-({[2-(1,1'-biphenyl-4-yl)ethyl]amino}carbonyl)-2-bromobenzyl](2-iodobenzyl amino](oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and 2-iodo-benzaldehyde in step d gave the title compound. M+(LC/MS(ESI)): 697.0

Example 181

[(2-bromo-4-{[(4-pentylbenzyl)amino]carbonyl}benzyl)(2-iodobenzyl)amino](oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 2-iodo-benzaldehyde in step d gave the title compound. M+(LC/MS(ESI)): 677.0

Example 182

[{2-bromo-4-[(dodecylamino)carbonyl]benzyl}(2-iodobenzyl)amino](oxo)acetic acid

The same procedure as employed in the preparation of Example 50 using dodecylamine in step a, N-(Fmoc)-2-bromo-4-(chlorocarbonyl)benzylcarbamate (Example 151) and DIEA in step b and 2-iodo-benzaldehyde in step d gave the title compound. M+(LC/MS(ESI)): 685.1

Example 183

([2-bromo-4-({[2-(4-phenoxyphenyl)ethyl]amino}carbonyl)benzyl]{[2'-(trifluoromethyl)-1,1'-biphenyl-4-yl]methyl}amino)(oxo)acetic acid The same procedure as employed in the preparation of Example 50 using 4-phenoxyphenethylamine in step a, N-(Fmoc)-2-bromo-4-(chlorocarbonyl)benzylcarbamate (Example 151) and DIEA in step b and 2'-trifluoromethyl-biphenyl-4-carbaldehyde in step d gave the title compound. M+(LC/MS(ESI)): 731.2

Example 184

([4-({[2-(1,1'-biphenyl-4-yl)ethyl]amino}carbonyl)-2-bromobenzyl]{[2'-(trifluoromethyl)-1,1'-biphenyl-4-yl]methyl}amino)(oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and 2'-trifluoromethyl-biphenyl-4-carbaldehyde in step d gave the title compound. M+(LC/MS(ESI): 715.2

Example 185

((2-bromo-4-{[(4-pentylbenzyl)amino]carbonyl}benzyl){[2'-(trifluoromethyl)-1,1'-biphenyl-4-yl]methyl}amino)(oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 2'-trifluoromethyl-biphenyl-4-carbaldehyde in step d gave the title compound. M+(LC/MS(ESI)): 695.2

Example 186

({2-bromo-4-[(dodecylamino)carbonyl]benzyl}{[2'-(trifluoromethyl)-1,1'-biphenyl-4-yl]methyl}amino)(oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and 2'-trifluoromethyl-biphenyl-4-carbaldehyde in step d gave the title compound. M+(LC/MS(ESI)): 703.3

Example 187

([4-({[2-(1,1'-biphenyl-4-yl)ethyl]amino}carbonyl)-2,6-dibromobenzyl]{[2'-(trifluoromethyl)-1,1'-biphenyl-4-yl]methyl}amino)(oxo)acetic acid The same procedure as employed in the preparation of Example 50 using 2-(4-biphenyl)ethylamine in step a, N-(Fmoc)-2,6-dibromo-4-carboxybenzylamine (Example 154) in step b and 2'-trifluoromethyl-biphenyl-4-carbaldehyde in step d gave the title compound. M+(LC/MS(ESI)): 793.1

Example 188

((2,6-dibromo-4-{[(4-pentylbenzyl)amino]carbonyl}benzyl){[2'-(trifluoromethyl)-1,1'-biphenyl-4-yl]methyl}amino)(oxo)acetic acid The same procedure as employed in the preparation of Example 50 using 4-pentylbenzylamine in step a, N-(Fmoc)-2,6-dibromo-4-carboxybenzylamine (Example 154) in step b and 2'-trifluoromethyl-biphenyl-4-carbaldehyde in step d gave the title compound. M+(LC/MS(ESI)): 773.2

Example 189

({2,6-dibromo-4-[(dodecylamino)carbonyl]benzyl}{[2'-(trifluoromethyl)-1,1'-biphenyl-4-yl]methyl}amino)(oxo)acetic acid The same procedure as employed in the preparation of Example 50 using dodecylamine in step a, N-(Fmoc)-2,6-dibromo-4-carboxybenzylamine (Example 154) in step b and 2'-trifluoromethyl-biphenyl-4-carbaldehyde in step d gave the title compound. M+(LC/MS(ESI)): 781.2

Example 190

(({4'-[(dodecylamino)carbonyl]-1,1'-biphenyl-4-yl}methyl){[2'-(trifluoromethyl)-1,1'-biphenyl-4-yl]methyl}amino)(oxo)acetic acid The same procedure as employed in the preparation of Example 50 using dodecylamine in step a, N-Fmoc-4-(4-carboxyphenyl)benzylamine (Example 155) in step b and 2'-trifluoromethyl-biphenyl-4-carbaldehyde in step d gave the title compound. M+(LC/MS(ESI)): 701.5

Example 191

[[4-({[2-(1,1'-biphenyl-4-yl)ethyl]amino}carbonyl)-2-bromobenzyl](1,1'-biphenyl-2-ylmethyl)amino](oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and biphenyl-2-carbaldehyde in step d gave the title compound. M+(LC/MS(ESI)): 647.3

Example 192

[(1,1'-biphenyl-2-ylmethyl)(2-bromo-4-{[(4-pentylbenzyl)amino]carbonyl}-benzyl)amino](oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and biphenyl-2-carbaldehyde in step d gave the title compound. M+(LC/MS(ESI)): 627.3

Example 193

((1,1'-biphenyl-2-ylmethyl){2-bromo-4-[(dodecylamino)carbonyl]benzyl}-amino)(oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and biphenyl-2-carbaldehyde in step d gave the title compound. M+(LC/MS(ESI)): 635.4

Example 194

{(1,1'-biphenyl-2-ylmethyl)[2,6-dibromo-4-({[2-(4-phenoxyphenyl)ethyl]-amino}carbonyl)benzyl]amino}(oxo)acetic acid The same procedure as employed in the preparation of Example 50 using 4-phenoxyphenethylamine in step a, N-(Fmoc)-2,6-dibromo-4-carboxybenzylamine (Example 154) in step b and biphenyl-2-carbaldehyde in step d gave the title compound. M+(LC/MS(ESI)): 741.2

Example 195

[[4-({[2-(1,1'-biphenyl-4-yl)ethyl]amino}carbonyl)-2,6-dibromobenzyl](1,1'-biphenyl-2-ylmethyl)amino](oxo)acetic acid The same procedure as employed in the preparation of Example 50 using 2-(4-biphenyl)ethylamine in step a, N-(Fmoc)-2,6-dibromo-4-carboxybenzylamine (Example 154) in step b and biphenyl-2-carbaldehyde in step d gave the title compound. M+(LC/MS(ESI)): 725.2

Example 196

[(1,1'-biphenyl-2-ylmethyl)(2,6-dibromo-4-{[(4-pentylbenzyl)amino]-carbonyl}benzyl)amino](oxo)acetic acid The same procedure as employed in the preparation of Example 50 using 4-pentylbenzylamine in step a, N-(Fmoc)-2,6-dibromo-4-carboxybenzylamine (Example 154) in step b and biphenyl-2-carbaldehyde in step d gave the title compound. M+(LC/MS/(ESI)): 705.3

Example 197

((1,1'-biphenyl-2-ylmethyl){2,6-dibromo-4-[(dodecylamino)carbonyl]-benzyl}amino)(oxo)acetic acid The same procedure as employed in the preparation of Example 50 using dodecylamine in step a, N-(Fmoc)-2,6-dibromo-4-carboxybenzylamine (Example 154) in step b and biphenyl-2-carbaldehyde in step d gave the title compound. M+(LC/MS(ESI)): 713.3

Example 198

{(2-bromo-4-{[(4-pentylbenzyl)amino]carbonyl}benzyl)[4-(trifluoromethoxy)benzyl]amino}(oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 4-(trifluoromethoxy)benzaldehyde in step d gave the title compound. M+(LC/MS(ESI)): 635.2

Example 199

{{2-bromo-4-[(dodecylamino)carbonyl]benzyl}[4-(trifluoromethoxy)-benzyl]amino}(oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and 4-(trifluoromethoxy)benzaldehyde in step d gave the title compound. M+(LC/MS(ESI)): 643.3

Example 200

{(2,6-dibromo-4-{[(4-pentylbenzyl)amino]carbonyl}benzyl)[4-(trifluoromethoxy)benzyl]amino}(oxo)acetic acid The same procedure as employed in the preparation of Example 50 using 4-pentylbenzylamine in step a, N-(Fmoc)-

2,6-dibromo-4-carboxybenzylamine (Example 154) in step b and 4-(trifluoromethoxy)benzaldehyde in step d gave the title compound. M⁺(LC/MS(ESI)): 714.3

Example 201

{(2-bromo-4-{[(4-pentylbenzyl)amino]carbonyl}benzyl)[3-(trifluoromethoxy)benzyl]amino}(oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 3-(trifluoromethoxy)benzaldehyde in step d gave the title compound. M⁺(LC/MS(ESI)): 635.2

Example 202

{{2-bromo-4-[(dodecylamino)carbonyl]benzyl}[3-(trifluoromethoxy)benzyl]amino}(oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and 3-(trifluoromethoxy)benzaldehyde in step d gave the title compound. M⁺(LC/MS(ESI)): 634.3

Example 203

{(2,6-dibromo-4-{[(4-pentylbenzyl)amino]carbonyl}benzyl)[3-(trifluoromethoxy)benzyl]amino}(oxo)acetic acid The same procedure as employed in the preparation of Example 50 using 4-pentylbenzylamine in step a, N-(Fmoc)-2,6-dibromo-4-carboxybenzylamine (Example 154) in step b and 3-(trifluoromethoxy)benzaldehyde in step d gave the title compound. M⁺(LC/MS(ESI)): 715.2

Example 204

{{2,6-dibromo-4-[(dodecylamino)carbonyl]benzyl}[3-(trifluoromethoxy)benzyl]amino}(oxo)acetic acid The same procedure as employed in the preparation of Example 50 using dodecylamine in step a, N-(Fmoc)-2,6-dibromo-4-carboxybenzylamine (Example 154) in step b and 3-(trifluoromethoxy)benzaldehyde in step d gave the title compound. M⁺(LC/MS(ESI)): 723.3

Example 205

{({4'-[(dodecylamino)carbonyl]-1,1'-biphenyl-4-yl}methyl)[3-(trifluoromethoxy)benzyl]amino}(oxo)acetic acid The same procedure as employed in the preparation of Example 50 using dodecylamine in step a, N-Fmoc-4-(4-carboxyphenyl)benzylamine (Example 155) in step b and 3-(trifluoromethoxy)benzaldehyde in step d gave the title compound. M⁺(LC/MS(ESI)): 641.4

Example 206

[[2-bromo-4-({[2-(4-phenoxyphenyl)ethyl]amino}carbonyl)benzyl](4-phenoxybenzyl)amino](oxo)acetic acid The same procedure as employed in the preparation of Example 50 using 4-phenoxyphenethylamine in step a, N-(Fmoc)-2-bromo-4-(chlorocarbonyl)benzylcarbamate (Example 151) and DIEA in step b and 4-phenoxy-benzaldehyde in step d gave the title compound. M⁺(LC/MS(ESI)): 679.3

Example 207

[[4-({[2-(1,1'-biphenyl-4-yl)ethyl]amino}carbonyl)-2-bromobenzyl](4-phenoxybenzyl)amino](oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and 4-phenoxy-benzaldehyde in step d gave the title compound. M⁺(LC/MS(ESI)): 663.3

Example 208

[(2-bromo-4-{[(4-pentylbenzyl)amino]carbonyl}benzyl)(4-phenoxybenzyl)amino](oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 4-phenoxy-benzaldehyde in step d gave the title compound. M⁺(LC/MS(ESI)): 643.3

Example 209

[{2-bromo-4-[(dodecylamino)carbonyl]benzyl}(4-phenoxybenzyl)amino](oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and 4-phenoxy-benzaldehyde in step d gave the title compound. M⁺(LC/MS(ESI)): 651.3

Example 210

[[4-({[2-(1,1'-biphenyl-4-yl)ethyl]amino}carbonyl)-2,6-dibromobenzyl](4-phenoxybenzyl)amino](oxo)acetic acid The same procedure as employed in the preparation of Example 50 using 2-(4-biphenyl)ethylamine in step a, N-(Fmoc)-2,6-dibromo-4-carboxybenzylamine (Example 154) in step b and 4-phenoxy-benzaldehyde in step d gave the title compound. M⁺(LC/MS(ESI)): 743.3

Example 211

[(2,6-dibromo-4-{[(4-pentylbenzyl)amino]carbonyl}benzyl)(4-phenoxybenzyl)amino](oxo)acetic acid The same procedure as employed in the preparation of Example 50 using 4-pentylbenzylamine in step a, N-(Fmoc)-2,6-dibromo-4-carboxybenzylamine (Example 154) in step b and 4-phenoxy-benzaldehyde in step d gave the title compound. M⁺(LC/MS(ESI)): 723.2

Example 212

{[4-({[2-(1,1'-biphenyl-4-yl)ethyl]amino}carbonyl)-2-bromobenzyl][4-(trifluoromethyl)benzyl]amino}(oxo)acetic acid The same procedure as employed in the preparation of Example 50 using 2-(4-biphenyl)ethylamine in step a, N-(Fmoc)-2-bromo-4-(chlorocarbonyl)benzylcarbamate (Example 151) and DIEA in step b and 4-(trifluoromethyl) benzaldehyde in step d gave the title compound. M+(LC/MS (ESI)): 639.2

Example 213

{(2-bromo-4-{[(4-pentylbenzyl)amino] carbonyl}benzyl)[4-(trifluoromethyl)benzyl]amino} (oxo)acetic acid The same procedure as employed in the preparation of Example 50 using 4-pentylbenzylamine in step a, N-(Fmoc)-2-bromo-4-(chlorocarbonyl)benzylcarbamate (Example 151) and DIEA in step b and 4-(trifluoromethyl)benzaldehyde in step d gave the title compound. M+(LC/MS(ESI)): 619.3

Example 214

{{2-bromo-4-[(dodecylamino)carbonyl]benzyl}[4-(trifluoromethyl)benzyl]amino}(oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and 4-(trifluoromethyl)benzaldehyde in step d gave the title compound. M+(LC/MS(ESI)): 627.3

Example 215

{(2,6-dibromo-4-{[(4-pentylbenzyl)amino] carbonyl}benzyl)[4-(trifluoromethyl)benzyl]amino} (oxo)acetic acid The same procedure as employed in the preparation of Example 50 using 4-pentylbenzylamine in step a, N-(Fmoc)-2,6-dibromo-4-carboxybenzylamine (Example 154) in step b and 4-(trifluoromethyl)benzaldehyde in step d gave the title compound. M+(LC/MS(ESI)): 699.2

Example 216

{{2,6-dibromo-4-[(dodecylamino)carbonyl]benzyl} [4-(trifluoromethyl)benzyl]amino}(oxo)acetic acid The same procedure as employed in the preparation of Example 50 using dodecylamine in step a, N-(Fmoc)-2,6-dibromo-4-carboxybenzylamine (Example 154) in step b and 4-(trifluoromethyl)benzaldehyde in step d gave the title compound. M+(LC/MS(ESI)): 707.3

Example 217 oxo{[(4'-{[(4-pentylbenzyl)amino]carbonyl}-1,1'-biphenyl-4-yl)methyl][4-(trifluoromethyl)benzyl] amino}acetic acid The same procedure as employed in the preparation of Example 50 using 4-pentylbenzylamine in step a, N-Fmoc-4-(4-carboxyphenyl)benzylamine (Example 155) in step b and 4-(trifluoromethyl)benzaldehyde in step d gave the title compound. M+(LC/MS(ESI)): 617.4

Example 218

{{2-bromo-4-[(dodecylamino)carbonyl]benzyl}[3-(trifluoromethyl)benzyl]amino}(oxo)acetic acid The same procedure as employed in the preparation of Example 50 using dodecylamine in step a, N-(Fmoc)-2-bromo-4-(chlorocarbonyl)benzylcarbamate (Example 151) and DIEA in step b and 3-(trifluoromethyl)benzaldehyde in step d gave the title compound. M+(LC/MS(ESI)): 627.3

Example 219

{{2,6-dibromo-4-[(dodecylamino)carbonyl]benzyl} [3-(trifluoromethyl)benzyl]amino}(oxo)acetic acid The same procedure as employed in the preparation of Example 50 using dodecylamine in step a, N-(Fmoc)-2,6-dibromo-4-carboxybenzylamine (Example 154) in step b and 3-(trifluoromethyl)benzaldehyde in step d gave the title compound. M+(LC/MS(ESI)): 707.3

Example 220 oxo{[(4'-{[(4-pentylbenzyl)amino]carbonyl}-1,1'-biphenyl-4-yl)methyl][3-(trifluoromethyl)benzyl] amino}acetic acid The same procedure as employed in the preparation of Example 50 using 4-pentylbenzylamine in step a, N-Fmoc-4-(4-carboxyphenyl)benzylamine (Example 155) in step b and 3-(trifluoromethyl)benzaldehyde in step d gave the title compound. M+(LC/MS(ESI)): 617.4

Example 221

{(4-dibenzo[b,d]furan-4-ylbenzyl)[4-(trifluoromethyl)benzyl]amino}(oxo)acetic acid Step a) Preparation of 4-dibenzo[b,d]furan-4-ylbenzonitrile To a mixture of dibenzofuran-4-boronic acid (40 g, 0.19 mol), 4-bromobenzonitrile (34 g, 0.19 mol), sodium carbonate (120 g) in toluene (500 mL) and water (500 mL) was added tetrakis (triphenylphosphine)palladium (0) (11 g, 0.0095 mol) with stirring under $N_2$ atmosphere. The reaction mixture was refluxed for 20 h. Toluene layer was separated, washed with water, dried and concentrated. The crude product was purified by column chromatography over silica gel (chloroform) to give the title compound (40 g, 79%).

Step b) Preparation of 1-(4-dibenzo[b,d]furan-4-ylphenyl)methanamine

To a solution of 4-(4-cyanophenyl) dibenzofuran (20 g, 0.074 mol) in isopropylalcohol (1.5 L) was added Raney-Nickel (10 g) with stirring. The reaction mixture was heated to reflux, treated with hydrazine hydrate (100 mL) and refluxed for 6 h. The reaction mixture was cooled, filtered through celite and washed with isopropylalcohol. The filtrate was concentrated and crude purified by column chromatography over silica gel ($CHCl_3$/MeOH; 9:1) to give the title compound as a solid (6.5 g, 32%). $^1$H NMR (THF-$d_8$, 300 MHz) δ 7.30-8.30 (m, 13H), 3.98 (s, 2H)

Step c) Preparation of N-(4-dibenzo[b,d]furan-4-ylbenzyl)-N-[4-(trifluoromethyl) benzyl]amine The same procedure as employed in the preparation of Example 1 (step a) using 1-(4-dibenzo[b,d]furan-4-ylphenyl) methanamine and 4-(trifluoromethyl)benzaldehyde gave the title compound (51%). M+(LC/MS(ESI)): 432.4

HPLC (Condition A), Rt: 4.28 min (HPLC purity: 97.9%). $^1$H NMR ($CDCl_3$, 300 MHz) δ 7.75-8.00 (m, 5H), 7.35-7.61 (m, 11H), 3.93 (s, 2H), 3.90 (s, 2H)

Step c) Preparation of ethyl{(4-dibenzo[b,d]furan-4-ylbenzyl)[4-(trifluoromethyl)benzyl]amino}(oxo)acetate The same procedure as employed in the preparation of Example 1 (step b) using N-(4-dibenzo[b,d]furan-4-ylbenzyl)-N-[4-(trifluoromethyl)benzyl]amine gave the title compound (98%). M⁺(LC/MS(ESI)): 531.6. HPLC (Condition A), Rt: 6.38 min (HPLC purity: 100%). ¹H NMR (CDCl₃, 300 MHz) δ 7.85-8.05 (m, 4H), 7.55-7.72 (m, 4H), 7.55-7.30 (m, 7H), 4.30-4.67 (m, OH), 1.25-1.45 (m, 3H)

Step d) Preparation of {(4-dibenzo[b,d]furan-4-ylbenzyl)[4-(trifluoromethyl)benzyl]amino}(oxo)acetic acid The same procedure as employed in the preparation of Example 1 (step e) using {(4-dibenzo[b,d]furan-4-ylbenzyl)[4-(trifluoromethyl)benzyl]amino}(oxo)acetate gave the title compound (90%). M⁻(LC/MS(ESI)): 502.0. HPLC (Condition A), Rt: 5.95 min (HPLC purity: 98.5%). ¹H NMR (CD₃OD, 300 MHz) δ 7.90-8.05 (m, 2H), 7.75-7.90 (m, 2H), 7.25-7.90 (m, 11H), 4.59 (s, 2H), 4.56 (s, 2H)

Example 222

{(4-dibenzo[b,d]furan-4-ylbenzyl)[4-(trifluoromethyl)benzyl]amino}-(oxo)acetic acid. N-methyl-D-glucamine (i.e. 1-deoxy-1-(methylamino)glucitol) salt The same procedure as employed in the preparation of Example 2 using {(4-dibenzo[b,d]furan-4-ylbenzyl)[4-(trifluoromethyl)benzyl]amino}(oxo)acetic acid and N-methyl-D-glucamine gave the title compound as a white fluffy solid (95%). M⁻(APCI): 562.6. HPLC (Condition A), Rt: 5.98 min (HPLC purity: 98.3%). Analysis calculated for C₂₉H₁₉F₃NO₄·C₇H₁₈NO₅■1.1H₂O: C, 60.18; H, 5.50; N, 3.90%. Found: C, 60.12; H, 5.56; N, 3.82%.

Example 223

({4-[(dodecylamino)carbonyl]benzyl}{1-[4-(trifluoromethyl)phenyl]ethyl}-amino)(oxo)acetic acid Step a) Formation of 4-(aminomethyl)-N-dodecylbenzamide At 0° C., to a solution of 4-{([(tert-butoxycarbonyl)amino]methyl}benzoic acid (2.0 g) and NMM (1.02 g, 1.11 mL) in anhydrous THF (50 mL) was added dropwise isobutyl chloroformate (1.2 mL). After stirring for 20 min, dodecylamine (1.875 g) was added dropwise. After 1 h the ice-water bath was removed and the mixture was stirred for 14 h at rt. A 1N aqueous solution of HCl (50 mL) was added and the mixture was extracted with AcOEt (2×50 mL). The combined organic layers were washed with water (150 mL), dried over MgSO₄ and evaporated off to give an oil (3.61 g). This crude product was purified by flash chromatography over silica gel (c-Hex/AcOEt 2/1) to give tert-butyl 4-[(dodecylamino)carbonyl]benzylcarbamate as a colorless oil (2.35 g, 70%). M⁻(LC/MS(ESI)): 419.5; M⁺(LC/MS(ESI)): 418.5. HPLC (Condition A), Rt: 6.35 min (HPLC purity: 99.6%).

To a solution of tert-butyl 4-[(dodecylamino)carbonyl] benzylcarbamate (2.35 g) in DCM (30 mL) was added a HCl solution (4N in dioxane, 30 mL). The resulting mixture was stirred at rt for 1 h. Evaporation of the solvents gave 4-(aminomethyl)-N-dodecylbenzamide hydrochloride compound as a white powder (1.97 g, 98%). M⁺(LC/MS(ESI)): 319.4; M⁻(LC/MS(ESI)): 317.4. HPLC (Condition A), Rt: 4.20 min (HPLC purity: 100%). ¹H NMR (DMSO-d₆, 300 MHz) δ 8.52 (br s, 3H), 7.87 (d, J=7.5 Hz, 2H), 7.56 (d, J=7.5 Hz, 2H), 4.06 (br s, 2H), 3.25-3.30 (m, 2H), 1.45-1.55 (m, 2H), 1.30-1.56 (m, 18H), 0.84 (t, J=8.3 Hz, 3H).

A suspension of 4-(aminomethyl)-N-dodecylbenzamide hydrochloride (1.97 g) in AcOEt (100 mL) was washed with a saturated aqueous solution of NaHCO₃ (50 mL). The organic layer was dried over MgSO₄ and evaporated to give the title compound as a white solid (1.6 g).

Step b) Formation of N-dodecyl-4-[({1-[4-(trifluoromethyl)phenyl]ethyl}amino)methyl]benzamide At 0° C., to a solution of 4-(aminomethyl)-N-dodecylbenzamide (0.955 g) and 4-trifluoro acetophenone (0.564 g) in THF (20 mL) was added titanium tetraisopropoxide (1.065 g).

The resulting mixture was stirred for 1 h at rt. MeOH (4 mL) was added and the reaction mixture was chilled at 0° C. NaBH₄ (0.227 g) was then added portion wise (rapid evolution of gas). After 1 h at rt, a 1N aqueous solution of NaOH was added and the resulting reaction mixture was extracted with AcOEt (3×50 mL). The combined organic layers were dried over MgSO₄ and evaporated to give a white solid (1.523 g). Purification by flash chromatography on silica gel (40/60 AcOEt/c-Hex) gave the title compound as a white solid (1.001 g, 68%). M (APCI): 491.2. HPLC (Condition A), Rt: 5.12 min (HPLC purity: 96.6%). ¹H NMR (CDCl₃, 300 MHz) δ 7.10-7.71 (m, 8H), 4.93 (br s, 1H), 3.90-3.96 (m, 1H), 3.70 (br s, 1H), 3.42 (s, 2H), 3.32 (s, 2H), 1.42-1.55 (m, 2H), 1.10-1.43 (m, 21H), 0.86 (m, 3H)

Step c) Formation of ethyl({4-[(dodecylamino)carbonyl]benzyl}{1-[4-(trifluoromethyl)phenyl]ethyl}amino)(oxo)acetate The same procedure as employed for the preparation of Example 1 (step b) using N-dodecyl-4-[({1-[4-(trifluoromethyl)phenyl]ethyl}amino)methyl]benzamide gave the title compound as a colorless oil (80%). ¹H NMR (CDCl₃, 300 MHz) δ 7.55-7.64 (m, 4H), 7.38 (m, 2H), 7.13 (m, 2H), 5.81-6.00 (m, 1H), 4.30-4.75 (m, 2H), 3.41 (m, 2H), 1.41-1.70 (m, 6H), 1.10-1.40 (m, 19H), 0.86 (m, 3H).

Step d) Formation of ({4-[(dodecylamino)carbonyl]benzyl}{1-[4-(trifluoromethyl)phenyl]ethyl}amino)(oxo)acetic acid The same procedure as employed in the preparation of Example 1 (step e) using ethyl({4-[(dodecylamino)carbonyl]benzyl}{1-[4-(trifluoromethyl)phenyl]ethyl}amino)(oxo)acetate gave the title compound as a colorless oil (95%). ¹H NMR (DMSO-d₆, 300 MHz) δ 8.24-8.41 (m, 1H), 7.78-8.28 (m, 8H), 7.15 (q, 0.4H, J=5.5 Hz), 5.13 (q, 0.6H, J=6.9 Hz), 4.38-4.65 (m, 1.4H), 4.10-4.22 (m, 0.6H), 3.08-3.27 (m, 2H), 1.37-1.60 (m, 5H), 1.10-1.35 (m, 18H), 0.84 (t, 3H, J=6.7 Hz). M⁻(LC/MS(ESI)): 560.9; M⁺(LC/MS(ESI)): 562.9 HPLC (Condition A), Rt: 6.36 min (HPLC purity: 99.6%). Analysis calculated for C₃₁H₄₀F₃N₂O₄■0.1H₂O: C, 65.96; H, 7.36; N, 4.96%. Found: C, 65.92; H, 7.41; N, 4.89%.

Example 224

({4-[(dodecylamino)carbonyl]benzyl}{1-[4-(trifluoromethyl)phenyl]ethyl}-amino)-(oxo)acetic acid, N-methyl-D-glucamine (i.e. 1-deoxy-1-(methylamino)glucitol) salt The same procedure as employed in the preparation of Example 2 using ({4-[(dodecylamino)carbonyl]benzyl}{1-[4-(trifluoromethyl)phenyl]ethyl}amino)(oxo)acetic acid and N-methyl-D-glucamine gave the title compound as a white powder (95%). M⁻(LC/MS(ESI)): 560.9; M⁺(LC/MS(ESI)): 56.2.9. HPLC (Condition A), Rt: 6.38 min (HPLC purity: 99.8%). Analysis calculated for $C_{31}H_{40}F_3N_2O_4 \cdot C_7H_{18}NO_5 \blacksquare 0.7H_2O$: C, 59.24; H, 7.77; N, 5.45%. Found: C, 59.36; H, 7.90; N, 5.43%.

Example 225

{({4'-[(octylamino)carbonyl]-1,1'-biphenyl-4-yl}methyl)[4-(trifluoromethyl)benzyl]amino}(oxo) acetic acid

Step a) Preparation of tert-butyl-4-bromobenzoate

To a stirred solution of 4-bromobenzoic acid (100 g, 0.5 mol) in dry $CH_2Cl_2$ (1.5 L) was added silver carbonate (275 g, 1 mol) and molecular sieves (4A, 100 g). The reaction mixture was cooled to 0° C. and then tert-butyl bromide (115 mL) was added dropwise over a period of 45 min. The reaction mixture was allowed to stir at Rt for 20 h and filtered off the solid. The filtrate was washed with an aqueous solution of $NaHCO_3$ (10%), water, brine and dried. The solvent was removed under vacuum to the title compound (100 g, 79%) as colorless liquid.

Step b) Preparation of tert-butyl 4'-methyl-1,1'-biphenyl-4-carboxylate

To a solution of tert-butyl-4-bromobenzoate (48 g, 0.186 mol), 4-tolyl-benzeneboronic acid (25.3 g, 0.186 mol), $Na_2CO_3$ (200 g in 500 mL of water) in toluene (750 mL) under $N_2$ was added Pd $(PPh_3)_4$ (10.7 g, 0.009 mol) and reaction mixture was refluxed for 10 h. After cooling to rt, organic layer was separated and aqueous layer was extracted with EtOAc (2×200 mL). The combined layer was washed with brine and concentrated. The crude was purified by column chromatography over silica gel (pet. ether/ethylacetate, 4:1) to give tert-butyl-4-(4-tolyl)benzoate (40 g, 800%) as a solid.

Step c) Preparation of tert-butyl 4'-(bromomethyl)-1,1'-biphenyl-4-carboxylate A mixture of tert-butyl 4'-methyl-1,1'-biphenyl-4-carboxylate (40.0 g, 0.15 mol), NBS (32.0 g, 0.18 mol) and benzoylperoxide (5.0 g) in $CCl_4$ (600 mL) was heated to reflux for 6 h under $N_2$. After cooling to rt, solid was filtered and concentrated under vacuum to give crude product. The crude solid was washed with PetEther/chloroform to give the title compound as solid (40 g, 78%).

Step d) Preparation of tert-butyl 4'-(aminomethyl)-1,1'-biphenyl-4-carboxylate To a solution of tert-butyl 4'-(bromomethyl)-1,1'-biphenyl-4-carboxylate (35.0 g) in methanol (1 L) at −30° C. was purged ammonia gas for 2 h. The reaction mixture was then allowed to stir at 0° C. for 30 h. The solid precipitate was filtered off, washed with water (2×1 L), dried under suction. The solid was recrystallised from methanol to the title compound as white solid (20 g, 71%).

Step e) Formation of tert-butyl 4'-({[4-(trifluoromethyl)benzyl]amino}methyl)-1,1'-biphenyl-4-carboxylate To a solution of tert-butyl 4'-(aminomethyl)-1,1'-biphenyl-4-carboxylate (2.0 g) and 4-(trifluormethyl)-benzaldehyde (0.88 mL) in DCE (40 mL) was added at once sodium triacetoxyborohydride (1.904 g). The resulting mixture was stirred for 14 h at rt. Water (50 mL) was added and the mixture extracted with DCM (3×). The combined organic layers were washed with water (50 mL), then dried over $MgSO_4$, evaporated off to give a yellow oil. This crude was purified by flash chromatography (c-Hex/AcOEt 4/1) to give the title compound as a white powder (1.30 g, 43%). M⁺(LC/MS(ESI)): 442.02

HPLC (Condition A), Rt: 4.25 min (HPLC purity: 93.7%). ¹H NMR (DMSO, 300 MHz): δ 7.97 (d, 2H, J=7.9 Hz), 7.80 (d, 2H, J=7.9 Hz), 7.69 (d, 2H, J=8.3 Hz), 7.60 (d, 2H, J=7.9 Hz), 7.48 (d, 2H, J=7.9 Hz), 3.79 (s, 2H), 3.74 (s, 2H), 1.56 (s, 9H).

Step f) Formation of tert-butyl 4'-({[ethoxy(oxo)acetyl][4-(trifluoromethyl)benzyl]amino}-methyl)-1,1'-biphenyl-4-carboxylate To a solution of tert-butyl 4'-({[4-(trifluoromethyl)benzyl]amino}methyl)-1,1'-biphenyl-4-carboxylate (1.29 g) and triethylamine (0.81 mL) in cold anhydrous DCM (40 mL) was added dropwise a solution of ethyl oxalyl chloride (0.49 mL, in anhydrous DCM (2 mL)). The resulting mixture was stirred for 2 h then water was added. After extraction with DCM (3×50 mL), the combined organic layers were washed with water (3×30 mL), dried on $MgSO_4$ and evaporated to give a yellow oil (1.44 g). This crude product was purified by flash chromatography over silica gel (c-Hex/AcOEt 6/1 then 4/1) to give the title compound as yellow oil (1.38 g, 79%). M⁺(LC/MS(ESI)): 542.0; M⁻(LC/MS(ESI)): 540.8. HPLC (Condition A), Rt: 6.67 min (HPLC purity: 90.9%)

Step g) Formation of 4'-({[(ethoxy(oxo)acetyl][4-(trifluoromethyl)benzyl]amino}methyl)-1,1'-biphenyl-4-carboxylic acid To a solution of tert-butyl 4'-({[ethoxy(oxo)acetyl][4-(trifluoromethyl)benzyl]amino}methyl)-1,1'-biphenyl-4-carboxylate (1.37 g) in DCM (15 mL) was added TFA (15 mL). The resulting mixture was stirred for 30 min. Evaporation of the solvents gave the title compound as a colorless oil (1.10 g, 67%). M⁺(LC/MS(ESI)): 486.1; M⁻(LC/MS(ESI)): 484.6. HPLC (Condition A), Rt: 4.13 min (HPLC purity: 91.7%) ¹H NMR (DMSO, 300 MHz) δ 7.94 (d, 2H, J=7.9 Hz), 7.72-7.61 (m, 6H), 7.42 (d, 1H, J=7.9 Hz), 7.33 (t, 2H, J=7.5 Hz), 7.25 (d, 1H, J=8.3 Hz), 4.49 (m, 4H), 4.20 (m, 2H), 1.10 (m, 3H).

Step h) Formation of ethyl{({4'-[(octylamino)carbonyl]-1,1'-biphenyl-4-yl}methyl)[4-(trifluoromethyl)benzyl]amino}(oxo)acetate To a solution of 4'-({[ethoxy(oxo)acetyl][4-(trifluoromethyl)benzyl]amino}methyl)-1,1'-biphenyl-4-carboxylic acid (100 mg), EDC (47 mg) and HOBt (28 mg) in DCM (4 mL) was added octylamine (0.041 mL). The resulting reaction mixture was stirred for 3 h. DCM (15 mL) and an aqueous solution of HCl (1N, 10 mL) was added. The aqueous layer was extracted with DCM (3×15 mL). The combined organic layers were washed with a saturated solution of NaHCO$_3$ (15 mL) and dried over MgSO$_4$. Evaporation of the solvents gave an oil which was purified by flash chromatography over silica gel (c-Hex/AcOEt 2/1) to give the title compound as a colorless oil (41 mg, 33%). M$^+$(LC/MS(ESI)): 597.8; M$^-$(LC/MS (ESI)): 595.0. HPLC (Condition A), Rt: 6.61 min (HPLC purity: 99.87%)

Step i) Formation of {({4'-[(octylamino)carbonyl]-1, 1'-biphenyl-4-yl}methyl)[4-(trifluoromethyl)benzyl] amino}(oxo)acetic acid The same procedure as employed in the preparation of Example 1 (step e) using ethyl{({4'-[(octylamino)carbonyl]-1,1'-biphenyl-4-yl}methyl)[4-(trifluoromethyl)benzyl] amino}(oxo)acetate gave the title compound as a colorless oil (77%). M$^+$(LC/MS(ESI)): 570.5; M (LC/MS(ESI)): 567.5. HPLC (Condition A), Rt: 5.70 min (HPLC purity: 97.7%). $^1$H NMR (CDCl$_3$, 300 MHz) δ 7.72-7.17 (m, 12H), 6.45-6.26 (m, 1H), 4.47 (s, 4H), 3.41 (s, 2H), 1.56-1.18 (m, 12H), 0.81 (m, 3H).

Example 226 oxo{(4-tetradec-1-ynylbenzyl)[4-(trifluoromethyl) benzyl]amino}acetic acid

Step a) Formation of N-(4-bromobenzyl)-N-[4-(trifluoromethyl)benzyl]amine hydrochloride A solution of 4-bromobenzaldehyde (5.81 g, 31.4 mmol) and 4-(trifluoromethyl)-benzylamine (5.00 g, 28.6 mmol) in toluene (100 mL) was heated at reflux for 75 min with azeotropic removal of water. The toluene was evaporated off under reduce pressure. The residue was taken up in methanol (100 mL) and cooled to 0° C. NaBH$_4$ (2.16 g, 57.1 mmol) was added portionwise and the reaction mixture was stirred at 0° C. for 1.5 h. The reaction mixture was poured into water (200 mL)/brine (200 mL) and extracted with Et$_2$O (500 mL and 200 mL). The organic layers were washed with brine, combined and dried over MgSO$_4$. The solvent was removed under reduce pressure. The residue was diluted with Et$_2$O (200 mL) and HCl (1N in Et$_2$O, 40 mL) was added. A white solid precipitated out. Filtration, washing with Et$_2$O (3×20 mL) and drying under vacuum at 50° C. for 18 hrs gave the title compound as a white solid (9.74 g, 89%). $^1$H NMR (DMSO-d$_6$, 300 MHz) δ 9.77 (s, 2H), 7.82 (d, 2H, J=8.5 Hz), 7.76 (d, 2H, J=8.5 Hz), 7.64 (d, 2H, J=8.3 Hz), 7.51 (d, 2H, J=8.3 Hz), 4.25 (s, 2H), 4.17 (s, 2H). M$^+$(LC/MS(ESI)): 344.1. HPLC (Condition A), Rt: 3.16 min (HPLC purity: 99.7%).

Step b) Formation of ethyl{(4-bromobenzyl)[4-(trifluoromethyl)benzyl]amino}(oxo) acetate The same procedure as employed for the preparation of Example 1 (step b) using N-(4-bromobenzyl)-N-[4-(trifluoromethyl)benzyl]amine gave the title compound as a white solid (83%). $^1$H NMR (CDCl$_3$, 300 MHz) δ 7.63 (m, 2H), 7.51 (m, 2H), 7.40 (d, 1H, J=7.9 Hz), 7.34 (d, 1H, J=7.9 Hz), 7.16 (d, 1H, J=8.3 Hz), 7.11 (d, 1H, J=8.3 Hz), 4.55 (s, 1H), 4.47 (s, 1H), 4.41-4.32 (m, 4H), 1.36 (m, 3H). M$^+$(LC/MS (ESI)): 444.0, M$^-$(LC/MS(ESI)): 442.1. HPLC (Condition A), Rt: 5.99 min (HPLC purity: 99.1%).

Step c) Formation of ethyl oxo{(4-tetradec-1-ynyl-benzyl)[4-(trifluoromethyl)benzyl]amino}acetate A mixture of ethyl{(4-bromobenzyl)[4-(trifluoromethyl) benzyl]amino}(oxo)acetate (100 mg, 0.23 mmol), 1-tetradecyne (66 mg, 0.34 mmol), copper(I) bromide (4.5 mg, 0.031 mmol) and palladium tetrakis(triphenylphosphine) (11 mg, 0.0095 mmol) in Et$_3$N (1 mL) was heated at 90° C. for 75 min. After cooling to rt, the reaction mixture was diluted with an aqueous HCl solution (1N, 10 mL) and extracted with Et$_2$O (2×20 mL). The combined organic layers were dried over MgSO$_4$ and the solvent was removed under reduce pressure. The residue was purified by flash chromatography (cyclohex./Et$_2$O 4:1) to give the title compound as yellow oil (63 mg, 50%). $^1$H NMR (CDCl$_3$, 300 MHz) δ 7.61 (m, 2H), 7.33 (m, 4H), 7.14 (m, 2H), 4.51 (s, 1H), 4.47 (s, 1H), 4.34 (m, 4H), 2.40 (m, 2H), 1.58-1.26 (m, 23H), 0.88 (m, 3H). HPLC (Condition A), Rt: 8.21 min (HPLC purity: 99.3%).

Step d) Formation of the oxo{(4-tetradec-1-ynylbenzyl)[4-(trifluoromethyl)benzyl]-amino}acetic acid The same procedure as employed in the preparation of Example 1 (step e) using ethyl oxo{(4-tetradec-1-ynylbenzyl)[4-(trifluoromethyl)benzyl]amino}acetate gave the title compound as a pale yellow oil (77%). $^1$H NMR (CDCl$_3$, 300 MHz) δ 7.60 (m, 2H), 7.34 (m, 4H), 7.12 (m, 2H), 5.01 (s, 1H), 4.95 (s, 1H), 4.57 (s, 1H), 4.53 (s, 1H), 2.38 (m, 2H), 1.57 (m, 2H), 1.41 (m, 2H), 1.24 (brs, 16H), 0.86 (m, 3H). M$^-$(LC/MS(ESI)): 528.0. HPLC (Condition A), Rt: 7.85 min (HPLC purity: 98%).

Example 227

{(4-dodec-1-ynylbenzyl)[4-(trifluoromethyl)benzyl] amino}(oxo)acetic acid

Step a) Formation of ethyl{(4-dodec-1-ynylbenzyl) [4-(trifluoromethyl)benzyl]amino)}(oxo)acetate The same procedure as employed in the preparation of Example 226 (step c) using 1-dodecyne gave the title compound as a pale yellow oil (21%). $^1$H NMR (CDCl$_3$, 300 MHz) δ 7.58 (m, 2H), 7.32 (m, 4H), 7.13 (d, 1H, J=8.2 Hz), 7.09 (d, 1H, J=8.1 Hz), 4.48 (s, 1H), 4.44 (s, 1H), 4.31 (m, 4H), 2.38 (dt, 2H, J=7.0, 1.3 Hz), 1.57 (m, 2H), 1.41 (m, 2H), 1.33-1.24 (m, 15H), 0.85 (t, 3H, J=6.7 Hz). HPLC (Condition A), Rt: 7.87 min (HPLC purity: 99.9%).

Step b) Preparation of {(4-dodec-1-ynylbenzyl)[4-(trifluoromethyl)benzyl]amino}(oxo)-acetic acid The same procedure as employed in the preparation of Example 1 (step e) using ethyl{(4-dodec-1-ynylbenzyl)[4-(trifluoromethyl)benzyl]amino}(oxo)acetate gave the title compound as a pale yellow oil (95%). $^1$H NMR (CDCl$_3$, 300 MHz) δ 8.78 (brs, 1H), 7.53 (m, 2H), 7.28 (m, 4H), 7.08 (m, 2H), 4.81 (brs, 1H), 4.74 brs, 1H), 4.47 (m, 2H), 2.36 (m, 2H), 1.57 (m, 2H), 1.41 (m, 2H), 1.25 (brs, 12H), 0.86 (t, 3H, J=7.0). M$^-$(LC/MS(ESI)): 499.9. HPLC (Condition A), Rt: 7.36 min (HPLC purity: 99.3%).

Example 228

{{4-[(dodecylamino)carbonyl]benzyl}[4-(trifluoromethyl)phenyl]amino}-(oxo)acetic acid Step a) Preparation of N-dodecyl-4-({[4-(trifluoromethyl)phenyl]amino}methyl)benzamide To a solution of N-dodecyl-4-formyl-benzamide (Example 10, step a) (1.00 g, 3.115 mmol), acetic acid (0.227 g, 3.78 mmol) and 4-trifluoromethyl-phenylamine (0.609 g, 3.78 mmol) in DCE (25 mL) was added at once NaBH(OAc)$_3$ (0.801 g, 3.78 mmol). The resulting mixture was stirred overnight at 70° C. A saturated solution of NaHCO$_3$ (10 mL) was added to the reaction mixture, the aqueous layer was separated and extracted with DCM (3×50 mL). The combined organic layers were dried over MgSO$_4$, filtered and concentrated to give a colorless oil. This crude product was purified by column chromatography over silica gel (4/1 c-Hex/AcOEt to 3/1 in about 0.5 h) to give the title compound as a colorless oil (0.824 g, 63%). $^1$H NMR (CD$_3$OD, 300 MHz) δ 7.74 (d, 2H, J=8.3 Hz), 7.43 (d, 2H, J=8.3 Hz), 7.29 (d, 2H, J=8.7 Hz), 6.63 (d, 2H, J=8.3 Hz), 4.42 (s, 2H), 3.35 (m, 2H), 1.58 (m, 2H), 1.27 (m, 18H), 0.88 (m, 3H). M$^+$(LC/MS(ESI)): 463.0; M$^-$(LC/MS(ESI)): 461.3. HPLC (Condition A), Rt: 6.84 min (HPLC purity: 98.5%).

Step b) Preparation of ethyl{{4-[(dodecylamino) carbonyl]benzyl}[4-(trifluoromethyl) phenyl]amino} (oxo)acetate The same procedure as employed for the preparation of Example 1 (step b) using N-dodecyl-4-({[4-(trifluoromethyl) phenyl]amino}methyl)benzamide gave the title compound as a colorless oil (56%). $^1$H NMR (CDCl$_3$, 300 MHz) δ 7.68 (m, 2H), 7.57 (m, 2H), 7.27 (m, 2H), 7.17 (m, 2H), 6.04 (s, 1H), 4.59 (s, 2H), 4.03 (m, 2H), 3.41 (m, 2H), 1.55 (m, 2H), 1.24 (m, 18H), 1.00 (m, 3H), 0.87 (m, 3H). M$^+$(APCI): 563.2; M$^-$(APCI): 561.2. HPLC (Condition A), Rt: 6.74 min (HPLC purity: 98.7%).

Step c) Preparation of {{4-[(dodecylamino)carbonyl] benzyl}[4-(trifluoromethyl)phenyl]amino}(oxo)acetic acid The same procedure as employed in the preparation of Example 1 (step c) using ethyl{{4-[(dodecylamino)carbonyl] benzyl}[4-(trifluoromethyl)phenyl]amino}(oxo)acetate and lithium hydroxide dihydrate gave the title compound as a white solid (89%). $^1$H NMR (DMSO-d$_6$, 300 MHz) δ 8.39 (s, 1H), 7.77 (m, 4H), 7.45 (d, 2H, J=7.9 Hz), 7.27 (d, 2H, J=7.5 Hz), 5.07 (s, 2H), 3.20 (m, 2H), 1.48 (m, 2H), 1.28 (m, 18H), 0.84 (t, 3H, J=5.9 Hz). M$^-$(APCI): 489.2 (M-CO$_2$). HPLC (Condition A), Rt: 6.44 min (HPLC purity: 97.4%).

Example 229

[{4-[(dodecylamino)carbonyl]benzyl}(2-methoxyphenol)amino](oxo)acetic acid

The same procedure as employed in the preparation of Example 28 using dodecylamine in step a, 4-chloromethylbenzoyl chloride in step b and 2-methoxyaniline in step c gave the title compound as a yellow oil (1.9 mg). M$^-$(LC/MS (ESI)): 495.2; M$^+$(LC/MS(ESI)): 497.2 HPLC (Condition A), Rt: 6.00 min (HPLC purity: 90.2%).

Example 230

((1,2-diphenylethyl){4-[(dodecylamino)carbonyl] benzyl}amino)(oxo)acetic acid

The same procedure as employed in the preparation of Example 28 using dodecylamine in step a, 4-chloromethylbenzoyl chloride in step b and 1,2-diphenylethylamine in step c gave the title compound as a colorless oil (6.3 mg). M$^-$(LC/MS(ESI)): 570.5; M$^+$(LC/MS(ESI)): 571.0. HPLC (Condition A), Rt: 6.60 min (HPLC purity: 94.4%).

Example 231

N-(carboxycarbonyl)-N-{4-[(dodecylamino)carbonyl]benzyl}-L-phenylalanine

The same procedure as employed in the preparation of Example 28 using dodecylamine in step a, 4-chloromethylbenzoyl chloride in step b and L-phenylalanine t-butyl ester hydrochloride in step c gave the title compound as a yellow oil (8.0 mg). M$^-$(LC/MS(ESI)): 537.0; M$^+$(LC/MS(ESI)): 539.2. HPLC (Condition A), Rt: 5.82 min (HPLC purity: 89.2%).

Example 232

[{4-[(dodecylamino)carbonyl]benzyl}(3-phenoxyphenyl)amino](oxo)acetic acid

The same procedure as employed in the preparation of Example 28 using dodecylamine in step a, 4-chloromethylbenzoyl chloride in step b and 3-phenoxyaniline in step c gave the title compound as a yellow oil (2.4 mg). M$^+$(LC/MS (ESI)): 559.2. HPLC (Condition A), Rt: 6.50 min (HPLC purity: 89.9%).

Example 233

[{4-[(dodecylamino)carbonyl]benzyl}(2-isopropoxyphenyl)amino]-(oxo)acetic acid

The same procedure as employed in the preparation of Example 28 using dodecylamine in step a, 4-chloromethylbenzoyl chloride in step b and 2-isopropoxy aniline in step c gave the title compound as a colorless oil (6.7 mg). M$^-$(LC/MS(ESI)): 523.2; M$^+$(LC/MS(ESI)): 524.2. HPLC (Condition A), Rt: 6.33 min (HPLC purity: 91.7%).

Example 234

[{4-[(dodecylamino)carbonyl]benzyl}(4-iodophenyl) amino](oxo)acetic acid

The same procedure as employed in the preparation of Example 28 using dodecylamine in step a, 4-chloromethylbenzoyl chloride in step b and 4-iodoaniline in step c gave the title compound as a colorless oil (7.2 mg). M$^+$(LC/MS(ESI)): 592.7. HPLC (Condition A), Rt: 6.34 min (HPLC purity: 81.9%).

Example 235

{{4-[(dodecylamino)carbonyl]benzyl}[3-fluoro-4-(trifluoromethyl)-benzyl]amino}(oxo)acetic acid The same procedure as employed in the preparation of Example 28 using dodecylamine in step a, 4-chloromethylbenzoyl chloride in step b and 3-fluoro-4-(trifluoromethyl) benzylamine in step c gave the title compound as a colorless oil (2.7 mg). M$^-$(LC/MS(ESI)): 564.9; M$^+$(LC/MS(ESI)): 566.9. HPLC (Condition A), Rt: 6.58 min (HPLC purity: 88.5%).

Example 236

((3-chloro-2-methylphenyl){4-[(dodecylamino)carbonyl]benzyl}-amino)(oxo)acetic acid The same procedure as employed in the preparation of Example 28 using dodecylamine in step a, 4-chloromethylbenzoyl chloride in step b and 3-chloro-2-methylaniline in step c gave the title compound as a colorless oil (3.3 mg). M⁺(LC/MS(ESI)): 515.5. HPLC (Condition A), Rt: 6.38 min (HPLC purity: 92.9%).

Example 237

4'-((carboxycarbonyl){4-[(dodecylamino)carbonyl]benzyl}amino)-1,1'-biphenyl-2-carboxylic acid The same procedure as employed in the preparation of Example 28 using dodecylamine in step a, 4-chloromethylbenzoyl chloride in step b and 4-(2-methoxycarbonylphenyl)aniline in step c gave the title compound as a white solid (3.9 mg). M⁻(LC/MS(ESI)): 585.5; M⁺(LC/MS(ESI)): 586.9. HPLC (Condition A), Rt: 5.96 min (HPLC purity: 67.6%).

Example 238

((2,4-dichlorobenzyl){4-[(dodecylamino)carbonyl]benzyl}amino)(oxo)acetic acid

The same procedure as employed in the preparation of Example 28 using dodecylamine in step a, 4-chloromethylbenzoyl chloride in step b and 2,4-dichlorobenzylamine in step c gave the title compound as a colorless oil (7.1 mg). M⁻(LC/MS(ESI)): 546.9; M⁺(LC/MS(ESI)): 549. HPLC (Condition A), Rt: 6.70 min (HPLC purity: 92.1%).

Example 239

[{4-[(dodecylamino)carbonyl]benzyl}(1-phenylpropyl)amino](oxo)acetic acid

The same procedure as employed in the preparation of Example 28 using dodecylamine in step a, 4-chloromethylbenzoyl chloride in step b and I-phenyl-propylamine in step c gave the title compound as a colorless oil (3.6 mg). M⁻(LC/MS(ESI)): 507.1; M⁺(LC/MS(ESI)): 509.2. HPLC (Condition A), Rt: 6.41 min (HPLC purity 95.2%).

Example 240

([2-(4-chlorophenyl)propyl]{4-[(dodecylamino)carbonyl]benzyl}amino)-(oxo)acetic acid The same procedure as employed in the preparation of Example 28 using dodecylamine in step a, 4-chloromethylbenzoyl chloride in step b and 2-(4-chloro-phenyl)-propylamine hydrochloride in step c gave the title compound as a colorless oil (8.1 mg). M⁻(LC/MS(ESI)): 541.0; M⁺(LC/MS (ESI)): 543.0. HPLC (Condition A), Rt: 6.67 min (HPLC purity: 86.2%).

Example 241

[{4-[(dodecylamino)carbonyl]benzyl}(4-isopropoxyphenyl)amino]-(oxo)acetic acid

The same procedure as employed in the preparation of Example 28 using dodecylamine in step a, 4-chloromethylbenzoyl chloride in step b and 4-isopropoxyaniline in step c gave the title compound as a colorless oil (5.8 mg). M⁺(LC/MS(ESI)): 525.2. HPLC (Condition A), Rt: 6.36 min (HPLC purity: 77.3%).

Example 242

([4-(benzyloxy)phenyl]{4-[(dodecylamino)carbonyl]benzyl}amino)-(oxo)acetic acid

The same procedure as employed in the preparation of Example 28 using dodecylamine in step a, 4-chloromethylbenzoyl chloride in step b and 4-benzyloxyaniline hydrochloride in step c gave the title compound as a colorless oil (4.8 mg). M⁻(LC/MS(ESI)): 571.0; M⁺(LC/MS(ESI)): 573.5. HPLC (Condition A), Rt: 6.54 min (HPLC purity: 71.9%).

Example 243

{{4-[(dodecylamino)carbonyl]benzyl}[2-(trifluoromethyl)benzyl]amino}-(oxo)acetic acid The same procedure as employed in the preparation of Example 28 using dodecylamine in step a, 4-chloromethylbenzoyl chloride in step b and 2-(trifluoromethyl)benzylamine in step c gave the title compound as a white solid (4.7 mg). M⁻(LC/MS(ESI)): 547.2; M⁺(LC/MS(ESI)): 549.2. HPLC (Condition A), Rt: 6.52 min (HPLC purity: 94.8%).

Example 244

[{4-[(dodecylamino)carbonyl]benzyl}(2-methoxybenzyl)amino](oxo)acetic acid

The same procedure as employed in the preparation of Example 28 using dodecylamine in step a, 4-chloromethylbenzoyl chloride in step b and 2-methoxybenzylamine in step c gave the title compound as a colorless oil (3.9 mg). M⁻(LC/MS(ESI)): 509.1; M⁺(LC/MS(ESI)): 511.0. HPLC (Condition A), Rt: 6.20 min (HPLC purity: 78.4%).

Example 245

([(1R)-1-(4-chlorophenyl)ethyl]{4-[(dodecylamino)carbonyl]benzyl}-amino)(oxo)acetic acid The same procedure as employed in the preparation of Example 28 using dodecylamine in step a, 4-chloromethylbenzoyl chloride in step b and (1R)-1-(4-chlorophenyl)ethanamine in step c gave the title compound as a colorless oil (3.0 mg). M⁻(LC/MS(ESI)): 527.0; M⁺(LC/MS(ESI)): 529. HPLC (Condition A), Rt: 6.50 min (HPLC purity: 93.4%).

Example 246

((3,4-dichlorobenzyl){4-[(dodecylamino)carbonyl]benzyl}amino)(oxo)acetic acid

The same procedure as employed in the preparation of Example 28 using dodecylamine in step a, 4-chloromethylbenzoyl chloride in step b and 3,4-dichlorobenzylamine in step c gave the title compound as a colorless oil (8.6 mg). M⁻(LC/MS(ESI)): 546.9; M⁺(LC/MS(ESI)): 550.7. HPLC (Condition A), Rt: 6.65 min (HPLC purity: 91.6%).

Example 247

((1-benzothien-3-ylmethyl){4-[(dodecylamino)carbonyl]benzyl}-amino)(oxo)acetic acid The same procedure as employed in the preparation of Example 28 using dodecylamine in step a, 4-chloromethylbenzoyl chloride in step b and benzo[b]thiophen-3-ylmethylamine in step c gave the title compound as a colorless oil (5.3 mg). M⁻(LC/MS(ESI)): 535.0; M⁺(LC/MS(ESI)): 536.9. HPLC (Condition A), Rt: 6.48 min (HPLC purity: 87.9%).

Example 248

([2-(2,6-dichlorophenyl)ethyl]{4-[(dodecylamino)carbonyl]-benzyl}amino)-(oxo)acetic acid The same procedure as employed in the preparation of Example 28 using dodecylamine in step a, 4-chloromethylbenzoyl chloride in step b and 2,6-dichlorophenethylamine in step c gave the title compound as a colorless oil (5.1 mg). M⁻(LC/MS(ESI)): 560.9; M⁺(LC/MS(ESI)): 565.0. HPLC (Condition A), Rt: 6.52 min (HPLC purity: 87.0%).

Example 249

({4-[(dodecylamino)carbonyl]benzyl}{2-[3-(trifluoromethyl)phenyl]ethyl}amino)(oxo)acetic acid The same procedure as employed in the preparation of Example 28 using dodecylamine in step a, 4-chloromethylbenzoyl chloride in step b and 2-(3-trifluormethylphenyl)ethylamine in step c gave the title compound as a yellow oil (6.1 mg). M⁻(LC/MS(ESI)): 561.0; M⁺(LC/MS(ESI)): 563.7. HPLC (Condition A), Rt: 6.59 min (HPLC purity: 83.9%).

Example 250

{{4-[(dodecylamino)carbonyl]benzyl}[2-(3-fluorophenyl)ethyl]amino}-(oxo)acetic acid The same procedure as employed in the preparation of Example 28 using dodecylamine in step a, 4-chloromethylbenzoyl chloride in step b and 3-fluorophenethylamine in step c gave the title compound as a white solid (4.1 mg). M⁻(LC/MS(ESI)): 511.0; M⁺(LC/MS(ESI)): 513. HPLC (Condition A), Rt: 6.30 min (HPLC purity: 84.2%).

Example 251

([(1S)-1-(4-chlorophenyl)ethyl]{4-[(dodecylamino)carbonyl]-benzyl}-amino)(oxo)acetic acid The same procedure as employed in the preparation of Example 28 using dodecylamine in step a, 4-chloromethylbenzoyl chloride in step b and (1S)-1-(4-chlorophenyl)ethanamine in step c gave the title compound as a colorless oil (12 mg). M⁻(LC/MS(ESI)): 527.0; M⁺(LC/MS(ESI)): 529. HPLC (Condition A), Rt: 6.50 min (HPLC purity: 93.0%).

Example 252

{{4-[(dodecylamino)carbonyl]benzyl}[(1S)-1-phenylethyl]amino}(oxo)-acetic acid

The same procedure as employed in the preparation of Example 28 using dodecylamine in step a, 4-chloromethylbenzoyl chloride in step b and (1S)-1-phenylethanamine in step c gave the title compound as a pale yellow powder (96 mg). M⁻(LC/MS(ESI)): 493.3; M⁺(LC/MS(ESI)): 495.2. HPLC (Condition A), Rt: 6.25 min (HPLC purity: 92.2%).

Example 253

{{4-[(dodecylamino)carbonyl]benzyl}[(1R)-1-phenylethyl]amino}(oxo)-acetic acid

The same procedure as employed in the preparation of Example 28 using dodecylamine in step a, 4-chloromethylbenzoyl chloride in step b and (1R)-1-phenylethanamine in step c gave the title compound as a pale yellow oil (43 mg). M⁻(LC/MS(ESI)): 493.0; M⁺(LC/MS(ESI)): 495.2. HPLC (Condition A), Rt: 6.26 min (HPLC purity: 91.3%).

Example 254

([3-(benzyloxy)phenyl]{4-[(dodecylamino)carbonyl]benzyl}-amino)(oxo)acetic acid

The same procedure as employed in the preparation of Example 28 using dodecylamine in step a, 4-chloromethylbenzoyl chloride in step b and 3-(benzyloxy)aniline in step c gave the title compound as a white solid (10.4 mg). M⁺(LC/MS(ESI)): 572.9. HPLC (Condition A), Rt: 6.53 min (HPLC purity: 89.2%).

Example 255

N-(carboxycarbonyl)-N-{4-[(dodecylamino)carbonyl]benzyl}-D-phenylalanine

The same procedure as employed in the preparation of Example 28 using dodecylamine in step a, 4-chloromethylbenzoyl chloride in step b and D-phenylalanine t-butyl ester hydrochloride in step c gave the title compound as a colorless solid (8.0 mg). M⁻(LC/MS(ESI)): 537.0; M⁺(LC/MS(ESI)): 539.0. HPLC (Condition A), Rt: 5.83 min (HPLC purity: 80.3%).

Example 256

{{4-[(dodecylamino)carbonyl]phenyl}[4-(trifluoromethyl)benzyl]-amino}(oxo)acetic acid Step a) Preparation of N-dodecyl-4-{[4-(trifluoromethyl)benzyl]amino}benzamide The same procedure as employed in the preparation of Example 228 (step a) using 4-amino-N-dodecylbenzamide (Example 150, step b) and 4-(trifluoromethyl)benzaldehyde gave the title compound as colorless oil (74%). ¹H NMR (DMSO-$d_6$, 300 MHz) δ 7.68 (d, 2H, J=8.3 Hz), 7.47-7.60 (m, 4H), 6.53 (d, 2H, J=8.6 Hz), 4.41 (s, 2H), 3.31 (s, 2H), 3.14 (t, 2H, J=6.8 Hz), 1.35-1.51 (m, 2H), 1.11-1.32 (m, 18H), 0.83 (t, 3H, J=6.7 Hz). HPLC (Condition A), Rt: 7.00 min (HPLC purity: 91.2%).

Step b) Preparation of ethyl{{4-[(dodecylamino)carbonyl]phenyl}[4-(trifluoromethyl)benzyl]amino}(oxo)acetate The same procedure as employed in the preparation of Example 1 (step b) using N-dodecyl-4-{[4-(trifluoromethyl)benzyl]amino}benzamide gave the title compound as colorless oil (93%).

Step c) Preparation of {{4-[(dodecylamino)carbonyl]phenyl}[4-(trifluoromethyl)benzyl]amino}(oxo)acetic acid The same procedure as employed in the preparation of Example 1 (step e) using ethyl{{4-[(dodecylamino)carbonyl]phenyl}[4-(trifluoromethyl)benzyl]amino}(oxo)acetate gave the title compound as colorless oil (96%). ¹H NMR (DMSO-$d_6$, 300 MHz) δ 8.5 (br s, 1H), 7.78 (d, 2H, J=8.3 Hz), 7.68 (d, 2H, J=7.9 Hz), 7.42 (d, 2H, J=7.9 Hz), 7.31 (d, 2H, J=8.3 Hz), 5.08 (s, 2H), 3.15-3.22 (m, 2H), 1.37-1.52 (m, 2H), 1.11-1.32

(m, 18H), 0.83 (t, 3H, 3=6.7 Hz). M⁺(LC/MS(ESI)): 535.0. HPLC (Condition A), Rt: 6.73 min (HPLC purity: 100%).

Example 257

{{4-[(dodecylamino)carbonyl]phenyl}[4-(trifluoromethyl)benzyl]amino}-(oxo)acetic acid. N-methyl-D-glucamine (i.e. 1-deoxy-1-(methylamino)glucitol) salt The same procedure as employed in the preparation of Example 2 using {{4-[(dodecylamino)carbonyl]phenyl}[4-(trifluoromethyl)benzyl]amino}(oxo)acetic acid and N-methyl-D-glucamine gave the title compound as a white powder (97%).

M⁺(LC/MS(ESI)): 535.4. HPLC (Condition A), Rt: 6.30 min (HPLC purity: 98.9%). Analysis calculated for $C_{29}H_{37}F_3N_2O_4 \cdot C_7H_{17}NO_5 \cdot 1H_2O$: C, 57.82; H, 7.55; N, 5.62%. Found: C, 57.87; H, 7.58; N, 5.62%.

Example 258 oxo{{1-[4-(trifluoromethyl)phenyl]ethyl}[4-(3-undecyl-1,2,4-oxadiazol-5-yl)benzyl]amino}acetic acid

Step a) Preparation of tert-butyl 4-({[(1-aminododecylidene)amino]oxy}carbonyl)benzylcarbamate At 0° C., to a solution of boc-(4-aminomethyl)-benzoic acid (5.000 g, 19.9 mmol), NMM (2.214 g, 21.89 mmol) in anhydrous THF (50 mL) was added dropwise isobutyl chloroformate (2.853 g, 20.89 mmol). The resulting mixture was stirred for 10 min, then N-hydroxydodecanimidamide (Example 23, step a) (6.398 g, 29.85 mmol) was added at once. After 1 h the ice-water bath was removed and the mixture was stirred for 14 h at rt. An aqueous solution of HCl (1N, 50 mL) was added and the mixture was extracted with AcOEt (3×70 mL). The combined organic layers were washed with water (150 mL), dried over MgSO₄ and evaporated to give a white solid (9.2 g). This crude product was purified by flash chromatography over silica gel (c-Hex/AcOEt 4/1) to give the title compound as a white solid (7.91 g, 89%). ¹H NMR (CDCl₃, 300 MHz) δ 7.80 (d, 2H, J=8.0 Hz), 7.50 (t, 1H, J=5.7 Hz) 7.32 (d, 2H, J=8.0 Hz), 6.42 (br s, 1H), 6.27 (br s, 1H), 4.20 (s, 1H), 4.18 (s, 1H), 1.91-2.15 (m, 2H), 1.08-1.66 (m, 27H), 0.86 (t, 3H, J=6.9 Hz). M⁺(LC/MS(ESI)): 448.4; M⁻(LC/MS (ESI)): 446.3. HPLC (Condition A), Rt: 5.74 min (HPLC purity: 96.7%).

Step b) Preparation of tert-butyl 4-(3-undecyl-1,2,4-oxadiazol-5-yl)benzylcarbamate The same procedure as employed in the preparation of Example 23 (step e) using tert-butyl 4-({[(1-aminododecylidene)amino]oxy}carbonyl)benzylcarbamate gave the title compound as a colorless oil (78%). ¹H NMR (CDCl₃, 300 MHz) δ 8.10 (d, 2H, J=7.9 Hz), 7.44 (d, 2H, J=7.9 Hz), 4.97 (br s, 1H), 4.41 (s, 2H), 2.81 (t, 2H, J=7.7 Hz), 1.71-1.91 (m, 27H), 0.89 (t, 3H, J=6.8 Hz). HPLC (Condition A), Rt: 7.06 min (HPLC purity: 99.4%).

Step c) Preparation of 1-[4-(3-undecyl-1,2,4-oxadiazol-5-yl)phenyl]methanamine The same procedure as employed in the preparation of Example 23 (step f) using tert-butyl 4-(3-undecyl-1,2,4-oxadiazol-5-yl)benzylcarbamate gave the hydrochloride salt of the title compound as a white solid (98%). A suspension of this solid (2.085 g, 5.70 mmol) in AcOEt (100 mL) was washed twice with a saturated aqueous solution of NaHCO₃ (50 mL).

The organic layer was dried over MgSO₄ and evaporated to give the title compound as a white solid (1.878 g). ¹H NMR (DMSO-d₆, 300 MHz) δ 8.00 (d, 2H, J=8.3 Hz), 7.56 (d, 2H, J=8.3 Hz), 3.79 (s, 2H), 2.72 (t, 2H, J=7.3 Hz), 1.60-1.76 (m, 2H), 1.10-1.40 (m, 18H), 0.83 (t, 3H, J=7.0 Hz). M⁺(LC/MS (ESI)): 330.3. HPLC (Condition A), Rt: 4.55 min (HPLC purity: 99.8%).

Step d) Preparation of N-{1-[4-(trifluoromethyl)phenyl]ethyl}-N-[4-(3-undecyl-1,2,4-oxadiazol-5-yl)benzyl]amine The same procedure as employed in the preparation of Example 223 (step b) using 1-[4-(3-undecyl-1,2,4-oxadiazol-5-yl)phenyl]methanamine gave the title compound as a white solid (84%). ¹H NMR (CDCl₃, 300 MHz) δ 8.08 (d, 2H, J=8.3 Hz), 7.63 (d, 2H, J=8.3 Hz), 7.41 (d, 2H, J=8.0 Hz), 7.46 (d, 2H, J=8.0 Hz), 3.90 (q, 1H, J=6.7 Hz), 3.72 (s, 1H), 3.70 (s, 1H), 2.81 (t, 2H, J=7.7 Hz), 1.75-1.90 (m, 2H), 1.19-1.49 (m, 19H), 0.89 (t, 3H, J=6.8 Hz) HPLC (Condition A), Rt: 5.42 min (HPLC purity: 93.2%).

Step e) Preparation of ethyl oxo{{1-[4-(trifluoromethyl)phenyl]ethyl}[4-(3-undecyl-1,2,4-oxadiazol-5-yl)benzyl]amino}acetate The same procedure as employed for the preparation of Example 1 (step b) using N-{1-[4-(trifluoromethyl)phenyl]ethyl}-N-[4-(3-undecyl-1,2,4-oxadiazol-5-yl)benzyl]amine gave the title compound as a colorless oil (93%). HPLC (Condition A), Rt: 7.84 min (HPLC purity: 99.9%).

Step f) Preparation of oxo{{1-[4-(trifluoromethyl)phenyl]ethyl}[4-(3-undecyl-1,2,4-oxadiazol-5-yl)benzyl]amino}acetic acid The same procedure as employed in the preparation of Example 1 (step e) using ethyl oxo{{1-[4-(trifluoromethyl)phenyl]ethyl}[4-(3-undecyl-1,2,4-oxadiazol-5-yl)benzyl]amino}acetate gave the title compound as a white solid (91%). ¹H NMR ((DMSO-d₆, 300 MHz) δ 7.97-7.11 (m, 8H), 5.56 (q, 0.35H, J=7.1 Hz), 5.15 (q, 0.65H, J=6.8 Hz), 4.31-4.71 (m, 2H), 2.65-2.79 (m, 2H), 1.43-1.77 (m, 5H), 1.06-1.38 (m, 16H), 0.83 (t, 3H, J=6.8 Hz). M⁻(LC/MS(ESI)): 571.9. HPLC (Condition A), Rt: 6.93 (HPLC purity: 99.9%)

Example 259 oxo{{1-[4-(trifluoromethyl)phenyl]ethyl}[4-(3-undecyl-1,2,4-oxadiazol-5-yl)benzyl]amino}acetic acid N-methyl-D-glucamine (i.e. 1-deoxy-1-(methylamino)glucitol) salt The same procedure as employed in the preparation of Example 2 using oxo{{1-[4-(trifluoromethyl)phenyl]ethyl}[4-(3-undecyl-1,2,4-oxadiazol-5-yl)benzyl]amino}acetic acid and N-methyl-D-glucamine gave the title compound as a white powder (99%). M⁻(LC/MS(ESI)): 572.5. HPLC (Condition A), Rt: 6.90 min (HPLC purity: 99.4%).

Example 260

{[(2-butyl-1-benzofuran-3-yl)methyl]{4-[(dodecylamino)carbonyl]benzyl}-amino)(oxo)acetic acid

Step a) Formation of 2-butyl-1-benzofuran-3-carbaldehyde

To a solution of DMF (59 g, 0.805 mol) in anhydrous DCM (300 mL) was added slowly at 0° C. under N₂ atmosphere phosphorous oxy-chloride (123 g, 0.84 mol). The mixture was stirred at rt for 2 h. To this was added slowly 2-butyl-1-benzofuran (35 g, 0.21 mol) in anhydrous DCM (100 mL). The reaction mixture was slowly heated to 60° C. for 72 h, cooled to rt and poured into ice and extracted with EtOAc. The organic layer was washed with water, brine and dried over MgSO$_4$. The solvent was removed under vacuum and the crude product purified by column chromatography over silica gel (PetEther/EtOAc) to give 2-butyl-1-benzofuran-3-carbaldehyde (30 g, 74%) as a light brown liquid.

Step b) Formation of 2-butyl-1-benzofuran-3-carbaldehyde oxime

To a mixture of 2-butyl-1-benzofuran-3-carbaldehyde (25 g, 0.124 mol) and sodium acetate (12.2 g, 0.124 mol) in methanol (100 mL) was added hydroxylamine hydrochloride (10.3 g, 0.149 mol) in water (25 mL) at 0° C. The mixture was stirred at rt for 2 h. Water (300 mL) was added to the reaction mixture and the product was extracted with EtOAc. The organic layer was dried and concentrated under vacuum to give crude 2-butyl-1-benzofuran-3-carbaldehyde oxime (25 g, 93%) as a light brown liquid.

Step c) Formation of (2-butyl-1-benzofuran-3-yl)methylamine hydrochloride

To a suspension of LiAlH$_4$ (6.6 g, 0.173 mol) in anhydrous THF (400 mL) was added a solution of 2-butyl-1-benzofuran-3-carbaldehyde oxime (25 g, 0.11 mol) in dry THF (100 mL) drop-wise at 0° C. under N$_2$. The reaction mixture was stirred at rt for 18 h and then quenched with an aqueous NaOH solution (30 mL, 10%) at −15° C. The solid was filtered off, washed with THF and the filtrates were concentrated. The residue was dissolved in DCM (100 mL), washed with water, brine and dried over MgSO$_4$. The solvent was removed and the resulting crude product was dissolved in Et$_2$O. A saturated HCl solution of ether was added while a white solid precipitated out. The white solid was filtered, washed with EtOAc to give the title compound as a white solid (15 g, 54%). $^1$H NMR (DMSO-d$_6$, 300 MHz) δ 8.45 (br s, 3H), 7.82 (m, 1H), 7.52 (m, 1H), 7.27 (m, 2H), 2.85 (t, 2H, J=7.5 Hz), 1.72-1.50 (m, 2H), 1.81-1.51 (m, 2H), 1.43-1.29 (m, 2H), 0.83 (t, 3H, J=7.3 Hz)

Step d) Formation of 4-({[(2-butyl-1-benzofuran-3-yl)methyl]amino}methyl)-N-dodecylbenzamide The same procedure as employed in the preparation of Example 1 (step a) but using (2-butyl-1-benzofuran-3-yl)methylamine hydrochloride, triethylamine and N-dodecyl-4-formylbenzamide gave the title compound as a colorless oil (59%). $^1$H NMR (CDCl$_3$, 300 MHz) δ 7.76 (m, 2H), 7.58 (m, 1H), 7.42 (m, 3H), 7.29-7.18 (m, 2H), 6.23 (m, 1H), 3.87 (m, 4H), 3.46 (m, 2H), 2.75 (t, 2H, J=7.5 Hz), 1.77-1.56 (m, 5H), 1.45-1.23 (m, 20H), 0.98-0.86 (m, 6H). HPLC (Condition A), Rt: 5.49 min (HPLC purity: 97.4%).

Step e) Formation of ethyl([[(2-butyl-1-benzofuran-3-yl)methyl]{4-[(dodecylamino)carbonyl]benzyl}amino)(oxo)acetate The same procedure as employed in the preparation of Example 15 (step b) but using 4-({[(2-butyl-1-benzofuran-3-yl)methyl]amino}methyl)-N-dodecylbenzamide gave the title compound as a colorless oil (83%). $^1$H NMR (CDCl$_3$, 300 MHz) δ 7.71 (d, 1.3H, J=8.1 Hz), 7.62 (d, 0.7H, J=8.1 Hz), 7.48-7.30 (m, 2H), 7.24-7.07 (m, 4H), 6.18 (m, 1H), 4.55 (s, 1.3H), 4.45 (s, 0.7H), 4.40-4.18 (m, 4H), 3.37 (m, 2H), 2.48-2.5 (m, 2H), 1.61-1.45 (m, 4H), 1.35-1.10 (m, 23H), 0.88-0.72 (m, 6H). HPLC (Condition A), Rt: 7.34 min (HPLC purity: 99.7%).

Step f) Formation of ([(2-butyl-1-benzofuran-3-yl)methyl]{4-[(dodecylamino)carbonyl]benzyl}amino)(oxo)acetic acid The same procedure as employed in the preparation of Example 1 (step e) but using ethyl ([(2-butyl-1-benzofuran-3-yl)methyl]{4-[(dodecylamino)carbonyl]benzyl}amino)(oxo)acetate gave the title compound as a white solid (99%). $^1$H NMR (CDCl$_3$, 300 MHz) δ 10.6 (m, 1H), 7.58 (t, 2H, J=8.0 Hz), 7.40-7.30 (m, 2H), 7.18-6.95 (m, 4H), 6.65 (m, 0.7H), 6.50 (m, 0.3H), 4.60-4.46 (m, 2H), 4.38-4.21 (m, 2H), 3.36 (m, 2H), 2.39 (m, 2H), 1.54 (m, 4H), 1.17 (m, 20H), 0.80 (m, 6H) M$^-$(LC/MS(ESI)): 575.2. HPLC (Condition A), Rt: 7.22 min (HPLC purity: 99.7%).

Example 261

{(1-{4-[(dodecylamino)carbonyl]phenyl}ethyl)[4-(trifluoromethyl)benzyl]-amino}(oxo)acetic acid Step a) Formation of 4-acetyl-N-dodecylbenzamide The same procedure as employed in the preparation of Example 10 (step a) but using 4-acetylbenzoic acid and dodecylamine gave the title compound as a white solid (54%). $^1$H NMR (CDCl$_3$, 300 MHz) δ 8.00-7.90 (m, 2H), 7.85-7.71 (m, 2H), 6.05 (br s, 1H), 3.41-3.30 (m, 2H), 2.56 (s, 1.5H), 2.54 (s, 1.5H), 1.63-1.73 (m, 2H), 1.72-1.05 (m, 18H), 0.78 (m, 3H). M$^-$(LC/MS(ESI)): 330.4; M$^+$(LC/MS(ESI)): 332.4. HPLC (Condition A), Rt: 5.87 min (HPLC purity: 99.7%).

Step b) Formation of N-dodecyl-4-(1-{[4-(trifluoromethyl)benzyl]amino}ethyl)benzamide The same procedure as employed in the preparation of Example 223 (step b) but using 4-acetyl-N-dodecylbenzamide and 4-(trifluoromethyl)benzylamine gave the title compound as a colorless oil (71%). M$^-$(LC/MS(ESI)): 489.1; M$^+$(LC/MS(ESI)): 491.5. HPLC (Condition A), Rt: 5.51 min (HPLC purity: 50.0%).

Step c) Formation of ethyl{(1-{4-[(dodecylamino)carbonyl]phenyl}ethyl)[4-(trifluoromethyl)benzyl]amino}(oxo)acetate The same procedure as employed in the preparation of Example 15 (step b) but using N-dodecyl-4-(1-{[4-(trifluoromethyl)benzyl]amino}ethyl)benzamide gave the title compound as a white foam (54%). $^1$H NMR (CDCl$_3$, 300 MHz) δ 7.70 (m, 2H), 7.64-7.41 (m, 2H), 7.39-7.30 (m, 2H), 7.28-7.12 (m, 2H), 6.09-5.90 (m, 1H), 4.67-4.37 (m, 2H), 4.30-4.08 (m, 2H), 3.50-3.38 (m, 2H), 1.68-1.48 (m, 6H), 1.43-1.10 (m, 21H), 0.88 (m, 3H). M$^+$(LC/MS(ESI)): 591.7. HPLC (Condition A), Rt: 7.24 min (HPLC purity: 99.6%).

Step d) Formation of {(1-{4-[(dodecylamino)carbonyl]phenyl}ethyl)[4-(trifluoromethyl)benzyl]amino}(oxo)acetic acid The same procedure as employed in the preparation of Example 1 (step e) but using ethyl{(1-{4-[(dodecylamino)carbonyl]phenyl}ethyl)[4-(trifluoromethyl)benzyl]amino}(oxo)acetate gave the title compound as a white solid (91%). $^1$H NMR (CD$_3$OD, 300 MHz) δ 7.75 (t, 2H, J=7.5 Hz), 7.48-7.19 (m, 6H), 5.75 (m, 0.3H), 5.28 (m, 0.7H), 4.60-4.31 (m, 2H), 3.38 (t, 2H, J=7.1 Hz), 1.66-1.56 (m, 5H), 1.36 (m, 18H), 0.90 (m, 3H). M⁻(LC/MS(ESI)): 562.6; M⁺(LC/MS (ESI)): 563.7. HPLC (Condition A), Rt: 6.68 min (HPLC purity: 98.7%).

Example 262

{(1-{4-[(dodecylamino)carbonyl]phenyl}ethyl)[4-(trifluoromethyl)-benzyl]amino}(oxo)acetic acid, N-methyl-D-glucamine (i.e. 1-deoxy-1-(methylamino)glucitol) salt The same procedure as employed in the preparation of Example 2 but using N-methyl-D-glucamine and {(1-{4 [(dodecylamino)carbonyl]phenyl}ethyl)[4-(trifluoromethyl) benzyl]amino}(oxo)acetic acid gave the title compound as a white solid (82%). M⁻(LC/MS(ESI)): 562.5; M⁺(LC/MS (ESI)): 564.1. HPLC (Condition A), Rt: 6.27 min (HPLC purity: 99.0%). Analysis calculated for $C_{31}H_{41}F_3N_2O_4 \cdot C_7H_{17}NO_5 \blacksquare 1.0H_2O$: C, 58.82; H, 7.79; N, 5.42%. Found: C, 58.92; H, 7.96; N, 5.35%.

Example 263

{(4-{[(4-octylphenyl)amino]carbonyl}benzyl)[4-(trifluoromethyl)benzyl]-amino}(oxo)acetic acid Step a) Formation of ethyl{(4-{[(4-octylphenyl) amino]carbonyl}benzyl)[4-(trifluoromethyl)benzyl] amino}(oxo)acetate The same procedure as employed in the preparation of Example 10 (step a) but using 4-({[ethoxy(oxo)acetyl][4-(trifluoromethyl)benzyl]amino}methyl)benzoic acid and 4-octylaniline gave the title compound as a colorless oil (22%). ¹H NMR (CDCl₃, 300 MHz) δ 7.89-6.60 (m, 12H), 4.48 (s, 2H), 4.44-4.21 (m, 4H), 2.65-2.36 (m, 2H), 1.68-1.40 (m, 3H), 1.38-1.08 (m, 13H), 0.81 (t, J=6.9 Hz, 3H). M⁺(LC/MS(ESI)): 597.7. HPLC (Condition A), Rt: 6.75 min (HPLC purity: 98.9%).

Step b) Formation of {(4-{[(4-octylphenyl)amino] carbonyl}benzyl)[4-(trifluoromethyl)benzyl]amino} (oxo)acetic acid The same procedure as employed in the preparation of Example 1 (step e) but using ethyl{(4-{[(4-octylphenyl) amino]carbonyl}benzyl)[4-(trifluoromethyl)benzyl]amino} (oxo)acetate gave the title compound as a brown oil (95%). ¹H NMR (CDCl₃, 300 MHz) δ 8.30 (m, 1H), 7.74 (m, 2H), 7.53 (m, 2H), 7.46 (m, 3H), 7.27-7.04 (m, 6H), 4.62-4.46 (m, 4H), 2.55 (t, 2H, J=7.5 Hz), 1.56 (m, 2H), 1.25 (m, 10H), 0.86 (t, 3H, J=6.5 Hz). M⁻(LC/MS(ESI)): 567.2; M⁺(LC/MS (ESI)): 569.6. HPLC (Condition A), Rt: 6.24 min (HPLC purity: 97.0%).

Example 264

{(3-chlorobenzyl)[4-(3-undecyl-1,2,4-oxadiazol-5-yl)benzyl]amino}-(oxo)acetic acid Step a) Formation of N-(3-chlorobenzyl)-N-[4-(3-undecyl-1,2,4-oxadiazol-5-yl)benzyl]amine The same procedure as employed in the preparation of Example 226 (step a) but using 1-[4-(3-undecyl-1,2,4-oxadiazol-5-yl)phenyl]methanamine and 3-chlorobenzaldehyde gave the title compound as a colorless oil (86%). ¹H NMR (DMSO-d₆, 300 MHz) δ 8.03 (d, J=8.3 Hz, 2H), 7.58 (d, J=8.3 Hz, 2H), 7.43 (s, 1H), 7.65-7.23 (m, 3H), 3.77 (s, 2H), 3.70 (s, 2H), 3.30 (s, 1H), 2.75 (t, J=7.2 Hz, 2H), 1.79-1.65 (m, 2H), 1.41-1.16 (m, 16H), 0.84 (t, J=7.0 Hz, 3H). HPLC (Condition A), Rt: 5.19 min (HPLC purity: 98.4%).

Step b) Formation of ethyl{(3-chlorobenzyl)[4-(3-undecyl-1,2,4-oxadiazol-5-yl)benzyl]amino}(oxo) acetate The same procedure as employed in the preparation of Example 15 (step b) but using N-(3-chlorobenzyl)-N-[4-(3-undecyl-1,2,4-oxadiazol-5-yl)benzyl]amine gave the title compound as a yellow oil (95%). ¹H NMR (DMSO-d, 300 MHz) δ 8.07 (d, J=8.3 Hz, 1H), 8.04 (d, J=8.3 Hz, 1H), 7.55-7.13 (m, 6H), 4.60 (d, 2H), 4.51 (d, 2H), 4.34-4.21 (m, 2H), 2.75 (m, 2H), 1.79-1.62 (m, 2H), 1.41-1.11 (m, 19H), 0.84 (t, J=6.8 Hz, 3H). HPLC (Condition A), Rt: 7.72 min (HPLC purity: 99.9%).

Step c) Formation of {(3-chlorobenzyl)[4-(3-undecyl-1,2,4-oxadiazol-5-yl)benzyl]amino}(oxo)acetic acid The same procedure as employed in the preparation of Example 1 (step e) but using ethyl{(3-chlorobenzyl)[4-(3-undecyl-1,2,4-oxadiazol-5-yl)benzyl]amino}(oxo)acetate gave the title compound as a colorless oil (91%). ¹H NMR (DMSO-d₆, 300 MHz) δ 7.91 (d, J=8.0 Hz, 2H), 7.87 (d, J=8.3 Hz, 1H), 7.36 (d, J=8.3 Hz, 1H), 7.29-6.97 (m, 41), 4.48-4.23 (m, 4H), 2.60 (t, J=7.3 Hz, 2H), 1.64-1.47 (m, 21), 1.25-0.95 (m, 16H), 0.67 (t, J=7.0 Hz, 3H). M⁻(LC/MS (ESI)): 524.2. HPLC (Condition A), Rt: 7.23 min (HPLC purity: 100%).

Example 265

{(3-chlorobenzyl)[4-(3-undecyl-1,2,4-oxadiazol-5-yl)benzyl]amino}(oxo)-acetic acid, N-methyl-D-glucamine (i.e. 1-deoxy-1-(methylamino)glucitol) salt The same procedure as employed in the preparation of Example 2 but using N-methyl-D-glucamine and {(3-chlorobenzyl)[4-(3-undecyl-1,2,4-oxadiazol-5-yl)benzyl] amino}(oxo)acetic acid gave the title compound as a white powder (93%). M⁻(LC/MS(ESI)): 523.9. HPLC (Condition A), Rt: 7.24 min (HPLC purity: 99.9%). Analysis calculated for $C_{29}H_{36}ClN_3O_4 \cdot C_7H_{17}NO_5 \blacksquare 0.4H_2O$: C, 59.35; H, 7.44; N, 7.69%. Found: C, 59.32; H, 7.37; N, 7.63%.

Example 266

{{cyclopentyl[4-(trifluoromethyl)phenyl]methyl}[4-(tridecanoylamino)-benzyl]amino}(oxo)acetic acid Step a) Preparation of N-methoxy-N-methyl-4-(trifluoromethyl)benzamide To a cold (0° C.) solution of N,O-dimethylhydroxylamine hydrochloride (2.5 g, 25.6 mmol) and 4-(trifluoromethyl) benzoyl chloride (prepared by refluxing a solution of 4-(trifluoromethyl)benzoic acid in SOCl₂, 4.86 g, 23.3 mmol) in DCM (50 mL) was added dropwise pyridine (4.06 g, 51.26 mmol). The reaction mixture was stirred overnight and evaporated. The residue was dissolved in a mixture of DCM/Et₂O (1/1) (45 mL) and brine (45 mL) was added. The aqueous layer was separated and extracted twice with DCM/Et₂O (1/1) (45 mL). The combined organic layers were washed with brine (45 mL), dried over MgSO₄, filtered and concentrated under vacuum to give the title compound as a yellow oil (4.88 g, 90%). ¹H NMR (CDCl₃, 300 MHz) δ 7.90-7.70 (m, 2H), 7.76-7.60 (m, 2H), 3.65-3.45 (m, 3H), 3.43-3.33 (m, 3H). HPLC (Condition A), Rt: 3.41 min (HPLC purity: 98.0%).

Step b) Preparation of cyclopentyl[4-(trifluoromethyl)phenyl]methanone

To a cold (0° C.) solution of N-methoxy-N-methyl-4-(trifluoromethyl)benzamide (3.44 g, 14.75 mmol) in anhydrous THF (70 mL) was added dropwise over a period of 30 minutes a solution of cyclopentylmagnesium bromide (2 M in diethyl ether, 29.5 mmol, 14.75 mL) under inert atmosphere of N₂. The reaction mixture was slowly allowed to warm to rt overnight. An aqueous solution of HCl (1N, 50 mL) was added and the resulting mixture was extracted with diethyl ether (3×50 mL). The combined organic layers were washed with brine (1×50 mL), dried over MgSO₄, filtered and evaporated under vacuum to give a brown oil (3.0 g). Purification by chromatography (SiO₂, DCM/c-Hex 1/3) gave the title compound as a colorless oil (610 mg, 17%). ¹H NMR (CDCl₃, 300 MHz) δ 8.24 (d, J=8.1 Hz, 2H), 7.90 (d, J=8.1 Hz, 2H), 3.96-3.79 (m, 1H), 2.21-2.00 (m, 4H), 2.01-1.71 (m, 4H). HPLC (Condition A), Rt: 5.22 min (HPLC purity: 98.6%).

Step c) Formation of N-{cyclopentyl[4-(trifluoromethyl)phenyl]methyl}-N-(4-nitrobenzyl)-amine The same procedure as employed in the preparation of Example 223 (step b) but using cyclopentyl[4-(trifluoromethyl)phenyl]methanone and 4-nitrobenzylamine gave the title compound as an oil (67%). M⁻(LC/MS(ESI)): 377.2; M⁺(LC/MS(ESI)): 379.2

Step d) Formation of ethyl[{cyclopentyl[4-(trifluoromethyl)phenyl]methyl}(4-nitrobenzyl)amino](oxo)acetate The same procedure as employed in the preparation of Example 15 (step b) but using N-{cyclopentyl[4-(trifluoromethyl)phenyl]methyl}-N-(4-nitrobenzyl)amine gave the title compound as a colorless oil (68%). ¹H NMR (CDCl₃, 300 MHz) δ 8.02-7.90 (m, 2H), 7.55-7.38 (m, 4H), 7.11-6.99 (m, 2H), 4.60-4.30 (m, 4H), 4.20-4.02 (m, 1H), 2.78-2.61 (m, 1H), 1.78-1.38 (m, 7H), 1.30-0.91 (m, 4H). M⁻(LC/MS (ESI)): 477.8; M⁺(LC/MS(ESI)): 479.1 HPLC (Condition A), Rt: 5.72 min (HPLC purity: 98.4%).

Step e) Formation of ethyl((4-aminobenzyl){cyclopentyl[4-(trifluoromethyl)phenyl]-methyl}amino)(oxo)acetate The same procedure as employed in the preparation of Example 1 (step c) but using ethyl[{cyclopentyl[4-(trifluoromethyl)phenyl]methyl}(4-nitrobenzyl)amino](oxo)acetate and gave the title compound as a brown oil (36%). M⁺(LC/MS(ESI)): 449.1. HPLC (Condition A), Rt: 4.0 min (HPLC purity: 88.2%).

Step f) Formation of ethyl{{cyclopentyl[4-(trifluoromethyl)phenyl]methyl}[4-(tridecanoylamino)benzyl]amino}(oxo)acetate The same procedure as employed in the preparation of Example 15 (step d) but using ethyl ((4-aminobenzyl){cyclopentyl[4-(trifluoromethyl)phenyl]methyl}amino)(oxo)acetate and tridecanoyl chloride gave the title compound as a colorless oil (76%). ¹H NMR (CDCl₃, 300 MHz) δ 7.52-7.21 (m, 6H), 6.95 (d, 1H, J=8.5 Hz) 6.8 (d, 1H, J=8.5 Hz), 5.30 (m, 1H), 4.47-4.05 (m, 4H), 2.85-2.60 (m, 1H), 2.45-2.26 (m, 2H), 1.80-1.10 (m, 31H), 1.05-0.86 (m, 4H). M⁻(LC/MS (ESI)): 643.9; M⁺(LC/MS(ESI)): 645.2. HPLC (Condition A), Rt: 6.85 min (HPLC purity: 98.0%).

Step g) Formation of {{cyclopentyl[4-(trifluoromethyl)phenyl]methyl}[4 (tridecanoylamino)benzyl]amino}(oxo)acetic acid The same procedure as employed in the preparation of Example 1 (step e) but using ethyl{{cyclopentyl[4-(trifluoromethyl)phenyl]methyl}[4-(tridecanoylamino)benzyl]amino}(oxo)acetate gave the title compound as a yellow oil (94%). ¹H NMR (CDCl₃, 300 MHz) δ 7.85-7.24 (m, 6H), 6.85 (m, 2H), 5.30 (m, 0.6H), 4.62-4.32 (m, 1.4H), 2.74-2.65 (m, 0.6H), 2.31-2.21 (m, 1.4H), 1.68-1.45 (m, 8H), 1.24 (m, 22H), 1.05-0.86 (m, 4H). M⁻(LC/MS(ESI)): 615.1; M⁺(LC/MS(ESI)): 617.3. HPLC (Condition A), Rt: 6.30 min (HPLC purity: 97.0%).

Example 267 oxo([4-(trifluoromethyl)benzyl]{[4-(3-undecyl-1,2,4-oxadiazol-5-yl)-1-naphthyl]methyl}amino)acetic acid Step a) Preparation of methyl 4-methyl-1-naphthoate To a stirred solution of 4-methyl-1-naphthoic acid (25 g, 0.13 mol) in methanol (350 mL), thionylchloride (39 g, 0.33 mol) was added and the reaction mixture was refluxed for 15 h.

Excess of thionylchloride and methanol was distilled off. The residue was taken up in DCM (400 mL), washed with an aqueous solution of NaHCO₃ (10%), water, brine and dried over MgSO₄. The solvent was removed under vacuum to give 4-methyl-1-naphthoic acid methyl ester (22.5 g, 83%) as pale yellow solid.

Step b) Preparation of methyl 4-(bromomethyl)-1-naphthoate

To a stirred solution of methyl 4-methyl-1-naphthoate (22.5 g, 0.112 mol) in CCl₄ (500 mL) was added NBS (22 g, 0.123 mol) and benzoylperoxide (10% w/w). The reaction mixture was allowed to reflux at 80° C. for 7 h. The reaction mixture was cooled to rt and filtered off. The solid and concentrated under vacuum and the obtained crude product (30 g) was used for further reaction.

Step c) Preparation of methyl 4-(azidomethyl)-1-naphthoate

To a solution of methyl 4-(bromomethyl)-1-naphthoate (30 g, 0.107 mol) in anhydrous DMSO (300 mL) was added NaN₃ portion wise (14 g, 0.215 mol) at 0° C. and stirred at rt for 16 h. Then the reaction mixture was diluted with water (500 mL), extracted with EtOAc (2×250 mL), washed with water, brine and dried over MgSO₄. The solvent was removed under vacuum to give methyl 4-(azidomethyl)-1-naphthoate (20 g, 77%).

Step d) Preparation of methyl 4-(aminomethyl)-1-naphthoate hydrochloride

To a mixture of methyl 4-(azidomethyl)-1-naphthoate (17 g, 0.078 mol) in THF (400 mL) and water (210 mL), was added triphenylphosphine (31 g, 0.118 mol). The reaction mixture was stirred at rt for 4 h then concentrated under vacuum, extracted with EtOAc (350 mL).

The combined organic layers were washed with brine, dried over MgSO$_4$ and the solvent was removed under vacuum. The resulting residue was taken up in an aqueous solution of HCl (75 mL, 2N), washed with diethylether (2×150 mL). The aqueous layer was treated with an aqueous solution of NaHCO$_3$ (10%) until pH 7. The mixture was then extracted with ethylacetate (2×150 mL), washed with brine, dried over MgSO$_4$ and concentrated. The product was slowly added to a saturated solution of HCl (g) in diethyl ether (75 mL) and filtered off the solid hydrochloride product. The product was washed with dry ether (2×100 mL) to give methyl-4-(aminomethyl)-1-naphthoate hydrochloride (5.5 g). M$^+$(LC/MS(ESI)): 216.2. $^1$H NMR (DMSO-d$_6$, 300 MHz) δ 8.75 (m, 1H), 8.25 (m, 1H), 8.12 (d, 1H, J=7.5 Hz), 7.74 (m, 3H), 4.60 (s, 21), 3.93 (s, 3H).

Step e) Preparation of methyl 4-({[4-(trifluoromethyl)benzyl]amino}methyl)-1-naphthoate The same procedure as employed in the preparation of example 226 (step a) gave the title compound (74%). $^1$H NMR (DMSO-d$_6$, 300 MHz) δ 8.77 (m, 1H), 8.24 (m, 1H), 8.09 (d, 1H, J=7.5 Hz), 7.71-7.57 (m, 7H), 4.20 (s, 2H), 3.93 (s, 3H), 3.90 (s, 2H). M$^+$(LC/MS(ESI)): 374.2

Step f) Preparation of 4-({[4-(trifluoromethyl)benzyl]amino}methyl)-1-naphthoic acid The same procedure as employed in the preparation of example 1 (step e) but using 4-({[4-(trifluoromethyl)benzyl]amino}methyl)-1-naphthoic acid gave the title compound (74%). M$^+$(LC/MS(ESI)): 360.2; M$^-$(LC/MS(ESI)): 358.3. $^1$H NMR (DMSO-d$_6$, 300 MHz) δ 13.3 (m, 1H), 9.90 (m, 1H), 8.91-8.84 (m, 1H), 8.28-8.22 (m, 1H), 8.12 (d, 1H, J=7.5 Hz), 7.98-7.89 (m, 5H), 7.76-7.65 (m, 2H), 4.76 (s, 2H), 4.47 (s, 2H).

Step g) Formation of 4-({{(tert-butoxycarbonyl)[4-(trifluoromethyl)benzyl]amino}methyl)-1-naphthoic acid The same procedure as employed in the preparation of Example 23 (step b) but using 4-({[4-(trifluoromethyl)benzyl]amino}methyl)-1-naphthoic acid gave the title compound as a white foam (55%). $^1$H NMR (DMSO-d$_6$, 300 MHz) δ 8.89 (m, 1H), 8.22-8.06 (m, 2H), 7.69-7.56 (m, 4H), 7.45-7.31 (m, 3H), 4.97 (s, 2H), 4.55-4.41 (m, 2H), 1.40-1.35 (m, 9H). M$^-$(LC/MS(ESI)): 458.3. HPLC (Condition A), Rt: 5.72 min (HPLC purity: 100%).

Step h) Formation of tert-butyl 4-(trifluoromethyl)benzyl{[4-(3-undecyl-1,2,4-oxadiazol-5-yl)-1-naphthyl]methyl}carbamate The same procedure as employed in the preparation of Example 258 (step a and b) but using 4-({{(tert-butoxycarbonyl)[4-(trifluoromethyl)benzyl]amino}methyl)-1-naphthoic acid and gave the title compound as a colorless oil (76%). $^1$H NMR (CDCl$_3$, 300 MHz) δ 9.15 (d, 1H, J=8.7 Hz), 8.30-7.76 (m, 2H), 7.70 (m, 1H), 7.64-7.50 (m, 3H), 7.37 (d, 1H, J=8.7 Hz), 7.33-7.18 (m, 2H), 5.02-4.87 (m, 2H), 4.55-4.33 (m, 2H), 2.88 (t, 2H, J=7.5 Hz), 1.93-1.82 (m, 2H), 1.50 (m, 9H), 1.46-1.22 (m, 16H), 0.86 (m, 3H). HPLC (Condition A), Rt: 7.84 min (HPLC purity: 100%).

Step i) Formation of N-[4-(trifluoromethyl)benzyl]-N-{([4-(3-undecyl-1,2,4-oxadiazol-5-yl)-1-naphthyl]methyl}amine Hydrochloride The same procedure as employed in the preparation of Example 23 (step f) but using tert-butyl 4-(trifluoromethyl)benzyl{[4-(3-undecyl-1,2,4-oxadiazol-5-yl)-1-naphthyl]methyl}carbamate gave the title compound as a foam (98%). $^1$H NMR (CDCl$_3$, 300 MHz) δ 10.68 (m, 1H), 9.07 (m, 1H), 8.23 (d, 1H, J=7.5 Hz), 7.84 (m, 2H), 7.69-7.51 (m, 6H), 4.31 (br s, 2H), 3.91 (br s, 2H), 2.82 (t, 2H, J=7.5 Hz), 1.82 (m, 2H), 1.47-1.17 (m, 18H), 0.88 (m, 3H). HPLC (Condition A), Rt: 5.50 min (HPLC purity: 98.9%).

Step j) Formation of ethyl oxo([4-(trifluoromethyl)benzyl]{[4-(3-undecyl-1,2,4-oxadiazol-5-yl)-1-naphthyl]methyl}amino)acetate The same procedure as employed in the preparation of Example 15 (step b) but using N-[4-(trifluoromethyl)benzyl]-N-{[4-(3-undecyl-1,2,4-oxadiazol-5-yl)-1-naphthyl]methyl}amine hydrochloride gave the title compound as a colorless oil (87%). $^1$H NMR (CDCl$_3$, 300 MHz) 59.17 (m, 1H), 8.30 (d, 0.4H, J=7.5 Hz), 8.22 (d, 0.6H, J=7.5 Hz), 8.05 (m, 0.6H), 7.95 (m, 0.4H), 7.76-7.46 (m, 4H), 7.33-7.24 (m, 3H), 5.08 (s, 1.2H), 4.88 (s, 0.8H), 4.65 (s, 0.8H), 4.37 (s, 1.2H), 4.36-4.24 (m, 2H), 2.89 (m, 2H), 1.88 (m, 2H), 1.50-1.20 (m, 19H), 0.88 (m, 3H). HPLC (Condition A), Rt: 7.17 min (HPLC purity: 100%).

Step k) Formation of oxo([4-(trifluoromethyl)benzyl]{[4-(3-undecyl-1,2,4-oxadiazol-5-yl)-1-naphthyl]methyl}amino)acetic acid The same procedure as employed in the preparation of Example 1 (step e) but using ethyl oxo([4-(trifluoromethyl)benzyl]{[4-(3-undecyl-1,2,4-oxadiazol-5-yl)-1-naphthyl]methyl}amino)acetate gave the title compound as a colorless oil (35%). $^1$H NMR (DMSO-d$_6$, 300 MHz) δ 9.03 (d, J=8.3 Hz, 1H), 8.32-8.15 (m, 2H), 7.80-7.30 (m, 7H), 5.17 (s, 1H), 5.07 (s, 1H), 4.68 (s, 1H), 4.62 (s, 1H), 2.86 (t, J=7.2 Hz, 2H), 1.83-1.69 (m, 2H), 1.45-1.05 (m, 16H), 0.83 (t, J=7.0 Hz, 3H). M$^-$(LC/MS(ESI)): 608.1. HPLC (Condition A), Rt: 6.51 min (HPLC purity: 100%).

Example 268 oxo([4-(trifluoromethyl)benzyl]{[4-(3-undecyl-1,2,4-oxadiazol-5-yl)-1-naphthyl]methyl}amino)acetic acid. N-methyl-D-glucamine (i.e. 1-deoxy-1-(methylamino)-glucitol) salt The same procedure as employed in the preparation of Example 2 but using N-methyl-D-glucamine and oxo([4-(trifluoromethyl)benzyl]{[4-(3-undecyl-1,2,4-oxadiazol-5-yl)-1-naphthyl]methyl}amino)acetic acid gave the title compound as a white powder (87%). M$^-$(LC/MS(ESI)): 608.1. HPLC (Condition A), Rt: 6.45 min (HPLC purity: 98.5%). Analysis calculated for C$_{34}$H$_{38}$F$_3$N$_3$O$_4$.C$_7$H$_{17}$NO$_5$: C, 61.18; H, 6.89; N, 6.96%. Found: C, 57.94; H, 6.90; N, 6.58%.

Example 269

{{cyclopentyl[4-(trifluoromethyl)phenyl]methyl}[4-(3-undecyl-1,2,4-oxadiazol-5-1)benzyl]amino}(oxo)acetic acid Step a) Formation of N-{cyclopentyl[4-(trifluoromethyl)phenyl]methyl}-N-[4-(3-undecyl-1,2,4-oxadiazol-5-yl)benzyl]amine The same procedure as employed in the preparation of Example 223 (step b) but using cyclopentyl[4-(trifluoromethyl)phenyl]methanone and 4-(3-undecyl-1,2,4-oxadiazol- 5-yl)benzylamine gave the title compound as a colorless oil (55%). ¹H NMR (DMSO-d₆, 300 MHz) δ 8.00 (d, 2H), 7.64 (m, 2H), 7.50 (m, 4H), 3.62-3.34 (m, 2H), 2.74 (m, 2H), 2.12-1.85 (m, 2H), 1.70 (m, 2H), 1.60-0.92 (m, 25H), 0.83 (m, 3H). HPLC (Condition A), Rt: 5.42 min (HPLC purity: 98.3%).

Step b) Formation of ethyl{{cyclopentyl[4-(trifluoromethyl)phenyl]methyl}[4-(3-undecyl-1,2,4-oxadiazol-5-yl)benzyl]amino}(oxo)acetate The same procedure as employed in the preparation of Example 15 (step b) but using N-{cyclopentyl[4-(trifluoromethyl)phenyl]methyl}-N-[4-(3-undecyl-1,2,4-oxadiazol-5-yl)benzyl]amine gave the title compound as a colorless oil (86%). ¹H NMR (CDCl₃, 300 MHz) δ 7.89 (m, 2H), 7.62-7.41 (m, 5H), 7.15-7.04 (m, 2H), 4.57-4.31 (m, 5H), 2.81-2.63 (m, 3H), 1.83-1.13 (m, 28H), 0.88 (m, 3H). HPLC (Condition A), Rt: 7.09 min (HPLC purity: 99.3%).

Step c) Formation of {{cyclopentyl[4-(trifluoromethyl)phenyl]methyl}[4-(3-undecyl-1,2,4-oxadiazol-5-yl)benzyl]amino}(oxo)acetic acid The same procedure as employed in the preparation of Example 1 (step e) but using ethyl{{cyclopentyl[4-(trifluoromethyl)phenyl]methyl}[4-(3-undecyl-1,2,4-oxadiazol-5-yl)benzyl]amino}(oxo)acetate gave the title compound as a colorless oil (92%). ¹H NMR (DMSO-d₆, 300 MHz) 37.87-7.68 (m, 2H), 7.63 (d, J=7.9 Hz, 2H), 7.51 (d, J=8.2 Hz, 2H), 7.02 (d, J=8.3 Hz, 3H), 4.72-4.43 (m, 3H), 3.19-2.85 (m, 2H), 2.72 (t, J=7.0 Hz, 2H), 1.76-1.37 (m, 8H), 1.26-1.10 (m, 16H), 0.84 (t, J=6.9 Hz, 3H). M⁻(LC/MS(ESI)): 626.2. HPLC (Condition A), Rt: 6.56 min (HPLC purity: 99.1%).

Example 270

{{cyclopentyl[4-(trifluoromethyl)phenyl]methyl}[4-(3-undecyl-1,2,4-oxadiazol-5-yl)benzyl]amino}(oxo) acetic acid, N-methyl-D-glucamine (i.e. 1-deoxy-1-(methylamino)glucitol) salt The same procedure as employed in the preparation of Example 2 but using N-methyl-D-glucamine and {{cyclopentyl[4-(trifluoromethyl)phenyl]methyl}[4-(3-undecyl-1,2,4-oxadiazol-5-yl)benzyl]amino}(oxo)acetic acid gave the title compound as a white powder (90%). M⁻(LC/MS(ESI)): 626.9. HPLC (Condition A), Rt: 6.52 min (HPLC purity: 99.1%). Analysis calculated for $C_{35}H_{44}F_3N_3O_4 \cdot C_7H_{17}NO_5 \blacksquare 1.2H_2O$: C, 59.73; H, 7.57; N, 6.63%. Found: C, 59.67; H, 7.65; N, 6.59%.

Example 271

{(4-dibenzo[b,d]furan-4-ylphenyl)[4-(trifluoromethyl)benzyl]amino}-(oxo)-acetic acid Step a) Formation of 4-(4-nitrophenyl)dibenzo[b,d]furan To a mixture of dibenzofuran-4-boronic acid (30 g, 0.14 mol), 4-bromonitrobenzene (25.7 g, 0.127 mol), sodium carbonate (150 g) in toluene/water (500 mL/500 mL) was added tetrakis(triphenylphosphine)palladium(0) (8.2 g, 0.7 mol %) and the resulting reaction mixture was refluxed for 20 h under N₂ atmosphere. The toluene layer was separated and concentrated to 200 mL. The concentrated solution was cooled to 0° C. and filtered off. The collected solid was dried and dissolved in chloroform and the obtained solution was filtered through celite bed to remove insoluble materials. The filtrate was concentrated under vacuum to give the title compound (23 g, 58%).

Step b) Formation of 4-dibenzo[b,d]furan-4-ylaniline

A solution of 4-(4-nitrophenyl)dibenzo[b,d]furan (22 g) in EtOAc (800 mL) was hydrogenated in presence of Pd/C (10%, 4.2 g) for 12 h at rt under 2 Kg of pressure. The reaction mixture was filtered, and the filtrates were concentrated. The residue was crystallized from chloroform/PetEther (6/4) to give the title compound (16 g, 84%) as a white solid. ¹H NMR (DMSO-d₆, 300 MHz) δ 8.15 (d, 1H, J=7.6 Hz), 7.97 (d, 1H, J=7.6 Hz), 7.72 (d, 1H, J=8.1 Hz), 7.65 (d, 2H, J=8.4 Hz), 7.57 (d, 1H, J=8.6 Hz), 7.50 (m, 1H), 7.38 (m, 2H), 6.72 (d, 2H, J=8.4 Hz), 7.35 (s, 2H). M⁺(LC/MS(ESI)): 260.2

Step c) Formation of N-(4-dibenzo[b,d]furan-4-ylphenyl)-N-[4-(trifluoromethyl)-benzyl]amine The same procedure as employed in the preparation of Example 226 (step a) but using 4-dibenzo[b,d]furan-4-ylaniline and 4-(trifluoromethyl)benzaldehyde gave the title compound as a colorless oil (78%). ¹H NMR (DMSO-d₆, 300 MHz) δ 8.15 (d, 1H, J=7.1 Hz), 8.01 (m, 1H), 7.7548 (m, 9H), 7.44-7.37 (m, 2H), 6.74 (m, 3H), 4.47 (m, 2H). M⁻(LC/MS (ESI)): 416.2; M⁺(LC/MS(ESI)): 418.2. HPLC (Condition A), Rt: 5.72 min (HPLC purity: 99.3%).

Step d) Formation of ethyl{(4-dibenzo[b,d]furan-4-ylphenyl)[4-(trifluoromethyl)-benzyl]amino}(oxo) acetate The same procedure as employed in the preparation of Example 15 (step b) but using N-(4-dibenzo[b,d]furan-4-ylphenyl)-N-[4-(trifluoromethyl)benzyl]amine gave the title compound as a colorless oil (89%). ¹H NMR (CDCl₃, 300 MHz) δ 8.26-8.11 (m, 4H), 7.87-7.77 (m, 4H), 7.75-7.58 (m, 5H), 7.52-7.45 (m, 2H), 5.31 (s, 2H), 4.32 (q, 2H, J=7.2 Hz), 1.27 (t, 3H, J=7.2 Hz). M⁺(LC/MS(ESI)): 518.2. HPLC (Condition A), Rt: 5.78 min (HPLC purity: 99.4%).

Step e) Formation of {(4-dibenzo[b,d]furan-4-ylphenyl)[4-(trifluoromethyl)benzyl]amino}-(oxo)acetic acid The same procedure as employed in the preparation of Example 1 (step e) but using ethyl{(4-dibenzo[b,d]furan-4-ylphenyl)[4-(trifluoromethyl)benzyl]amino}(oxo)acetate gave the title compound as a colorless oil (95%). ¹H NMR (DMSO-d₆, 300 MHz) δ 8.04 (t, J=7.6 Hz, 2H), 7.82 (d, J=8.3 Hz, 2H), 7.65-7.51 (m, 4H), 7.46-7.22 (m, 7H), 5.00 (s, 2H). M⁻(LC/MS(ESI)): 416.3 (M-CO—CO₂); M⁺(LC/MS(ESI)): 489.9. HPLC (Condition A), Rt: 5.07 min (HPLC purity: 99.1%).

Example 272

{(4-dibenzo[b,d]furan-4-ylphenyl)[4-(trifluoromethyl)benzyl]amino}(oxo)-acetic acid N-methyl-D-glucamine (i.e. 1-deoxy-1-methylamino)glucitol) salt The same procedure as employed in the preparation of Example 2 but using N-methyl-D-glucamine and {(4-dibenzo[b,d]furan-4-ylphenyl)[4-(trifluoromethyl)benzyl]

amino}(oxo)acetic acid gave the title compound as a white powder (96%). M⁺(LC/MS(ESI)): 490.2. HPLC (Condition A), Rt: 5.03 min (HPLC purity: 98.4%). Analysis calculated for $C_{28}H_{18}F_3NO_4 \cdot C_7H_{17}NO_5 \blacksquare 1.5H_2O$: C, 59.07; H, 5.38; N, 3.94%. Found: C, 59.26; H, 5.39; N, 3.91%.

Example 273

{[4-(octyloxy)benzyl][4-(trifluoromethyl)benzyl]amino}(oxo)acetic acid

Step a) Formation of N-[4-(octyloxy)benzyl]-N-[4-(trifluoromethyl)benzyl]amine

The same procedure as employed in the preparation of Example 226 (step a) but using 4-(octyloxy)benzaldehyde and 4-(trifluoromethyl)benzylamine gave the title compound as a colorless oil (86%). ¹H NMR (CDCl₃, 300 MHz) δ 7.57 (d, 2H, J=7.9 Hz), 7.45 (d, 2H, J=7.9 Hz), 7.22 (m, 2H), 6.85 (m, 2H), 3.93 (t, 2H, J=6.5 Hz), 3.84 (s, 2H), 3.72 (s, 2H), 1.82-1.70 (m, 2H), 1.50-1.23 (m, 10H), 0.89 (m, 3H). M⁻(LC/MS(ESI)): 406.3 HPLC (Condition A), Rt: 4.42 min (HPLC purity: 98.7%).

Step b) Formation of ethyl{[4-(octyloxy)benzyl][4-(trifluoromethyl)benzyl]-amino}(oxo)-acetate The same procedure as employed in the preparation of Example 15 (step b) but using N-[4-(octyloxy)benzyl]-N-[4-(trifluoromethyl)benzyl]amine gave the title compound as a colorless oil (79%). ¹H NMR (CDCl₃, 300 MHz) δ 7.60 (m, 2H), 7.36 (d, 1H, J=7.9 Hz), 7.31 (d, 1H, J=7.9 Hz), 7.17-7.07 (m, 2H), 6.89-6.81 (m, 2H), 4.50 (s, 1H), 4.43 (s, 1H), 4.41-4.24 (m, 4H), 3.93 (m, 2H), 1.77 (m, 2H), 1.51-1.24 (m, 13H), 0.89 (m, 3H). M⁺(LC/MS(ESI)): 494.2. HPLC (Condition A), Rt: 6.22 min (HPLC purity: 99.4%).

Step c) Formation of {[4-(octyloxy)benzyl][4-(trifluoromethyl)benzyl]amino}(oxo)acetic acid The same procedure as employed in the preparation of Example 1 (step e) but using ethyl{[4-(octyloxy)benzyl][4-(trifluoromethyl)benzyl]amino}(oxo)acetate gave the title compound as a white solid (51%). ¹H NMR (CD₃OD, 300 MHz) δ 7.64 (m, 2H), 7.48 (d, 0.8H, J=8.3 Hz), 7.37 (d, 1.2H, J=8.3 Hz), 7.23 (d, 1.2H, J=8.3 Hz), 7.21 (d, 0.8H, J=8.5 Hz), 6.95-6.80 (m, 2H), 4.55 (s, 2H), 4.45 (s, 2H), 3.96 (t, 2H, J=6.4 Hz), 1.85-1.70 (m, 2H), 1.55-1.30 (m, 10H), 0.91 (m, 3H). M⁻(LC/MS(ESI)): 464.3. HPLC (Condition A), Rt: 5.57 min (HPLC purity: 96.8%). Analysis calculated for $C_{25}H_{30}F_3NO_4 \blacksquare 0.9H_2O$: C, 62.33; H, 6.65; N, 2.91%. Found: C, 62.09; H, 6.28; N, 2.78%.

Example 274

{[4-(octyloxy)benzyl][4-(trifluoromethyl)benzyl]amino}(oxo)acetic acid, N-methyl-D-glucamine (i.e. 1-deoxy-1-(methylamino)glucitol) salt The same procedure as employed in the preparation of Example 2 but using N-methyl-D-glucamine and {[4-(octyloxy)benzyl][4-(trifluoromethyl)benzyl]amino}(oxo)acetic acid gave the title compound as a white solid (82%). M⁻(LC/MS(ESI)): 464.3. HPLC (Condition A), Rt: 5.57 min (HPLC purity: 100%). Analysis calculated for $C_{25}H_{30}F_3NO_4 \cdot C_7H_{17}NO_5 \blacksquare 2.0H_2O$: C, 55.16; H, 7.38; N, 4.02%. Found: C, 55.21; H, 7.18; N, 4.02%.

Example 275

[[2-(3-chlorophenyl)ethyl](4-dec-1-ynylbenzyl)amino](oxo)acetic acid

Step a) Formation of 4-dec-1-ynylbenzaldehyde

To a solution of 4-bromobenzaldehyde (30.0 g, 162.2 mmol), 1-decyne (26.9 g, 35 mL, 194.6 mmol), CuI (309 mg, 1.62 mmol) and of Et₃N (68 mL) in anhydrous THF (450 mL) were added PPh₃ (1.7 g, 6.49 mmol) and Pd(OAc)₂ (728 mg). The reaction mixture was refluxed under argon for 1 hour. After cooling to rt, the solution was concentrated under reduced pressure and the residual oil was dissolved in hexane (480 mL). The solution was washed with an aqueous solution of HCl (0.1N, 1×), brine (2×), water (2×), dried over MgSO₄, filtered and concentrated under reduced pressure to give a brown oil. Purification by chromatography on silicagel (c-Hex/EtOAc 20/1) gave the title compound as a yellow solid (34.7 g, 88%). ¹H NMR (CDCl₃, 300 MHz) δ 9.97 (s, 1H), 7.78 (d, 2H, J=8.7 Hz), 7.51 (d, 2H, J=8.3 Hz), 2.42 (t, 2H, J=7.0 Hz), 1.67-1.55 (m, 2H), 1.50-1.38 (m, 2H), 1.36-1.21 (m, 8H), 0.87 (m, 3I). HPLC (Condition A), Rt: 5.50 min (HPLC purity: 93.2%).

Step b) Formation of N-[2-(3-chlorophenyl)ethyl]-N-(4-dec-1-ynylbenzyl)amine and N-[2-(3-chlorophenyl)ethyl]-N-{4-[(1Z)-dec-1-enyl]benzyl}amine in hplc ratio (74.3/24.3)

The same procedure as employed in the preparation of Example 226 (step a) but using 4-dec-1-ynylbenzaldehyde and [2-(3-chlorophenyl)ethyl]amine gave the title compounds as a colorless oil (53%). M⁺(LC/MS(ESI)): 382.4. HPLC (Condition A), Rt: 4.65 (alkyne) and 4.73 (alkene) min (HPLC purity: 74.3 (alkyne) and 24.3 (akene) %).

Step c) Formation of ethyl[[2-(3-chlorophenyl)ethyl](4-dec-1-ynylbenzyl)amino]-(oxo)acetate The same procedure as employed in the preparation of Example 15 (step b) but using N-[2-(3-chlorophenyl)ethyl]-N-(4-dec-1-ynylbenzyl)amine and N-[2-(3-chlorophenyl)ethyl]-N-{4-[(1Z)-dec-1-enyl]benzyl}amine in hplc ratio (74.3/24.3) gave (after chromatography) the title compound as a colorless oil (2%). ¹H NMR (CDCl₃, 300 MHz) δ 7.37 (d, 2H, J=7.9 Hz), 7.24-6.91 (m, 6H), 4.57 (s, 1H), 4.38-4.23 (m, 3H), 3.50-3.34 (m, 2H), 2.84-2.76 (m, 2H), 2.38 (t, 2H, J=6.9 Hz), 1.65-1.53 (m, 2H), 1.47-1.22 (m, 13H), 0.89 (m, 3H) M⁺(LC/MS(ESI)): 482.4. HPLC (Condition A), Rt: 6.40 min (HPLC purity: 98.5%).

Step d) Formation of [[2-(3-chlorophenyl)ethyl](4-dec-1-ynylbenzyl)amino](oxo)acetic acid The same procedure as employed in the preparation of Example 1 (step e) but using ethyl[[2-(3-chlorophenyl)ethyl](4-dec-1-ynylbenzyl)amino](oxo)acetate gave the title compound as a colorless oil (32%). ¹H NMR (CDCl₃, 300 MHz) δ 7.38 (m, 2H), 7.25-6.93 (m, 6H), 4.95 (s, 0.811), 4.59 (s, 1.21), 3.95 (m, 1H), 3.53 (m, 1H), 2.90-2.73 (m, 2H), 2.39 (t, 2H, J=6.9 Hz), 1.65-1.52 (m, 2H), 1.48-1.37 (m, 2H), 1.34-1.20 (m, 8H), 0.85 (m, 3H). M⁻(LC/MS(ESI)): 452.2; M⁺(LC/MS(ESI)): 455.3. HPLC (Condition A), Rt: 5.85 min (HPLC purity: 97.4%). Analysis calculated for $C_{27}H_{32}ClNO_3 \blacksquare 0.5H_2O$: C, 70.04; H, 7.18; N, 3.03%. Found: C, 70.39; H, 7.12; N, 2.96%.

Example 276

([2-(3-chlorophenyl)ethyl]{4-[(1Z)-dec-1-enyl]benzyl}amino)(oxo)acetic acid

Step a) Formation of ethyl([2-(3-chlorophenyl)ethyl]{4-[(1Z)-dec-1-enyl]benzyl}amino) (oxo)acetate The same procedure as employed in the preparation of Example 15 (step b) but using N-[2-(3-chlorophenyl)ethyl]-N-(4-dec-1-ynylbenzyl)amine and N-[2-(3-chlorophenyl)ethyl]-N-{4-[(1Z)-dec-1-enyl]benzyl}amine in hplc ratio (74.3/24.3) gave (after chromatography) the title compound as a colorless oil (2%). $^1$H NMR (CDCl$_3$, 300 MHz) δ 7.32-6.96 (m, 8H), 6.39 (d, 1H, J=11.7 Hz), 5.70 (m, 1H), 4.61 (s, 1H), 4.36 (q, 2H, J=7.1 Hz), 4.30 (s, 1H), 3.54-3.38 (m, 2H), 2.90-2.76 (m, 2H), 2.32 (m, 2H), 1.52-1.22 (m, 13H), 0.89 (m, 3H) M$^+$(LC/MS(ESI)): 484.3. HPLC (Condition A), Rt: 6.55 min (HPLC purity: 96.6%).

Step b) Formation of ([2-(3-chlorophenyl)ethyl]{4-[(1Z)-dec-1-enyl]benzyl}amino)(oxo)-acetic acid The same procedure as employed in the preparation of Example 1 (step e) but using ethyl ([2-(3-chlorophenyl)ethyl]{4-[(1Z)-dec-1-enyl]benzyl}amino)(oxo)acetate gave the title compound as a colorless oil (69%). $^1$H NMR (CDCl$_3$, 300 MHz) δ 7.29-6.99 (m, 8H), 6.37 (d, 1H, J=6.7 Hz), 5.68 (m, 1H), 4.93 (s, 1H), 4.92 (s, 1H), 3.92 (m, 1H), 3.54 (m, 1H), 2.88 (m, 1H), 2.78 (m, 1H), 2.29 (m, 2H), 1.49-1.37 (m, 2H), 1.33-1.18 (m, 10H), 0.86 (m, 3H) M$^-$(LC/MS(ESI)): 454.2. HPLC (Condition A), Rt: 5.96 min (HPLC purity: 95.9%).

Example 277

{[2-(3-chlorophenyl)ethyl][4-(3-undecyl-1,2,4-oxadiazol-5-yl)benzyl]-amino}(oxo)acetic acid

Step a) Formation of 4-(3-undecyl-1,2,4-oxadiazol-5-yl)benzaldehyde

To a solution of 4-carboxybenzaldehyde (20.0 g, 133.2 mmol) in anhydrous DCM (500 mL) was added DIC (18.42 g, 146.5 mmol). The mixture was stirred at rt for 30 min then a solution of N-hydroxydodecanimidamide (31.41 g, 146.5 mmol) in anhydrous DCM (500 mL) was added in one portion. The resulting reaction mixture was stirred overnight at rt. The reaction was filtered, the collected solid washed with DCM and the solvent was concentrated in vacuo. The residue was heated at 115° C. for 5 h in a mixture of toluene (285 mL) and pyridine (115 mL). The solvents were evaporated off and the resulting residue was purified on column (SiO$_2$, c-Hex/EtOAc 20/1) to give the title compound as a white solid (24.0 g, 55%). $^1$H NMR (CDCl$_3$, 300 MHz) δ 10.1 (s, 1H), 8.18 (d, 2H, J=8.3 Hz), 7.94 (d, 2H, J=8.3 Hz), 2.33 (t, 2H, J=7.4 Hz), 1.74-1.58 (m, 2H), 1.43-1.18 (m, 16H), 0.87 (m, 3H). HPLC (Condition A), Rt: 5.83 min (HPLC purity: 99.6%).

Step b) Formation of N-[2-(3-chlorophenyl)ethyl]-N-[4-(3-undecyl-1,2,4-oxadiazol-5-yl)benzyl]amine The same procedure as employed in the preparation of Example 226 (step a) but using 4-(3-undecyl-1,2,4-oxadiazol-5-yl)benzaldehyde and [2-(3-chlorophenyl)ethyl]amine gave the title compound as a colorless oil (62%). $^1$H NMR (CDCl$_3$, 300 MHz) δ 7.99 (d, J=8.3 Hz, 2H, 7.37 (d, J=8.3 Hz, 2H), 7.21-6.96 (m, 4H), 3.80 (s, 2H), 2.87-2.78 (m, 2H), 2.77-2.66 (m, 4H), 1.80-1.66 (m, 2H), 1.40-1.10 (m, 16H), 0.80 (t, J=7.2 Hz, 3H). M$^+$(LC/MS(ESI)): 468.4. HPLC (Condition A), Rt: 5.1 min (HPLC purity: 99.1%).

Step c) Formation of ethyl{[2-(3-chlorophenyl)ethyl][4-(3-undecyl-1,2,4-oxadiazol-5-yl)benzyl]amino}(oxo)acetate The same procedure as employed in the preparation of Example 15 (step b) but using N-[2-(3-chlorophenyl)ethyl]-N-[4-(3-undecyl-1,2,4-oxadiazol-5-yl)benzyl]amine gave the title compound as a colorless oil (99%). $^1$H NMR (CDCl$_3$, 300 MHz) δ 8.13 (dd, J1=1.7 Hz, J2=8.5 Hz, 2H), 7.46-7.37 (m, 2H), 7.26-7.20 (m, 2H), 7.18-6.95 (m, 2H), 4.67 (s, 1H), 4.42-4.30 (m, 3H), 3.57-3.44 (m, 2H), 2.92-2.76 (m, 4H), 1.89-1.75 (m, 2H), 1.49-1.19 (m, 19H), 0.89 (t, J=7.0 Hz, 3H). M$^+$(LC/MS(ESI)): 568.2. HPLC (Condition A), Rt: 6.78 min (HPLC purity: 99.8%).

Step d) Formation of {[2-(3-chlorophenyl)ethyl][4-(3-undecyl-1,2,4-oxadiazol-5-yl)benzyl]amino}(oxo)acetic acid The same procedure as employed in the preparation of Example 1 (step e) but using ethyl{[2-(3-chlorophenyl)ethyl][4-(3-undecyl-1,2,4-oxadiazol-5-yl)benzyl]amino}(oxo)acetate gave the title compound as a white powder (85%). $^1$H NMR (CDCl$_3$, 300 MHz) δ 8.08 (d, J=8.1 Hz, 2H), 7.94 (br s, 1H), 7.36-7.26 (m, 2H), 7.20-6.91 (m, 4H), 4.86 (s, 1H), 4.61 (s, 1H), 3.84 (t, J=7.6 Hz, 1H), 3.51 (t, J=7.6 Hz, 1H), 2.91-2.67 (m, 4H), 1.80-1.65 (m, 2H), 1.41-1.09 (m, 16H), 0.80 (t, J=6.8 Hz, 3H). M$^-$(LC/MS(ESI)): 538.0. HPLC (Condition A), Rt: 6.21 min (HPLC purity: 98.4%). Analysis calculated for C$_{30}$H$_{38}$ClN$_3$O$_4$■0.2H$_2$O: C, 66.27; H, 7.12; N, 7.73%. Found: C, 66.10; H, 7.16; N, 7.64%.

Example 278

{[2-(3-chlorophenyl)ethyl][4-(3-undecyl-1,2,4-oxadiazol-5-yl)benzyl]-amino}(oxo)acetic acid, N-methyl-D-glucamine (i.e. 1-deoxy-1-(methylamino)glucitol) salt The same procedure as employed in the preparation of Example 2 but using N-methyl-D-glucamine and {[2-(3-chlorophenyl)ethyl][4-(3-undecyl-1,2,4-oxadiazol-5-yl)benzyl]amino}(oxo)acetic acid gave the title compound as a white solid (84%). M$^-$(LC/MS(ESI)): 538.4. HPLC (Condition A), Rt: 6.17 min (HPLC purity: 99.8%). Analysis calculated for C$_{30}$H$_{38}$ClN$_3$O$_4$·C$_7$H$_{17}$NO$_5$■0.3H$_2$O: C, 60.00; H, 7.57; N, 7.56%. Found: C, 59.84; H, 7.70; N, 7.48%.

Example 279 oxo{{(1R)-1-[4-(trifluoromethyl)phenyl]ethyl}[4-(3-undecyl-1,2,4-oxadiazol-5-yl)benzyl]amino}acetic acid

Step a) Formation of N-{(1R)-1-[4-(trifluoromethyl)phenyl]ethyl}-N-[4-(3-undecyl-1,2,4-oxadiazol-5-yl)benzyl]amine The same procedure as employed in the preparation of Example 226 (step a) but using 4-(3-undecyl-1,2,4-oxadiazol-5-yl)benzaldehyde and (1R)-1-[4-(trifluoromethyl)phenyl]ethylamine gave the title compound as a colorless oil (71%). M⁺(LC/MS(ESI)): 502.4. HPLC (Condition A), Rt: 5.04 min (HPLC purity: 99.6%).

Step b) Formation of Ethyl oxo{{(1R)-1-[4-(trifluoromethyl)phenyl]ethyl}[4-(3-undecyl-1,2,4-oxadiazol-5-yl)benzyl]amino}acetate The same procedure as employed in the preparation of Example 15 (step b) but using N-{(1R)-1-[4-(trifluoromethyl)phenyl]ethyl}-N-[4-(3-undecyl-1,2,4-oxadiazol-5-yl)benzyl]amine gave the title compound as a colorless oil (89%). $^1$H NMR (CDCl$_3$, 300 MHz) δ 8.04 (d, J=8.3 Hz, 1H), 7.99 (d, J=8.3 Hz, 1H), 7.64-7.55 (m, 2H), 7.50-7.38 (m, 2H), 7.30 (d, J=8.3 Hz, 1H), 7.24 (d, J=8.3 Hz, 1H), 5.94 (q, J=7.2 Hz, 0.5H), 5.12 (q, J=7.0 Hz, 0.5H), 4.80-4.06 (m, 4H), 2.86-2.73 (m, 2H), 1.86-1.73 (m, 2H), 1.60 (d, J=7.2 Hz, 1.5H), 1.54 (d, J=7.3 Hz, 1.5H), 1.49-1.13 (m, 19H), 0.89 (t, J=6.9 Hz, 3H). M⁻(LC/MS(ESI)): 600.1; M⁺(LC/MS(ESI)): 602.5. HPLC (Condition A), Rt: 6.75 min (HPLC purity: 100%).

Step c) Formation of oxo{{(1R)-1-[4-(trifluoromethyl)phenyl]ethyl}[4-(3-undecyl-1,2,4-oxadiazol-5-yl)benzyl]amino}acetic acid The same procedure as employed in the preparation of Example 1 (step e) but using ethyl oxo{{(1R)-1-[4-(trifluoromethyl)phenyl]ethyl}[4-(3-undecyl-1,2,4-oxadiazol-5-yl)benzyl]amino}acetate gave the title compound as a white powder (88%). $^1$H NMR (CDCl$_3$, 300 MHz) δ 7.94 (d, J=7.0 Hz, 1H), 7.89 (d, J=8.1 Hz, 1H), 7.56-7.44 (m, 2H), 7.37 (d, J=8.1 Hz, 1H), 7.31 (d, 3=8.1 Hz, 1H), 7.18 (d, 8.1 Hz, 1H), 7.10 (d, J=8.1 Hz, 1H), 6.02 (q, J=6.5 Hz, 0.5H), 5.75 (q, J=6.5 Hz, 0.5H), 4.99 (d, J=17 Hz, 0.5H), 4.67-4.49 (m, 1H), 4.14 (d, J=17 Hz, 0.5H), 2.78-2.64 (m, 2H), 1.81-1.63 (m, 2H), 1.55 (d, 3=6.4 Hz, 1.5H), 1.45 (d, J=6.5 Hz, 1.5H), 1.40-1.07 (m, 16H), 0.80 (t, J=6.8 Hz, 3H). M⁻(LC/MS (ESI)): 572.3. HPLC (Condition A), Rt: 6.21 min (HPLC purity: 97.9%).

Example 280 oxo{{(1R)-1-[4-(trifluoromethyl)phenyl]ethyl}[4-(3-undecyl-1,2,4-oxadiazol-5-yl)benzyl]amino}acetic acid, N-methyl-D-glucamine (i.e. 1-deoxy-1-(methylamino)glucitol) salt The same procedure as employed in the preparation of Example 2 but using N-methyl-D-glucamine and oxo{{(1R)-1-[4-(trifluoromethyl)phenyl]ethyl}[4-(3-undecyl-1,2,4-oxadiazol-5-yl)benzyl]amino}acetic acid gave the title compound as a white powder (86%). M⁻(LC/MS(ESI)): 572.4. HPLC (Condition A), Rt: 6.18 min (HPLC purity: 99.2%). Analysis calculated for C$_{31}$H$_{38}$F$_3$N$_3$O$_4$·C$_7$H$_{17}$NO$_5$■0.5H$_2$O: C, 58.67; H, 7.26; N, 7.20%. Found: C, 58.58; H, 7.31; N, 7.12%.

Example 281 oxo{[4-(trifluoromethyl)phenyl][4-(3-undecyl-1,2,4-oxadiazol-5-yl)benzyl]-amino}acetic acid Step a) Formation of N-[4-(trifluoromethyl)phenyl]-N-[4-(3-undecyl-1,2,4-oxadiazol-5-yl)benzyl]amine The same procedure as employed in the preparation of Example 226 (step a) but using 4-(3-undecyl-1,2,4-oxadiazol-5-yl)benzaldehyde and 4-(trifluoromethyl)aniline gave the title compound as a colorless oil (76%). $^1$H NMR (CDCl$_3$, 300 MHz) δ 8.03 (d, J=8.3 Hz, 2H), 7.42 (d, J=8.3 Hz, 2H), 7.32 (d, J=8.3 Hz, 2H), 6.54 (d, J=8.3 Hz, 2H), 4.40 (s, 2H), 2.71 (t, J=7.5 Hz, 2H), 1.80-1.65 (m, 2H), 1.40-1.07 (m, 16H), 0.80 (t, J=6.8 Hz, 3H). M⁻(LC/MS(ESI)): 472.5; M⁺(LC/MS(ESI)): 474.2. HPLC (Condition A), Rt: 6.78 min (HPLC purity: 97.5%).

Step b) Formation of ethyl oxo{[4-(trifluoromethyl)phenyl][4-(3-undecyl-1,2,4-oxadiazol-5-yl)benzyl]amino}acetate The same procedure as employed in the preparation of Example 15 (step b) but using N-[4-(trifluoromethyl)phenyl]-N-[4-(3-undecyl-1,2,4-oxadiazol-5-yl)benzyl]amine gave the title compound as a colorless oil (95%). $^1$H NMR (CDCl$_3$, 300 MHz) δ 8.09 (d, J=8.3 Hz, 2H), 7.61 (d, J=8.3 Hz, 2H), 7.4 (d, J=8.3 Hz, 2H), 7.23 (d, J=8.3 Hz, 2H), 5.07 (s, 2H), 4.08 (q, J=7.2 Hz, 2H), 2.80 (t, J=7.9 Hz, 2H), 1.88-1.72 (m, 2H), 1.51-1.17 (m, 16H), 1.04 (t, J=7.2 Hz, 3H), 0.89 (t, J=7.2 Hz, 3H). M⁻(LC/MS(ESI)): 572.3; M⁺(LC/MS(ESI)): 574.4. HPLC (Condition A), Rt: 6.68 min (HPLC purity: 99.4%).

Step c) Formation of oxo{[4-(trifluoromethyl)phenyl][4-(3-undecyl-1,2,4-oxadiazol-5-yl)benzyl]amino}acetic acid The same procedure as employed in the preparation of Example 1 (step e) but using ethyl oxo{[4-(trifluoromethyl)phenyl][4-(3-undecyl-1,2,4-oxadiazol-5-yl)benzyl]amino}acetate gave the title compound as a white powder (54%). $^1$H NMR (CDCl$_3$, 300 MHz) δ 7.98 (d, J=8.3 Hz, 2H), 7.50 (d, J=8.0 Hz, 2H), 8.00 (d, J=8.0 Hz, 2H), 7.11 (d, J=8.0 Hz, 2H), 4.97 (s, 2H), 2.70 (t, J=7.53 Hz, 2H), 1.76-1.61 (m, 2H), 1.39-1.09 (m, 16H), 0.8 (t, J=7.0 Hz, 3H). M⁻(LC/MS (ESI)): 472.5 (M-CO—CO$_2$); M⁺(LC/MS(ESI)): 546.4. HPLC (Condition A), Rt: 6.12 min (HPLC purity: 97.5%). Analysis calculated for C$_{29}$H$_{34}$F$_3$N$_3$O$_4$: C, 63.84; H, 6.28; N, 7.70%. Found: C, 63.77; H, 6.32; N, 7.60%.

Example 282 oxo{[4-(trifluoromethyl)phenyl][4-(3-undecyl-1,2,4-oxadiazol-5-yl)benzyl]amino}acetic acid, N-methyl-D-glucamine (i.e. 1-deoxy-1-(methylamino)glucitol) salt The same procedure as employed in the preparation of Example 2 but using N-methyl-D-glucamine and oxo{[4-(trifluoromethyl)phenyl][4-(3-undecyl-1,2,4-oxadiazol-5-yl)benzyl]amino}acetic acid gave the title compound as a white powder (89%). M⁻(LC/MS(ESI)): 472.5 (M-CO—CO$_2$). HPLC (Condition A), Rt: 6.09 min (HPLC purity: 100%). Analysis calculated for C$_{29}$H$_{34}$F$_3$N$_3$O$_4$·C$_7$H$_{17}$NO$_5$■0.5H$_2$O: C, 57.67; H, 6.99; N, 7.47%. Found: C, 57.40; H, 7.13; N, 7.36%.

Example 283 oxo{{(1S)-1-[4-(trifluoromethyl)phenyl]ethyl}[4-(3-undecyl-1,2,4-oxadiazol-5-yl)benzyl]amino}acetic acid Step a) Formation of benzyl 4-[({(1S)-1-[4-(trifluoromethyl)phenyl]ethyl}amino)methyl]benzoate The same procedure as employed in the preparation of Example 226 (step a) but using benzyl 4-formylbenzoate and (1S)-1-[4-(trifluoromethyl)phenyl]ethylamine gave the title compound as a pale yellow oil (83%). M⁺(LC/MS(ESI)): 414.3. HPLC (Condition A), Rt: 3.77 min (HPLC purity: 99.1%).

Step b) Formation of benzyl 4-[((tert-butoxycarbonyl){(1S)-1-[4-(trifluoromethyl)phenyl]ethyl}amino)methyl]benzoate The same procedure as employed in the preparation of Example 23 (step b) but using benzyl 4-[({(1S)-1-[4-(trifluoromethyl)phenyl]ethyl}amino)methyl]benzoate gave the title compound as a colorless oil (90%). HPLC (Condition A), Rt: 6.48 min (HPLC purity: 66.5%).

Step c) Formation of tert-butyl(1S)-1-[4-(trifluoromethyl)phenyl]ethyl[4-(3-undecyl-1,2,4-oxadiazol-5-yl)benzyl]carbamate The same procedure as employed in the preparation of Example 258 (step a and b) but using benzyl 4-[((tert-butoxycarbonyl){(1S)-1-[4-(trifluoromethyl)phenyl]ethyl}amino)methyl]benzoate and N-hydroxydodecanimidamide gave the title compound as a colorless oil (85%). $^1$H NMR (CDCl$_3$, 300 MHz) δ 8.02 (d, J=8.1 Hz, 2H), 7.53 (d, J=8.1 Hz, 2H), 7.34-7.17 (m, 4H), 4.47 (br s, 1H), 4.35 (br s, 1H), 2.75 (t, J=7.5 Hz, 2H), 1.83-1.69 (m, 2H), 1.60-1.14 (m, 29H), 0.90 (t, J=7.0 Hz, 3H). HPLC (Condition A), Rt: 8.02 min (HPLC purity: 95.7%).

Step d) Formation of N-{(1S)-1-[4-(trifluoromethyl)phenyl]ethyl}-N-[4-(3-undecyl-1,2,4-oxadiazol-5-yl)benzyl]amine The same procedure as employed in the preparation of Example 23 (step f) but using tert-butyl(1S)-1-[4-(trifluoromethyl)phenyl]ethyl[4-(3-undecyl-1,2,4-oxadiazol-5-yl)benzyl]carbamate and gave the hydrochloride salt of the title compound. The salt was poured in DCM and the resulting solution washed with an aqueous solution of NaOH (1N). The solvent was dried over MgSO$_4$ filtered and evaporated to give the title compound as a colorless oil (98%). $^1$H NMR (DMSO-d$_6$, 300 MHz) δ 10.18 (br s, 0.5H), 9.76 (br s, 0.5H), 8.1 (d, J=8.3 Hz, 2H), 7.90-7.79 (m, 4H), 7.75 (d, J=8.3 Hz, 2H), 4.63-4.48 (m, 1H), 4.30-5.16 (m, 1H), 4.04-3.90 (m, 1H), 3.00 (t, J=7.5 Hz, 2H), 1.78-1.63 (m, 5H), 1.41-1.24 (m, 16H), 0.84 (t, J=7.3 Hz, 3H). HPLC (Condition A), Rt: 5.59 min (HPLC purity: 99.5%).

Step e) Formation of ethyl oxo{{(1S)-1-[4-(trifluoromethyl)phenyl]ethyl}[4-(3-undecyl-1,2,4-oxadiazol-5-yl)benzyl]amino}acetate The same procedure as employed in the preparation of Example 15 (step b) but using N-{(1S)-1-[4-(trifluoromethyl)phenyl]ethyl}-N-[4-(3-undecyl-1,2,4-oxadiazol-5-yl)benzyl]amine gave the title compound as a colorless oil (93%).

Step f) Formation of oxo{{(1S)-1-[4-(trifluoromethyl)phenyl]ethyl}[4-(3-undecyl-1,2,4-oxadiazol-5-yl)benzyl]amino}acetic acid The same procedure as employed in the preparation of Example 1 (step e) but using ethyl oxo{{(S)-1-[4-(trifluoromethyl)phenyl]ethyl}[4-(3-undecyl-1,2,4-oxadiazol-5-yl)benzyl]amino}acetate gave the title compound as a colorless oil (93%). $^1$H NMR (DMSO-D$_6$, 300 MHz) δ 7.80-7.60 (m, 2H), 7.45-7.16 (m, 6H), 7.02 (d, J=8.3 Hz, 2H), 5.36 (m, 0.3H), 4.95 (m, 0.7H), 4.55-4.23 (m, 2H), 2.59-2.48 (m, 2H), 1.40 (d, J=6.5 Hz, 2.1H), 1.35 (d, J=6.5 Hz, 0.9H), 1.19-0.90 (m, 16H), 0.65 (t, J=6.9 Hz, 3H). M$^-$(LC/MS(ESI)): 572.3; M$^+$(LC/MS(ESI)): 573.9. HPLC (Condition A), Rt: 7.29 min (HPLC purity: 100%).

Example 284 oxo{{(1S)-1-[4-(trifluoromethyl)phenyl]ethyl}[4-(3-undecyl-1,2,4-oxadiazol-5-yl)benzyl]amino}acetic acid, N-methyl-D-glucamine (i.e. 1-deoxy-1-(methylamino)glucitol) salt The same procedure as employed in the preparation of Example 2 but using N-methyl-D-glucamine and oxo{{(1S)-1-[4-(trifluoromethyl)phenyl]ethyl}[4-(3-undecyl-1,2,4-oxadiazol-5-yl)benzyl]amino}acetic acid gave the title compound as a white solid (92%). M$^-$(LC/MS(ESI)): 572.3; M$^+$(LC/MS(ESI)): 574.3. HPLC (Condition A), Rt: 7.32 min (HPLC purity: 98.7%). Analysis calculated for C$_{31}$H$_{38}$F$_3$N$_3$O$_4$·C$_7$H$_{17}$NO$_5$■0.9H$_2$O: C, 58.14; H, 7.29; N, 7.14%. Found: C, 58.18; H, 7.27; N, 7.19%.

Example 285

[(3-chlorobenzyl)(4-dec-1-ynylbenzyl)amino](oxo)acetic acid

Step a) Formation of N-(3-chlorobenzyl)-N-(4-dec-1-ynylbenzyl)amine

The same procedure as employed in the preparation of Example 226 (step a) but using 4-dec-1-ynylbenzaldehyde and 3-chlorobenzylamine gave the title compound as a colorless oil (60%). $^1$H NMR (CDCl$_3$, 300 MHz) δ 7.37-7.19 (m, 8H), 3.75 (s, 2H), 3.74 (s, 2H), 2.37 (t, J=7.2 Hz, 2H), 1.64-1.52 (m, 2H), 1.48-1.37 (m, 2H), 1.36-1.19 (m, 8H), 0.91-0.81 (m, 3H). M$^+$(LC/MS(ESI)): 368.4. HPLC (Condition A), Rt: 4.60 min (HPLC purity: 84.1%).

Step b) Formation of ethyl[(3-chlorobenzyl)(4-dec-1-ynylbenzyl)amino](oxo)acetate The same procedure as employed in the preparation of Example 15 (step b) but using N-(3-chlorobenzyl)-N-(4-dec-1-ynylbenzyl)amine gave the title compound as a colorless oil (52%). $^1$H NMR (CDCl$_3$, 300 MHz) δ 7.21-7.12 (m, 2H), 7.11-7.00 (m, 3H), 6.99-6.84 (m, 3H), 4.25 (s, 1H), 4.22 (s, 1H), 4.18-4.04 (m, 4H), 2.19 (t, 2H), 1.52-0.95. (m, 15H), 0.69 (t, 3=6.9 Hz, 3H). HPLC (Condition A), Rt: 6.35 min (HPLC purity: 95.4%).

Step c) Formation of [(3-chlorobenzyl)(4-dec-1-ynylbenzyl)amino](oxo)acetic acid The same procedure as employed in the preparation of Example 1 (step e) but using ethyl[(3-chlorobenzyl)(4-dec-1-ynylbenzyl)amino](oxo)acetate gave the title compound as a colorless oil (92%). $^1$H NMR (CD$_3$OD, 300 MHz) δ 7.49-7.04 (m, 8H), 4.50 (s, 4H), 2.43 (t, J=6.8 Hz, 2H), 1.71-1.25 (m, 12H), 0.94 (t, J=7.0 Hz, 3H). M$^-$(LC/MS(ESI)): 438.1 HPLC (Condition A), Rt: 5.73 min (HPLC purity: 96.1%). Analysis calculated for C$_{26}$H$_{30}$ClNO$_3$■0.3H$_2$O: C, 70.12; H, 6.92; N, 3.14%. Found: C, 69.95; H, 6.73; N, 3.01%.

Example 286

[(3-chlorobenzyl)(4-dec-1-ynylbenzyl)amino](oxo) acetic acid, N-methyl-D-glucamine (i.e. 1-deoxy-1-(methylamino)glucitol) salt The same procedure as employed in the preparation of Example 2 but using N-methyl-D-glucamine and [(3-chlorobenzyl)(4-dec-1-ynylbenzyl)amino](oxo)acetic acid gave the title compound as a white powder (78%). M$^-$(ESI): 438.0; M$^+$(ESI): 440.2. HPLC (Condition A), Rt: 5.70 min (HPLC purity: 98.3%). Analysis calculated for C$_{26}$H$_{30}$ClNO$_3$.C$_7$H$_{17}$NO$_5$■0.3H$_2$O: C, 61.87; H, 7.49; N, 4.37%. Found: C, 61.59; H, 7.48; N, 4.29%.

Example 287

[[2-(3-chlorophenyl)ethyl](4-oct-1-ynylbenzyl)amino](oxo)acetic acid

Step a) Formation of 4-oct-1-ynylbenzaldehyde

The same procedure as employed in the preparation of Example 275 (step a) but using 4-bromobenzaldehyde and 1-octyne gave the title compound as a yellow oil (84%). $^1$H NMR (CDCl$_3$, 300 MHz) δ 9.97 (s, 1H), 7.78 (d, 2H, J=8.3 Hz), 7.51 (d, 2H, J=8.3 Hz), 2.42 (t, 2H, J=7.0 Hz), 1.67-1.54 (m, 2H), 1.50-1.24 (m, 6H), 0.89 (m, 3H). M$^-$(LC/MS(ESI)): 215.4. HPLC (Condition A), Rt: 5.17 min (HPLC purity: 78.6%).

Step b) Formation of N-[2-(3-chlorophenyl)ethyl]-N-(4-oct-1-ynylbenzyl)amine The same procedure as employed in the preparation of Example 1 (step a) but using 4-oct-1-ynylbenzaldehyde and [2-(3-chlorophenyl)ethyl]amine gave the title compound as a colorless oil (62%). $^1$H NMR (CDCl$_3$, 300 MHz) δ 7.26 (d, J=8.3 Hz, 2H), 7.19-7.08 (m, 5H), 7.03-6.96 (m, 1H), 3.71 (s, 2H), 2.83-2.67 (m, 2H), 2.32 (t, J=7.2 Hz, 2H), 1.63-1.44 to (m, 2H), 1.44-1.31 (m, 2H), 1.31-1.15 (m, 6H), 0.83 (t, J=8.3 Hz, 3H). M$^+$(LC/MS(ESI)): 354.4. HPLC (Condition A), Rt: 4.31 min (HPLC purity: 97.5%).

Step c) Formation of ethyl[[2-(3-chlorophenyl)ethyl](4-oct-1-ynylbenzyl)amino](oxo)-acetate The same procedure as employed in the preparation of Example 15 (step b) but using N-[2-(3-chlorophenyl)ethyl]-N-(4-oct-1-ynylbenzyl)amine gave the title compound as a colorless oil (81%). $^1$H NMR (CDCl$_3$, 300 MHz) δ 7.39 (d, J=7.7 Hz, 2H), 7.29-6.91 (m, 6H), 4.59 (s, 1H), 4.41-4.25 (m, 3H), 3.53-3.35 (m, 2H), 2.82 (q, J=7.3 Hz, 2H), 2.41 (t, J=7.0 Hz, 2H), 1.69-1.55 (m, 2H), 1.54-1.25 (m, 9H), 0.90 (t, J=6.9 Hz, 3H). M$^+$(LC/MS(ESI)): 454.3 HPLC (Condition A), Rt: 5.92 min (HPLC purity: 99.8%).

Step d) Formation of [[2-(3-chlorophenyl)ethyl](4-oct-1-ynylbenzyl)amino](oxo)acetic acid The same procedure as employed in the preparation of Example 1 (step e) but using ethyl[[2-(3-chlorophenyl)ethyl](4-oct-1-ynylbenzyl)amino](oxo)acetate gave the title compound as a colorless oil (96%). $^1$H NMR (CD$_3$OD, 300 MHz) δ 7.39-6.85 (m, 8H), 4.49 (s, 1H), 4.32 (s, 1H), 3.48-3.28 (m, 2H), 2.78 (t, J=7.6 Hz, 1H), 2.66 (t, J=7.5 Hz, 1H), 2.30 (t, J=6.4 Hz, 2H), 1.59-1.10 (m, 8H), 0.80 (t, J=6.9 Hz, 3H). M$^-$(LC/MS(ESI)): 424.2 HPLC (Condition A), Rt: 5.31 min (HPLC purity: 99.7%). Analysis calculated for C$_{25}$H$_{28}$ClNO$_3$■0.1H$_2$O: C, 70.20; H, 6.64; N, 3.27%. Found: C, 69.97; H, 6.76; N, 3.20%.

Example 288

[[2-(3-chlorophenyl)ethyl](4-oct-1-ynylbenzyl)amino](oxo)acetic acid, N-methyl-D-glucamine (i.e. 1-deoxy-1-(methylamino)glucitol) salt The same procedure as employed in the preparation of Example 2 but using N-methyl-D-glucamine and [[2-(3-chlorophenyl)ethyl](4-oct-1-ynylbenzyl)amino](oxo)acetic acid gave the title compound as a white solid (92%). M$^-$(LC/MS (ESI)): 424.3. HPLC (Condition A), Rt: 5.32 min (HPLC purity: 99.7%). Analysis calculated for C$_{25}$H$_{28}$ClNO$_3$.C$_7$H$_{17}$NO$_5$■0.5H$_2$O: C, 60.99; H, 7.36; N, 4.45%. Found: C, 60.98; H, 7.46; N, 4.40%.

Example 289

{(4-dec-1-ynylbenzyl)[4-(trifluoromethyl)phenyl]amino}(oxo)acetic acid

Step a) Formation of N-(4-dec-1-ynylbenzyl)-N-[4-(trifluoromethyl)phenyl]amine The same procedure as employed in the preparation of Example 226 (step a) but using 4-dec-1-ynylbenzaldehyde and 4-(trifluoromethyl)aniline gave the title compound as a colorless oil (50%). $^1$H NMR (CDCl$_3$, 300 MHz) δ 7.32 (d, J=8.3 Hz, 2H), 7.29 (d, J=8.3 Hz, 2H), 7.21-7.13 (m, 2H), 6.50 (d, J=8.7 Hz, 2H), 4.28 (s, 2H), 2.32 (t, J=7.2 Hz, 2H), 1.60-1.43 (m, 2H), 1.43-1.31 (m, 2H), 1.30-1.11 (m, 8H), 0.87-0.75 (m, 3H). M$^-$(LC/MS(ESI)): 386.4. HPLC (Condition A), Rt: 6.43 min (HPLC purity: 82.6%).

Step b) Formation of tert-butyl {(4-dec-1-ynylbenzyl)[4-(trifluoromethyl)phenyl]amino)}(oxo)acetate The same procedure as employed in the preparation of Example 15 (step b) but using N-(4-dec-1-ynylbenzyl)-N-[4-(trifluoromethyl)phenyl]amine and tert-butyl chloro(oxo)acetate gave the title compound as a colorless oil (27%). $^1$H NMR (CDCl$_3$, 300 MHz) δ 7.58 (d, J=8.3 Hz, 2H), 7.31 (d, J=8.3 Hz, 2H), 7.18 (d, J=8.3 Hz, 2H), 7.12 (d, J=8.3 Hz, 2H), 5.01 (s, 2H), 2.38 (t, J=7.2 Hz, 2H), 1.65-1.69 (m, 2H), 1.49-1.37 (m, 2H), 1.37-1.22 (m, 8H), 1.17 (s, 9H), 0.87 (t, J=6.8 Hz, 3H). M$^+$(LC/MS(ESI)): 460.1 (M-t-Bu). HPLC (Condition A), Rt: 6.52 min (HPLC purity: 97.1%).

Step c) Formation of {(4-dec-1-ynylbenzyl)[4-(trifluoromethyl)phenyl]amino}(oxo)acetic acid The same procedure as employed in the preparation of Example 15 (step c) but using tert-butyl{(4-dec-1-ynylbenzyl)[4-(trifluoromethyl)phenyl]amino}(oxo)acetate gave the title compound as a yellow foam (60%). $^1$H NMR (CDCl$_3$, 300 MHz) δ 7.65 (m, 2H), 7.43 (m, 2H), 7.27 (m, 2H), 5.76 (s, 1H), 4.96 (s, 2H), 2.38 (t, 2H), 1.59-1.45 (in 2H), 1.44-1.15 (m, 12H), 0.84 (t, J=6.7 Hz, 3H) M$^-$(ESI): 458. HPLC (Condition A), Rt: 5.70 min (HPLC purity: 94.6%).

Example 290

((4-dec-1-ynylbenzyl){1-[4-(trifluoromethyl)phenyl]ethyl}amino)(oxo)acetic acid

Step a) Formation of N-(4-dec-1-ynylbenzyl)-N-{1-[4-(trifluoromethyl)phenyl]ethyl}amine The same procedure as employed in the preparation of Example 226 (step a) but using 4-dec-1-ynylbenzaldehyde and 1-[4-(trifluoromethyl)phenyl]ethanamine gave the title compound as a colorless oil (54%). M$^+$(ESI): 416.2. HPLC (Condition A), Rt: 4.67 min (HPLC purity: 87.6%).

Step b) Formation of ethyl((4-dec-1-ynylbenzyl){1-[4-(trifluoromethyl)phenyl]ethyl}-amino)(oxo)acetate The same procedure as employed in the preparation of Example 15 (step b) but using N-(4-dec-1-ynylbenzyl)-N-{1-

[4-(trifluoromethyl)phenyl]ethyl}amine gave the title compound as a colorless oil (60%). $^1$H NMR (CDCl$_3$, 300 MHz) δ 7.63-7.52 (m, 2H), 7.43-7.34 (m, 2H), 7.32-7.20 (m, 2H), 7.07-6.95 (m, 2H), 5.81 (m, 0.5H), 5.03 (m, 0.5H), 4.77-3.86 (m, 4H), 2.38 (t, J=7.2 Hz, 2H), 1.66-1.21 (m, 18H), 0.88 (t, J=7.1 Hz, 3H). M$^+$(ESI): 516.2. HPLC (Condition A), Rt: 6.38 min (HPLC purity: 98.2%).

Step c) Formation of ((4-dec-1-ynylbenzyl){1-[4-(trifluoromethyl)phenyl]ethyl}amino)-(oxo)acetic acid The same procedure as employed in the preparation of Example 1 (step e) but using ethyl ((4-dec-1-ynylbenzyl){1-[4-(trifluoromethyl)phenyl]ethyl}amino)(oxo)acetate gave the title compound as a colorless oil (85%). $^1$H NMR (DMSO-d$_6$, 300 MHz) δ 7.53-7.39 (m, 2H), 7.38-7.18 (m, 2H), 7.10-6.70 (m, 3H), 6.78 (d, J=8.3 Hz, 1H), 5.24 (q, J=7.2 Hz, 0.4H), 4.93 (q, J=7.2 Hz, 0.6H), 4.39-4.15 (m, 1.4H), 4.00-3.89 (m, 0.6H), 2.20-2.13 (m, 2H), 1.41-0.96 (m, 15H), 0.66 (t, J=7.1 Hz, 3H). M$^-$(LC/MS(ESI)): 486.3. HPLC (Condition A), Rt: 5.76 min (HPLC purity: 98.2%). Analysis calculated for C$_{28}$H$_{32}$F$_3$NO$_3$■1.0H$_2$O: C, 66.52; H, 6.78; N, 2.77%. Found: C, 66.73; H, 6.82; N, 2.72%.

Example 291

((4-dec-1-ynylbenzyl){1-[4-(trifluoromethyl)phenyl]ethyl}amino)(oxo)acetic acid, N-methyl-D-glucamine (i.e. 1-deoxy-1-(methylamino)glucitol) salt The same procedure as employed in the preparation of Example 2 but using N-methyl-D-glucamine and ((4-dec-1-ynylbenzyl){1-[4-(trifluoromethyl)phenyl]ethyl}amino)(oxo)-acetic acid gave the title compound as a white solid (84%). M$^-$(LC/MS(ESI)): 486.1. HPLC (Condition A), Rt: 5.79 min (HPLC purity: 98.3%). Analysis calculated for C$_{28}$H$_{32}$F$_3$NO$_3$.C$_7$H$_{17}$NO$_5$■1.0H$_2$O: C, 59.99; H, 7.33; N, 4.00%. Found: C, 60.22; H, 7.37; N, 3.96%.

Example 292

{{1-methyl-1-[4-(trifluoromethyl)phenyl]ethyl}[4-(3-undecyl-1,2,4-oxadiazol-5-yl)benzyl]amino}(oxo)acetic acid Step a) Formation of N-{1-methyl-1-[4-(trifluoromethyl)phenyl]ethyl}acetamide To a cold (0° C.) solution H$_2$SO$_4$ (2.68 g, 27.3 mmol) in CH$_3$CN (91 mL) was added dropwise a solution of 2-(4-(trifluoromethyl)-phenyl)-2-propanol (1.86 g, 9.1 mmol) in CH$_3$CN (9.1 mL). The resulting reaction mixture was stirred at 0° C. for 1 h then at rt for 23 h. The solvent was evaporated under vacuo and H$_2$O was added (20 mL). The mixture was extracted with Et$_2$O (2×50 mL) and the combined organic layers were washed with H$_2$O (2×20 mL), an aqueous solution of NaOH (1N) (2×20 mL), dried over MgSO$_4$, filtered and evaporated to give the title compound as white solid (2.00 g, 90%). $^1$H NMR (CDCl$_3$, 300 MHz) δ 7.69 (d, J=8.3 Hz, 2H), 7.59 (d, J=8.3 Hz, 2H), 2.10 (s, 3H), 1.79 (s, 6H). HPLC (Condition A), Rt: 3.18 min (HPLC purity: 97.2%).

Step b) Formation of 1-methyl-1-[4-(trifluoromethyl)phenyl]ethylamine

To a solution N-{1-methyl-1-[4-(trifluoromethyl)phenyl]ethyl}acetamide (2.0 g, 8.16 mmol) in ethylene glycol (5 mL) was added KOH (3.66 g, 8.16 mmol) and the resulting mixture was heated for 48 h at 170° C. After cooling to rt, the reaction mixture was extracted with Et$_2$O (3×20 mL). The combined organic layers were washed with water (4×), dried over MgSO$_4$, filtered and evaporated to give a colorless oil. This oil was dissolved in Et$_2$O (30 mL) and a saturated solution of HCl in Et$_2$O (10 mL) was added. The white precipitate was collected, washed with Et$_2$O (3×10 mL) and dried under vacuo. This solid was then poured into Et$_2$O (50 mL) and a 1N aqueous solution of NaOH (20 mL) were added. The organic layer was separated and the aqueous layer was extracted with Et$_2$O. The combined organic layers were washed with water (2×20 mL), dried over MgSO$_4$, filtered and evaporated to give the title compound as colorless oil (1.2 g, 72%). $^1$H NMR (CDCl$_3$, 300 MHz) δ 7.60-7.46 (m, 4H), 1.53 (br s, 2H), 1.43 (s, 6H). HPLC (Condition A), Rt: 1.73 min (HPLC purity: 94.0%).

Step c) Formation of N-{1-methyl-1-[4-(trifluoromethyl)phenyl]ethyl}-N-[4-(3-undecyl-1,2,4-oxadiazol-5-yl)benzyl]amine The same procedure as employed in the preparation of Example 226 (step a) but using 4-(3-undecyl-1,2,4-oxadiazol-5-yl)benzaldehyde and 1-methyl-1-[4-(trifluoromethyl)phenyl]ethylamine gave the title compound as a colorless oil (78%). $^1$H NMR (CDCl$_3$, 300 MHz) δ 8.07 (d, J=7.9 Hz, 2H), 7.73-7.59 (m, 4H), 7.49 (d, J=8.3 Hz, 2H), 3.57 (s, 2H), 2.80 (t, J=7.5 Hz, 2H), 1.89-1.74 (m, 2H), 1.57 (s, 3H), 1.47-1.17 (m, 19H), 0.88 (t, J=7.0 Hz, 3H). M$^+$(LC/MS(ESI)): 516.3. HPLC (Condition A), Rt: 5.02 min (HPLC purity: 98.2%).

Step d) Formation of ethyl{{1-methyl-1-[4-(trifluoromethyl)phenyl]ethyl}[4-(3-undecyl-1,2,4-oxadiazol-5-yl)benzyl]amino}(oxo)acetate The same procedure as employed in the preparation of Example 15 (step b) but using N-{1-methyl-1-[4-(trifluoromethyl)phenyl]ethyl}-N-[4-(3-undecyl-1,2,4-oxadiazol-5-yl)benzyl]amine gave the title compound as a yellow oil (87%). $^1$H NMR (CDCl$_3$, 300 MHz) δ 8.15 (d, J=8.3 Hz, 2H), 7.70-7.50 (m, 4H), 7.42 (d, J=8.3 Hz, 2H), 4.92-4.75 (m, 2H), 4.31-4.18 (m, 1.3H), 3.65-3.52 (m, 0.7H), 2.79 (t, J=7.2 Hz, 2H), 1.91-1.75 (m, 2H), 1.75-1.60 (m, 3H), 1.54 (s, 3H), 1.48-1.00 (m, 19H), 0.87 (t, J=7.0 Hz, 3H). M$^-$(LC/MS (ESI)): 614.2; M$^+$(LC/MS(ESI)): 616.4. HPLC (Condition A), Rt: 6.64 min (HPLC purity: 99.7%).

Step e) Formation of {{1-methyl-1-[4-(trifluoromethyl)phenyl]ethyl}[4-(3-undecyl-1,2,4-oxadiazol-5-yl)benzyl]amino}(oxo)acetic acid The same procedure as employed in the preparation of Example 1 (step e) but using ethyl{{1-methyl-1-[4-(trifluoromethyl)phenyl]ethyl}[4-(3-undecyl-1,2,4-oxadiazol-5-yl)benzyl]amino}(oxo)acetate gave the title compound as a colorless foam (94%). $^1$H NMR (CD$_3$OD, 300 MHz) δ 8.08 (d, J=8.3 Hz, 2H), 7.67 (d, J=8.3 Hz, 2H), 7.51 (d, J=8.3 Hz, 2H), 7.45 (d, J=8.3 Hz, 2H), 5.03 (s, 2H), 2.80 (t, J=7.5 Hz, 2H), 1.82-1.48 (m, 8H), 1.40-1.10 (m, 16H), 0.89 (t, J=7.0 Hz, 3H). M$^-$(LC/MS(ESI)): 586.2. HPLC (Condition A), Rt: 6.21 min (HPLC purity: 99.6%). Analysis calculated for C$_{32}$H$_{40}$F$_3$N$_3$O$_4$0.2H$_2$O: C, 65.00; H, 6.89; N, 7.11%. Found: C, 64.64; H, 6.69; N, 6.84%.

Example 293

{{1-methyl-1-[4-(trifluoromethyl)phenyl]ethyl}[4-(3-undecyl-1,2,4-oxadiazol-5-yl)benzyl]amino}(oxo)acetic acid N-methyl-D-glucamine (i.e. 1-deoxy-1-(methylamino)glucitol) salt The same procedure as employed in the preparation of Example 2 but using N-methyl-D-glucamine and {{1-methyl-1-[4-(trifluoromethyl)phenyl]ethyl}[4-(3-undecyl-1,2,4-oxadiazol-5-yl)benzyl]amino}(oxo)acetic acid gave the title compound as a white powder (95%). M⁻(LC/MS(ESI)): 586.3. HPLC (Condition A), Rt: 6.22 min (HPLC purity: 99.9%). Analysis calculated for C$_{32}$H$_{40}$F$_3$N$_3$O$_4$·C$_7$H$_{17}$NO$_5$■1.5H$_2$O: C, 57.84; H, 7.47; N, 6.92%. Found: C, 57.79; H, 7.46; N, 6.88%.

Example 294

{[2-(3-chlorophenyl)ethyl][4-(3-octyl-1,2,4-oxadiazol-5-yl)benzyl]-amino}-(oxo)acetic acid Step a) Formation of 4-(3-octyl-1,2,4-oxadiazol-5-yl)benzaldehyde The same procedure as employed in the preparation of Example 277 (step a) but using 4-carboxybenzaldehyde and N-hydroxynonanimidamide gave the title compound as a beige solid (34%). $^1$H NMR (CDCl$_3$, 300 MHz) δ 10.1 (s, 1H), 8.29 (d, 2H, J=8.3 Hz), 8.03 (d, 2H, J=8.3 Hz), 2.81 (t, 2H, J=7.4 Hz), 1.86-1.75 (m, 2H), 1.46-1.21 (m, 10H), 0.87 (m, 3H). HPLC (Condition A), Rt: 5.16 min (HPLC purity: 95.4%).

Step b) Formation of N-[2-(3-chlorophenyl)ethyl]-N-[4-(3-octyl-1,2,4-oxadiazol-5-yl)benzyl]amine The same procedure as employed in the preparation of Example 226 (step a) but using 4-(3-octyl-1,2,4-oxadiazol-5-yl)benzaldehyde and [2-(3-chlorophenyl)ethyl]amine gave the title compound as a colorless oil (76%). $^1$H NMR (CDCl$_3$, 300 MHz) δ 8.06 (d, J=8.3 Hz, 2H), 7.44 (d, J=8.3 Hz, 2H), 7.23-7.00 (m, 4H), 3.88 (s, 2H), 2.95-2.68 (m, 6H), 1.75-1.65 (m, 2H), 1.41-1.20 (m, 10H), 0.87 (t, J=7.1 Hz, 3H). M$^+$(LC/MS(ESI)): 426.4. HPLC (Condition A), Rt: 4.35 min (HPLC purity: 99.6%).

Step c) Formation of ethyl{[2-(3-chlorophenyl)ethyl][4-(3-octyl-1,2,4-oxadiazol-5-yl)benzyl]amino}(oxo)acetate The same procedure as employed in the preparation of Example 15 (step b) but using N-[2-(3-chlorophenyl)ethyl]-N-[4-(3-octyl-1,2,4-oxadiazol-5-yl)benzyl]amine gave the title compound as a colorless oil (59%). $^1$H NMR (CDCl$_3$, 300 MHz) δ 8.05 (dd, J1=8.3 Hz, J2=1.5 Hz, 2H), 7.37-7.39 (m, 2H), 7.18-7.12 (m, 2H), 7.09-6.87 (m, 2H), 4.59 (s, 1H), 4.43-4.22 (m, 3H), 3.48-3.35 (m, 2H), 2.84-2.68 (m, 4H), 1.80-1.68 (m, 2H), 1.38-1.14 (m, 13H), 0.87 (t, J=7.0 Hz, 3H). M⁻(LC/MS(ESI)): 524.4; M$^+$(LC/MS(ESI)): 526.4. HPLC (Condition A), Rt: 6.06 min (HPLC purity: 99.8%).

Step d) Formation of {[2-(3-chlorophenyl)ethyl][4-(3-octyl-1,2,4-oxadiazol-5-yl)benzyl]-amino}(oxo)acetic acid The same procedure as employed in the preparation of Example 1 (step e) but using ethyl{[2-(3-chlorophenyl)ethyl][4-(3-octyl-1,2,4-oxadiazol-5-yl)benzyl]amino}(oxo)acetate gave the title compound as a colorless oil (79%). $^1$H NMR (CD$_3$OD, 300 MHz) δ 8.14 (d, J=8.3 Hz, 2H), 7.60-7.49 (m, 2H), 7.34-7.09 (m, 4H), 4.72 (s, 1.2H), 4.57 (s, 0.8H), 3.67-3.49 (m, 2H), 3.03-2.76 (m, 4H), 1.90-1.75 (m, 2H), 1.51-1.24 (m, 10H), 0.89 (t, J=7.0 Hz, 3H). M⁻(LC/MS(ESI)): 496.3. HPLC (Condition A), Rt: 5.48 min (HPLC purity: 100%). Analysis calculated for C$_{27}$H$_{32}$ClN$_3$O$_4$■0.5H$_2$O: C, 63.96; H, 6.56; N, 8.29%. Found: C, 63.96; H, 6.59; N, 8.20%.

Example 295

{[2-(3-chlorophenyl)ethyl][4-(3-octyl-1,2,4-oxadiazol-5-yl)benzyl]amino}-(oxo)acetic acid, N-methyl-D-glucamine (i.e. 1-deoxy-1-methylamino)glucitol) salt The same procedure as employed in the preparation of Example 2 but using N-methyl-D-glucamine and {[2-(3-chlorophenyl)ethyl][4-(3-octyl-1,2,4-oxadiazol-5-yl) benzyl]amino}(oxo)acetic acid gave the title compound as a white solid (68%). M⁻(LC/MS(ESI)): 496.2. HPLC (Condition A), Rt: 5.51 min (HPLC purity: 99.4%). Analysis calculated for C$_{27}$H$_{32}$ClN$_3$O$_4$·C$_7$H$_{17}$NO$_5$■1.5H$_2$O: C, 56.70; H, 7.28; N, 7.78%. Found: C, 56.83; H, 7.48; N, 7.77%.

Example 296

{[4-(3-octyl-1,2,4-oxadiazol-5-yl)benzyl][4-(trifluoromethyl)benzyl]amino}-(oxo)acetic acid Step a) Formation of N-[4-(3-octyl-1,2,4-oxadiazol-5-yl)benzyl]-N-[4-(trifluoromethyl)-benzyl]amine The same procedure as employed in the preparation of Example 223 (step b) but using 4-(3-octyl-1,2,4-oxadiazol-5-yl)benzaldehyde and 4-(trifluoromethyl)benzylamine gave the title compound as a colorless oil (49%). M$^+$(LC/MS (ESI)): 446.4.

Step b) Formation of ethyl{[4-(3-octyl-1,2,4-oxadiazol-5-yl)benzyl][4-(trifluoromethyl)-benzyl]amino}(oxo)acetate The same procedure as employed in the preparation of Example 15 (step b) but using N-[4-(3-octyl-1,2,4-oxadiazol-5-yl)benzyl]-N-[4-(trifluoromethyl)benzyl]amine gave the title compound as a colorless oil (89%). $^1$H NMR (CDCl$_3$, 300 MHz) δ 8.05 (d, J=8.3 Hz, 1H), 8.02 (d, J=8.3 Hz, 1H), 7.60-7.49 (m, 2H), 7.39-7.22 (m, 4H), 4.50 (s, 2H), 4.37 (s, 2H), 4.34-4.23 (m, 2H), 2.78-2.67 (m, 2H), 1.82-1.66 (m, 2H), 1.42-1.11 (m, 13H), 0.81 (t, J=7.2 Hz, 3H). M⁻(LC/MS (ESI)): 544.3; M$^+$(LC/MS(ESI)): 546.2. HPLC (Condition A), Rt: 5.98 min (HPLC purity: 98.5%).

Step c) Formation of {[4-(3-octyl-1,2,4-oxadiazol-5-yl)benzyl][4-(trifluoromethyl)benzyl]-amino}(oxo) acetic acid The same procedure as employed in the preparation of Example 1 (step e) but using ethyl {[4-(3-octyl-1,2,4-oxadiazol-5-yl)benzyl][4-(trifluoromethyl)benzyl]amino}(oxo)acetate gave the title compound as a colorless oil (90%). $^1$H NMR (CD$_3$OD, 300 MHz) δ 8.16-8.04 (m, 2H), 7.71-7.38 (m, 6H), 4.66 (s, 2H), 4.64 (s, 2H), 2.80 (m, 2H), 1.91-1.76 (m, 2H), 1.52-1.25 (m, 10H), 0.91 (t, J=7.0 Hz, 3H). M⁻(LC/MS(ESI)): 516.2. HPLC (Condition A), Rt: 5.45 min (HPLC purity: 98.3%). Analysis calculated for C$_{27}$H$_{30}$F$_3$N$_3$O$_4$■0.2H$_2$O: C, 62.23; H, 5.88; N, 8.06%. Found: C, 62.10; H, 6.04; N, 7.87%.

Example 297

{[4-(3-octyl-1,2,4-oxadiazol-5-yl)benzyl][4-(trifluoromethyl)benzyl]amino}(oxo)acetic acid, N-methyl-D-glucamine (i.e. 1-deoxy-1-(methylamino)glucitol) salt The same procedure as employed in the preparation of Example 2 but using N-methyl-D-glucamine and {[4-(3-octyl-1,2,4-oxadiazol-5-yl)benzyl][4-(trifluoromethyl)benzyl]-amino}(oxo)acetic acid gave the title compound as a white solid (82%). M⁻(LC/MS(ESI)): 516.3. HPLC (Condition A), Rt: 5.43 min (HPLC purity: 98.6%). Analysis calculated for $C_{27}H_{30}F_3N_3O_4 \cdot C_7H_{17}NO_5 \blacksquare 1.0H_2O$: C, 55.88; H, 6.76; N, 7.67%. Found: C, 55.54; H, 6.79; N, 7.55%.

Example 298

{{[4-(dodecyloxy)-1-naphthyl]methyl}[4-(trifluoromethyl)benzyl]amino}-(oxo)acetic acid Step a) Formation of 4-(dodecyloxy)-1-naphthaldehyde To a solution of 1-bromodecane (10.0 g, 40.12 mmol) and 4-hydroxy-1-naphthaldehyde (6.29 g, 36.5 mmol) in anhydrous DMF (150 mL) was added NaOMe (2.38 g, 44.1 mmol). The mixture was stirred at 50° C. for 5 h. The reaction mixture was cooled to rt and concentrated under vacuo. The residue was dissolved in EtOAc and washed with brine (3×), dried over MgSO₄, filtered and concentrated under reduced pressure to give an orange solid. Purification by chromatography (SiO₂, c-Hex/EtOAc 9/1) gave the title product as a beige powder (11.12 g, 81%). ¹H NMR (CDCl₃, 300 MHz) δ 10.2 (s, 1H), 9.29 (d, 1H, J=8.7 Hz), 8.35 (d, 1H, J=8.7 Hz), 7.90 (d, 1H, J=8.3 Hz), 7.69 (m, 1H), 7.57 (m, 1H), 6.90 (d, 1H, J=7.9 Hz), 4.23 (t, 2H, J=6.4 Hz), 2.01-1.79 (m, 2H), 1.68-1.48 (m, 2H), 1.45-1.20 (m, 16H), 0.87 (m, 3H). HPLC (Condition A), Rt: 6.61 min (HPLC purity: 85.8%).

Step b) Formation of N-{[4-(dodecyloxy)-1-naphthyl]methyl}-N-[4-(trifluoromethyl)-benzyl]amine The same procedure as employed in the preparation of Example 226 (step a) but using 4-(dodecyloxy)-1-naphthaldehyde and 4-(trifluoromethyl)benzylamine gave the title compound as a colorless oil (66%). ¹H NMR (CDCl₃, 300 MHz) δ 8.20 (d, J=7.9 Hz, 1H), 7.91 (d, J=7.9 Hz, 1H), 7.76-7.41 (m, 6H), 7.32 (d, J=7.5 Hz, 1H), 6.72 (d, J=7.5 Hz, 1H), 4.19-4.11 (m, 4H), 3.63 (s, 2H), 1.96-1.84 (m, 2H), 1.63-1.47 (m, 2H), 1.45-1.20 (m, 16H), 0.87 (t, J=6.8 Hz, 3H). HPLC (Condition A), Rt: 5.41 min (HPLC purity: 100%).

Step c) Formation of ethyl{{[4-(dodecyloxy)-1-naphthyl]methyl}[4-(trifluoromethyl)-benzyl]amino}(oxo)acetate The same procedure as employed in the preparation of Example 15 (step b) but using N-{[4-(dodecyloxy)-1-naphthyl]methyl}-N-[4-(trifluoromethyl)benzyl]amine gave the title compound as a colorless oil (88%). ¹H NMR (CDCl₃, 300 MHz) δ 8.20 (d, J=7.5 Hz, 1H), 7.91 (d, J=8.0 Hz, 0.5H), 7.76 (m, 0.5H), 7.60-7.44 (m, 4H), 7.28 (m, 1.5H), 7.19 (t, J=8.3 Hz, 1H), 7.02 (d, J=7.9 Hz, 0.5H), 6.72 (d, J=7.9 Hz, 0.5H), 6.68 (d, J=7.9 Hz, 0.5H), 4.93 (s, 1H), 4.79 (s, 1H), 4.52 (s, 1H), 4.40-4.23 (m, 3H), 4.11 (m, 2H), 1.93 (m, 2H), 1.40-1.15 (m, 21H), 0.87 (t, J=6.9 Hz, 3H). HPLC (Condition A), Rt: 6.98 min (HPLC purity: 96.6%).

Step d) Formation of {{[4-(dodecyloxy)-1-naphthyl]methyl}[4-(trifluoromethyl)benzyl]-amino}(oxo)acetic acid The same procedure as employed in the preparation of Example 1 (step e) but using ethyl {{[4-(dodecyloxy)-1-naphthyl]methyl}[4-(trifluoromethyl)benzyl]amino}(oxo)acetate gave the title compound as a white powder (67%). ¹H NMR (CD₃OD, 300 MHz) δ 8.30-8.19 (m, 1H), 8.00-7.91 (m, 1H), 7.61-7.26 (m, 6H), 7.21-7.09 (s, 1H), 4.98 (s, 2H), 4.54 (s, 1H), 4.46 (s, 1H), 4.17 (m, 2H), 2.05-1.88 (m, 2H), 1.71-1.55 (m, 2H), 1.55-1.21 (m, 16H), 0.91 (t, J=6.8 Hz, 3H). M⁻(LC/MS(ESI)): 570.2. HPLC (Condition A), Rt: 6.44 min (HPLC purity: 100%).

Example 299

{{[4-(dodecyloxy)-1-naphthyl]methyl}[4-(trifluoromethyl)benzyl]amino}-(oxo)acetic acid N-methyl-D-glucamine (i.e. 1-deoxy-1-(methylamino)glucitol) salt The same procedure as employed in the preparation of Example 2 but using N-methyl-D-glucamine and {{[4-(dodecyloxy)-1-naphthyl]methyl}[4-(trifluoromethyl)benzyl]amino}(oxo)acetic acid gave the title compound as a pink solid (68%). M⁻(LC/MS(ESI)): 570.3. HPLC (Condition A), Rt: 6.45 min (HPLC purity: 99.7%). Analysis calculated for $C_{33}H_{40}F_3NO_4 \cdot C_7H_{17}NO_5 \blacksquare 1.5H_2O$: C, 60.52; H, 7.62; N, 3.53%. Found: C, 60.71; H, 7.50; N, 3.56%.

Example 300

[(4-bromobenzyl)(4-oct-1-ynylbenzyl)amino](oxo)acetic acid

Step a) Formation of N-(4-bromobenzyl)-N-(4-oct-1-ynylbenzyl)amine

The same procedure as employed in the preparation of Example 226 (step a) but using 4-oct-1-ynylbenzaldehyde and 4-bromobenzylamine gave the title compound as a colorless oil (86%). ¹H NMR (CDCl₃, 300 MHz) δ 7.47 (d, J=8.3 Hz, 2H), 7.38 (d, J=8.3 Hz, 2H), 7.30-7.19 (m, 4H), 3.78 (s, 2H), 3.75 (s, 2H), 2.42 (t, J=6.8 Hz, 2H), 1.69-1.55 (m, 2H), 1.54-1.42 (m, 2H), 1.42-1.27 (m, 4H), 0.93 (t, J=6.8 Hz, 3H). M⁺(LC/MS(ESI)): 384.4 HPLC (Condition A), Rt: 4.18 min (HPLC purity: 97.6%).

Step b) Formation of ethyl[(4-bromobenzyl)(4-oct-1-ynylbenzyl)amino](oxo)acetate The same procedure as employed in the preparation of Example 15 (step b) but using N-(4-bromobenzyl)-N-(4-oct-1-ynylbenzyl)amine gave the title compound as a yellow oil (93%). ¹H NMR (CDCl₃, 300 MHz) δ 7.56-7.44 (m, 2H), 7.45-7.34 (m, 2H), 7.22-7.06 (m, 4H), 4.51-4.23 (m, 6H), 2.49-2.37 (m, 2H), 1.75-1.56 (m, 2H), 1.54-1.24 (m, 9H), 0.92 (t, J=7.0 Hz, 3H). HPLC (Condition A), Rt: 98.9 min (HPLC purity: 95.2%).

Step c) Formation of [(4-bromobenzyl)(4-oct-1-ynylbenzyl)amino](oxo)acetic acid

The same procedure as employed in the preparation of Example 1 (step e) but using ethyl [(4-bromobenzyl)(4-oct-1-ynylbenzyl)amino](oxo)acetate gave the title compound as a colorless oil (87%). ¹H NMR (CD₃OD, 300 MHz) δ 7.57-7.47 (m, 2H), 7.39-7.31 (m, 2H), 7.29-7.22 (m, 2H), 7.18-7.11 (m, 2H), 4.47 (s, 2H), 4.45 (s, 2H), 2.42 (t, J=6.8 Hz, 2H), 1.69-1.30 (m, 8H), 0.96 (t, J=7.0 Hz, 3H). M⁻(LC/MS(ESI)): 455.8. HPLC (Condition A), Rt: 5.28 min (HPLC purity: 98.7%).

Example 301

[{4-[(dodecylamino)carbonyl]benzyl}(2-hydroxy-1-phenylethyl)amino]-(oxo)acetic acid

Step a) Formation of N-dodecyl-4-{[(2-hydroxy-1-phenylethyl)amino]methyl}benzamide The same procedure as employed in the preparation of Example 226 (step a) but using N-dodecyl-4-formylbenzamide and 2-amino-2-phenylethanol gave the title compound as a white powder (83%). $^1$H NMR (CD$_3$OD, 300 MHz) δ 7.79 (d, J=8.3 Hz, 2H), 7.44-7.26 (m, 7H), 3.85-3.56 (m, 5H), 3.39 (t, J=7.2 Hz, 2H), 1.71-1.58 (m, 2H), 1.47-1.25 (m, 18H), 0.92 (t, J=6.8 Hz, 3H) M$^-$(LC/MS(ESI)): 437.5; M$^+$(LC/MS(ESI)): 439.6 HPLC (Condition A), Rt: 4.26 min (HPLC purity: 98.8%).

Step b) Formation of 4-[(2,3-dioxo-5-phenylmorpholin-4-yl)methyl]-N-dodecylbenzamide The same procedure as employed in the preparation of Example 15 (step b) but using N-dodecyl-4-{[(2-hydroxy-1-phenylethyl)amino]methyl}benzamide gave the title compound as a colorless oil (39%). $^1$H NMR (CDCl$_3$, 300 MHz) δ 7.66 (d, J=8.3 Hz, 2H), 7.41-7.31 (m, 3H), 7.19 (d, J=8.3 Hz, 2H), 7.15-7.05 (m, 2H), 6.17 (t, J=6.0 Hz, 1H), 5.43 (s, 0.5H), 5.38 (s, 0.5H), 4.64-4.47 (m, 2H), 4.41-4.31 (m, 1H), 3.77 (s, 0.5H), 3.72 (s, 0.5H), 3.37 (m, 2H), 1.61-1.48 (m, 2H), 1.38-1.09 (m, 18H), 0.81 (t, J=7.1 Hz, 3H). M$^-$(LC/MS(ESI)): 491.4; M$^+$(LC/MS(ESI)): 493.4. HPLC (Condition A), Rt: 5.48 min (HPLC purity: 98.8%).

Step c) Formation of [{4-[(dodecylamino)carbonyl]benzyl}(2-hydroxy-1-phenylethyl)-amino](oxo)acetic acid The same procedure as employed in the preparation of Example 1 (step e) but using 4-[(2,3-dioxo-5-phenylmorpholin-4-yl)methyl]-N-dodecylbenzamide gave the title compound as a colorless oil (87%). $^1$H NMR (CDCl$_3$, 300 MHz) δ 7.54 (m, 2H), 7.31-7.20 (m, 3H), 7.15-6.91 (m, 4H), 6.02 (br s, 1H), 5.30 (d, J=14.6 Hz, 1H), 4.56-4.20 (m, 3H), 3.63 (d, J=14.6 Hz, 1H), 3.26 (m, 2H), 1.51-1.35 (m, 2H), 1.32-0.97 (m, 18H), 0.70 (t, J=6.9 Hz, 3H). M$^-$(LC/MS(ESI)): 509.4; M$^+$(LC/MS(ESI)): 511.4. HPLC (Condition A), Rt: 5.47 min (HPLC purity: 90.2%).

Example 302

((4-dec-1-ynylbenzyl){1-methyl-1[4-(trifluoromethyl)phenyl]ethyl}-amino)(oxo)acetic acid

Step a) Formation of N-(4-dec-1-ynylbenzyl)-N-{1-methyl-1-[4-(trifluoromethyl)phenyl]ethyl}amine The same procedure as employed in the preparation of Example 226 (step a) but using 4-dec-1-ynylbenzaldehyde and 1-methyl-1-[4-(trifluoromethyl)phenyl]ethylamine gave the title compound as a colorless oil (79%). $^1$H NMR (CDCl$_3$, 300 MHz) δ 7.74-7.57 (m, 4H), 7.36 (d, J=8.1 Hz, 2H), 7.24 (d, J=8.3 Hz, 2H), 3.48 (s, 2H), 2.41 (t, J=7.2 Hz, 2H), 1.73-1.22 (m, 18H), 0.91 (t, J=7.0 Hz, 3H). M$^+$(LC/MS(ESI)): 430.4. HPLC (Condition A), Rt: 4.69 min (HPLC purity: 99.8%).

Step b) Formation of ethyl((4-dec-1-ynylbenzyl){1-methyl-1-[4-(trifluoromethyl)phenyl]-ethyl}amino)(oxo)acetate The same procedure as employed in the preparation of Example 15 (step b) but using N-(4-dec-1-ynylbenzyl)-N-{1-methyl-1-[4-(trifluoromethyl)phenyl]ethyl}amine gave the title compound as a colorless oil (91%). $^1$H NMR (CDCl$_3$, 300 MHz) δ 7.58 (d, J=8.1 Hz, 2H), 7.51-7.25 (m, 6H), 4.90-4.71 (m, 2H), 4.33-4.17 (m, 1.5H), 3.66-3.46 (m, 0.5H), 2.43 (t, J=7.2 Hz, 2H), 1.77-1.54 (m, 8H), 1.53-1.18 (m, 13H), 0.91 (t, J=7.0 Hz, 3H) HPLC (Condition A), Rt: 6.38 min (HPLC purity: 99.8%).

Step c) Formation of ((4-dec-1-ynylbenzyl){1-methyl-1-[4-(trifluoromethyl)phenyl]ethyl}-amino)(oxo)acetic acid The same procedure as employed in the preparation of Example 1 (step e) but using ethyl ((4-dec-1-ynylbenzyl){1-methyl-1-[4-(trifluoromethyl)phenyl]ethyl}amino)(oxo)acetate gave the title compound as a colorless oil (95%). $^1$H NMR (CD$_3$OD, 300 MHz) δ 7.60-7.04 (m, 8H), 4.80 (s, 2H), 2.31 (t, J=6.8 Hz, 2H), 1.70-1.10 (m, 18H), 0.80 (t, J=6.9 Hz, 3H). M$^-$(LC/MS(ESI)): 500.2. HPLC (Condition A), Rt: 5.84 min (HPLC purity: 99.8%). Analysis calculated for C$_{29}$H$_{34}$F$_3$NO$_3$: C, 69.44; H, 6.83; N, 2.79%. Found: C, 69.55; H, 7.07; N, 2.77%.

Example 303

((4-dec-1-ynylbenzyl){1-methyl-1-[4-(trifluoromethyl)phenyl]ethyl}amino)-(oxo)acetic acid, N-methyl-D-glucamine (i.e. 1-deoxy-1-(methylamino)glucitol) salt The same procedure as employed in the preparation of Example 2 but using N-methyl-D-glucamine and ((4-dec-1-ynylbenzyl){1-methyl-1-[4-(trifluoromethyl)phenyl]-amino)(oxo)acetic acid gave the title compound as a white solid (80%). M$^-$(LC/MS(ESI)): 500.2. HPLC (Condition A), Rt: 5.89 min (HPLC purity: 98.6%). Analysis calculated for C$_{29}$H$_{34}$F$_3$NO$_3$.C$_7$H$_{17}$NO$_5$■1.0H$_2$O: C, 60.49; H, 7.47; N, 3.92%. Found: C, 60.75; H, 7.76; N, 3.89%.

Example 304 oxo{{4-[(9Z)-tetradec-9-enoylamino]benzyl}[4-(trifluoromethyl)-benzyl]amino}acetic acid

Step a) Formation of Ethyl oxo{{4-[(9Z)-tetradec-9-enoylamino]benzyl}[4-(trifluoromethyl)benzyl]amino}acetate To a cold (0° C.) solution of ethyl{(4-aminobenzyl)[4-(trifluoromethyl)benzyl]amino}-(oxo)acetate (140 mg, 0.37 mmol) in anhydrous pyridine (2 mL) was added (9Z)-tetradec-9-enoyl chloride (100 mg, 0.40 mmol) under inert atmosphere. The resulting reaction mixture was stirred for 1 h at 0° C. A 5 N aqueous solution of HCl (10 mL) was added and the mixture was extracted with Et$_2$O (3×10 mL). The combined organic layers were dried over MgSO$_4$, filtered and concentrated to give a yellow oil. This crude product was purified by SPE (NH$_2$ Isolute column) to give the title compound as a pale yellow oil (191 mg, 88%). $^1$H NMR (CDCl$_3$, 300 MHz) δ 7.62 (m, 2H), 7.52 (m, 2H), 7.39 (d, 1H, J=8.0 Hz), 7.33 (d, 1H, J=7.9 Hz), 7.20 (m, 3H), 5.36 (m, 2H), 4.52

(s, 1H), 4.46 (s, 1H), 4.42-4.30 (m, 4H), 2.37 (t, 2H, J=7.5 Hz), 2.03 (m, 4H), 1.74 (m, 2H), 1.39-1.29 (m, 15H), 0.90 (t, 3H, 3=6.9 Hz). M⁻(LC/MS(ESI)): 587; M⁺(LC/MS(ESI)): 589. HPLC (Condition A), Rt: 7.24 min (HPLC purity: 97.3%).

Step b) Formation of oxo{{4-[(9Z)-tetradec-9-enoylamino]benzyl}[4-(trifluoromethyl)-benzyl]amino}acetic acid The same procedure as employed in the preparation of Example 1 (step e) but using ethyl oxo{{4-[(9Z)-tetradec-9-enoylamino]benzyl}[4-(trifluoromethyl)benzyl]amino}acetate gave the title compound as a yellow oil (84%). ¹H NMR (CD₃OD, 300 MHz) δ 7.64 (m, 2H), 7.50 (m, 3H), 7.36 (d, 1H, J=8.18 Hz), 7.25 (d, 1H, J=8.67 Hz), 7.15 (d, 1H, J=8.67 Hz), 5.35 (m, 2H), 4.55 (s, 2H), 4.47 (s, 2H), 2.36 (t, 2H, J=7.2 Hz), 2.03 (m, 4H), 1.33 (m, 14H), 0.91 (m, 3H). M⁻(LC/MS(ESI)): 559; M⁺(LC/MS(ESI)): 561. HPLC (Condition A), Rt: 6.25 min (HPLC purity: 99.1%).

Example 305

{(4-dec-1-ynylbenzyl)[4-(trifluoromethyl)benzyl]amino}(oxo)acetic acid

Step a) Formation of ethyl{(4-dec-1-ynylbenzyl)[4-(trifluoromethyl)benzyl]-amino}-(oxo)acetate The same procedure as employed in the preparation of Example 226 (step c) but using 1-decyne gave the title compound as a yellow oil (58%). ¹H NMR (CDCl₃, 300 MHz) δ 7.62 (m, 2H), 7.36 (m, 4H), 7.15 (m, 2H), 4.50 (m, 2H), 4.35 (m, 4H), 2.42 (dt, 2H, J=7.0, 1.5 Hz), 1.62 (m, 2H), 1.47 (m, 2H), 1.34 (m, 1H), 0.90 (t, 3H, J=6.7 Hz). HPLC (Condition A), Rt: 7.16 min (HPLC purity: 99.5%).

Step b) Formation of {(4-dec-1-ynylbenzyl)[4-(trifluoromethyl)benzyl]amino}(oxo)acetic acid The same procedure as employed in the preparation of Example 1 (step e) but using ethyl{(4-dec-1-ynylbenzyl)[4-(trifluoromethyl)benzyl]amino}(oxo)acetate gave the title compound as a yellow oil (91%). ¹H NMR (CDCl₃, 300 MHz) δ 7.60 (m, 3H), 7.34 (m, 4H), 7.12 (m, 2H), 6.28 (br s, 1H), 4.89 (s, 1H), 4.82 (s, 1H), 4.55 (s, 1H), 4.52 (s, 1H), 2.38 (t, 2H, J=6.7 Hz), 1.58 (m, 2H), 1.41 (m, 2H), 1.27 (br s, 8H), 0.87 (m, 3H) M⁻(LC/MS(ESI)): 472. HPLC (Condition A), Rt: 6.57 min (HPLC purity: 98.5%).

Example 306 oxo{[4-(trifluoromethyl)benzyl][3-(3-undecyl-1,2,4-oxadiazol-5-yl)benzyl]-amino}acetic acid Step a) Formation of 3-({[4-(trifluoromethyl)benzyl]amino}methyl)benzoic acid The same procedure as employed in the preparation of Example 226 (step a) but using 3-formylbenzoic acid gave the title compound as a white solid (72%). ¹H NMR (CD₃OD, 300 MHz) δ 8.20 (br s, 1H), 8.11 (d, 1H, J=7.9 Hz), 7.80-7.70 (m, 4H), 7.59 (m, 2H), 4.38 (m, 4H). M⁻(LC/MS(ESI)): 308; M⁺(LC/MS(ESI)): 310. HPLC (Condition A), Rt: 2.60 min (HPLC purity: 78.7%).

Step b) Formation of 3-({(tert-butoxycarbonyl)[4-(trifluoromethyl)benzyl]amino}-methyl)-benzoic acid To a solution of 3-({[4-(trifluoromethyl)benzyl]amino}methyl)benzoic acid hydrochloride (4.00 g, 11.6 mmol) and 1N aqueous solution of NaOH (25 mL) in dioxane (25 mL) at 0° C. was added the di-tert-butyl dicarbonate (2.78 g, 12.7 mmol) and the resulting reaction mixture was stirred at 0° C. for 30 min. The solvents were evaporated off. The residue was diluted with a 1N aqueous solution of HCl (35 mL) and extracted with EtOAc (3×30 mL). The combined organic layers were dried over MgSO₄ and the solvent was removed under reduced pressure. The residue was purified by flash chromatography over silica gel (DCM/MeOH 95/5) to give the title compound as a yellow oil (3.05 g, 64%). ¹H NMR (CDCl₃, 300 MHz) δ 8.03 (d, 1H, J=7.1 Hz), 7.94 (br s, 1H), 7.59 (d, 2H, J=7.9 Hz), 7.45 (m, 2H), 7.33 (m, 2H), 4.50 (br s, 2H), 4.42 (br s, 2H), 1.50 (s, 9H). M⁻(LC/MS(ESI)): 408 HPLC (Condition A), Rt: 5.41 min (HPLC purity: 98.2%).

Step c) Formation of Tert-Butyl 3-{[(dodecanimidoylamino)oxy]carbonyl}benzyl[4-(trifluoromethyl)benzyl]carbamate The same procedure as employed in the preparation of Example 10 (step a) but using 3-({(tert-butoxycarbonyl)[4-(trifluoromethyl)benzyl]amino}methyl)benzoic acid and N-hydroxydodecanimidamide gave the title compound as a pale yellow oil (99%). ¹H NMR (CDCl₃, 300 MHz) δ 7.91 (m, 2H), 7.59 (m, 2H), 7.36 (m, 4H), 4.78 (br s, 2H), 4.48 (br s, 2H), 4.41 (br s, 2H), 2.34 (m, 2H), 1.65 (m, 2H), 1.50 (s, 9H), 1.26 (br s, 16H), 0.88 (m, 3H). HPLC (Condition A), Rt: 7.34 min (HPLC purity: 95.6%).

Step d) Formation of Tert-Butyl 4-(trifluoromethyl)benzyl[3-(3-undecyl-1,2,4-oxadiazol-5-yl)benzyl]carbamate The same procedure as employed in the preparation of Example 23 (step e) but using tert-butyl 3-{[(dodecanimidoylamino)oxy]carbonyl}benzyl[4-(trifluoromethyl)benzyl]carbamate gave the title compound as a yellow oil (54%). ¹H NMR (CDCl₃, 300 MHz) δ 8.04 (d, 1H, J=7.1 Hz), 7.95 (br s, 1H), 7.59 (d, 2H, J=8.3 Hz), 7.48 (m, 2H), 7.32 (m, 2H), 4.51 (br s, 2H), 4.44 (br s, 2H), 2.80 (t, 2H, J=7.5 Hz), 1.80 (m, 2H), 1.51 (s, 9H), 1.43-1.27 (m, 16H), 0.88 (m, 3H). HPLC (Condition A), Rt: 8.35 min (HPLC purity: 96.4%).

Step e) Formation of N-[4-(trifluoromethyl)benzyl]-N-[3-(3-undecyl-1,2,4-oxadiazol-5-yl)benzyl]amine hydrochloride The same procedure as employed in the preparation of Example 23 (step f) but using tert-butyl 4-(trifluoromethyl)benzyl[3-(3-undecyl-1,2,4-oxadiazol-5-yl)benzyl]carbamate gave the title compound as a white solid (90%). ¹H NMR (CD₃OD, 300 MHz) δ 8.31 (br s, 1H), 8.23 (d, 1H, J=7.9 Hz), 7.80 (m, 3H), 7.71 (m, 3H), 4.43 (s, 2H), 4.41 (s, 2H), 2.80 (t, 2H, J=7.5 Hz), 1.80 (m, 2H), 1.33 (m, 16H), 0.89 (t, 3H, J=6.6 Hz). HPLC (Condition A), Rt: 5.4 min (HPLC purity: 99.7%).

Step f) Formation of Ethyl oxo{[4-(trifluoromethyl)benzyl][3-(3-undecyl-1,2,4-oxadiazol-5-yl)benzyl]amino}acetate The same procedure as employed in the preparation of Example 15 (step b) but using N-[4-(trifluoromethyl)benzyl]-N-[3-(3-undecyl-1,2,4-oxadiazol-5-yl)benzyl]amine hydrochloride gave the title compound as a pale yellow oil (89%). $^1$H NMR (CDCl$_3$, 300 MHz) δ 8.08 (m, 1H), 7.98 (br s, 0.5H), 7.88 (br s, 0.5H), 7.61 (m, 2H), 7.52 (m, 2H), 7.39 (d, 1H, J=7.9 Hz), 7.34 (d, 1H, J=7.9 Hz), 4.58 (m, 2H), 4.46 (m, 2H), 4.36 (m, 2H), 2.79 (m, 2H), 1.81 (m, 2H), 1.42-1.23 (m, 19H), 0.87 (t, 3H, J=6.6 Hz). HPLC (Condition A), Rt: 7.43 min (HPLC purity: 99.4%).

Step g) Formation of oxo{[4-(trifluoromethyl)benzyl][3-(3-undecyl-1,2,4-oxadiazol-5-yl)benzyl]amino}acetic acid The same procedure as employed in the preparation of Example 1 (step e) but using ethyl oxo{[4-(trifluoromethyl)benzyl][3-(3-undecyl-1,2,4-oxadiazol-5-yl)benzyl]amino}acetate gave the title compound as a yellow oil (77%). $^1$H NMR (CDCl$_3$, 300 MHz) δ 8.08 (br s, 1H), 7.96 (m, 1H), 7.61-7.33 (m, 6H), 4.98 (m, 2H), 4.64 (br s, 2H), 2.80 (m, 2H), 1.79 (m, 2H), 1.25 (br s, 16H), 0.87 (m, 3H). M$^-$(LC/MS(ESI)): 558; M$^+$(LC/MS(ESI)): 560. HPLC (Condition A), Rt: 6.87 min (HPLC purity: 99.3%). Analysis calculated for C$_{30}$H$_{36}$F$_3$N$_3$O$_4$■0.2H$_2$O: C, 63.98; H, 6.51; N, 7.46%. Found: C, 63.90; H, 6.59; N, 7.46%.

Example 307 oxo{[4-(trifluoromethyl)benzyl][3-(3-undecyl-1,2,4-oxadiazol-5-yl)benzyl]amino}acetic acid, N-methyl-D-glucamine (i.e. 1-deoxy-1-(methylamino)glucitol) salt The same procedure as employed in the preparation of Example 2 but using oxo{[4-(trifluoromethyl)benzyl][3-(3-undecyl-1,2,4-oxadiazol-5-yl)benzyl]amino}acetic acid and N-methyl-D-glucamine gave the title compound as a white powder (98%). M$^-$(LC/MS(ESI)): 558. HPLC (Condition A), Rt: 6.85 min (HPLC purity: 99.2%). Analysis calculated for C$_{30}$H$_{36}$F$_3$N$_3$O$_4$.C$_7$H$_{17}$NO$_5$■1.5H$_2$O: C, 56.84; H, 7.22; N, 7.17%. Found: C, 56.88; H, 7.13; N, 7.10%.

Example 308

{(4-dodecylbenzyl)[4-(trifluoromethyl)benzyl]amino}(oxo)acetic acid

Step a) Formation of ethyl{(4-dodecylbenzyl)[4-(trifluoromethyl)benzyl]amino}-(oxo)-acetate The same procedure as employed in the preparation of Example 1 (step c) but using ethyl {(4-dodec-1-ynylbenzyl)[4-(trifluoromethyl)benzyl]amino}(oxo)acetate in EtOAc gave the title compound as a colorless oil (95%). $^1$H NMR (CDCl$_3$, 300 MHz) δ 7.63 (d, 0.7H, J=8.2 Hz), 7.60 (d, 1.3H, J=8.1 Hz), 7.39 (d, 0.7H, J=8.2 Hz), 7.33 (d, 1.3H, J=8.1 Hz), 7.15 (m, 4H), 4.54 (s, 1.3H), 4.48 (s, 0.7H), 4.41-4.30 (m, 4H), 2.61 (m, 2H), 1.61 (m, 2H), 1.38-1.27 (m, 2H), 0.89 (t, 3H, J=6.7 Hz). HPLC (Condition A), Rt: 7.24 min (HPLC purity: 99.5%).

Step b) Formation of {(4-dodecylbenzyl)[4-(trifluoromethyl)benzyl]amino}(oxo)acetic acid The same procedure as employed in the preparation of Example 1 (step e) but using ethyl{(4-dodecylbenzyl)[4-(trifluoromethyl)benzyl]amino}(oxo)acetate gave the title compound to as a colorless oil (95%). $^1$H NMR (CDCl$_3$, 300 MHz) δ 7.62 (m, 2H), 7.35 (m, 2H), 7.16 (m, 4H), 5.06 (s, 1H), 4.97 (s, 1H), 4.61 (s, 1H), 4.56 (s, 1H), 2.61 (t, 2H, J=7.7 Hz), 1.61 (m, 2H), 1.29 (m, 18H), 0.89 (t, 3H, J=6.6 Hz). M$^-$(LC/MS(ESI)): 504. HPLC (Condition A), Rt: 6.64 min (HPLC purity: 99.6%). Analysis calculated for C$_{29}$H$_{38}$F$_3$NO$_3$: C, 68.89; H, 7.57; N, 2.77%. Found: C, 68.72; H, 7.52; N, 2.66%.

Example 309

{(4-dodecylbenzyl)[4-(trifluoromethyl)benzyl]amino}(oxo)acetic acid, N-methyl-D-glucamine (i.e. 1-deoxy-1-(methylamino)glucitol) salt The same procedure as employed in the preparation of Example 2 but using {(4-dodecylbenzyl)[4-(trifluoromethyl)benzyl]amino}(oxo)acetic acid and N-methyl-D-glucamine gave the title compound as a white powder (94%). M$^-$(LC/MS(ESI)): 504 HPLC (Condition A), Rt: 6.58 min (HPLC purity: 99.9%). Analysis calculated for C$_{29}$H$_{38}$F$_3$NO$_3$.C$_7$H$_{17}$NO$_5$: C, 61.70; H, 7.91; N, 4.00%. Found: C, 61.32; H, 7.97; N, 3.91%.

Example 310

{[4-({[(2-butyl-1-benzofuran-3-yl methyl]amino}carbonyl)benzyl][4-(trifluoromethyl)benzyl]amino}(oxo)acetic acid Step a) Formation of ethyl{[4-({[(2-butyl-1-benzofuran-3-yl)methyl]amino}carbonyl)-benzyl][4-(trifluoromethyl)benzyl]amino}(oxo)acetate The same procedure as employed in the preparation of Example 1 (step d) but using 4-({[ethoxy(oxo)acetyl][4-(trifluoromethyl)benzyl]amino}methyl)benzoic acid and [(2-butyl-1-benzofuran-3-yl)methyl]amine hydrochloride, HOBT and TEA in DCM gave the title compound as a white solid (33%). $^1$H NMR (CDCl$_3$, 300 MHz) δ 7.66 (m, 2H), 7.51 (m, 3H), 7.35-7.18 (m, 7H), 6.05 (br s, 1H), 4.64 (s, 2H), 4.44 (s, 2H), 4.29 (m, 4H), 2.78 (m, 2H), 1.66 (m, 2H), 1.46 (m, 2H), 1.24 (m, 3H), 0.88 (m, 3H). M$^-$(LC/MS(ESI)): 593; M$^+$(LC/MS(ESI)): 595. HPLC (Condition A), Rt: 6.38 min (HPLC purity: 99.6%).

Step b) Formation of {[4-({[(2-butyl-1-benzofuran-3-yl)methyl]amino}carbonyl)benzyl][4-(trifluoromethyl)benzyl]amino}(oxo)acetic acid The same procedure as employed in the preparation of Example 1 (step e) but using ethyl{[4-({[(2-butyl-1-benzofuran-3-yl)methyl]amino}carbonyl)benzyl][4-(trifluoromethyl)-benzyl]amino}(oxo)acetate gave the title compound as a white powder (93%). $^1$H NMR (CDCl$_3$, 300 MHz) δ 7.71-7.26 (m, 12H), 6.22 (br s, 1H), 4.89 (s, 1H), 4.74 (br s, 31), 4.55 (s, 2H), 2.86 (m, 2H), 2.10-1.27 (m, 4H), 0.95 (m, 3H). M$^-$(LC/MS(ESI)): 565; M$^+$(LC/MS(ESI)): 567. HPLC (Condition A), Rt: 5.71 min (HPLC purity: 99.8%).

Example 311

{(4-{[4-(benzyloxy)benzoyl]amino}benzyl)[4-(trifluoromethyl)benzyl]-amino}(oxo)acetic acid Step a) Formation of ethyl{(4-{[4-(benzyloxy)benzoyl]amino}benzyl)[4-(trifluoromethyl)benzyl]amino}(oxo)acetate To a solution of 4-(benzyloxy)benzoic acid (180 mg, 0.79 mmol) in anhydrous pyridine (3 mL) at rt was added dropwise isobutyl chloroformate (0.100 mL, 0.79 mmol) under inert atmosphere. After 30 min, a solution of ethyl{(4-aminobenzyl)[4-trifluoromethyl)benzyl]amino}(oxo)acetate (100 mg, 0.26 mmol) in anhydrous pyridine (1 mL) was added dropwise and the resulting mixture was heated at 70° C. for 30 min. The reaction mixture was diluted with a 5N aqueous solution of HCl (11 mL) and extracted with Et$_2$O (2×5 mL). The combined organic layers were dried over MgSO$_4$ and the solvent was removed under reduced pressure. This residue was purified by flash chromatography over silica gel (Et$_2$O/c-Hex 1/1 to Et$_2$O) to give the title compound as a colorless oil (125 mg, 79%). $^1$H NMR (CDCl$_3$, 300 MHz) δ 7.86 (m, 2H), 7.77 (br s, 1H), 7.63 (m, 4H), 7.44-7.21 (m, 9H), 7.08 (m, 2H), 5.16 (s, 2H), 4.54-4.33 (m, 6H), 1.35 (m, 3H). M$^-$(LC/MS (ESI)): 589; M$^+$(LC/MS(ESI)): 591. HPLC (Condition A), Rt: 6.04 min (HPLC purity: 99.7%).

Step b) Formation of {(4-{[4-(benzyloxy)benzoyl]amino}benzyl)[4-(trifluoromethyl)-benzyl]amino}(oxo)acetic acid The same procedure as employed in the preparation of Example 1 (step e) but using ethyl{(4-{[4-(benzyloxy)benzoyl]amino}benzyl)[4-(trifluoromethyl)benzyl]amino}(oxo)acetate gave the title compound as a beige solid (48%). $^1$H NMR (CD$_3$OD, 300 MHz) δ 7.96 (d, 2H, J=8.7 Hz), 7.69 (m, 4H), 7.55-7.33 (m, 8H), 7.25. (d, 1H, 3=8.3 Hz), 7.16 (d, 2H, J=8.7 Hz), 5.22 (s, 2H), 4.62 (s, 2H), 4.54 (s, 2H). M$^-$(LC/MS(ESI)): 561; M$^+$(LC/MS(ESI)): 563. HPLC (Condition A), Rt: 5.35 min (HPLC purity: 97.0%).

Example 312

{(3,5-dichlorobenzyl)[4-(tridecanoylamino)benzyl]amino}(oxo)acetic acid

Step a) Formation of (3,5-dichlorobenzyl)(4-nitrobenzyl)amine hydrochloride

The same procedure as employed in the preparation of Example 226 (step a) but using 3,5-dichlorobenzylamine and 4-nitrobenzaldehyde gave the title compound as a yellow powder (71%). $^1$H NMR (CD$_3$OD, 300 MHz) δ 8.37 (d, 2H, J=8.8 Hz), 7.83 (d, 2H, J=8.8 Hz), 7.61 (br s, 3H), 4.48 (s, 2H), 4.38 (s, 2H). M$^-$(LC/MS(ESI)): 309; M$^+$(LC/MS(ESI)): 311 HPLC (Condition A), Rt: 2.78 min (HPLC purity: 93.0%).

Step b) Formation of ethyl[(3,5-dichlorobenzyl)(4-nitrobenzyl)amino](oxo)acetate The same procedure as employed in the preparation of Example 15 (step b) but using (3,5-dichlorobenzyl)(4-nitrobenzyl)amine hydrochloride gave the title compound as a yellow powder (77%). $^1$H NMR (CDCl$_3$, 300 MHz) δ 8.22 (m, 2H), 7.46-7.30 (m, 3H), 7.13 (br s, 1H), 7.06 (br s, 1H), 4.60 (s, 1H), 4.51 (s, 1H), 4.45 (s, 1H), 4.37 (m, 3H), 1.35 (m, 3H). M$^-$(LC/MS(ESI)): 409. HPLC (Condition A), Rt: 5.57 min (HPLC purity: 97.7%).

Step c) Formation of ethyl[(4-aminobenzyl)(3,5-dichlorobenzyl)amino](oxo)acetate A suspension of PtO$_2$ (250 mg) in EtOAc (5 mL) was added to a solution of ethyl[(3,5-dichlorobenzyl) (4-nitrobenzyl) amino](oxo)acetate (2.00 g, 4.86 mmol) in EtOH/EtOAc (2/1, 90 mL) under H$_2$ (1 atm). The reaction mixture was stirred vigorously at rt for 30 min. The reaction mixture was filtered over a pad of Celite and silica gel to remove the catalyst. The solvents were removed under reduced pressure. The residue was purified by flash chromatography over silica gel (c-Hex/EtOAc 2/1) to give the title compound as a pale yellow oil (1.21 g, 61%). $^1$H NMR (CDCl$_3$, 300 MHz) δ 7.31-7.05 (m, 5H), 6.71 (m, 2H), 4.39 (m, 4H), 4.25 (br s, 2H), 1.36 (m, 3H). HPLC (Condition A), Rt: 3.4 min (HPLC purity: 94.1%).

Step d) Formation of ethyl{(3,5-dichlorobenzyl)[4-(tridecanoylamino)-benzyl]amino}(oxo)acetate The same procedure as employed in the preparation of Example 15 (step d) but using ethyl[(4-aminobenzyl)(3,5-dichlorobenzyl)amino](oxo)acetate gave the title compound as a pale yellow oil (59%). $^1$H NMR (CDCl$_3$, 300 MHz) δ 7.52 (m, 2H), 7.32-7.05 (m, 6H), 4.47-4.27 (m, 6H), 2.37 (t, 2H, J=7.5 Hz), 1.73 (m, 2H), 1.38-1.26 (m, 21H), 0.88 (t, 3H, J=6.6 Hz). HPLC (Condition A), Rt: 7.52 min (HPLC purity: 99.0%).

Step e) Formation of {(3,5-dichlorobenzyl)[4-(tridecanoylamino)benzyl]amino}(oxo)acetic acid The same procedure as employed in the preparation of Example 1 (step e) but using ethyl{(3,5-dichlorobenzyl)[4-(tridecanoylamino)benzyl]amino}(oxo)acetate gave the title compound as a white powder (81%). $^1$H NMR (CDCl$_3$, 300 MHz) δ 7.50 (br s, 2H), 7.30-7.06 (m, 6H), 4.91 (s, 2H), 4.50 (m, 2H), 2.36 (m, 2H), 1.72 (m, 2H), 1.25 (br s, 18H), 0.88 (br s, 3H). M$^-$(LC/MS(ESI)): 547; M$^+$(LC/MS(ESI)): 549. HPLC (Condition A), Rt: 6.46 min (HPLC purity: 99.5%).

Example 313

{(3,5-dichlorobenzyl [4-(tridecanoylamino)benzyl]amino}(oxo)acetic acid, N-methyl-D-glucamine (i.e. 1-deoxy-1-(methylamino)glucitol) salt The same procedure as employed in the preparation of Example 2 but using {(3,5-dichlorobenzyl)[4-(tridecanoylamino)benzyl]amino}(oxo)acetic acid and N-methyl-D-glucamine gave the title compound as a white powder (88%). M$^-$(LC/MS(ESI)): 547; M$^+$(LC/MS(ESI)): 549. HPLC (Condition A), Rt: 6.48 min (HPLC purity: 99.5%). Analysis calculated for C$_{29}$H$_{38}$Cl$_2$N$_2$O$_4$·C$_7$H$_{17}$NO$_5$■1.1H$_2$O: C, 56.55; H, 7.54; N, 5.50%. Found: C, 56.52; H, 7.50; N, 5.47%.

Example 314

{{4-[(4-octylphenyl)ethynyl]benzyl}[4-(trifluoromethyl)benzyl]amino}(oxo)acetic acid Step a) Formation of ethyl{{4-[(4-octylphenyl)ethynyl]benzyl}[4-(trifluoromethyl)benzyl]amino}(oxo)acetate The same procedure as employed in the preparation of Example 226 (step c) but using 1-ethynyl-4-octylbenzene under microwave conditions (300 W, 120° C., 5 min) gave the title compound as a pale yellow oil (37%). $^1$H NMR (CDCl$_3$, 300 MHz) δ 7.63 (m, 2H), 7.54-7.33 (m, 6H), 7.21 (m, 4H), 4.55 (s, 1H), 4.52 (s, 1H), 4.36 (m, 4H), 2.62 (m, 2H), 1.62 (m, 2H), 1.32 (m, 13H), 0.89 (m, 3H). HPLC (Condition A), Rt: 7.91 min (HPLC purity: 97.2%).

Step b) Formation of {{4-[(4-octylphenyl)ethynyl]benzyl}[4-(trifluoromethyl)benzyl]-amino}(oxo) acetic acid The same procedure as employed in the preparation of Example 1 (step e) but using ethyl{{4-[(4-octylphenyl)ethynyl]benzyl}[4-(trifluoromethyl)benzyl]amino}(oxo)acetate gave the title compound as a pale yellow oil (89%). $^1$H NMR (CDCl₃, 300 MHz) δ 7.64 (m, 2H), 7.50 (m, 4H), 7.36 (m, 2H), 7.19 (m, 4H), 5.04 (s, 1H), 4.98 (s, 1H), 4.62 (s, 1H), 4.59 (s, 1H), 2.62 (m, 2H), 1.62 (m, 2H), 1.27 (br s, 10H), 0.89 (m, 3H). M⁻(LC/MS(ESI)): 548. HPLC (Condition A), Rt: 7.53 min (HPLC purity: 98.5%).

Example 315 oxo{[4-(trifluoromethyl)benzyl][4-(5-undecyl-1,2,4-oxadiazol-3-yl)benzyl]-amino}acetic acid

Step a) Formation of tert-butyl 4-(trifluoromethyl)benzyl[4-(5-undecyl-1,2,4-oxadiazol-3-yl)benzyl]carbamate The same procedure as employed in the preparation of Example 23 (step e) but using tert-butyl 4-[[(dodecanoyloxy)amino](imino)methyl]benzyl[4-(trifluoromethyl)benzyl]carbamate gave the title compound as a colorless oil (71%). ¹H NMR (CDCl₃, 300 MHz) δ 8.05 (d, 2H, J=8.1 Hz), 7.60 (d, 2H, J=37.9 Hz), 7.31 (m, 4H), 4.45 (m, 4H), 2.95 (t, 2H, J=7.5 Hz), 1.88 (m, 2H), 1.50 (s, 9H), 1.27 (br s, 16H), 0.88 (m, 3H). HPLC (Condition A), Rt: 7.93 min (HPLC purity: 99.9%).

Step b) Formation of Tert-Butyl 4-[[(dodecanoyloxy)amino](imino)methyl]benzyl[4-(trifluoromethyl)benzyl]carbamate The same procedure as employed in the preparation of Example 10 (step a) but using tert-butyl 4-[(hydroxyamino)(imino)methyl]benzyl[4-(trifluoromethyl)benzyl]carbamate and dodecanoic acid gave the title compound as a colorless oil (95%). ¹H NMR (CD₃OD, 300 MHz) δ 7.68 (d, 2H, J=7.9 Hz), 7.59 (d, 2H, J=8.0 Hz), 7.27 (m, 4H), 5.08 (br s, 2H), 4.42 (m, 4H), 2.49 (m, 2H), 1.72 (m, 2H), 1.49 (s, 9H), 1.27 (br s, 16H), 0.88 (m, 3H). HPLC (Condition A), Rt: 7.06 min (HPLC purity: 86.0%).

Step c) Formation of Tert-Butyl 4-[(hydroxyamino)(imino)methyl]benzyl[4-(trifluoromethyl)benzyl]carbamate The same procedure as employed in the preparation of Example 23 (step a) but using tert-butyl 4-cyanobenzyl[4-(trifluoromethyl)benzyl]carbamate gave the title compound as a white foam (88%). ¹H NMR (CDCl₃, 300 MHz) δ 7.60 (m, 4H), 7.28 (m, 4H), 5.05 (br s, 3H), 4.43 (m, 4H), 1.49 (s, 9H). M⁻(LC/MS(ESI)): 422; M⁺(LC/MS(ESI)): 424. HPLC (Condition A), Rt: 3.67 min (HPLC purity: 96.1%).

Step d) Formation of Tert-Butyl 4-cyanobenzyl[4-(trifluoromethyl)benzyl]carbamate The same procedure as employed in the preparation of Example 23 (step b) but using 4-({[4-(trifluoromethyl)benzyl]amino}methyl)benzonitrile hydrochloride and DIEA gave the title compound as a colorless oil (92%): ¹H NMR (CDCl₃, 300 MHz) δ 7.62 (m, 4H), 7.30 (m, 4H), 4.44 (m, 4H), 1.48 (s, 9H). M⁻(LC/MS(ESI)): 389. HPLC (Condition A), Rt: 6.02 min (HPLC purity: 99.8%).

Step e) Formation of 4-({[4-(trifluoromethyl)benzyl]amino}methyl)benzonitrile hydrochloride The same procedure as employed in the preparation of Example 226 (step a) but using 4-cyanobenzaldehyde gave the title compound as a white solid (83%). ¹H NMR (DMSO-d₆, 300 MHz) δ 10.01 (br s, 2H), 7.92 (d, 2H, J=8.4 Hz), 7.80 (s, 4H), 7.77 (d, 2H, J=8.4 Hz), 4.28 (s, 4H). HPLC (Condition A), Rt: 2.59 min (HPLC purity: 98.3%).

Step f) Formation of N-[4-(trifluoromethyl)benzyl]-N-[4-(5-undecyl-1,2,4-oxadiazol-3-yl)benzyl]amine hydrochloride The same procedure as employed in the preparation of Example 23 (step f) but using tert-butyl 4-(trifluoromethyl)benzyl[4-(5-undecyl-1,2,4-oxadiazol-3-yl)benzyl]carbamate gave the title compound as a white powder (94%). ¹H NMR (DMSO-d₆, 300 MHz) δ 9.64 (br s, 2H), 8.05 (m, 2H), 7.76 (m, 6H), 4.30 (br s, 4H), 2.99 (m, 2H), 1.77 (m, 2H), 1.23 (br s, 16H), 0.84 (m, 3H). HPLC (Condition A), Rt: 5.35 min (HPLC purity: 99.9%).

Step g) Formation of Ethyl oxo{[4-(trifluoromethyl)benzyl][4-(5-undecyl-1,2,4-oxadiazol-3-yl)benzyl]amino}acetate The same procedure as employed in the preparation of Example 15 (step b) but using N-[4-(trifluoromethyl)benzyl]-N-[4-(5-undecyl-1,2,4-oxadiazol-3-yl)benzyl]amine hydrochloride gave the title compound as a colorless oil (96%). ¹H NMR (CDCl₃, 300 MHz) δ 8.08 (m, 2H), 7.63 (m, 2H), 7.36 (m, 4H), 4.57 (s, 2H), 4.42 (s, 2H), 4.39 (m, 2H), 2.96 (m, 2H), 1.88 (m, 2H), 1.43-1.27 (m, 19H), 0.89 (m, 3H). HPLC (Condition A), Rt: 7.36 min (HPLC purity: 99.9%).

Step h) Formation of oxo{[4-(trifluoromethyl)benzyl][4-(5-undecyl-1,2,4-oxadiazol-3-yl)benzyl]amino}acetic acid The same procedure as employed in the preparation of Example 1 (step e) but using ethyl oxo{[4-(trifluoromethyl)benzyl][4-(5-undecyl-1,2,4-oxadiazol-3-yl)benzyl]amino}acetate gave the title compound as a colorless oil (90%). ¹H NMR (CDCl₃, 300 MHz) δ 8.08 (m, 2H), 7.64 (m, 2H), 7.35 (m, 4H), 5.04 (m, 2H), 4.64 (s, 2H), 2.96 (m, 2H), 1.88 (m, 2H), 1.50-1.15 (m, 16H), 0.88 (m, 3H). M⁻(LC/MS (ESI)): 558. HPLC (Condition A), Rt: 6.85 min (HPLC purity: 99.9%). Analysis calculated for C₃₀H₃₆F₃N₃O₄■0.2H₂O: C, 63.98; H, 6.51; N, 7.46%. Found: C, 63.93; H, 6.56; N, 7.44%.

Example 316 oxo{[4-(trifluoromethyl)benzyl][4-(5-undecyl-1,2,4-oxadiazol-3-yl)benzyl]amino}acetic acid, N-methyl-D-glucamine (i.e. 1-deoxy-1-(methylamino)glucitol) salt The same procedure as employed in the preparation of Example 2 but using oxo{[4-(trifluoromethyl)benzyl][4-(5-undecyl-1,2,4-oxadiazol-3-yl)benzyl]amino}acetic acid and N-methyl-D-glucamine gave the title compound as a white powder (79%). M⁻(LC/MS(ESI)): 558. HPLC (Condition A), Rt: 6.85 min (HPLC purity: 99.9%). Analysis calculated for C₃₀H₃₆F₃N₃O₄·C₇H₁₇NO₅■0.8H₂O: C, 57.77; H, 7.15; N, 7.28%. Found: C, 57.76; H, 7.16; N, 7.29%.

Example 317

{{4-[2-(4-octylphenyl ethyl]benzyl}[4-(trifluoromethyl)benzyl]amino}-(oxo)acetic acid The same procedure as employed in the preparation of Example 1 (step c) but using {{4-[(4-octylphenyl)ethynyl]benzyl}[4-(trifluoromethyl)benzyl]amino}(oxo)acetic acid in EtOAc gave the title compound as a colorless oil (54%). ¹H NMR (CDCl₃, 300 MHz) δ 7.61 (m, 2H), 7.34 (m, 2H), 7.13 (m, 8H), 5.42 (br s, 1H), 4.97 (s, 1H), 4.87 (s, 1H), 4.59 (s, 1H), 4.55 (s, 1H), 2.89 (br s, 4H), 2.57 (m, 2H), 1.59 (m, 2H), 1.27 (br s, 10H), 0.89 (m, 3H). M⁻(LC/MS(ESI)): 552; M⁺(LC/MS(ESI)): 554. HPLC (Condition A), Rt: 7.13 min (HPLC purity: 98.5%).

Example 318

{(4-{[4-(heptyloxy)phenyl]ethyl}benzyl)[4-(trifluoromethyl)benzyl]-amino}(oxo)acetic acid Step a) Formation of ethyl{(4-{[4-(heptyloxy)phenyl]ethynyl}benzyl)[4-(trifluoromethyl)-benzyl]amino}(oxo)acetate The same procedure as employed in the preparation of Example 226 (step c) but using 1-ethynyl-4-(heptyloxy)benzene under microwave conditions (300 W, 120° C., 10 min) gave the title compound as a pale yellow oil (43%). HPLC (Condition A), Rt: 7.57 min (HPLC purity: 94.2%).

Step b) Formation of {(4-{[4-(heptyloxy)phenyl]ethynyl}benzyl)[4-(trifluoromethyl)benzyl]-amino}(oxo)acetic acid The same procedure as employed in the preparation of Example 1 (step e) but using ethyl{(4-{[4-heptyloxy)phenyl]ethynyl}benzyl)[4-(trifluoromethyl)benzyl]amino}(oxo)acetate gave the title compound as a pale yellow oil (90%). M⁻(LC/MS(ESI)): 550. HPLC (Condition A), Rt: 6.71 min (HPLC purity: 94.6%).

Example 319

{{4-[(4-butylphenyl)ethynyl]benzyl}[4-(trifluoromethyl)benzyl]amino}-(oxo)acetic acid Step a) Formation of ethyl{{4-[(4-butylphenyl)ethynyl]benzyl}[4-(trifluoromethyl)benzyl]-amino}(oxo)acetate The same procedure as employed in the preparation of Example 226 (step c) but using 1-butyl-4-ethynylbenzene under microwave conditions (300 W, 120° C., 10 min) gave the title compound as a pale yellow oil (50%). HPLC (Condition A), Rt: 7.24 min (HPLC purity: 96.8%).

Step b) Formation of {{4-[(4-butylphenyl)ethynyl]benzyl}[4-(trifluoromethyl)benzyl]-amino}(oxo) acetic acid The same procedure as employed in the preparation of Example 1 (step e) but using ethyl{{4-[(4-butylphenyl)ethynyl]benzyl}[4-(trifluoromethyl)benzyl]amino}(oxo)acetate gave the title compound as a pale yellow oil (92%). M⁻(LC/MS(ESI)): 492. HPLC (Condition A), Rt: 6.25 min (HPLC purity: 96.2%).

Example 320

{{4-[(4-hexylphenyl)ethynyl]benzyl}[4-(trifluoromethyl)benzyl]amino}-(oxo)acetic acid Step a) Formation of 4-[(4-hexylphenyl)ethynyl]benzaldehyde A mixture of 4-bromobenzaldehyde (5.00 g, 27.0 mmol), 1-ethynyl-4-hexylbenzene (6.29 g, 33.4 mmol), Et₃N (4.70 mL, 33.4 mmol), bis(triphenylphosphine)palladium chloride (950 mg, 1.35 mmol) and triphenylphosphine (180 mg, 0.68 mmol) in anhydrous THF (100 mL) was stirred at rt for 30 min under inert atmosphere. Then copper(I) bromide (82 mg, 0.43 mmol) was added and the resulting mixture was stirred overnight at rt. The solvent was evaporated off. The residue was dissolved in Et₂O (100 mL), washed with water (50 mL), dried over MgSO₄ and the solvent was removed under reduced pressure. The resulting brown solid was triturated in hexane (25 mL), filtered off and washed with hexane to give the title compound as a beige solid (7.73 g, 91%). HPLC (Condition A), Rt: 5.88 min (HPLC purity: 91.9%).

Step b) Formation of N-{4-[(4-hexylphenyl)ethynyl]benzyl}-N-[4-(trifluoromethyl)benzyl]-amine hydrochloride The same procedure as employed in the preparation of Example 226 (step a) but using 4-(trifluoromethyl)benzylamine and 4-[(4-hexylphenyl)ethynyl]benzaldehyde gave the title compound as a beige solid (68%). ¹H NMR (DMSO-d₆, 300 MHz) δ 9.74 (br s, 2H), 7.83 (d, 2H, J=8.5 Hz), 7.77 (d, 2H, J=8.5 Hz), 7.59 (m, 4H), 7.46 (d, 2H, J=8.3 Hz), 7.25 (d, 2H, J=8.3 Hz), 4.28 (s, 2H), 4.22 (s, 2H), 2.59 (t, 2H, J=7.5 Hz), 1.56 (m, 2H), 1.27 (br s, 6H), 0.84 (t, 3H, J=6.7 Hz). M⁺(LC/MS(ESI)): 450. HPLC (Condition A), Rt: 4.87 min (HPLC purity: 99.6%).

Step c) Formation of ethyl{{4-[(4-hexylphenyl)ethynyl]benzyl}[4-(trifluoromethyl)benzyl]-amino}(oxo) acetate The same procedure as employed in the preparation of Example 15 (step b) but using N-{4-[(4-hexylphenyl)ethynyl]benzyl}-N-[4-(trifluoromethyl)benzyl]amine hydrochloride gave the title compound as a pale yellow oil (96%). ¹H NMR (CDCl₃, 300 MHz) δ 7.63 (m, 2H), 7.52 (m, 2H), 7.46 (m, 2H), 7.37 (m, 2H), 7.21 (m, 4H), 4.55 (s, 1H), 4.52 (s, 1H), 4.37 (m, 4H), 2.63 (t, 2H, J=7.7 Hz), 1.62 (m, 2H), 1.35 (m, 9H), 0.89 (t, 3H, J=6.7 Hz). HPLC (Condition A), Rt: 6.50 min (HPLC purity: 99.2%).

Step d) Formation of {{4-[(4-hexylphenyl)ethynyl]benzyl}[4-(trifluoromethyl)benzyl]-amino}(oxo) acetic acid The same procedure as employed in the preparation of Example 1 (step e) but using ethyl{{4-[(4-hexylphenyl)ethynyl]benzyl}[4-(trifluoromethyl)benzyl]amino}(oxo)acetate gave the title compound as a pale yellow gummy solid (90%). ¹H NMR (CDCl₃, 300 MHz) δ 7.64 (m, 2H), 7.52 (m, 2H), 7.46 (m, 2H), 7.37 (m, 2H), 7.21 (m, 4H), 6.12 (br s, 1H), 4.95 (s, 1H), 4.89 (s, 1H), 4.61 (s, 1H), 4.58 (s, 1H), 2.63 (t, 2H, J=7.8 Hz), 1.63 (m, 2H), 1.32 (m, 6H), 0.90 (t, 3H, J=6.8 Hz). M⁻(LC/MS(ESI)): 520. HPLC (Condition A), Rt: 5.94 min (HPLC purity: 99.1%).

Example 321

{{4-[(4-hexylphenyl)ethynyl]benzyl}[4-(trifluoromethyl)benzyl]amino}-(oxo)acetic acid, N-methyl-D-glucamine (i.e. 1-deoxy-1-(methylamino)glucitol) salt The same procedure as employed in the preparation of Example 2 but using {{4-[(4-hexylphenyl)ethynyl]benzyl}[4-(trifluoromethyl)benzyl]amino}(oxo)acetic acid and N-methyl-D-glucamine gave the title compound as a white powder (94%). M⁻(LC/MS(ESI)): 520. HPLC (Condition A), Rt: 5.94 min (HPLC purity: 99.6%). Analysis calculated for $C_{31}H_{30}F_3NO_3 \cdot C_7H_{17}NO_5 \blacksquare 1.3H_2O$: C, 61.66; H, 6.75; N, 3.78%. Found: C, 61.63; H, 6.63; N, 3.70%.

Example 322 oxo{(4-{[4-(pentyloxy)phenyl]ethynyl}benzyl)[4-(trifluoromethyl)benzyl]-amino}acetic acid Step a) Formation of Ethyl oxo{(4-{[4-(pentyloxy)phenyl]ethynyl}benzyl)[4-(trifluoromethyl)benzyl]amino}acetate The same procedure as employed in the preparation of Example 226 (step c) but using 1-ethynyl-4-(pentyloxy)benzene under microwave conditions (300 W, 120° C., 10 min) gave the title compound as a pale yellow oil (33%). HPLC (Condition A), Rt: 6.80 min (HPLC purity: 74.0%).

Step b) Formation of oxo{(4-{[4-(pentyloxy)phenyl]ethynyl}benzyl)[4-(trifluoromethyl)-benzyl]amino}acetic acid The same procedure as employed in the preparation of Example 1 (step e) but using ethyl oxo{(4-{[4-(pentyloxy)phenyl]ethynyl}benzyl)[4-(trifluoromethyl)benzyl]amino}acetate gave the title compound as a pale yellow oil (79%). M⁻(LC/AS(ESI)): 522. HPLC (Condition A), Rt: 6.68 min (HPLC purity: 74.9%).

Example 323 oxo{{4-[(4-propylphenyl)ethynyl]benzyl}[4-(trifluoromethyl)benzyl]-amino}acetic acid Step a) Formation of Ethyl oxo{{4-[(4-propylphenyl)ethynyl]benzyl}[4-(trifluoromethyl)-benzyl]amino}acetate The same procedure as employed in the preparation of Example 226 (step c) but using 1-ethynyl-4-propylbenzene under microwave conditions (300 W, 120° C., 10 min) gave the title compound as a pale yellow oil (45%). HPLC (Condition A), Rt: 6.65 min (HPLC purity: 97.5%).

Step b) Formation of oxo{{4-[(4-propylphenyl)ethynyl]benzyl}[4-(trifluoromethyl)benzyl]-amino}acetic acid The same procedure as employed in the preparation of Example 1 (step e) but using ethyl oxo{{4-[(4-propylphenyl)ethynyl]benzyl}[4-(trifluoromethyl)benzyl]amino}acetate gave the title compound as a pale yellow oil (80%). M⁻(LC/MS(ESI)): 478. HPLC (Condition A), Rt: 6.44 min (HPLC purity: 96.9%).

Example 324

[[2-(3-chlorophenyl)ethyl](4-dodec-1-ynylbenzyl amino](oxo)acetic acid

Step a) Formation of 4-dodec-1-ynyl benzaldehyde

The same procedure as employed in the preparation of Example 275 (step a) but using 1-dodecyne gave the title compound as a yellow oil (77%). ¹H NMR (CDCl₃, 300 MHz) δ 9.97 (s, 1H), 7.78 (d, 2H, J=8.4 Hz), 7.51 (d, 2H, J=8.4 Hz), 2.43 (t, 2H, J=7.0 Hz), 1.66-1.55 (m, 2H), 1.50-1.38 (m, 2H), 1.36-1.21 (m, 12H), 0.87 (t, 3H, J=6.9 Hz). HPLC (Condition A), Rt: 5.92 min (HPLC purity: 89.4%).

Step b) Formation of N-[2-(3-chlorophenyl)ethyl]-N-(4-dodec-1-ynylbenzyl)amine hydrochloride The same procedure as employed in the preparation of Example 226 (step a) but using [2-(3-chlorophenyl)ethyl]amine and 4-dodec-1-ynylbenzaldehyde gave the title compound as a white powder (50%). ¹H NMR (DMSO-dr, 300 MHz) δ 9.27 (br s, 1H), 7.51-7.24 (m, 8H), 4.15 (br s, 2H), 3.14 (br s, 2H), 2.98 (m, 2H), 1.99 (m, 2H), 1.55-1.40 (m, 16H), 0.85 (t, 3H, J=6.6 Hz). M⁻(LC/MS(ESI)): 411. HPLC (Condition A), Rt: 5.30 min (HPLC purity: 99.9%).

Step c) Formation of ethyl[[2-(3-chlorophenyl)ethyl](4-dodec-1-ynylbenzyl)amino](oxo)acetate The same procedure as employed in the preparation of Example 15 (step b) but using N-[2-(3-chlorophenyl)ethyl]-N-(4-dodec-1-ynylbenzyl)amine hydrochloride gave the title compound as a pale yellow oil (80%). ¹H NMR (CDCl₃, 300 MHz) δ 7.37-6.93 (m, 8H), 4.30 (m, 2H), 4.43-4.07 (m, 4H), 3.40 (m, 2H), 2.77 (m, 2H), 2.39 (m, 2H), 1.53-1.30 (m, 16H), 0.87 (t, 3H, J=6.6 Hz). M⁺(LC/MS(ESI)): 511. HPLC (Condition A), Rt: 7.04 min (HPLC purity: 99.6%).

Step d) Formation of [[2-(3-chlorophenyl)ethyl](4-dodec-1-ynylbenzyl)amino](oxo)acetic acid The same procedure as employed in the preparation of Example 1 (step e) but using ethyl[[2-(3-chlorophenyl)ethyl](4-dodec-1-ynylbenzyl)amino](oxo)acetate gave the title compound as a white foam (87%). ¹H NMR (DMSO-ds, 300 MHz) δ 7.39-7.22 (m, 6H), 7.11 (m, 2H), 4.56 (s, 1H), 4.43 (s, 1H), 3.32 (br s, 2H), 2.84 (m, 1H), 2.72 (m, 1H), 2.39 (m, 2H), 1.54-1.23 (m, 16H), 0.88 (t, 3H, J=6.6 Hz). M⁻(LC/MS (ESI)): 480. HPLC (Condition A), Rt: 6.44 min (HPLC purity: 99.8%).

Example 325

[[2-(3-chlorophenyl)ethyl](4-dodec-1-ynylbenzyl) amino](oxo)acetic acid, N-methyl-D-glucamine (i.e. 1-deoxy-1-(methylamino)glucitol) salt The same procedure as employed in the preparation of Example 2 but using [[2-(3-chlorophenyl)ethyl](4-dodec-1-ynylbenzyl)amino](oxo)acetic acid and N-methyl-D-glucamine gave the title compound as a white powder (90%). M⁺(LC/MS(ESI)): 481. HPLC (Condition A), Rt: 6.33 min (HPLC purity: 99.1%).

Example 326

{(4-oct-ynylbenzyl)[4-(trifluoromethyl)-benzyl]amino}(oxo)acetic acid

Step a) Formation of ethyl{(4-oct-1-ynylbenzyl)[4-(trifluoromethyl)-benzyl]amino}(oxo)acetate The same procedure as employed in the preparation of Example 226 (step c) but using 1-octyne gave the title compound as a pale yellow oil (9%). ¹H NMR (CDCl₃, 300 MHz) δ 7.62 (m, 2H), 7.36 (m, 4H), 7.15 (m, 2H), 4.52 (s, 1H), 4.48

(s, 1H), 4.35 (m, 4H), 2.42 (dt, 2H, J=6.9, 1.4 Hz), 1.62 (m, 2H), 1.46 (m, 2H), 1.34 (m, 7H), 0.92 (t, 3H, J=6.7 Hz) M⁺(LC/MS(ESI)): 474. HPLC (Condition A), Rt: 6.10 min (HPLC purity: 99.1%).

Step b) Formation of {(4-oct-1-ynylbenzyl)[4-(trifluoromethyl)benzyl]amino}(oxo)acetic acid The same procedure as employed in the preparation of Example 1 (step e) but using ethyl{(4-oct-1-ynylbenzyl)[4-(trifluoromethyl)benzyl]amino}(oxo)acetate gave the title compound as a yellow oil (92%). ¹H NMR (CDCl₃, 300 MHz) δ 7.63 (m, 2H), 7.37 (m, 4H), 7.15 (m, 2H), 6.11 (br s, 1H), 4.89 (s, 1H), 4.82 (s, 1H), 4.58 (s, 1H), 4.54 (s, 1H), 2.42 (t, 2H, J=7.0 Hz), 1.62 (m, 2H), 1.48 (m, 2H), 1.34 (m, 4H), 0.92 (t, 3H, 3=6.8 Hz). M⁻(LC/MS(ESI)): 444. HPLC (Condition A), Rt: 5.43 min (HPLC purity: 94.8%).

Example 327

{[4-(11-hydroxyundec-1-ynyl)benzyl][4-(trifluoromethyl)benzyl]amino}-(oxo)acetic acid Step a) Formation of ethyl{[4-(11-hydroxyundec-1-ynyl)benzyl][4-(trifluoromethyl)-benzyl]amino}(oxo)acetate The same procedure as employed in the preparation of Example 226 (step c) but using 10-undecyn-1-ol gave the title compound as a yellow oil (30%). ¹H NMR (CDCl₃, 300 MHz) δ 7.62 (m, 2H), 7.36 (m, 4H), 7.15 (m, 2H), 4.53 (s, 1H), 4.48 (s, 1H), 4.35 (m, 4H), 3.65 (t, 2H, J=6.6 Hz), 2.42 (dt, 2H, J=7.0, 1.4 Hz), 1.64-1.30 (m, 17H). M⁺(LC/MS (ESI)): 532. HPLC (Condition A), Rt: 5.61 min (HPLC purity: 98.2%).

Step b) Formation of {[4-(11-hydroxyundec-1-ynyl)benzyl][4-(trifluoromethyl)benzyl]-amino}(oxo)acetic acid The same procedure as employed in the preparation of Example 1 (step e) but using ethyl{[4-(11-hydroxyundec-1-ynyl)benzyl][4-(trifluoromethyl)benzyl]amino}(oxo)acetate gave the title compound as a yellow oil (86%). ¹H NMR (CDCl₃, 300 MHz) δ 7.62 (m, 2H), 7.36 (m, 4H), 7.15 (m, 2H), 4.85 (s, 1H), 4.75 (s, 1H), 4.69 (br s, 2H), 4.58 (s, 1H), 4.52 (s, 1H), 3.66 (m, 2H), 2.42 (t, 2H, J=6.8 Hz), 1.64-1.24 (m, 14H). M⁻(LC/MS(ESI)): 502; M⁺(LC/MS(ESI)): 504. HPLC (Condition A), Rt: 4.93 min (HPLC purity: 91.7%).

Example 328

{[4-(11-methoxy-11-oxoundec-1-ynyl)benzyl][4-(trifluoromethyl)benzyl]amino}(oxo)acetic acid Step a) Formation of methyl 11-[4-({[ethoxy(oxo) acetyl][4-(trifluoromethyl)benzyl]amino-}methyl) phenyl]undec-10-ynoate The same procedure as employed in the preparation of Example 226 (step c) but using methyl 10-undecynoate gave the title compound as a colorless oil (20%). ¹H NMR (CDCl₃, 300 MHz) δ 7.62 (m, 2H), 7.36 (m, 4H), 7.15 (m, 2H), 4.51 (m, 2H), 4.36 (m, 4H), 3.68 (s, 3H), 2.42 (dt, 2H, J=6.9, 1.4 Hz), 2.32 (t, 2H, J=7.5 Hz), 1.63 (m, 4H), 1.47-1.24 (m, 11H). M⁻(LC/MS(ESI)): 558; M⁺(LC/MS(ESI)): 560. HPLC (Condition A), Rt: 5.98 min (HPLC purity: 97.3%).

Step b) Formation of {[4-(11-methoxy-11-oxoundec-1-ynyl)benzyl][4-(trifluoromethyl)-benzyl]amino} (oxo)acetic acid The same procedure as employed in the preparation of Example 1 (step e) but using methyl 11-[4-({[ethoxy(oxo) acetyl][4-(trifluoromethyl)benzyl]amino}methyl)phenyl] undec-10-ynoate and quenching after one minute gave the title compound as a colorless oil (61%). M⁻(LC/MS(ESI)): 530. HPLC (Condition A), Rt: 5.35 min (HPLC purity: 83.6%).

Example 329

11-[4-({(carboxycarbonyl)[4-(trifluoromethyl)benzyl]amino}-methyl)phenyl]undec-10-ynoic acid The same procedure as employed in the preparation of Example 1 (step e) but using methyl 11-[4-({[ethoxy(oxo) acetyl][4-(trifluoromethyl)benzyl]amino}methyl)phenyl] undec-10-ynoate gave the title compound as a pale yellow oil (84%). ¹H NMR (CDCl₃, 300 MHz) δ 8.60 (br s, 2H), 7.62 (m, 2H), 7.35 (m, 4H), 7.14 (m, 2H), 4.77 (s, 1H), 4.68 (s, 1H), 4.57 (s, 1H), 4.51 (s, 1H), 2.39 (m, 4H), 1.64-1.24 (m, 12H). M⁻(LC/MS(ESI)): 516. HPLC (Condition A), Rt: 4.78 min (HPLC purity: 95.7%).

Example 330

{(4-{[4-(benzyloxy)phenyl]ethynyl}benzyl)[4-(trifluoromethyl)benzyl]-amino}(oxo)acetic acid Step a) Formation of ethyl{(4-{[4-(benzyloxy)phenyl]ethynyl}benzyl)[4-(trifluoromethyl)-benzyl] amino}(oxo)acetate The same procedure as employed in the preparation of Example 226 (step c) but using 1-(benzyloxy)-4-ethynylbenzene under microwave conditions (300 W, 120° C., 10 min) gave the title compound as a pale yellow solid (28%). HPLC (Condition A), Rt: 6.36 min (HPLC purity: 95.9%).

Step b) Formation of {(4-{[4-(benzyloxy)phenyl] ethynyl}benzyl)[4-(trifluoromethyl)-benzyl]amino} (oxo)acetic acid The same procedure as employed in the preparation of Example 1 (step e) but using ethyl{(4-{[4-(benzyloxy)phenyl]ethynyl}benzyl)[4-(trifluoromethyl)benzyl]amino} (oxo)acetate gave the title compound as a pale yellow oil (86%). M⁻(LC/MS(ESI)): 542. HPLC (Condition A), Rt: 6.21 min (HPLC purity: 96.5%).

Example 331

{(4-{2-[4-(heptyloxy)phenyl]ethyl}benzyl)[4-(trifluoromethyl)benzyl]-amino}(oxo)acetic acid The same procedure as employed in the preparation of Example 1 (step c) but using {(4-{[4-(heptyloxy)phenyl] ethynyl}benzyl)[4-(trifluoromethyl)benzyl]amino}(oxo) acetic acid in EtOAc gave the title compound as a colorless oil (54%). M⁻(LC/MS(ESI)): 554. HPLC (Condition A), Rt: 5.95 min (HPLC purity: 95.1%).

Example 332

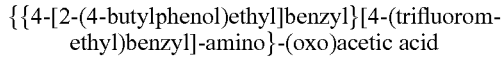
{{4-[2-(4-butylphenol)ethyl]benzyl}[4-(trifluoromethyl)benzyl]-amino}-(oxo)acetic acid The same procedure as employed in the preparation of Example 1 (step c) but using {{4-[(4-butylphenyl)ethynyl] benzyl}[4-(trifluoromethyl)benzyl]amino}(oxo)acetic acid in EtOAc gave the title compound as a colorless oil (38%). M⁻(LC/MS(ESI)): 496. HPLC (Condition A), Rt: 5.62 min (HPLC purity: 95.5%).

Example 333

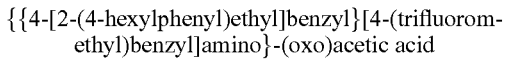
{{4-[2-(4-hexylphenyl)ethyl]benzyl}[4-(trifluoromethyl)benzyl]amino}-(oxo)acetic acid Step a) Formation of ethyl{{4-[2-(4-hexylphenyl) ethyl]benzyl}[4-(trifluoromethyl)-benzyl]amino} (oxo)acetate The same procedure as employed in the preparation of Example 1 (step c) but using ethyl{{4-[(4-hexylphenyl)ethynyl]benzyl}[4-(trifluoromethyl)benzyl]amino}(oxo)acetate in EtOAc gave the title compound as a colorless oil (94%). ¹H NMR (CDCl₃, 300 MHz) δ 7.64 (d, 0.8H, J=8.1 Hz), 7.60 (d, 1.2H, J=8.1 Hz), 7.39 (d, 0.8H, J=8.1 Hz), 7.33 (d, 1.2H, J=8.1 Hz), 7.18 (m, 4H), 7.11 (s, 4H), 4.54 (s, 1.2H), 4.49 (s, 0.8H), 4.42-4.30 (m, 4H), 2.90 (m, 4H), 2.59 (t, 2H, J=7.8 Hz), 1.61 (m, 2H), 1.39-1.30 (m, 9H), 0.89 (t, 3H, J=6.8 Hz). M⁻(LC/MS(ESI)): 552; M⁺(LC/MS(ESI)): 554. HPLC (Condition A), Rt: 6.46 min (HPLC purity: 99.2%).

Step b) Formation of {{4-[2-(4-hexylphenyl)ethyl]benzyl}[4-(trifluoromethyl)benzyl]-amino}(oxo) acetic acid The same procedure as employed in the preparation of Example 1 (step e) but using ethyl{{4-[2-(4-hexylphenyl) ethyl]benzyl}[4-(trifluoromethyl)benzyl]amino}(oxo)acetate gave the title compound as a colorless oil (95%). ¹H NMR (CDCl₃, 300 MHz) δ 7.63 (m, 2H), 7.35 (m, 2H), 7.19 (m, 41), 7.11 (s, 4H), 5.03 (s, 1H), 4.93 (s, 1H), 4.61 (s, 1H), 4.56 (s, 1H), 2.90 (m, 4H), 2.59 (t, 2H, J=7.8 Hz), 1.61 (m, 2H), 1.32 (m, 6H), 0.89 (t, 3H, J=6.8 Hz). M⁻(LC/MS(ESI)): 524; M⁺(LC/MS(ESI)): 526. HPLC (Condition A), Rt: 5.95 min (HPLC purity: 99.5%). Analysis calculated for $C_{31}H_{34}F_3NO_3$.■$2H_2O$: C, 70.36; H, 6.55; N, 2.65%. Found: C, 70.32; H, 6.56; N, 2.57%.

Example 334

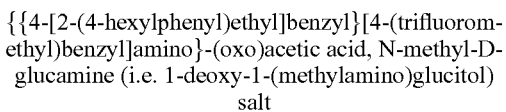
{{4-[2-(4-hexylphenyl)ethyl]benzyl}[4-(trifluoromethyl)benzyl]amino}-(oxo)acetic acid, N-methyl-D-glucamine (i.e. 1-deoxy-1-(methylamino)glucitol) salt The same procedure as employed in the preparation of Example 2 but using {{4-[2-(4-hexylphenyl)ethyl]benzyl} [4-(trifluoromethyl)benzyl]amino}(oxo)acetic acid and N-methyl-D-glucamine gave the title compound as a white powder (92%). M⁻(LC/MS(ESI)): 524; M⁺(LC/MS(ESI)): 526. HPLC (Condition A), Rt: 5.90 min (HPLC purity: 99.5%). Analysis calculated for $C_{31}H_{34}F_3NO_3$.$C_7H_{17}NO_5$■$0.4H_2O$: C, 62.69; H, 7.17; N, 3.85%. Found: C, 62.63; H, 7.25; N, 3.83%.

Example 335

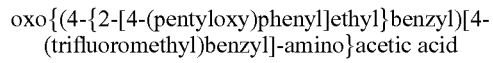
oxo{(4-{2-[4-(pentyloxy)phenyl]ethyl}benzyl)[4-(trifluoromethyl)benzyl]-amino}acetic acid The same procedure as employed in the preparation of Example 1 (step c) but using oxo{(4-{[4-(pentyloxy)phenyl] ethynyl}benzyl)[4-(trifluoromethyl)benzyl]amino}acetic acid in EtOAc gave the title compound as a yellow oil (49%). M⁻(LC/MS(ESI)): 526. HPLC (Condition A), Rt: 5.62 min (HPLC purity: 74.1%).

Example 336

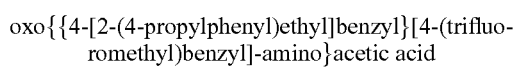
oxo{{4-[2-(4-propylphenyl)ethyl]benzyl}[4-(trifluoromethyl)benzyl]-amino}acetic acid The same procedure as employed in the preparation of Example 1 (step c) but using oxo{{4-[(4-propylphenyl)ethynyl]benzyl}[4-(trifluoromethyl)benzyl]amino}acetic acid in EtOAc gave the title compound as a colorless oil (51%). M⁻(LC/MS(ESI)): 482. HPLC (Condition A), Rt: 5.43 min (HPLC purity: 89.2%).

Example 337

11-[4-({(carboxycarbonyl)[4-(trifluoromethyl)benzyl]amino}-methyl)-phenyl]undecanoic acid The same procedure as employed in the preparation of Example 1 (step c) but using 11-[4-({(carboxycarbonyl)[4-(trifluoromethyl)benzyl]amino}methyl)phenyl]undec-10-ynoic acid in EtOAc gave the title compound as a colorless oil (20%). M⁻(LC/MS(ESI)): 520. HPLC (Condition A), Rt: 5.03 min (HPLC purity: 96.1%).

Example 338

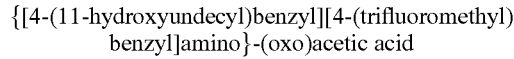
{[4-(11-hydroxyundecyl)benzyl][4-(trifluoromethyl) benzyl]amino}-(oxo)acetic acid The same procedure as employed in the preparation of Example 1 (step c) but using {[4-(11-hydroxyundec-1-ynyl) benzyl][4-(trifluoromethyl)benzyl]amino}(oxo)acetic acid gave the title compound as a colorless oil (45%). M⁻(LC/MS (ESI)): 506; M⁺(LC/MS(ESI)): 508. HPLC (Condition A), Rt: 5.19 min (HPLC purity: 86.3%).

Example 339

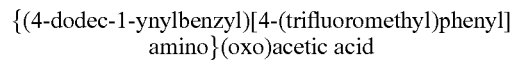
{(4-dodec-1-ynylbenzyl)[4-(trifluoromethyl)phenyl] amino}(oxo)acetic acid Step a) Formation of N-(4-dodec-1-ynylbenzyl)-N-[4-(trifluoromethyl)phenyl]amine The same procedure as employed in the preparation of Example 226 (step a) but using 4-(trifluoromethyl)aniline and 4-dodec-1-ynylbenzaldehyde gave the title compound as a pale yellow oil (42%). ¹H NMR (CDCl₃, 300 MHz) δ 7.40-7.23 (m, 8H), 4.35 (s, 2H), 2.40 (m, 2H), 1.62-1.27 (m, 16H), 0.88 (t, 3H, J=6.8 Hz). HPLC (Condition A), Rt: 7.0 min (HPLC purity: 99.4%).

Step b) Formation of ethyl{(4-dodec-1-ynylbenzyl)[4-(trifluoromethyl)phenyl]amino}-(oxo)acetate The same procedure as employed in the preparation of Example 15 (step b) but using N-(4-dodec-1-ynylbenzyl)-N-[4-(trifluoromethyl)phenyl]amine gave the title compound as a colorless oil (81%). $^1$H NMR (CDCl$_3$, 300 MHz) δ 7.60 (m, 2H), 7.33 (m, 2H), 7.20 (m, 4H), 4.94 (s, 2H), 4.04 (q, 2H, J=7.14 Hz), 2.39 (m, 2H), 1.58 (m, 2H), 1.43 (m, 2H), 1.26 (m, 12H), 0.99 (m, 3H), 0.88 (t, 3H, J=6.8 Hz). M$^+$(LC/MS (ESI)): 516. HPLC (Condition A), Rt: 6.81 min (HPLC purity: 91.8%).

Step c) Formation of {(4-dodec-1-ynylbenzyl)[4-(trifluoromethyl)phenyl]amino}(oxo)acetic acid The same procedure as employed in the preparation of Example 1 (step e) but using ethyl{(4-dodec-1-ynylbenzyl)[4-(trifluoromethyl)phenyl]amino}(oxo)acetate gave the title compound as a colorless oil (95%). $^1$H NMR (CDCl$_3$, 300 MHz) δ 7.59 (d, 2H, J=8.31 Hz), 7.32 (d, 2H, J=8.28 Hz), 7.09 (m, 4H), 5.03 (s, 1H), 4.93 (s, 1H), 2.39 (m, 2H), 1.60 (m, 2H), 1.42 (m, 2H), 1.27 (br s, 12H), 0.87 (m, 3H). HPLC (Condition A), Rt: 6.22 min (HPLC purity: 97.1%).

Example 340

{(4-dodec-1-ynylbenzyl)[4-(trifluoromethyl)phenyl]amino}(oxo)acetic acid, N-methyl-D-glucamine (i.e. 1-deoxy-1-(methylamino)glucitol) salt The same procedure as employed in the preparation of Example 2 but using {(4-dodec-1-ynylbenzyl)[4-(trifluoromethyl)phenyl]amino}(oxo)acetic acid and N-methyl-D-glucamine gave the title compound as a white powder (99%). HPLC (Condition A), Rt: 6.07 min (HPLC purity: 96.7%).

Example 341 oxo([4-(trifluoromethyl)benzyl]{4-[2-(3-undecyl-1,2,4-oxadiazol-5-yl)-ethyl]benzyl}amino)acetic acid Step a) Formation of Tert-Butyl 4-{3-[(dodecanimidoylamino)oxy]-3-oxopropyl}benzylcarbamate The same procedure as employed in the preparation of Example 10 (step a) but using 3-(4-{[(tert-butoxycarbonyl)amino]methyl}phenyl)propanoic acid gave the title compound as a pale yellow solid (99%). $^1$H NMR (CDCl$_3$, 300 MHz) δ 7.21 (s, 4H), 5.03-4.58 (m, 3H), 4.27 (d, 2H, J=5.6 Hz), 3.01 (t, 2H, J=7.4 Hz), 2.75 (t, 2H, J=7.4 Hz), 2.23 (t, 2H, J=7.9 Hz), 1.57 (m, 2H), 1.46 (s, 9H), 1.25 (br s, 16H), 0.89 (t, 3H, J=6.6 Hz). M$^-$(LC/MS(ESI)): 474; M$^+$(LC/MS(ESI)): 476. HPLC (Condition A), Rt: 5.29 min (HPLC purity: 99.0%).

Step b) Formation of Tert-Butyl 4-[2-(3-undecyl-1,2,4-oxadiazol-5-yl)ethyl]-benzyl-carbamate The same procedure as employed in the preparation of Example 23 (step e) but using tert-butyl 4-{3-[(dodecanimidoylamino)oxy]-3-oxopropyl}benzylcarbamate gave the title compound as a pale yellow solid (71%). $^1$H NMR (CDCl$_3$, 300 MHz) δ 7.22 (d, 2H, J=8.3 Hz), 7.16 (d, 2H, J=8.3 Hz), 4.80 (br s, 1H), 4.27 (m, 2H), 3.13 (m, 4H), 2.70 (t, 2H, J=7.5 Hz), 1.73 (m, 2H), 1.46 (s, 9H), 1.29 (m, 16H), 0.88 (t, 3H, J=6.8 Hz). HPLC (Condition A), Rt: 6.07 min (HPLC purity: 98.0%).

Step c) Formation of 4-[2-(3-undecyl-1,2,4-oxadiazol-5-yl)ethyl]benzylamine

The same procedure as employed in the preparation of Example 23 (step f) but using tert-butyl 4-[2-(3-undecyl-1,2,4-oxadiazol-5-yl)ethyl]benzylcarbamate gave the title compound as a white solid (82%). $^1$H NMR (CDCl$_3$, 300 MHz) δ 7.25 (d, 2H, J=8.3 Hz), 7.17 (d, 2H, J=8.3 Hz), 3.85 (s, 2H), 3.13 (m, 4H), 2.70 (t, 2H, J=7.7 Hz), 1.97 (br s, 2H), 1.73 (m, 2H), 1.30 (m, 16H), 0.88 (t, 3H, J=6.8 Hz). M$^+$(LC/MS (ESI)): 358. HPLC (Condition A), Rt: 4.17 min (HPLC purity: 98.0%).

Step d) Formation of N-[4-(trifluoromethyl)benzyl]-N-{4-[2-(3-undecyl-1,2,4-oxadiazol-5-yl)ethyl]benzyl}amine The same procedure as employed in the preparation of Example 226 (step a) but using 4-[2-(3-undecyl-1,2,4-oxadiazol-5-yl)ethyl]benzylamine and 4-(trifluoromethyl)benzaldehyde gave the title compound as a pale yellow oil (68%). $^1$H NMR (CDCl$_3$, 300 MHz) δ 7.60 (d, 2H, J=8.1 Hz), 7.53 (d, 2H, J=8.1 Hz), 7.33 (d, 2H, J=7.9 Hz), 7.19 (d, 2H, J=7.9 Hz), 3.86 (s, 2H), 3.79 (s, 2H), 3.13 (m, 4H), 2.70 (t, 2H, J=7.7 Hz), 1.72 (m, 2H), 1.29 (m, 16H), 0.88 (t, 3H, J=6.8 Hz). M$^-$(LC/MS(ESI)): 516. HPLC (Condition A), Rt: 4.83 min (HPLC purity 93.5%).

Step e) Formation of Ethyl oxo([4-(trifluoromethyl)benzyl]{4-[2-(3-undecyl-1,2,4-oxadiazol-5-yl)ethyl]benzyl}amino)acetate The same procedure as employed in the preparation of Example 15 (step b) but using N-[4-(trifluoromethyl)benzyl]-N-{4-[2-(3-undecyl-1,2,4-oxadiazol-5-yl)ethyl]benzyl}amine gave the title compound as a colorless oil (67%). $^1$H NMR (CDCl$_3$, 300 MHz) δ 7.60 (m, 2H), 7.37 (d, 1H, J=8.3 Hz), 7.32 (d, 1H, J=8.3 Hz), 7.17 (m, 4H), 4.52 (s, 1H), 4.47 (s, 1H), 4.35 (m, 4H), 3.15 (br s, 4H), 2.71 (t, 2H, J=7.7 Hz), 1.73 (m, 2H), 1.37-1.25 (m, 19H), 0.88 (t, 3H, J=6.8 Hz). M$^-$(LC/MS(ESI)): 614; M$^+$(LC/MS(ESI)): 616. HPLC (Condition A), Rt: 6.37 min (HPLC purity: 97.3%).

Step f) Formation of oxo([4-(trifluoromethyl)benzyl]{4-[2-(3-undecyl-1,2,4-oxadiazol-5-yl)ethyl]benzyl}amino)acetic acid The same procedure as employed in the preparation of Example 1 (step e) but using ethyl oxo([4-(trifluoromethyl)benzyl]{4-[2-(3-undecyl-1,2,4-oxadiazol-5-yl)ethyl]benzyl}amino)acetate gave the title compound as a colorless oil (92%). $^1$H NMR (CDCl$_3$, 300 MHz) δ 7.61 (m, 2H), 7.35 (m, 2H), 7.19 (m, 4H), 5.03 (s, 1H), 4.91 (s, 1H), 4.61 (s, 1H), 4.55 (s, 1H), 3.14 (br s, 4H), 2.70 (m, 2H), 1.71 (m, 2H), 1.32 (m, 16H), 0.88 (t, 3H, J=6.8 Hz). M$^-$(LC/MS(ESI)): 586. HPLC (Condition A), Rt: 5.87 min (HPLC purity: 99.9%). Analysis calculated for $C_{32}H_{40}F_3N_3O_4$■0.5H$_2$O C, 64.41; H, 6.93; N, 7.04%. Found: C, 64.31; H, 6.93; N, 6.97%.

Example 342 oxo([4-(trifluoromethyl)benzyl]{4-[2-(3-undecyl-1,2,4-oxadiazol-5-yl)ethyl]benzyl}amino)acetic acid, N-methyl-D-glucamine (i.e. 1-deoxy-1-(methylamino)-glucitol) salt The same procedure as employed in the preparation of Example 2 but using oxo([4-(trifluoromethyl)benzyl]{4-[2-(3-undecyl-1,2,4-oxadiazol-5-yl)ethyl]benzyl}amino)acetic acid and N-methyl-D-glucamine gave the title compound as a colorless oil (97%). M⁻(LC/MS(ESI)): 586; M⁺(LC/MS(ESI)): 588. HPLC (Condition A), Rt: 5.88 min (HPLC purity: 99.5%).

Example 343

{{4-[2-(3-octyl-1,2,4-oxadiazol-5-yl)ethyl]benzyl}[4-(trifluoromethyl)-benzyl]amino}(oxo)acetic acid Step a) Formation of Tert-Butyl 4-{3-[(nonanimidoylamino)oxy]-3-oxopropyl}-benzyl-carbamate The same procedure as employed in the preparation of Example 10 (step a) but using 3-(4-{[(tert-butoxycarbonyl)amino]methyl}phenyl)propanoic acid gave the title compound as a pale yellow solid (99%). $^1$H NMR (CDCl$_3$, 300 MHz) δ 7.21 (s, 4H), 5.00-4.50 (m, 3H), 4.27 (d, 2H, J=5.6 Hz), 3.00 (t, 2H, J=7.3 Hz), 2.73 (t, 2H, J=7.3 Hz), 2.19 (t, 2H, J=7.5 Hz), 1.56 (m, 2H), 1.46 (s, 9H), 1.26 (br s, 10H), 0.88 (t, 3H, J=6.8 Hz). M⁻(LC/MS(ESI)): 432; M⁺(LC/MS(ESI)): 434. HPLC (Condition A), Rt: 4.70 min (HPLC purity: 97.8%).

Step b) Formation of Tert-Butyl 4-[2-(3-octyl-1,2,4-oxadiazol-5-yl)ethyl]benzylcarbamate The same procedure as employed in the preparation of Example 23 (step e) but using tert-butyl 4-{3-[(nonanimidoylamino)oxy]-3-oxopropyl}benzylcarbamate gave the title compound as a pale yellow solid (76%).

Step c) Formation of 4-[2-(3-octyl-1,2,4-oxadiazol-5-yl)ethyl]benzylamine

The same procedure as employed in the preparation of Example 23 (step f) but using 4-[2-(3-octyl-1,2,4-oxadiazol-5-yl)ethyl]benzylamine gave the title compound as a white solid (87%). $^1$H NMR (CDCl$_3$, 300 MHz) δ 7.25 (d, 2H, J=7.7 Hz), 7.17 (d, 2H, J=7.7 Hz), 3.84 (s, 2H), 3.13 (m, 4H), 2.70 (t, 2H, J=7.7 Hz), 1.78 (br s, 2H), 1.73 (m, 2H), 1.30 (m, 10H), 0.88 (t, 3H, J=6.8 Hz). M⁺(LC/MS(ESI)): 316. HPLC (Condition A), Rt: 3.51 min (HPLC purity: 98.0%).

Step d) Formation of N-{4-[2-(3-octyl-1,2,4-oxadiazol-5-yl)ethyl]benzyl}-N-[4-(trifluoromethyl)benzyl]amine The same procedure as employed in the preparation of Example 226 (step a) but using 4-[2-(3-octyl-1,2,4-oxadiazol-5-yl)ethyl]benzylamine and 4-(trifluoromethyl)benzaldehyde gave the title compound as a pale yellow oil (65%). $^1$H NMR (CDCl$_3$, 300 MHz) δ 7.60 (d, 2H, J=8.3 Hz), 7.51 (d, 2H, J=8.3 Hz), 7.30 (d, 2H, J=7.9 Hz), 7.18 (d, 2H, J=7.9 Hz), 3.86 (s, 2H), 3.78 (s, 2H), 3.12 (m, 4H), 2.70 (t, 2H, J=7.7 Hz), 1.73 (m, 2H), 1.28 (m, 10H), 0.88 (t, 3H, J=6.6 Hz). M⁺(LC/MS(ESI)): 474. HPLC (Condition A), Rt: 4.31 min (HPLC purity: 97.9%).

Step e) Formation of ethyl{{4-[2-(3-octyl-1,2,4-oxadiazol-5-yl)ethyl]benzyl}[4-(trifluoromethyl)benzyl]amino}(oxo)acetate The same procedure as employed in the preparation of Example 15 (step b) but using N-{4-[2-(3-octyl-1,2,4-oxadiazol-5-yl)ethyl]benzyl}-N-[4-(trifluoromethyl)benzyl]amine gave the title compound as a colorless oil (74%). $^1$H NMR (CDCl$_3$, 300 MHz) δ 7.61 (m, 2H), 7.37 (d, 1H, J=7.9 Hz), 7.31 (d, 1H, J=7.9 Hz), 7.17 (m, 4H), 4.52 (s, 1H), 4.46 (s, 1H), 4.35 (m, 4H), 3.14 (m, 4H), 2.71 (t, 2H, J=7.5 Hz), 1.73 (m, 2H), 1.37-1.23 (m, 13H), 0.87 (t, 3H, J=6.8 Hz). M⁻(LC/MS(ESI)): 572; M⁺(LC/MS(ESI)): 574. HPLC (Condition A), Rt: 5.92 min (HPLC purity: 99.9%).

Step f) Formation of {{4-[2-(3-octyl-1,2,4-oxadiazol-5-yl)ethyl]benzyl}[4-(trifluoromethyl)-benzyl]amino}(oxo)acetic acid The same procedure as employed in the preparation of Example 1 (step e) but using ethyl{{4-[2-(3-octyl-1,2,4-oxadiazol-5-yl)ethyl]benzyl}[4-(trifluoromethyl)benzyl]amino}(oxo)acetate gave the title compound as a colorless oil (91%). $^1$H NMR (CDCl$_3$, 300 MHz) δ 7.64 (m, 2H), 7.37 (m, 2H), 7.19 (m, 4H), 5.04 (s, 1H), 4.93 (s, 1H), 4.63 (s, 1H), 4.56 (s, 1H), 3.17 (m, 4H), 2.73 (t, 2H, J=7.7 Hz), 1.75 (m, 2H), 1.31 (m, 10H), 0.89 (t, 3H, J=6.8 Hz). M⁻(LC/MS(ESI)): 544; M⁺(LC/MS(ESI)): 546 HPLC (Condition A), Rt: 5.38 min (HPLC purity: 99.2%).

Example 344

{{4-[2-(3-octyl-1,2,4-oxadiazol-5-yl)ethyl]benzyl}[4-(trifluoromethyl)-benzyl]amino}(oxo)acetic acid, N-methyl-D-glucamine (i.e. 1-deoxy-1-(methylamino)glucitol) salt The same procedure as employed in the preparation of Example 2 but using {{4-[2-(3-octyl-1,2,4-oxadiazol-5-yl)ethyl]benzyl}[4-(trifluoromethyl)benzyl]amino}(oxo)acetic acid and N-methyl-D-glucamine gave the title compound as a white gummy solid (96%). M⁻(LC/MS(ESI)): 544; M⁺(LC/MS(ESI)): 546. HPLC (Condition A), Rt: 5.37 min (HPLC purity: 99.0%).

Example 345

{{4-[(4-octylbenzoyl)amino]benzyl}[4-(trifluoromethyl)benzyl]-amino}-(oxo)acetic acid Step a) Formation of ethyl{{4-[(4-octylbenzoyl)amino]benzyl}[4-(trifluoromethyl)-benzyl]amino}(oxo)acetate The same procedure as employed in the preparation of Example 311 (step a) but using 4-octylbenzoic acid gave the title compound as a colorless oil (93%). $^1$H NMR (CDCl$_3$, 300 MHz) δ 7.81 (m, 3H), 7.63 (m, 4H), 7.42-7.21 (m, 6H), 4.54 (s, 1H), 4.49 (s, 1H), 4.37 (m, 4H), 2.68 (m, 2H), 1.64 (m, 2H), 1.28 (m, 13H), 0.89 (m, 3H). M⁻(LC/MS(ESI)): 595; M⁺(LC/MS(ESI)): 597. HPLC (Condition A), Rt: 7.19 min (HPLC purity: 99.2%).

Step b) Formation of {{4-[(4-octylbenzoyl)amino]benzyl}[4-(trifluoromethyl)benzyl]-amino}(oxo)acetic acid The same procedure as employed in the preparation of Example 1 (step e) but using ethyl{{4-[(4-octylbenzoyl)amino]benzyl}[4-(trifluoromethyl)benzyl]amino}(oxo)acetate gave the title compound as a white solid (93%). $^1$H NMR (CDCl$_3$, 300 MHz) δ 7.95 (m, 1H), 7.80 (m, 2H), 7.61 (m, 4H), 7.39-7.23 (m, 6H), 5.13 (br s, 1H), 4.91 (s, 1H), 4.77 (s, 1H), 4.58 (s, 1H), 4.53 (s, 1H), 2.68 (m, 2H), 1.63 (m, 2H), 1.28 (br s, 10H), 0.89 (m, 3H). M⁻(LC/MS(ESI)): 567; M⁺(LC/MS(ESI)): 569. HPLC (Condition A), Rt: 6.64 min (HPLC purity: 99.5%). Analysis calculated for C$_{32}$H$_{35}$F$_3$N$_2$O$_4$: C, 67.59; H, 6.20; N, 4.93%. Found: C, 67.32; H, 6.21; N, 4.86%.

Example 346

{{4[(4-octylbenzoyl)amino]benzyl}[4-(trifluoromethyl)benzyl]amino}-(oxo)acetic acid, N-methyl-D-glucamine (i.e. 1-deoxy-1-(methylamino)glucitol) salt The same procedure as employed in the preparation of Example 2 but using {{4-[(4octylbenzoyl)amino]benzyl}[4-(trifluoromethyl)benzyl]amino}(oxo)acetic acid and N-methyl-D-glucamine gave the title compound as a white powder (92%). M$^-$(LC/MS(ESI)): 567; M$^+$(LC/MS(ESI)): 569. HPLC (Condition A), Rt: 6.68 min (HPLC purity: 99.4%). Analysis calculated for $C_{32}H_{35}F_3N_2O_4 \cdot C_7H_{17}NO_5 \cdot 0.6H_2O$: C, 60.47; H, 6.92; N, 5.42%. Found: C, 60.48; H, 7.11; N, 5.41%.

Example 347 oxo{[(1-tridecanoylpiperidin-4-yl)methyl][4-(trifluoromethyl)benzyl]-amino}acetic acid

Step a) Formation of Tert-Butyl 4-(2-{[4-trifluoromethylbenzyl]amino}methyl)piperidine-1-carboxylate hydrochloride The same procedure as employed in the preparation of Example 226 (step a) but using tert-butyl 4-(aminomethyl)piperidine-1-carboxylate and 4-(trifluoromethyl)benzaldehyde gave the title compound as a white solid (65%). $^1$H NMR (DMSO-d$_6$, 300 MHz) δ 9.16 (br s, 1H), 7.84 (d, 2H, J=8.3 Hz), 7.77 (d, 2H, J=8.3 Hz), 4.25 (br s, 2H), 3.92 (m, 2H), 2.84 (m, 2H), 2.70 (br s, 2H), 1.89 (br s, 1H), 1.72 (br s, 2H), 1.39 (br s, 9H), 1.05 (m, 2H).

Step b) Formation of Tert-Butyl 4-(2-{ethoxy(oxo)acetyl][4-(trifluoromethyl)benzyl]amino}-methyl)piperidine-1-carboxylate The same procedure as employed in the preparation of Example 15 (step b) but using tert-butyl 4-(2-{[4-trifluoromethylbenzyl]amino}methyl)piperidine-1-carboxylate hydrochloride gave the title compound as a colourless oil (94%). M$^-$(LC/MS(ESI)): 471. HPLC, Rt: 5.78 min (HPLC purity 99.9%). $^1$H NMR (CDCl$_3$, 300 MHz) δ 7.62 (m, 2H), 7.39 (m, 2H), 4.68 (s, 1H), 4.54 (s, 1H), 4.45-4.20 (m, 2H), 4.19-4.00 (m, 2H), 3.19 (d, 1H, J=7.2 Hz), 3.12 (d, 1H, J=7.2 Hz), 2.63 (m, 2H), 1.81 (m, 1H), 1.59 (m, 2H), 1.48-0.95 (m, 14H).

Step c) Formation of Ethyl oxo-{(2-piperidin-4-ylmethyl)[4-(trifluoromethylbenzyl]amino}acetate hydrochloride The same procedure as employed in the preparation of Example 23 (step f) but using tert-butyl 4-(2-{ethoxy(oxo)acetyl][4-(trifluoromethyl)benzyl]amino}-methyl)piperidine-1-carboxylate gave the title compound as a gummy colorless solid (99%). HPLC, Rt: 3.12 min (HPLC purity: 99.5%).

Step d) Formation of Ethyl oxo{[(1-tridecanoylpiperidin-4-yl)methyl][4-(trifluoromethyl)-benzyl]amino}acetate The same procedure as employed in the preparation of Example 1 (step d) but using ethyl oxo-{(2-piperidin-4-ylmethyl)[4-(trifluoromethylbenzyl]amino}acetate hydrochloride, tridecanoic acid, HOBT, and TEA in DCM gave the title compound as a yellow oil (66%). M$^-$(LC/MS(ESI)): 567; M$^+$(LC/MS(ESI)): 569. HPLC (Condition A), Rt: 7.24 min (HPLC purity: 99.4%).

Step e) Formation of oxo{[(1-tridecanoylpiperidin-4-yl)methyl][4-(trifluoromethyl)benzyl]-amino}acetic acid The same procedure as employed in the preparation of Example 1 (step e) but using ethyl oxo{[(1-tridecanoylpiperidin-4-yl)methyl][4-trifluoromethyl)benzyl]amino}acetate gave the title compound as a gummy orange solid (58%). $^1$H NMR (DMSO-d$_6$, 300 MHz) δ 7.75 (m, 2H), 7.50 (m, 2H), 4.63 (m, 2H), 4.35 (br t, 1H), 3.83 (br d, 1H), 3.20-2.80 (m, 3H), 2.41 (br q, 1H), 2.24 (t, 2H, J=7.4 Hz), 1.90 (br s, 1H), 1.65-1.35 (m, 4H), 1.23 (br s, 18H), 1.15-0.70 (m, 5H). M$^-$(LC/MS(ESI)): 539. HPLC (Condition A), Rt: 6.68 min (HPLC purity: 98.3%).

Example 348

{{[1-(4-octylbenzoyl)piperidin-4-yl]methyl}[4-(trifluoromethyl)benzyl]-amino}(oxo)acetic acid

Step a) Formation of ethyl{{[1-(4-octylbenzoyl)piperidin-4-yl]methyl}[4-trifluoromethyl)-benzyl]amino}(oxo)acetate The same procedure as employed in the preparation of Example 1 (step d) but using ethyl oxo-{(2-piperidin-4-ylmethyl)[4-(trifluoromethylbenzyl]amino}acetate hydrochloride, 4-n-octylbenzoic acid, HOBT, and TEA in DCM gave the title compound as a colorless oil (84%). $^1$H NMR (CDCl$_3$, 300 MHz) δ 7.63 (m, 2H), 7.40 (m, 2H), 7.32-7.17 (m, 4H), 4.70 (s, 1H), 4.55 (s, 1H), 4.40 (q, 2H, J=7.2 Hz), 4.20 (q, 2H, J=7.2 Hz), 3.4-3.1 (m, 2H), 2.85 (br s, 2H), 2.6 (m, 2H), 1.95 (br s, 1H), 1.6 (m, 4H), 1.47-1.1 (m, 17H), 0.88 (m, 3H). M$^-$(LC/MS(ESI)): 587. HPLC (Condition A), Rt: 6.26 min (HPLC purity: 99.2%).

Step b) Formation of {{[1-(4-octylbenzoyl)piperidin-4-yl]methyl}[4-(trifluoromethyl)-benzyl]amino}(oxo)acetic acid The same procedure as employed in the preparation of Example 1 (step e) but using ethyl{{[1-(4-octylbenzoyl)piperidin-4-yl]methyl}[4-(trifluoromethyl)benzyl]amino}(oxo)acetate gave the title compound as a white foam (67%). $^1$H NMR (CDCl$_3$, 300 MHz) δ 7.61 (m, 2H), 7.39 (m, 2H), 7.31 (m, 2H), 7.22 (m, 2H), 4.80 (m, 3H), 3.86 (m, 1H), 3.49 (br s, 1H), 3.25 (br s, 1H), 2.94 (m, 2H), 2.60 (t, 2H, J=7.5 Hz), 2.15-1.45 (m, 4H), 1.28 (m, 13H), 0.88 (t, 3H, J=6.6 Hz). M$^-$(LC/MS(ESI)): 559; M$^+$(LC/MS(ESI)): 561. HPLC (Condition A), Rt: 5.68 min (HPLC purity: 99.5%).

Example 349

{{[1-(4-octylbenzoyl)piperidin-4-yl]methyl}[4-(trifluoromethyl)benzyl]-amino}(oxo)acetic acid, N-methyl-D-glucamine (i.e. 1-deoxy-1-(methylamino) glucitol) salt The same procedure as employed in the preparation of Example 2 but using {{[1-(4-octylbenzoyl)piperidin-4-yl]methyl}[4-(trifluoromethyl)benzyl]amino}(oxo)acetic acid and N-methyl-D-glucamine gave the title compound as a white powder (90%). M⁻(LC/MS(ESI)): 559; M⁺(LC/MS (ESI)): 561. HPLC (Condition A), Rt: 5.56 min (HPLC purity: 97.1%). Analysis calculated for C₃₁H₃₉F₃N₂O₄.C₇H₁₇NO₅■3.5H₂O: C, 55.73; H, 7.75; N, 5.13%. Found: C, 55.68; H, 7.56; N, 5.17%.

Example 350

{[(3-dec-1-ynyl-1-benzofuran-5-yl)methyl][4-(trifluoromethyl)benzyl]-amino}(oxo)acetic acid

Step a) Formation of 3-bromo-1-benzofuran-5-carbaldehyde

To a solution of 2,3-dibromo-2,3-dihydro-1-benzofuran-5-carbaldehyde (10 g) in dry ethanol (25 mL) was added a solution of KOH in dry ethanol (14 mL) and refluxed at 70° C. for 2 h. The reaction mixture was cooled, diluted with water and extracted with EtOAc (3×50 mL). The organic layer was washed with water, brine and dried. The solvent was removed under vacuum and the residue was purified by flash chromatography (PetEther/EtOAc 99.5/0.5) to give the title compound as a pale yellow solid (3.3 g, 45%). ¹H NMR (DMSO-d₆, 300 MHz) δ 10.12 (s, 1H), 8.47 (s, 1H), 8.14 (d, 1H, J=1.5 Hz), 7.97 (dd, 1H, J=8.6, 1.5 Hz), 7.87 (d, 1H, J=8.6 Hz).

Step b) Formation of N-[(3-bromo-1-benzofuran-5-yl)methyl]-N-[4-(trifluoromethyl)-benzyl]amine hydrochloride The same procedure as employed in the preparation of Example 226 (step a) but using 3-bromo-1-benzofuran-5-carbaldehyde gave the title compound as a beige solid (77%). ¹H NMR (DMSO-d₆, 300 MHz) δ 10.00 (br s, 2H), 8.35 (s, 1H), 7.81-7.64 (m, 7H), 4.32 (s, 2H), 4.26 (s, 2H). M⁺(LC/MS(ESI)): 386.1. HPLC (Condition A), Rt: 3.11 min (HPLC purity: 96.4%).

Step c) Formation of ethyl{[(3-bromo-1-benzofuran-5-yl)methyl][4-(trifluoromethyl)-benzyl]amino}(oxo)acetate The same procedure as employed in the preparation of Example 15 (step b) but using N-[(3-bromo-1-benzofuran-5-yl)methyl]-N-[4-(trifluoromethyl)benzyl]amine hydrochloride gave the title compound as a colorless oil (84%). ¹H NMR (CDCl₃, 300 MHz) δ 7.71 (s, 0.5H), 7.69 (s, 0.5H), 7.65 (d, 1H, J=8.1 Hz), 7.61 (d, 1H, J=8.1 Hz), 7.50 (d, 0.5H, J=8.4 Hz), 7.48 (d, 0.5H, J=8.5 Hz), 7.41-7.25 (m, 4H), 4.64 (s, 1H), 4.56 (s, 1H), 4.49 (s, 1H), 4.43 (s, 1H), 4.40 (q, 1H, J=7.2 Hz), 4.35 (q, 1H, J=7.2 Hz), 1.38 (t, 1.5H, J=7.2 Hz), 1.33 (t, 1.5H, J=7.2 Hz). M⁺(LC/MS(ESI)): 484.0. HPLC (Condition A), Rt: 4.95 min (HPLC purity: 99.0%).

Step d) Formation of ethyl{[(3-dec-1-ynyl-1-benzofuran-5-yl)methyl][4-(trifluoromethyl)-benzyl]amino}(oxo)acetate The same procedure as employed in the preparation of Example 226 (step c) but using ethyl{[(3-bromo-1-benzofuran-5-yl)methyl][4-(trifluoromethyl)benzyl]amino}(oxo)acetate and 1-decyne gave the title compound as a yellow oil (40%). ¹H NMR (CDCl₃, 300 MHz) δ 7.78 (s, 0.5H), 7.76 (s, 0.5H), 7.65 (d, 1H, J=7.9 Hz), 7.61 (d, 1H, J=7.9 Hz), 7.52-7.33 (m, 4H), 7.22 (m, 1H), 4.64 (s, 1H), 4.56 (s, 1H), 4.47 (s, 1H), 4.41 (s, 1H), 4.39 (q, 1H, J=7.2 Hz), 4.34 (q, 1H, J=7.2 Hz), 2.49 (m, 2H), 1.66 (m, 2H), 1.49 (m, 2H), 1.40-1.26 (m, 11H), 0.89 (t, 3H, J=6.8 Hz). M⁻(LC/MS(ESI)): 540.5; M⁺(LC/MS(ESI)): 542.7. HPLC (Condition A), Rt: 6.07 min (HPLC purity: 98.0%).

Step e) Formation of {[(3-dec-1-ynyl-1-benzofuran-5-yl)methyl][4-(trifluoromethyl)-benzyl]amino}(oxo)acetic acid The same procedure as employed in the preparation of Example 1 (step e) but using ethyl{[(3-dec-1-ynyl-1-benzofuran-5-yl)methyl][4-(trifluoromethyl)benzyl]amino}-(oxo)acetate gave the title compound as a yellow oil (91%). ¹H NMR (CDCl₃, 300 MHz) δ 7.78 (s, 0.5H), 7.77 (s, 0.5H), 7.63 (m, 2H), 7.47 (m, 2H), 7.36 (m, 2H), 7.22 (m, 1H), 5.07 to (s, 1H), 5.03 (s, 1H), 4.71 (s, 1H), 4.62 (s, 1H), 2.49 (t, 2H, J=7.0 Hz), 1.67 (m, 2H), 1.49 (m, 2H), 1.30 (m, 8H), 0.89 (t, 3H, J=6.8 Hz). M⁻(LC/MS(ESI)): 512.4. HPLC (Condition A), Rt: 5.54 min (HPLC purity: 92.4%).

Example 351

{[(3-dodec-1-ynyl-1-benzofuran-5-yl)methyl][4-(trifluoromethyl)benzyl]-amino}(oxo)acetic acid

Step a) Formation of ethyl{[(3-dodec-1-ynyl-1-benzofuran-5-yl)methyl][4-(trifluoromethyl)-benzyl]amino}(oxo)acetate The same procedure as employed in the preparation of Example 226 (step c) but using ethyl{[(3-bromo-1-benzofuran-5-yl)methyl][4-(trifluoromethyl)benzyl]amino}(oxo)acetate and 1-dodecyne gave the title compound as a yellow oil (34%). HPLC (Condition A), Rt: 6.39 min (HPLC purity: 99.2%).

Step b) Formation of {[(3-dodec-1-ynyl-1-benzofuran-5-yl)methyl][4-(trifluoromethyl)-benzyl]amino}(oxo)acetic acid The same procedure as employed in the preparation of Example 1 (step e) but using ethyl{[(3-dodec-1-ynyl-1-benzofuran-5-yl)methyl][4-(trifluoromethyl)benzyl]-amino}(oxo)acetate gave the title compound as a yellow oil (86%). M⁻(LC/MS(ESI)): 540.4. HPLC (Condition A), Rt: 5.91 min (HPLC purity: 96.3%).

Example 352 oxo{({3-[(4-propylphenyl)ethynyl]-1-benzofuran-5-yl}methyl)[4-(trifluoromethyl)benzyl]amino}acetic acid

Step a) Formation of ethyloxo{({3-[(4-propylphenyl)ethynyl]-1-benzofuran-5-yl}methyl)[4-(trifluoromethyl)benzyl]amino}acetate The same procedure as employed in the preparation of Example 226 (step c) but using ethyl{[(3-bromo-1-benzofuran-5-yl)methyl][4-(trifluoromethyl)benzyl]amino}(oxo)acetate and 1-ethynyl-4-propylbenzene under microwave conditions (300 W, 120° C., 10 min) gave the title compound as a yellow oil (5%). M⁻(LC/MS(ESI)): 545.8; M⁺(LC/MS (ESI)): 548.2 HPLC (Condition A), Rt: 5.85 min (HPLC purity: 92.4%).

Step b) Formation of oxo{({3-[(4-propylphenyl)ethynyl]-1-benzofuran-5-yl}methyl)[4-(trifluoromethyl)benzyl]amino}acetic acid The same procedure as employed in the preparation of Example 1 (step e) but using ethyloxo{({3-[(4-propylphenyl)ethynyl]-1-benzofuran-5-yl}methyl)[4-(trifluoromethyl)benzyl]amino}acetate gave the title compound as a pale yellow foam (75%). M⁻(LC/MS(ESI)): 518.2; M⁺(LC/MS (ESI)): 520.0. HPLC (Condition A), Rt: 5.30 min (HPLC purity: 84.0%).

Example 353

[(4-dodec-1-ynylbenzyl)(4-fluorobenzyl)amino] (oxo)acetic acid

Step a) Formation of N-(4-bromobenzyl)-N-(4-fluorobenzyl)amine hydrochloride

The same procedure as employed in the preparation of Example 226 (step a) but using 4-fluorobenzylamine gave the title compound as a white solid (98%). $^1$H NMR (CD$_3$OD, 300 MHz) δ 7.65 (m, 2H), 7.57 (m, 2H), 7.47 (m, 2H), 7.22 (m, 2H), 4.22 (s, 2H), 4.20 (s, 2H). HPLC (Condition A), Rt: 2.23 min (HPLC purity: 97.4%).

Step b) Formation of ethyl[(4-bromobenzyl)(4-fluorobenzyl)amino](oxo)acetate

The same procedure as employed in the preparation of Example 15 (step b) but using N-(4-bromobenzyl)-N-(4-fluorobenzyl)amine hydrochloride gave the title compound as a pale yellow oil (87%). $^1$H NMR (CDCl$_3$, 300 MHz) δ 7.51 (d, 1H, J=8.2 Hz), 7.48 (d, 1H, 3=8.3 Hz), 7.24-7.00 (m, 6H), 4.45 (s, 1H), 4.43 (s, 1H), 4.37 (q, 1H, J=7.2 Hz), 4.35 (q, 1H, J=7.2 Hz), 4.30 (s, 1H), 4.28 (s, 1H), 1.36 (t, 1.5H, J=7.2 Hz), 1.35 (t, 1.5H, J=7.2 Hz). M⁺(LC/MS(ESI)): 394.0. HPLC (Condition A), Rt: 4.58 min (HPLC purity: 95.3%).

Step c) Formation of ethyl[(4-dodec-1-ynylbenzyl) (4-fluorobenzyl)amino](oxo)acetate The same procedure as employed in the preparation of Example 226 (step c) but using ethyl[(4-bromobenzyl)(4-fluorobenzyl)amino](oxo)acetate and 1-dodecyne gave the title compound as a pale yellow oil (23%). $^1$H NMR (CDCl$_3$, 300 MHz) δ 7.39 (m, 2H), 7.25-7.00 (m, 6H), 4.45 (s, 1H), 4.44 (s, 1H), 4.36 (m, 2H), 4.30 (s, 1H), 4.28 (s, 1H), 2.42 (t, 2H, J=7.1 Hz), 1.62 (m, 2H), 1.46 (m, 2H), 1.37-1.25 (m, 15H), 0.89 (t, 3H, J=6.6 Hz). M⁺(LC/MS(ESI)): 480.3. HPLC (Condition A), Rt: 6.28 min (HPLC purity: 99.8%).

Step d) Formation of [(4-dodec-1-ynylbenzyl)(4-fluorobenzyl)amino](oxo)acetic acid The same procedure as employed in the preparation of Example 1 (step e) but using ethyl[(4-dodec-1-ynylbenzyl) (4-fluorobenzyl)amino](oxo)acetate gave the title compound as a yellow oil (87%). $^1$H NMR (CDCl$_3$, 300 MHz) δ 7.40 (m, 2H), 7.25-7.02 (m, 6H), 4.95 (s, 1H), 4.93 (s, 1H), 4.53 (s, 1H), 4.51 (s, 1H), 2.41 (t, 2H, J=6.8 Hz), 1.62 (m, 2H), 1.45 (m, 2H), 1.28 (br s, 12H), 0.89 (t, 3H, J=6.8 Hz). M⁻(LC/MS (ESI)): 450.2. HPLC (Condition A), Rt: 5.75 min (HPLC purity: 99.0%).

Example 354

[bis(4-oct-1-ynylbenzyl)amino](oxo)acetic acid

Step a) Formation of ethyl[bis(4-oct-1-ynylbenzyl)amino](oxo)acetate

The same procedure as employed in the preparation of Example 226 (step c) but using ethyl[(4-bromobenzyl)(4-oct-1-ynylbenzyl)amino](oxo)acetate and 1-octyne gave the title compound as a pale yellow oil (32%). $^1$H NMR (CDCl$_3$, 300 MHz) δ 7.38 (m, 4H), 7.16 (d, 2H, J=8.3 Hz), 7.12 (d, 2H, J=7.9 Hz), 4.45 (s, 2H), 4.35 (q, 2H, J=7.2 Hz), 4.28 (s, 2H), 2.42 (t, 4H, J=7.1 Hz), 1.62 (m, 4H), 1.47 (m, 4H), 1.33 (m, 11H), 0.92 (t, 6H, J=6.8 Hz). M⁺(LC/MS(ESI)): 514.0. HPLC (Condition A), Rt: 6.54 min (HPLC purity: 99.3%).

Step b) Formation of [bis(4-oct-1-ynylbenzyl)amino](oxo)acetic acid

The same procedure as employed in the preparation of Example 1 (step e) but using ethyl[bis(4-oct-1-ynylbenzyl) amino](oxo)acetate gave the title compound as a yellow oil (94%). $^1$H NMR (CDCl$_3$, 300 MHz) δ 7.39 (m, 4H), 7.14 (m, 4H), 4.93 (s, 2H), 4.52 (s, 2H), 2.42 (t, 4H, J=7.0 Hz), 1.62 (m, 4H), 1.47 (m, 4H), 1.34 (m, 8H), 0.92 (t, 6H, J=6.8 Hz). M⁻(LC/MS(ESI)): 484.3. HPLC (Condition A), Rt: 6.04 min (HPLC purity: 98.7%).

Example 355

{[(6-dodec-1-ynylpyridin-3-yl)methyl][4-(trifluoromethyl)benzyl]-amino}(oxo)acetic acid Step a) Formation of 6-dodec-1-ynylnicotinaldehyde A mixture of 6-bromonicotinaldehyde (500 mg, 2.69 mmol), 1-dodecyne (680 mg, 4.09 mmol), triphenylphosphine (23 mg, 0.09 mmol), triethylamine (470 ml, 3.38 mmol) and bis(triphenylphosphine)palladium(II) chloride (94 mg, 0.13 mmol) in THF (10 mL) was stirred under argon at rt for 30 min. Copper(I) iodide (21 mg, 0.11 mmol) was added and the mixture was stirred for 21 hours at rt. The solvent was removed under reduced pressure. The residue was diluted with a saturated aqueous solution of NH$_4$Cl (20 mL) and extracted with Et$_2$O (50 ml+2×20 mL). The combined organic layers were dried over MgSO$_4$ and the solvent was removed under reduce pressure. The residue was purified by flash chromatography (c-Hex/EtOAc 4/1) to give the title compound as yellow oil (218 mg, 29%). $^1$H NMR (CDCl$_3$, 300 MHz) δ 10.1 (s, 1H), 9.00 (s, 1H), 8.11 (d, 1H, J=8.1 Hz), 7.52 (d, 1H, J=8.1 Hz), 2.49 (t, 2H, J=7.1 Hz), 1.67 (m, 2H), 1.47 (m, 2H), 1.28 (m, 12H), 0.89 (t, 3H, J=6.8 Hz). M⁻(LC/MS(ESI)): 270.3; M⁺(LC/MS(ESI)): 272.4. HPLC (Condition A), Rt: 5.23 min (HPLC purity: 98.3%).

Step b) Formation of N-[(6-dodec-1-ynylpyridin-3-yl)methyl]-N-[4-(trifluoromethyl)-benzyl]amine The same procedure as employed in the preparation of Example 226 (step a) but using 6-dodec-1-ynylnicotinaldehyde gave the title compound as a pale yellow solid (54%). M⁺(LC/MS(ESI)): 431.4. HPLC (Condition A), Rt: 4.47 min (HPLC purity: 98.8%).

Step c) Formation of ethyl{[(6-dodec-1-ynylpyridin-3-yl)methyl][4-(trifluoromethyl)-benzyl]amino} (oxo)acetate The same procedure as employed in the preparation of Example 15 (step b) but using N-[(6-dodec-1-ynylpyridin-3-yl)methyl]-N-[4-(trifluoromethyl)benzyl]amine gave the title compound as a colorless oil (93%). $^1$H NMR (CDCl$_3$, 300 MHz) δ 8.38 (d, 0.5H, J=2.0 Hz), 8.34 (d, 0.5H, J=2.0 Hz), 7.64 (m, 2.5H), 7.56 (dd, 0.5H, J=7.9, 2.0 Hz), 7.41-7.31 (m, 3H), 4.54 (s, 1H), 4.49 (s, 1H), 4.42-4.32 (m, 4H), 2.46 (m, 2H), 1.65 (m, 2H), 1.46 (m, 2H), 1.39-1.28 (m, 15H), 0.89 (t, 3H, J=6.8 Hz). M⁻(LC/MS(ESI)): 529.3; M⁺(LC/MS(ESI)): 531.4. HPLC (Condition A), Rt: 5.60 min (HPLC purity: 100%).

Step d) Formation of {[(6-dodec-1-ynylpyridin-3-yl)methyl][4-(trifluoromethyl)benzyl]-amino}(oxo)acetic acid The same procedure as employed in the preparation of Example 1 (step e) but using ethyl{[(6-dodec-1-ynylpyridin-3-yl)methyl][4-(trifluoromethyl)benzyl]amino}(oxo)acetate gave the title compound as a white foam (90%). $^1$H NMR (CDCl$_3$, 300 MHz) δ 8.65 (s, 0.5H), 8.58 (s, 0.5H), 7.84 (d, 0.5H, J=8.3 Hz), 7.69 (d, 0.5H, J=8.2 Hz), 7.58 (m, 2H), 7.45 (m, 2H), 7.35 (d, 1H, J=7.9 Hz), 5.38 (br s, 1H), 4.72 (s, 1H), 4.70 (s, 1H), 4.60 (s, 1H), 4.50 (s, 1H), 2.45 (t, 2H, J=7.0 Hz), 1.63 (m, 2H), 1.42 (m, 2H), 1.27 (br s, 12H), 0.88 (t, 3H, J=6.6 Hz). M$^-$(LC/MS(ESI)): 501.2; M$^+$(LC/MS(ESI)): 503.0. HPLC (Condition A), Rt: 4.76 min (HPLC purity: 99.5%).

Example 356

{(3-dodec-1-ynylbenzyl)[4-(trifluoromethyl)benzyl]amino}(oxo)acetic acid

Step a) Formation of 3-dodec-1-ynylbenzaldehyde

The same procedure as employed in the preparation of Example 226 (step c) but using 3-bromobenzaldehyde gave the title compound (59%).

Step b) Formation of N-(3-dodec-1-ynylbenzyl)-N-[4-(trifluoromethyl)benzyl]amine The same procedure as employed in the preparation of Example 226 (step a) but using 3-dodec-1-ynylbenzaldehyde and 4-(trifluoromethyl)benzylamine gave the title compound (37%). M$^+$(LC/MS(ESI)): 430.5. HPLC (Condition A), Rt: 4.82 min (HPLC purity 94.7%).

Step c) Formation of ethyl{(3-dodec-1-ynylbenzyl)[4-(trifluoromethyl)benzyl]amino}-(oxo)acetate The same procedure as employed in the preparation of Example 15 (step b) but using N-(3-dodec-1-ynylbenzyl)-N-[4-(trifluoromethyl)benzyl]amine gave the title compound (99%). HPLC (Condition A), Rt: 6.48 min (HPLC purity: 100%).

Step d) Formation of {(3-dodec-1-ynylbenzyl)[4-(trifluoromethyl)benzyl]amino}(oxo)acetic acid The same procedure as employed in the preparation of Example 1 (step e) but using ethyl{(3-dodec-1-ynylbenzyl)[4-(trifluoromethyl)benzyl]amino}(oxo)acetate gave the title compound as a colorless oil (95%). $^1$H NMR (CD$_3$OD, 300 MHz) δ 7.71-7.61 (m, 2H), 7.52 (d, 1H, J=7.9 Hz), 7.41 (d, 1H, J=8.3 Hz), 7.34-7.14 (m, 4H), 4.62 (m, 2H), 4.54 (m, 2H), 2.45 (t, 2H, J=6.8 Hz), 1.70-1.58 (m, 2H), 1.57-1.46 (m, 2H), 1.45-1.28 (m, 12H), 0.92 (m, 3H). M$^-$(LC/MS(ESI)): 500.4. HPLC (Condition A), Rt: 5.94 min (HPLC purity: 98.4%).

Example 357

{[2-(2-fluorophenyl)ethyl][4-(3-undecyl-1,2,4-oxadiazol-5-yl)benzyl]-amino}(oxo)acetic acid

Step a) Formation of N-[2-(2-fluorophenyl)ethyl]-N-[4-(3-undecyl-1,2,4-oxadiazol-5-yl)benzyl]amine To a solution of 4-(3-undecyl-1,2,4-oxadiazol-5-yl)benzaldehyde (32.8 mg, 0.1 mmol) in anhydrous THF (0.6 mL) was added the 2-(2-fluorophenyl)ethylamine (11.8 mg, 0.1 mmol) and Ti(iPrO)$_4$ (0.035 mL, 0.12 mmol). The mixture was stirred for 3 h at 60° C. then sodium triacetoxyborohydride (53 mg, 0.25 mmol) was added and the reaction mixture was stirred overnight at rt. THF (0.75 mL) was added followed by the PS-DEAM resin (Argonaut, 148 mg, 1.68 mmol/g), and the reaction mixture was stirred at rt overnight. The reaction mixture was filtered and the filtrates were eluted through a SCX column (Isolute, 1 g) with DCM (6 mL), then NH$_3$ (2M in MeOH, 4 mL). The desired fractions (TLC monitoring) were concentrated under vacuum to give the title product.

Step b) Formation of ethyl{[2-(2-fluorophenyl)ethyl][4-(3-undecyl-1,2,4-oxadiazol-5-yl)benzyl]amino}(oxo)acetate To a solution of N-[2-(2-fluorophenyl)ethyl]-N-[4-(3-undecyl-1,2,4-oxadiazol-5-yl)benzyl]amine (45.1 mg, 0.1 mmol) in anhydrous DCM (0.6 mL) was added the morpholinomethyl polystyrene resin (Novabiochem, HL, 39.5 mg, 0.15 mmol, 3.8 mmol/g) and the resulting mixture was cooled at 0° C. Ethyloxalyl chloride (4.7 mg, 0.13 mmol) in anhydrous DCM (0.4 mL) was added. The reaction mixture was stirred for 2 h at rt, then the PL-AMS-Resin (Polymer Laboratories, 52 mg, 0.1 mmol, 1.93 mmol/g) was added and the mixture stirred for 1.5 h. The resins were filtered off, washed with DCM, and the filtrates were concentrated under vacuum to afford the title compound as an oil.

Step c) Formation of {[2-(2-fluorophenyl)ethyl][4-(3-undecyl-1,2,4-oxadiazol-5-yl)benzyl]amino}(oxo)acetic acid The same procedure as employed in the preparation of Example 1 (step e) but using ethyl{[2-(2-fluorophenyl)ethyl][4-(3-undecyl-1,2,4-oxadiazol-5-yl)benzyl]amino}(oxo)acetate gave the title compound as a colorless oil (26% (overall yield from step a)). M$^-$(LC/MS(ESI)): 522.3. HPLC (Condition A), Rt: 5.76 min (HPLC purity: 98.9%).

Example 358

{[2-(2-fluorophenyl)ethyl][3-(3-undecyl-1,2,4-oxadiazol-5-yl)benzyl]amino}(oxo)acetic acid

Step a) Formation of N-[2-(2-fluorophenyl)ethyl]-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 2-(2-fluorophenyl)ethylamine gave the title compound as an oil.

Step b) Formation of ethyl{[2-(2-fluorophenyl)ethyl][3-(3-undecyl-1,2,4-oxadiazol-5-yl)benzyl]amino}(oxo)acetate The same procedure as employed in the preparation of Example 357 (step b) but using N-[2-(2-fluorophenyl)ethyl]-N-[3-(3-undecyl-1,2,4-oxadiazol-5-yl)benzyl]amine gave the title compound as an oil. M$^+$(LC/MS(ESI)): 552.5. HPLC (Condition A), Rt: 6.31 min (HPLC purity: 91.2%).

Step c) Formation of {[2-(2-fluorophenyl)ethyl][3-(3-undecyl-1,2,4-oxadiazol-5-yl)benzyl]amino}(oxo)acetic acid The same procedure as employed in the preparation of Example 1 (step e) but using ethyl{[2-(2-fluorophenyl)ethyl][3-(3-undecyl-1,2,4-oxadiazol-5-yl)benzyl]amino}(oxo)acetate gave the title compound as a yellow oil (24% (overall yield from step a)). M⁻(LC/MS(ESI)): 522.4; M⁺(LC/MS (ESI)): 524.2. HPLC (Condition A), Rt: 5.76 min (HPLC purity: 98.5%).

Example 359

{[2-(2-fluorophenyl)ethyl][4-(3-octyl-1,2,4-oxadiazol-5-yl)benzyl]amino}-(oxo)acetic acid Step a) Formation of N-[2-(2-fluorophenyl)ethyl]-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 2-(2-fluorophenyl)ethylamine gave the title compound as an oil.

Step b) Formation of ethyl{[2-(2-fluorophenyl)ethyl][4-(3-octyl-1,2,4-oxadiazol-5-yl)benzyl]amino}(oxo)acetate The same procedure as employed in the preparation of Example 357 (step b) but using N-[2-(2-fluorophenyl)ethyl]-N-[4-(3-octyl-1,2,4-oxadiazol-5-yl)benzyl]amine gave the title compound as an oil.

Step c) Formation of {[2-(2-fluorophenyl)ethyl][4-(3-octyl-1,2,4-oxadiazol-5-yl)benzyl]amino}(oxo)acetic acid The same procedure as employed in the preparation of Example 1 (step e) but using ethyl{[2-(2-fluorophenyl)ethyl][4-(3-octyl-1,2,4-oxadiazol-5-yl)benzyl]amino}(oxo)acetate gave the title compound as a yellow oil (29% (overall yield from step a)). M⁻(LC/MS(ESI)): 480.2. HPLC (Condition A), Rt: 5.21 min (HPLC purity: 98.4%).

Example 360

{[2-(3,4-dichlorophenyl)ethyl][4-(3-undecyl-1,2,4-oxadiazol-5-yl benzyl]-amino}(oxo)acetic acid Step a) Formation of N-[2-(3,4-dichlorophenyl)ethyl]-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 2-(3,4-dichlorophenyl)ethylamine gave the title compound as an oil.

Step b) Formation of ethyl{[2-(3,4-dichlorophenyl)ethyl][4-(3-undecyl-1,2,4-oxadiazol-5-yl)benzyl]amino}(oxo)acetate The same procedure as employed in the preparation of Example 357 (step b) but using N-[2-(3,4-dichlorophenyl)ethyl]-N-[4-(3-undecyl-1,2,4-oxadiazol-5-yl)benzyl]amine gave the title compound as an oil.

Step c) Formation of {[2-(3,4-dichlorophenyl)ethyl][4-(3-undecyl-1,2,4-oxadiazol-5-yl)benzyl]amino}(oxo)acetic acid The same procedure as employed in the preparation of Example 1 (step e) but using ethyl{[2-(3,4-dichlorophenyl)ethyl][4-(3-undecyl-1,2,4-oxadiazol-5-yl)benzyl]amino}(oxo)acetate gave the title compound as a yellow oil (23% (overall yield from step a)). M⁻(LC/MS(ESI)): 572.2. HPLC (Condition A), Rt: 6.04 min (HPLC purity: 99.2%).

Example 361

{[2-3,4-dichlorophenyl)ethyl][3-(3-undecyl-1,2,4-oxadiazol-5-yl benzyl]-amino}(oxo)acetic acid Step a) Formation of N-[2-(3,4-dichlorophenyl)ethyl]-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 2-(3,4-dichlorophenyl)ethylamine gave the title compound as an oil.

Step b) Formation of ethyl{[2-(3,4-dichlorophenyl)ethyl][3-(3-undecyl-1,2,4-oxadiazol-5-yl)benzyl]amino}(oxo)acetate The same procedure as employed in the preparation of Example 357 (step b) but using N-[2-(3,4-dichlorophenyl)ethyl]-N-[3-(3-undecyl-1,2,4-oxadiazol-5-yl)benzyl]amine gave the title compound as an oil.

Step c) Formation of {[2-(3,4-dichlorophenyl)ethyl][3-(3-undecyl-1,2,4-oxadiazol-5-yl)benzyl]amino}(oxo)acetic acid The same procedure as employed in the preparation of Example 1 (step e) but using ethyl{[2-(3,4-dichlorophenyl)ethyl][3-(3-undecyl-1,2,4-oxadiazol-5-yl)benzyl]amino}(oxo)acetate gave the title compound as a colorless oil (18% (overall yield from step a)). M⁻(LC/MS(ESI)): 572.3; M⁺(LC/MS(ESI)): 574.0. HPLC (Condition A), Rt: 6.04 min (HPLC purity: 97.9%).

Example 362

{[2-(3,4-dichlorophenyl ethyl][4-(3-octyl-1,2,4-oxadiazol-5-yl)benzyl]-amino}(oxo)acetic acid Step a) Formation of N-[2-(3,4-dichlorophenyl)ethyl]-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 2-(3,4-dichlorophenyl)ethylamine gave the title compound as an oil.

Step b) Formation of ethyl{[2-(3,4-dichlorophenyl)ethyl][4-(3-octyl-1,2,4-oxadiazol-5-yl)benzyl]amino}(oxo)acetate The same procedure as employed in the preparation of Example 357 (step b) but using N-[2-(3,4-dichlorophenyl)ethyl]-N-[4-(3-octyl-1,2,4-oxadiazol-5-yl)benzyl]amine gave the title compound as an oil. M⁻(LC/MS(ESI)): 558.5; M⁺(LC/MS(ESI)): 560.1. HPLC (Condition A), Rt: 6.07 min (HPLC purity: 78.5%).

Step c) Formation of {[2-(3,4-dichlorophenyl)ethyl][4-(3-octyl-1,2,4-oxadiazol-5-yl)benzyl]amino}(oxo)acetic acid The same procedure as employed in the preparation of Example 1 (step e) but using ethyl{[2-(3,4-dichlorophenyl)ethyl][4-(3-octyl-1,2,4-oxadiazol-5-yl)benzyl]amino}(oxo)

acetate gave the title compound as a yellow oil (14% (overall yield from step a)). M⁻(LC/MS(ESI)): 532.0. HPLC (Condition A), Rt: 5.52 min (HPLC purity: 89.6%).

Example 363

{[2-(1,1'-biphenyl-4-yl)ethyl][4-(3-undecyl-1,2,4-oxadiazol-5-yl)benzyl]amino}(oxo)acetic acid Step a) Formation of N-[2-(1,1'-biphenyl-4-yl)ethyl]-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 2-(1,1'-biphenyl-4-yl)ethylamine gave the title compound as an oil.

Step b) Formation of ethyl{[2-(1,1-biphenyl-4-yl)ethyl][4-(3-undecyl-1,2,4-oxadiazol-5-yl)benzyl]amino}(oxo)acetate The same procedure as employed in the preparation of Example 357 (step b) but using N-[2-(1,1'-biphenyl-4-yl)ethyl]-N-[4-(3-undecyl-1,2,4-oxadiazol-5-yl)benzyl]amine gave the title compound as an oil. M⁺(LC/MS(ESI)): 610.3. HPLC (Condition A), Rt: 6.60 min (HPLC purity: 77.8%).

Step c) Formation of {[2-(1,1'-biphenyl-4-yl)ethyl][4-(3-undecyl-1,2,4-oxadiazol-5-yl)benzyl]amino}(oxo)acetic acid The same procedure as employed in the preparation of Example 1 (step e) but using ethyl{[2-(1,1'-biphenyl-4-yl)ethyl][4-(3-undecyl-1,2,4-oxadiazol-5-yl)benzyl]amino}(oxo)acetate gave the title compound as a yellow oil (4% (overall yield from step a)). M⁻(LC/MS(ESI)): 580.3. HPLC (Condition A), Rt: 6.10 min (HPLC purity: 95.3%).

Example 364

{[2-(1,1'-biphenyl-4-yl)ethyl][3-(3-undecyl-1,2,4-oxadiazol-5-yl)benzyl]-amino}(oxo)acetic acid Step a) Formation of N-[2-(1,1'-biphenyl-4-yl)ethyl]-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 2-(1,1'-biphenyl-4-yl)ethylamine gave the title compound as an oil.

Step b) Formation of ethyl{[2-(1,1-biphenyl-4-yl)ethyl][3-(3-undecyl-1,2,4-oxadiazol-5-yl)benzyl]amino}(oxo)acetate The same procedure as employed in the preparation of Example 357 (step b) but using N-[2-(1,1'-biphenyl-4-yl)ethyl]-N-[3-(3-undecyl-1,2,4-oxadiazol-5-yl)benzyl]amine gave the title compound as an oil.

Step c) Formation of {[2-(1,1'-biphenyl-4-yl)ethyl][3-(3-undecyl-1,2,4-oxadiazol-5-yl)benzyl]amino}(oxo)acetic acid The same procedure as employed in the preparation of Example 1 (step e) but using ethyl{[2-(1,1'-biphenyl-4-yl)ethyl][3-(3-undecyl-1,2,4-oxadiazol-5-yl)benzyl]amino}(oxo)acetate gave the title compound as a colorless oil (24% (overall yield from step a)). M⁻(LC/MS(ESI)): 580.1; M⁺(LC/MS(ESI)): 582.3. HPLC (Condition A), Rt: 6.10 min (HPLC purity: 97.8%).

Example 365

{[2-(1,1'-biphenyl-4-yl)ethyl][4-(3-octyl-1,2,4-oxadiazol-5-yl benzyl]-amino}(oxo)acetic acid Step a) Formation of N-[2-(1,1'-biphenyl-4-yl)ethyl]-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 2-(1,1'-biphenyl-4-yl)ethylamine gave the title compound as an oil.

Step b) Formation of ethyl{[2-(1,1'-biphenyl-4-yl)ethyl][4-(3-octyl-1,2,4-oxadiazol-5-yl)benzyl]amino}(oxo)acetate The same procedure as employed in the preparation of Example 357 (step b) but using N-[2-(1,1'-biphenyl-4-yl)ethyl]-N-[4-(3-octyl-1,2,4-oxadiazol-5-yl)benzyl]amine gave the title compound as an oil.

Step c) Formation of {[2-(1,1'-biphenyl-4-yl)ethyl][4-(3-octyl-1,2,4-oxadiazol-5-yl)benzyl]amino}(oxo)acetic acid The same procedure as employed in the preparation of Example 1 (step e) but using ethyl{[2-(1,1'-biphenyl-4-yl)ethyl][4-(3-octyl-1,2,4-oxadiazol-5-yl)benzyl]amino}(oxo)acetate gave the title compound as a colorless oil (13% (overall yield from step a)). M⁻(LC/MS(ESI)): 538.3. HPLC (Condition A), Rt: 5.63 min (HPLC purity: 97.8%).

Example 366 oxo{5,6,7,8-tetrahydronaphthalen-1-yl[4-(3-undecyl-1,2,4-oxadiazol-5-yl)benzyl]amino}acetic acid Step a) Formation of N-5,6,7,8-tetrahydronaphthalen-1-yl-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 5,6,7,8-tetrahydronaphthalen-1-ylamine gave the title compound as an oil. M⁺(LC/MS(ESI)): 460.4. HPLC (Condition A), Rt: 6.36 min (HPLC purity: 73.3%).

Step b) Formation of Ethyl oxo{5,6,7,8-tetrahydronaphthalen-1-yl[4-(3-undecyl-1,2,4-oxadiazol-5-yl)benzyl]amino}acetate The same procedure as employed in the preparation of Example 357 (step b) but using N-5,6,7,8-tetrahydronaphthalen-1-yl-N-[4-(3-undecyl-1,2,4-oxadiazol-5-yl)benzyl]amine gave the title compound as an oil.

Step c) Formation of oxo{5,6,7,8-tetrahydronaphthalen-1-yl[4-(3-undecyl-1,2,4-oxadiazol-5-yl)benzyl]amino}acetic acid The same procedure as employed in the preparation of Example 1 (step e) but using ethyl oxo{5,6,7,8-tetrahydronaphthalen-1-yl[4-(3-undecyl-1,2,4-oxadiazol-5-yl)benzyl]amino}acetate gave the title compound as a white powder (23% (overall yield from step a)). M⁻(LC/MS(ESI)): 530.3. HPLC (Condition A), Rt: 5.95 min (HPLC purity: 94.7%).

Example 367 oxo{5,6,7,8-tetrahydronaphthalen-1-yl[3-(3-undecyl-1,2,4-oxadiazol-5-yl)benzyl]amino}acetic acid Step a) Formation of N-5,6,7,8-tetrahydronaphthalen-1-yl-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 5,6,7,8-tetrahydronaphthalen-1-ylamine gave the title compound as an oil. M$^+$(LC/MS(ESI)): 460.4. HPLC (Condition A), Rt: 6.32 min (HPLC purity: 68.9%).

Step b) Formation of Ethyl oxo{5,6,7,8-tetrahydronaphthalen-1-yl[3-(3-undecyl-1,2,4-oxadiazol-5-yl)benzyl]amino}acetate The same procedure as employed in the preparation of Example 357 (step b) but using N-5,6,7,8-tetrahydronaphthalen-1-yl-N-[3-(3-undecyl-1,2,4-oxadiazol-5-yl)benzyl]amine gave the title compound as an oil. M$^+$(LC/MS(ESI)): 560.4. HPLC (Condition A), Rt: 6.52 min (HPLC purity: 73.3%).

Step c) Formation of oxo{5,6,7,8-tetrahydronaphthalen-1-yl[3-(3-undecyl-1,2,4-oxadiazol-5-yl)benzyl]amino}acetic acid The same procedure as employed in the preparation of Example 1 (step e) but using ethyl oxo{5,6,7,8-tetrahydronaphthalen-1-yl[3-(3-undecyl-1,2,4-oxadiazol-5-yl)benzyl]amino}acetate gave the title compound as a yellow solid (7% overall yield from step a)). M$^-$(LC/MS(ESI)): 530.2; M$^+$(LC/MS(ESI)): 532.3. HPLC (Condition A), Rt: 5.94 min (HPLC purity: 90.3%).

Example 368

[[4-(3-octyl-1,2,4-oxadiazol-5-yl)benzyl](5,6,7,8-tetrahydronaphthalen-1-yl)amino](oxo)acetic acid Step a) Formation of N-5,6,7,8-tetrahydronaphthalen-1-yl-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 5,6,7,8-tetrahydronaphthalen-1-ylamine gave the title compound as an oil. M$^+$(LC/MS(ESI)): 418.4. HPLC (Condition A), Rt: 5.83 min (HPLC purity: 82.3%).

Step b) Formation of Ethyl oxo{5,6,7,8-tetrahydronaphthalen-1-yl[4-(3-octyl-1,2,4-oxadiazol-5-yl)benzyl]amino}acetate The same procedure as employed in the preparation of Example 357 (step b) but using N-5,6,7,8-tetrahydronaphthalen-1-yl-N-[4-(3-octyl-1,2,4-oxadiazol-5-yl)benzyl]amine gave the title compound as an oil.

Step c) Formation of [[4-(3-octyl-1,2,4-oxadiazol-5-yl)benzyl](5,6,7,8-tetrahydronaphthalen-1-yl)amino](oxo)acetic acid The same procedure as employed in the preparation of Example 1 (step e) but using ethyl oxo{5,6,7,8-tetrahydronaphthalen-1-yl[4-(3-octyl-1,2,4-oxadiazol-5-yl)benzyl]amino}acetate gave the title compound as a white solid (11% overall yield from step a)). M$^-$(LC/MS(ESI)): 488.2. HPLC (Condition A), Rt: 5.43 min (HPLC purity: 95.6%).

Example 369

{(1,1'-biphenyl-3-ylmethyl)[4-(3-undecyl-1,2,4-oxadiazol-5-yl)benzyl]amino}(oxo)acetic acid Step a) Formation of N-(1,1'-biphenyl-3-ylmethyl)-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 1,1'-biphenyl-3-ylmethylamine hydrobromide gave the title compound as an oil. M$^+$(LC/MS(ESI)): 496.5. HPLC (Condition A), Rt: 4.99 min (HPLC purity: 90.9%).

Step b) Formation of ethyl{(1,1'-biphenyl-3-ylmethyl)[4-(3-undecyl-1,2,4-oxadiazol-5-yl)benzyl]amino}(oxo)acetate The same procedure as employed in the preparation of Example 357 (step b) but using N-(1,1'-biphenyl-3-ylmethyl)-N-[4-(3-undecyl-1,2,4-oxadiazol-5-yl)benzyl]amine gave the title compound as an oil. M$^+$(LC/MS(ESI)): 596.1. HPLC (Condition A), Rt: 6.51 min (HPLC purity: 91.8%).

Step c) Formation of {(1,1'-biphenyl-3-ylmethyl)[4-(3-undecyl-1,2,4-oxadiazol-5-yl)benzyl]amino}(oxo)acetic acid The same procedure as employed in the preparation of Example 1 (step e) but using ethyl{(1,1'-biphenyl-3-ylmethyl)[4-(3-undecyl-1,2,4-oxadiazol-5-yl)benzyl]amino}(oxo)acetate gave the title compound as a yellow oil (6% overall yield from step a)). M$^-$(LC/MS(ESI)): 566.3. HPLC (Condition A), Rt: 6.06 min (HPLC purity: 99.5%).

Example 370

{(1,1'-biphenyl-3-ylmethyl)[3-(3-undecyl-1,2,4-oxadiazol-5-yl)benzyl]amino}(oxo)acetic acid Step a) Formation of N-(1,1'-biphenyl-3-ylmethyl)-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 1,1'-biphenyl-3-ylmethylamine hydrobromide gave the title compound as an oil. M$^+$(LC/MS(ESI)): 496.5. HPLC (Condition A), Rt: 4.99 min (HPLC purity: 87.7%).

Step b) Formation of ethyl{(1,1'-biphenyl-3-ylmethyl)[3-(3-undecyl-1,2,4-oxadiazol-5-yl)benzyl]amino}(oxo)acetate The same procedure as employed in the preparation of Example 357 (step b) but using N-(1,1'-biphenyl-3-ylmethyl)-N-[3-(3-undecyl-1,2,4-oxadiazol-5-yl)benzyl]amine gave the title compound as an oil.

Step c) Formation of {(1,1'-biphenyl-3-ylmethyl)[3-(3-undecyl-1,2,4-oxadiazol-5-yl)benzyl]amino}(oxo)acetic acid The same procedure as employed in the preparation of Example 1 (step e) but using ethyl{(1,1'-biphenyl-3-ylmethyl)[3-(3-undecyl-1,2,4-oxadiazol-5-yl)benzyl]amino}(oxo)acetate gave the title compound as a yellow oil (17%

(overall yield from step a)). M⁻(LC/MS(ESI)): 566.1; M⁺(LC/MS(ESI)): 568.2. HPLC (Condition A), Rt: 5.99 min (HPLC purity: 94.5%).

Example 371

{(1,1'-biphenyl-3-ylmethyl)[4-(3-octyl-1,2,4-oxadiazol-5-yl)benzyl]-amino}(oxo)acetic acid Step a) Formation of N-(1,1'-biphenyl-3-ylmethyl)-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 1,1'-biphenyl-3-ylmethylamine hydrobromide gave the title compound as an oil. M⁺(LC/MS (ESI)): 454.6 HPLC (Condition A), Rt: 4.52 min (HPLC purity: 81%).

Step b) Formation of ethyl{(1,1'-biphenyl-3-ylmethyl)[4-(3-octyl-1,2,4-oxadiazol-5-yl)benzyl] amino}(oxo)acetate The same procedure as employed in the preparation of Example 357 (step b) but using N-(1,1'-biphenyl-3-ylmethyl)-N-[4-(3-octyl-1,2,4-oxadiazol-5-yl)benzyl]amine gave the title compound as an oil.

Step c) Formation of {(1,1'-biphenyl-3-ylmethyl)[4-(3-octyl-1,2,4-oxadiazol-5-yl)benzyl]amino}(oxo) acetic acid The same procedure as employed in the preparation of Example 1 (step e) but using ethyl{(1,1'-biphenyl-3-ylmethyl)[4-(3-octyl-1,2,4-oxadiazol-5-yl)benzyl]amino}(oxo)acetate gave the title compound as a colorless oil (4% overall yield from step a)). M⁻(LC/MS(ESI)): 524.2. HPLC (Condition A), Rt: 5.51 min (HPLC purity: 90.8%).

Example 372

{(1-benzothien-3-ylmethyl)[(3-undecyl-1,2,4-oxadiazol-5-yl)benzyl]-amino}(oxo)acetic acid Step a) Formation of N-(1-benzothien-3-ylmethyl)-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 1-benzothien-3-ylmethylamine gave the title compound as an oil. M⁺(LC/MS(ESI)): 476.4. HPLC (Condition A), Rt: 4.82 min (HPLC purity: 77.5%).

Step b) Formation of ethyl{(1-benzothien-3-ylmethyl)[4-(3-undecyl-1,2,4-oxadiazol-5-yl)-benzyl] amino}(oxo)acetate The same procedure as employed in the preparation of Example 357 (step b) but using N-(1-benzothien-3-ylmethyl)-N-[4-(3-undecyl-1,2,4-oxadiazol-5-yl)benzyl]amine gave the title compound as an oil.

Step c) Formation of {(1-benzothien-3-ylmethyl)[4-(3-undecyl-1,2,4-oxadiazol-5-yl)-benzyl]amino} (oxo)acetic acid The same procedure as employed in the preparation of Example 1 (step e) but using ethyl{(1-benzothien-3-ylmethyl)[4-(3-undecyl-1,2,4-oxadiazol-5-yl)benzyl]amino} (oxo)acetate gave the title compound as a colorless oil (15% overall yield from step a)). M⁻(LC/MS(ESI)): 546.2. HPLC (Condition A), Rt: 5.88 min (HPLC purity: 98.3%).

Example 373

{(1-benzothien-3-ylmethyl)[3-(3-undecyl-1,2,4-oxadiazol-5-yl)benzyl]-amino}(oxo)acetic acid Step a) Formation of N-(1-benzothien-3-ylmethyl)-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 1-benzothien-3-ylmethylamine gave the title compound as an oil. M⁺(LC/MS(ESI)): 476.3. HPLC (Condition A), Rt: 4.79 min (HPLC purity: 86.7%).

Step b) Formation of ethyl{(1-benzothien-3-ylmethyl)[3-(3-undecyl-1,2,4-oxadiazol-5-yl)benzyl] amino}(oxo)acetate The same procedure as employed in the preparation of Example 357 (step b) but using N-(1-benzothien-3-ylmethyl)-N-[3-(3-undecyl-1,2,4-oxadiazol-5-yl)benzyl]amine gave the title compound as an oil. M⁺(LC/MS(ESI)): 576.7. HPLC (Condition A), Rt: 6.37 min (HPLC purity: 87.9%).

Step c) Formation of {(1-benzothien-3-ylmethyl)[3-(3-undecyl-1,2,4-oxadiazol-5-yl)-benzyl]amino} (oxo)acetic acid The same procedure as employed in the preparation of Example 1 (step e) but using ethyl{(1-benzothien-3-ylmethyl)[3-(3-undecyl-1,2,4-oxadiazol-5-yl)benzyl]amino} (oxo)acetate gave the title compound as a colorless oil (23% overall yield from step a)). M⁻(LC/MS(ESI)): 546.1. HPLC (Condition A), Rt: 5.84 min (HPLC purity: 98.0%).

Example 374

{(1-benzothien-3-ylmethyl)[4-(3-octyl-1,2,4-oxadiazol-5-yl)benzyl]amino}-(oxo)acetic acid Step a) Formation of N-(1-benzothien-3-ylmethyl)-N-[4-(3-octyl-1,2,4-oxadiazol-5-yl)-benzyl]amine The same procedure as employed in the preparation of Example 357 (step a) but using 4-(3-octyl-1,2,4-oxadiazol-5-yl)benzaldehyde and 1-benzothien-3-ylmethylamine gave the title compound as an oil. M⁺(LC/MS(ESI)): 434.3. HPLC (Condition A), Rt: 4.30 min (HPLC purity: 89.9%).

Step b) Formation of ethyl{(1-benzothien-3-ylmethyl)[4-(3-octyl-1,2,4-oxadiazol-5-yl)-benzyl] amino}(oxo)acetate The same procedure as employed in the preparation of Example 357 (step b) but using N-(1-benzothien-3-ylmethyl)-N-[4-(3-octyl-1,2,4-oxadiazol-5-yl)benzyl]amine gave the title compound as an oil.

Step c) Formation of {(1-benzothien-3-ylmethyl)[4-(3-octyl-1,2,4-oxadiazol-5-yl)benzyl]-amino}(oxo) acetic acid The same procedure as employed in the preparation of Example 1 (step e) but using ethyl{(1-benzothien-3-ylmethyl][4-(3-octyl-1,2,4-oxadiazol-5-yl)benzyl]amino}(oxo)acetate gave the title compound as a yellow oil (9% (overall yield from step a)). M⁻(LC/MS(ESI)): 504.1. HPLC (Condition A), Rt: 5.34 min (HPLC purity: 88.7%).

Example 375 oxo{[2-(trifluoromethyl)benzyl][4-(3-undecyl-1,2,4-oxadiazol-5-yl)benzyl]-amino}acetic acid Step a) Formation of N-[2-(trifluoromethyl)benzyl]-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 2-(trifluoromethyl)benzylamine gave the title compound as an oil. M⁺(LC/MS(ESI)): 488.5. HPLC (Condition A), Rt: 4.78 min (HPLC purity: 95.4%).

Step b) Formation of Ethyl oxo{[2-(trifluoromethyl)benzyl][4-(3-undecyl-1,2,4-oxadiazol-5-yl)benzyl]amino}acetate The same procedure as employed in the preparation of Example 357 (step b) but using N-[2-(trifluoromethyl)benzyl]-N-[4-(3-undecyl-1,2,4-oxadiazol-5-yl)benzyl]amine gave the title compound as an oil.

Step c) Formation of oxo{[2-(trifluoromethyl)benzyl][4-(3-undecyl-1,2,4-oxadiazol-5-yl)-benzyl]amino}acetic acid The same procedure as employed in the preparation of Example 1 (step e) but using ethyl oxo{[2-(trifluoromethyl)benzyl][4-(3-undecyl-1,2,4-oxadiazol-5-yl)benzyl]amino}acetate gave the title compound as a colorless oil (38% (overall yield from step a)). M⁻(LC/MS(ESI)): 558.1. HPLC (Condition A), Rt: 5.94 min (HPLC purity: 98.7%).

Example 376 oxo{[2-(trifluoromethyl)benzyl][3-(3-undecyl-1,2,4-oxadiazol-5-yl)benzyl]amino}acetic acid Step a) Formation of N-[2-(trifluoromethyl)benzyl]-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 2-(trifluoromethyl)benzylamine gave the title compound as an oil. M⁺(LC/MS(ESI)): 488.4. HPLC (Condition A), Rt: 4.78 min (HPLC purity: 95.4%).

Step b) Formation of Ethyl oxo{[2-(trifluoromethyl)benzyl][3-(3-undecyl-1,2,4-oxadiazol-5-yl)benzyl]amino}acetate The same procedure as employed in the preparation of Example 357 (step b) but using N-[2-(trifluoromethyl)benzyl]-N-[3-(3-undecyl-1,2,4-oxadiazol-5-yl)benzyl]amine gave the title compound as an oil.

Step c) Formation of oxo{[2-(trifluoromethyl)benzyl][3-(3-undecyl-1,2,4-oxadiazol-5-yl)benzyl]amino}acetic acid The same procedure as employed in the preparation of Example 1 (step e) but using ethyl oxo{[2-(trifluoromethyl)benzyl][3-(3-undecyl-1,2,4-oxadiazol-5-yl)benzyl]amino}acetate gave the title compound as a colorless oil (13% (overall yield from step a)). M⁻(LC/MS(ESI)): 558.2. HPLC (Condition A), Rt: 5.87 min (HPLC purity: 97.8%).

Example 377

{[4-(3-octyl-1,2,4-oxadiazol-5-yl)benzyl][2-(trifluoromethyl)benzyl]amino}-(oxo)acetic acid Step a) Formation of N-[2-(trifluoromethyl)benzyl]-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 2-(trifluoromethyl)benzylamine gave the title compound as an oil. M⁺(LC/MS(ESI)): 446.4. HPLC (Condition A), Rt: 4.23 min (HPLC purity: 96.5%).

Step b) Formation of Ethyl oxo{[2-(trifluoromethyl)benzyl][4-(3-octyl-1,2,4-oxadiazol-5-yl)benzyl]amino}acetate The same procedure as employed in the preparation of Example 357 (step b) but using N-[2-(trifluoromethyl)benzyl]-N-[4-(3-octyl-1,2,4-oxadiazol-5-yl)benzyl]amine gave the title compound as an oil. M⁻(LC/MS(ESI)): 544.2; M⁺(LC/MS(ESI)): 546.1. HPLC (Condition A), Rt: 5.95 min (HPLC purity: 92.7%).

Step c) Formation of {[4-(3-octyl-1,2,4-oxadiazol-5-yl)benzyl][2-(trifluoromethyl)benzyl]amino}(oxo)acetic acid The same procedure as employed in the preparation of Example 1 (step e) but using ethyl oxo{[2-(trifluoromethyl)benzyl][4-(3-octyl-1,2,4-oxadiazol-5-yl)benzyl]amino}acetate gave the title compound as a colorless oil (18% (overall yield from step a)). M⁻(LC/MS(ESI)): 516.2. HPLC (Condition A), Rt: 5.35 min (HPLC purity: 99.0%).

Example 378 oxo{[3-(trifluoromethyl)benzyl][4-(3-undecyl-1,2,4-oxadiazol-5-yl)benzyl]amino}acetic acid Step a) Formation of N-[3-(trifluoromethyl)benzyl]-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 3-(trifluoromethyl)benzylamine gave the title compound as an oil. M⁺(LC/MS(ESI)): 488.4. HPLC (Condition A), Rt: 4.84 min (HPLC purity: 64.4%).

Step b) Formation of Ethyl oxo{[3-(trifluoromethyl)benzyl][4-(3-undecyl-1,2,4-oxadiazol-5-yl)benzyl]amino}acetate The same procedure as employed in the preparation of Example 357 (step b) but using N-[3-(trifluoromethyl)benzyl]-N-[4-(3-undecyl-1,2,4-oxadiazol-5-yl)benzyl]amine gave the title compound as an oil.

Step c) Formation of oxo{[3-(trifluoromethyl)benzyl][4-(3-undecyl-1,2,4-oxadiazol-5-yl)benzyl]amino}acetic acid The same procedure as employed in the preparation of Example 1 (step e) but using ethyl oxo{[3-(trifluoromethyl)benzyl][4-(3-undecyl-1,2,4-oxadiazol-5-yl)benzyl]

Example 379 oxo{[3-(trifluoromethyl)benzyl][3-(3-undecyl-1,2,4-oxadiazol-5-yl)benzyl]amino}acetic acid Step a) Formation of N-[3-(trifluoromethyl)benzyl]-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 3-(trifluoromethyl)benzylamine gave the title compound as an oil. M⁺(LC/MS(ESI)): 488.5. HPLC (Condition A), Rt: 4.86 min (HPLC purity: 66.8%).

Step b) Formation of Ethyl oxo{[3-(trifluoromethyl)benzyl][3-(3-undecyl-1,2,4-oxadiazol-5-yl)benzyl]amino}acetate The same procedure as employed in the preparation of Example 357 (step b) but using N-[3-(trifluoromethyl)benzyl]-N-[3-(3-undecyl-1,2,4-oxadiazol-5-yl)benzyl]amine gave the title compound as an oil.

Step c) Formation of oxo{[3-(trifluoromethyl)benzyl][3-(3-undecyl-1,2,4-oxadiazol-5-yl)benzyl]amino}acetic acid The same procedure as employed in the preparation of Example 1 (step e) but using ethyl oxo{[3-(trifluoromethyl)benzyl][3-(3-undecyl-1,2,4-oxadiazol-5-yl)benzyl]amino}acetate gave the title compound as a yellow oil (44% (overall yield from step a)). M⁻(LC/MS(ESI)): 558.1; M⁺(LC/MS(ESI)): 560.2. HPLC (Condition A), Rt: 5.84 min (HPLC purity: 97.3%).

Example 380

{[4-(3-octyl-1,2,4-oxadiazol-5-yl)benzyl][3-(trifluoromethyl)benzyl]-amino}(oxo)acetic acid Step a) Formation of N-[3-(trifluoromethyl)benzyl]-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 3-(trifluoromethyl)benzylamine gave the title compound as an oil. M⁺(LC/MS(ESI)): 446.4. HPLC (Condition A), Rt: 4.31 min (HPLC purity: 73.9%).

Step b) Formation of Ethyl oxo{[3-(trifluoromethyl)benzyl][4-(3-octyl-1,2,4-oxadiazol-5-yl)benzyl]amino}acetate The same procedure as employed in the preparation of Example 357 (step b) but using N-[3-(trifluoromethyl)benzyl]-N-[4-(3-octyl-1,2,4-oxadiazol-5-yl)benzyl]amine gave the title compound as an oil.

Step c) Formation of {[4-(3-octyl-1,2,4-oxadiazol-5-yl)benzyl][3-(trifluoromethyl)-benzyl]amino}(oxo)acetic acid The same procedure as employed in the preparation of Example 1 (step e) but using ethyl oxo{[3-(trifluoromethyl)benzyl][4-(3-octyl-1,2,4-oxadiazol-5-yl)benzyl]amino}acetate gave the tide compound as a yellow oil (20% (overall yield from step a)). M⁻(LC/MS(ESI)): 516.1. HPLC (Condition A), Rt: 97.9 min (HPLC purity: 97.9%).

Example 381

{(2-methoxybenzyl)[4-(3-undecyl-1,2,4-oxadiazol-5-yl)benzyl]-amino}-(oxo)acetic acid Step a) Formation of N-(2-methoxybenzyl)-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 2-methoxybenzylamine gave the title compound as an oil. M⁺(LC/MS(ESI)): 450.5. HPLC (Condition A), Rt: 4.70 min (HPLC purity: 92.7%).

Step b) Formation of ethyl{(2-methoxybenzyl)[4-(3-undecyl-1,2,4-oxadiazol-5-yl)benzyl]-amino}(oxo)acetate The same procedure as employed in the preparation of Example 357 (step b) but using N-(2-methoxybenzyl)-N-[4-(3-undecyl-1,2,4-oxadiazol-5-yl)benzyl]amine gave the title compound as an oil.

Step c) Formation of {(2-methoxybenzyl)[4-(3-undecyl-1,2,4-oxadiazol-5-yl)benzyl]amino}(oxo)acetic acid The same procedure as employed in the preparation of Example 1 (step e) but using ethyl{(2-methoxybenzyl)[4-(3-undecyl-1,2,4-oxadiazol-5-yl)benzyl]amino}(oxo)acetate gave the title compound as a colorless oil (43% (overall yield from step a)). M⁻(LC/MS(ESI)): 520.3; M⁺(LC/MS(ESI)): 522.4. HPLC (Condition A), Rt: 5.76 min (HPLC purity: 98.6%).

Example 382

{(2-methoxybenzyl)[3-(3-undecyl-1,2,4-oxadiazol-5-yl)benzyl]amino}-(oxo)acetic acid Step a) Formation of N-(2-methoxybenzyl)-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 2-methoxybenzylamine gave the title compound as an oil. M⁺(LC/MS(ESI)): 450.5. HPLC (Condition A), Rt: 4.72 min (HPLC purity: 92.6%).

Step b) Formation of ethyl{(2-methoxybenzyl)[3-(3-undecyl-1,2,4-oxadiazol-5-yl)benzyl]-amino}(oxo)acetate The same procedure as employed in the preparation of Example 357 (step b) but using N-(2-methoxybenzyl)-N-[3-(3-undecyl-1,2,4-oxadiazol-5-yl)benzyl]amine gave the title compound as an oil.

Step c) Formation of {(2-methoxybenzyl)[3-(3-undecyl-1,2,4-oxadiazol-5-yl)benzyl]amino}(oxo)acetic acid The same procedure as employed in the preparation of Example 1 (step e) but using ethyl{(2-methoxybenzyl)[3-(3- undecyl-1,2,4-oxadiazol-5-yl)benzyl]amino}(oxo)acetate gave the title compound as a white solid (17% (overall yield from step a)). M⁻(LC/MS(ESI)): 520.3; M⁺(LC/MS(ESI)): 522.3. HPLC (Condition A), Rt: 5.70 min (HPLC purity: 98.9%).

Example 383

{(2-methoxybenzyl)[4-(3-octyl-1,2,4-oxadiazol-5-yl)benzyl]amino}-(oxo)acetic acid Step a) Formation of N-(2-methoxybenzyl)-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 2-methoxybenzylamine gave the title compound as an oil. M⁺(LC/MS(ESI)): 408.4. HPLC (Condition A), Rt: 4.12 min (HPLC purity: 91.9%).

Step b) Formation of ethyl{(2-methoxybenzyl)[4-(3-octyl-1,2,4-oxadiazol-5-yl)benzyl]amino}(oxo)acetate The same procedure as employed in the preparation of Example 357 (step b) but using N-(2-methoxybenzyl)-N-[4-(3-octyl-1,2,4-oxadiazol-5-yl)benzyl]amine gave the title compound as an oil.

Step c) Formation of {(2-methoxybenzyl)[4-(3-octyl-1,2,4-oxadiazol-5-yl)benzyl]amino}(oxo)acetic acid The same procedure as employed in the preparation of Example 1 (step e) but using ethyl{(2-methoxybenzyl)[4-(3-octyl-1,2,4-oxadiazol-5-yl)benzyl]amino}(oxo)acetate gave the title compound as a yellow oil (33% (overall yield from step a)). M⁻(LC/MS(ESI)): 478.2. HPLC (Condition A), Rt: 5.15 min (HPLC purity: 98.0%).

Example 384 oxo{{4-[(trifluoromethyl)sulfonyl]benzyl}[4-(3-undecyl-1,2,4-oxadiazol-5-yl)benzyl]amino}acetic acid Step a) Formation of N-{4-[(trifluoromethyl)sulfonyl]benzyl}-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 4-[(trifluoromethyl)sulfonyl]benzylamine hydrochloride gave the title compound as an oil. M⁺(LC/MS(ESI)): 552.7. HPLC (Condition A), Rt: 4.85 min (HPLC purity: 36%).

Step b) Formation of Ethyl oxo{{4-[(trifluoromethyl)sulfonyl]benzyl}[4-(3-undecyl-1,2,4-oxadiazol-5-yl)benzyl]amino}acetate The same procedure as employed in the preparation of Example 357 (step b) but using N-{4-[(trifluoromethyl)sulfonyl]benzyl}-N-[4-(3-undecyl-1,2,4-oxadiazol-5-yl)benzyl]amine gave the title compound as an oil.

Step c) Formation of oxo{{4-[(trifluoromethyl)sulfonyl]benzyl}[4-(3-undecyl-1,2,4-oxadiazol-5-yl)benzyl]amino}acetic acid The same procedure as employed in the preparation of Example 1 (step e) but using ethyl oxo{{4-[(trifluoromethyl)sulfonyl]benzyl}[4-(3-undecyl-1,2,4-oxadiazol-5-yl)benzyl]amino}acetate gave the title compound as a yellow oil (15% (overall yield from step a)). M⁻(LC/MS(ESI)): 622.1; M⁺(LC/MS(ESI)): 624.1. HPLC (Condition A), Rt: 5.80 min (HPLC purity: 79.4%).

Example 385 oxo{{4-[(trifluoromethyl)sulfonyl]benzyl}[3-(3-undecyl-1,2,4-oxadiazol-5-yl)benzyl]amino}acetic acid Step a) Formation of N-{4-[(trifluoromethyl)sulfonyl]benzyl}-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 4-[(trifluoromethyl)sulfonyl]benzylamine hydrochloride gave the title compound as an oil. M⁺(LC/MS(ESI)): 552.5. HPLC (Condition A), Rt: 4.85 min (HPLC purity: 62.0%).

Step b) Formation of Ethyl oxo{{4-[(trifluoromethyl)sulfonyl]benzyl}[3-(3-undecyl-1,2,4-oxadiazol-5-yl)benzyl]amino}acetate The same procedure as employed in the preparation of Example 357 (step b) but using N-{4-[(trifluoromethyl)sulfonyl]benzyl}-N-[3-(3-undecyl-1,2,4-oxadiazol-5-yl)benzyl]amine gave the title compound as an oil.

Step c) Formation of oxo{{4-[(trifluoromethyl)sulfonyl]benzyl}[3-(3-undecyl-1,2,4-oxadiazol-5-yl)benzyl]amino}acetic acid The same procedure as employed in the preparation of Example 1 (step e) but using ethyl oxo{{4-[(trifluoromethyl)sulfonyl]benzyl}[3-(3-undecyl-1,2,4-oxadiazol-5-yl)benzyl]amino}acetate gave the title compound as a yellow oil (37% (overall yield from step a)). M⁻(LC/MS(ESI)): 622.1; M⁺(LC/MS/ESI)): 624.0. HPLC (Condition A), Rt: 5.79 min (HPLC purity: 81.4%).

Example 386

([4-(3-octyl-1,2,4-oxadiazol-5-yl)benzyl]{4-[(trifluoromethyl)sulfonyl]-benzyl}amino)(oxo)acetic acid Step a) Formation of N-{4-[(trifluoromethyl)sulfonyl]benzyl}-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 4-[(trifluoromethyl)sulfonyl]benzylamine hydrochloride gave the title compound as an oil. HPLC (Condition A), Rt: 4.36 min (HPLC purity: 43.4%).

Step b) Formation of Ethyl oxo{{4-[(trifluoromethyl)sulfonyl]benzyl}[4-(3-octyl-1,2,4-oxadiazol-5-yl)benzyl]amino}acetate The same procedure as employed in the preparation of Example 357 (step b) but using N-{4-[(trifluoromethyl)sulfonyl]benzyl}-N-[4-(3-octyl-1,2,4-oxadiazol-5-yl)benzyl]amine gave the title compound as an oil.

Step c) Formation of ([4-(3-octyl-1,2,4-oxadiazol-5-yl)benzyl]{4-[(trifluoromethyl)-sulfonyl]benzyl}amino)(oxo)acetic acid The same procedure as employed in the preparation of Example 1 (step e) but using ethyl oxo{{4-[(trifluoromethyl)sulfonyl]benzyl}[4-(3-octyl-1,2,4-oxadiazol-5-yl)benzyl]amino}acetate gave the title compound as a yellow oil (24% (overall yield from step a)). M$^-$(LC/MS(ESI)): 580.1; M$^+$(LC/MS(ESI)): 582.1. HPLC (Condition A), Rt: 5.26 min (HPLC purity: 81.1%).

Example 387

{1,3-benzodioxol-5-yl[4-(3-undecyl-1,2,4-oxadiazol-5-yl)benzyl]-amino}(oxo)acetic acid Step a) Formation of N-1,3-benzodioxol-5-yl-N-[4-(3-undecyl-1,2,4-oxadiazol-5-yl)benzyl]amine The same procedure as employed in the preparation of Example 357 (step a) but using 4-(3-undecyl-1,2,4-oxadiazol-5-yl)benzaldehyde and 1,3-benzodioxol-5-ylamine gave the title compound as an oil. HPLC (Condition A), Rt: 5.15 min (HPLC purity: 97.2%).

Step b) Formation of ethyl{1,3-benzodioxol-5-yl[4-(3-undecyl-1,2,4-oxadiazol-5-yl)benzyl]amino}(oxo)acetate The same procedure as employed in the preparation of Example 357 (step b) but using N-1,3-benzodioxol-5-yl-N-[4-(3-undecyl-1,2,4-oxadiazol-5-yl)benzyl]amine gave the title compound as an oil.

Step c) Formation of {1,3-benzodioxol-5-yl[4-(3-undecyl-1,2,4-oxadiazol-5-yl)benzyl]amino}(oxo)acetic acid The same procedure as employed in the preparation of Example 1 (step e) but using ethyl{1,3-benzodioxol-5-yl[4-(3-undecyl-1,2,4-oxadiazol-5-yl)benzyl]amino}(oxo)acetate gave the title compound as a brown oil (46% (overall yield from step a)). M$^+$(LC/MS(ESI)): 478.2 (—CO$_2$). HPLC (Condition A), Rt: 5.55 min (HPLC purity: 96.4%).

Example 388

{1,3-benzodioxol-5-yl[3-(3-undecyl-1,2,4-oxadiazol-5-yl)benzyl]-amino}-(oxo)acetic acid Step a) Formation of N-1,3-benzodioxol-5-yl-N-[3-(3-undecyl-1,2,4-oxadiazol-5-yl)benzyl]amine The same procedure as employed in the preparation of Example 357 (step a) but using 3-(3-undecyl-1,2,4-oxadiazol-5-yl)benzaldehyde and 1,3-benzodioxol-5-ylamine gave the title compound as an oil. M$^+$(LC/MS(ESI)): 450.4. HPLC (Condition A), Rt: 5.12 min (HPLC purity: 95.4%).

Step b) Formation of ethyl{1,3-benzodioxol-5-yl[3-(3-undecyl-1,2,4-oxadiazol-5-yl)benzyl]amino}(oxo)acetate The same procedure as employed in the preparation of Example 357 (step b) but using N-1,3-benzodioxol-5-yl-N-[3-(3-undecyl-1,2,4-oxadiazol-5-yl)benzyl]amine gave the title compound as an oil.

Step c) Formation of {1,3-benzodioxol-5-yl[3-(3-undecyl-1,2,4-oxadiazol-5-yl)benzyl]-amino}(oxo)acetic acid The same procedure as employed in the preparation of Example 1 (step e) but using ethyl{1,3-benzodioxol-5-yl[3-(3-undecyl-1,2,4-oxadiazol-5-yl)benzyl]amino}(oxo)acetate gave the title compound as a brown oil (56% (overall yield from step a)). M$^+$(LC/MS(ESI)): 522.1. HPLC (Condition A), Rt: 5.55 min (HPLC purity: 94.7%).

Example 389

{1,3-benzodioxol-5-yl[4-(3-octyl-1,2,4-oxadiazol-5-yl)benzyl]amino}(oxo)acetic acid Step a) Formation of N-1,3-benzodioxol-5-yl-N-[4-(3-octyl-1,2,4-oxadiazol-5-yl)benzyl]amine The same procedure as employed in the preparation of Example 357 (step a) but using 4-(3-octyl-1,2,4-oxadiazol-5-yl)benzaldehyde and 1,3-benzodioxol-5-ylamine gave the title compound as an oil. M$^+$(LC/MS(ESI)): 408.4. HPLC (Condition A), Rt: 4.54 min (HPLC purity: 85.5%).

Step b) Formation of ethyl{1,3-benzodioxol-5-yl[4-(3-octyl-1,2,4-oxadiazol-5-yl)benzyl]amino}(oxo)acetate The same procedure as employed in the preparation of Example 357 (step b) but using N-1,3-benzodioxol-5-yl-N-[4-(3-octyl-1,2,4-oxadiazol-5-yl)benzyl]amine gave the title compound as an oil.

Step c) Formation of {1,3-benzodioxol-5-yl[4-(3-octyl-1,2,4-oxadiazol-5-yl)benzyl]amino}(oxo)acetic acid The same procedure as employed in the preparation of Example 1 (step e) but using ethyl{1,3-benzodioxol-5-yl[4-(3-octyl-1,2,4-oxadiazol-5-yl)benzyl]amino}(oxo)acetate gave the title compound as a brown oil (48% (overall yield from step a)). M$^+$(LC/MS(ESI)): 478.2 (—CO$_2$). HPLC (Condition A), Rt: 4.91 min (HPLC purity: 97.5%).

Example 390

{[(4-dodec-1-ynyl-1-naphthyl)methyl][4-(trifluoromethyl)benzyl]amino}-(oxo)acetic acid Step a) Formation of (4-bromo-1-naphthyl)methylamine hydrochloride A mixture of 1-bromo-4-methylnaphthaline (25 g, 0.113 mol), NBS (22.2 g, 0.123 mol) and benzoylperoxide (5 g) in CCl$_4$ (750 mL) was refluxed for 5 h. The reaction mixture was cooled, filtered off the succinimide and concentrated to give crude bromide (34 g) and used for the next reaction without any purification. To a cold (−40° C.) solution of liquid ammonia (2 L) was added 1-bromo-4-bromomethyl naphthaline (crude 34 g) dissolved in 200 mL of CH$_2$Cl$_2$ over a period of 45 min. The reaction mixture was then stirred at −40° C. for 18 h. The reaction mixture was then allowed to stir at RT and concentrated under vacuum to give yellow residue. The residue was then treated with 3N HCl (250 mL), filtered off the solid obtained and washed with CH$_2$Cl$_2$ (2×250 mL). The solid was dried under vacuum to give (4-bromo-1-naphthyl) methylamine hydrochloride (25 g, 80%). HPLC purity: 96.6%

Step b) Formation of N-[(4-bromo-1-naphthyl)methyl]-N-[4-(trifluoromethyl)benzyl]amine hydrochloride The same procedure as employed in the preparation of Example 226 (step a) but using (4-bromo-1-naphthyl)methylamine and 4-(trifluoromethyl)benzaldehyde gave the title compound as a brown oil (58%). HPLC (Condition A), Rt: 3.40 min (HPLC purity: 98.4%).

Step c) Formation of ethyl{([(4-bromo-1-naphthyl)methyl][4-(trifluoromethyl)benzyl]-amino}(oxo)acetate The same procedure as employed in the preparation of Example 15 (step b) but using N-[(4-bromo-1-naphthyl)methyl]-N-[4-(trifluoromethyl)benzyl]amine hydrochloride gave the title compound (98%). M$^-$(LC/MS(ESI)): 491.4; M$^+$(LC/MS(ESI)): 496.1. HPLC (Condition A), Rt: 5.25 min (HPLC purity: 97.9%).

Step d) Formation of ethyl{[(4-dodec-1-ynyl-1-naphthyl)methyl][4-(trifluoromethyl)-benzyl]amino}(oxo)acetate The same procedure as employed in the preparation of Example 226 (step c) but using ethyl{[(4-bromo-1-naphthyl)methyl][4-(trifluoromethyl)benzyl]amino}(oxo)acetate gave the title compound as a yellow oil (74%). HPLC (Condition A), Rt: 6.64 min (HPLC purity: 100%).

Step e) Formation of {[(4-dodec-1-ynyl-1-naphthyl)methyl][4-(trifluoromethyl)benzyl]-amino}(oxo) acetic acid The same procedure as employed in the preparation of Example 1 (step e) but using ethyl{[(4-dodec-1-ynyl-1-naphthyl)methyl][4-(trifluoromethyl)benzyl]amino}(oxo)acetate gave the title compound as a yellow oil (48% (overall yield from step a)). M$^-$(LC/MS(ESI)): 550.2. HPLC (Condition A), Rt: 6.15 min (HPLC purity 99.3%). Analysis calculated for C$_{33}$H$_{36}$F$_3$NO$_3$■0.5H$_2$O: C, 70.70; H, 6.65; N, 2.50%. Found: C, 70.44; H, 6.72; N, 2.29%.

Example 391

{[(4-dec-1-ynyl-1-naphthyl)methyl][4-(trifluoromethyl)benzyl]amino}-(oxo)acetic acid Step a) Formation of N-[(4-bromo-1-naphthyl)methyl]-N-[4-(trifluoromethyl)benzyl]amine hydrochloride The same procedure as employed in the preparation of Example 226 (step a) but using (4-bromo-1-naphthyl)methylamine and 4-(trifluoromethyl)benzaldehyde gave the title compound as a brown oil (58%). HPLC (Condition A), Rt: 3.40 min (HPLC purity: 98.4%).

Step b) Formation of ethyl{[(4-bromo-1-naphthyl)methyl][4-(trifluoromethyl)benzyl]amino}(oxo)acetate The same procedure as employed in the preparation of Example 15 (step b) but using N-[(4-bromo-1-naphthyl)methyl]-N-[4-(trifluoromethyl)benzyl]amine hydrochloride gave the title compound as a colorless oil (98%).

Step c) Formation of ethyl{[(4-dec-1-ynyl-1-naphthyl)methyl][4-(trifluoromethyl)benzyl]-amino}(oxo)acetate The same procedure as employed in the preparation of Example 226 (step c) but using ethyl{[(4-bromo-1-naphthyl)methyl][4-(trifluoromethyl)benzyl]amino}(oxo)acetate gave the title compound as a yellow oil (87%). M$^-$(LC/MS(ESI)): 550.1; M$^+$(LC/MS(ESI)): 552.5. HPLC (Condition A), Rt: 6.36 min (HPLC purity: 96.4%).

Step d) Formation of {[(4-dec-1-ynyl-1-naphthyl)methyl][4-(trifluoromethyl)benzyl]-amino}(oxo) acetic acid The same procedure as employed in the preparation of Example 1 (step e) but using ethyl{[(4-dec-1-ynyl-1-naphthyl)methyl][4-(trifluoromethyl)benzyl]amino}(oxo)acetate gave the title compound as a brown oil (91%). $^1$H NMR (CDCl$_3$, 300 MHz) δ 8.43-8.37 (m, 1H), 7.90-7.76 (m, 1H), 7.61-7.48 (m, 5H), 7.28-7.08 (m, 3H), 5.37 (s, 0.7H), 5.05 (s, 1.3H), 4.79 (s, 1.3H), 4.61 (s, 0.7H), 2.57 (t, 2H, J=7.0 Hz), 1.77-1.65 (m, 2H), 1.59-1.48 (m, 2H), 1.42-1.25 (m, 8H), 0.89 (m, 3H). M$^-$(LC/MS(ESI)): 522.3. HPLC (Condition A), Rt: 5.83 min (HPLC purity: 97.7%).

Example 392

([1-(3-chlorophenyl)-1-methylethyl]{4-[(4-hexylphenyl ethynyl]benzyl}-amino)(oxo)acetic acid, N-methyl-D-glucamine (i.e. 1-deoxy-1-(methylamino) glucitol) salt Step a) Formation of N-[1-(3-chlorophenyl)-1-methylethyl]-N-{4-[(4-hexylphenyl)-ethynyl]benzyl}amine The same procedure as employed in the preparation of Example 226 (step a) but using 4-[(4-hexylphenyl)ethynyl]benzaldehyde and 1-(3-chlorophenyl)-1-methylethylamine gave the title compound as a brown oil (80%). HPLC (Condition A), Rt: 4.73 min (HPLC purity: 98.7%).

Step b) Formation of ethyl([1-(3-chlorophenyl)-1-methylethyl]{4-[(4-hexylphenyl)ethynyl]-benzyl}amino)(oxo)acetate The same procedure as employed in the preparation of Example 15 (step b) but using N-[1-(3-chlorophenyl)-1-methylethyl]-N-{4-[(4-hexylphenyl)ethynyl]benzyl}amine gave the title compound as a brown oil (95%). HPLC (Condition A), Rt: 6.26 min (HPLC purity: 99.3%).

Step c) Formation of ([1-(3-chlorophenyl)-1-methylethyl]{4-[(4-hexylphenyl)ethynyl]-benzyl}amino) (oxo)acetic acid The same procedure as employed in the preparation of Example 1 (step e) but using ethyl([1-(3-chlorophenyl)-1-methylethyl]{4-[(4-hexylphenyl)ethynyl]benzyl}-amino) (oxo)acetate gave the title compound as a yellow powder (89%). M⁻(LC/MS(ESI)): 514.1. HPLC (Condition A), Rt: 5.84 min (HPLC purity: 99.1%).

Step d) Formation of ([1-(3-chlorophenyl)-1-methylethyl]{4-[(4-hexylphenyl)ethynyl]-benzyl}amino)(oxo)acetic acid, N-methyl-D-glucamine (i.e. 1-deoxy-1-(methylamino)glucitol) salt The same procedure as employed in the preparation of Example 2 but using ([1-(3-chlorophenyl)-1-methylethyl]{4-[(4-hexylphenyl)ethynyl]benzyl}amino)(oxo)acetic acid gave the title compound as a white powder (94%). M⁻(LC/MS(ESI)): 514.7. HPLC (Condition A), Rt: 5.81 min (HPLC purity: 99.4%). Analysis calculated for $C_{32}H_{34}ClNO_3 \cdot C_7H_{17}NO_5 \blacksquare 0.8H_2O$: C, 64.55; H, 7.31; N, 3.86%. Found: C, 64.6; H, 7.43; N, 3.87%.

Example 393 oxo{[4-(trifluoromethyl)benzyl][4-(4-undecyl-1,3-thiazol-2-yl)benzyl]amino}acetic acid Step a) Formation of 4-(1,3-dioxolan-2-yl)benzonitrile To a solution of 4-cyanobenzaldehyde (25 g, 0.190 mol) in dry toluene (300 mL) was added ethyleneglycol (15 g, 0.228 mol) and PTSA (0.5 g) and allowed to reflux at 130° C. with azeotropic removal of water for 12 h. The reaction mixture was cooled, washed with 10% aqueous $NaHCO_3$ (100 mL), dried and concentrated under vacuum. The crude solid was recrystallised from PetEther/EtOAc to give the 4-(1,3-dioxolan-2-yl)benzonitrile (17 g, 51%) as white solid. TLC (PetEther/EtOAc 4/1), Rf=0.6

Step b) Formation of 4-(1,3-dioxolan-2-yl)benzenecarbothioamide

To a solution of 4-(1,3-dioxolan-2-yl)benzonitrile (2 g, 0.01 mol) in dry pyridine (50 mL) and TEA (5.75 g, 0.057 mol) was passed $H_2S$ gas (freshly generated) for 1 h with stirring at RT. The reaction mixture was diluted with water (100 mL), extracted with diethyl ether (100 mL), washed with brine (50 mL) and dried. The solvent was removed under vacuum and the crude product was purified by column chromatography over silica gel (PetEther/EtOAc, 3/7) to give 4-(1,3-dioxolan-2-yl)benzenecarbothioamide (1.9 g, 86%) as yellow solid. TLC (PetEther/EtOAc 3/7), Rf=0.35

Step c) Formation of 1-bromotridecan-2-one

To a solution of lauric acid chloride (10.0 g, 45.7 mmol) in anhydrous THF (91 mL) at 0° C. was added dropwise a solution of trimethylsilyldiazomethane (2 M in ether, 45.7 mL, 91.4 mmol). The mixture was stirred 1 h at 0° C. then overnight at RT. The solvents were evaporated under vacuum to give a yellow oil. This crude product was dissolved in DCM (50 mL) and stirred in the presence of the PL-AMS-Resin (Polymer Laboratories, 1.54 mmol/g, 5 g) for 5 h at RT. The resin was filtered off and washed with DCM. The combined filtrates were evaporated to give a yellow oil. This crude product was dissolved in $Et_2O$, chilled at 0° C. and a concentrated aqueous solution of HBr (48%, 10 mL) was added dropwise carefully. After 1 h of reaction, the mixture was decanted and the organic layer was dried over $MgSO_4$, filtered and evaporated to give the title product as a beige solid (8.32 g, 66%). ¹H NMR ($CDCl_3$, 300 MHz) δ 3.87 (s, 2H), 2.63 (t, 2H, J=7.5 Hz), 1.67-1.54 (m, 2H), 1.30-1.21 (m, 16H), 0.87 (m, 3H)

Step d) Formation of 4-(4-undecyl-1,3-thiazol-2-yl)benzaldehyde

A solution of 1-bromotridecan-2-one (5.54 g, 20 mmol) and 4-(1,3-dioxolan-2-yl)benzenecarbothioamide (4.19 g, 20 mmol) in EtOH (50 mL) was refluxed overnight. After evaporation of the solvent, the residue was taken up in ether, washed with water, brine, dried over $MgSO_4$, filtered. The solvents were evaporated under vacuum to give a yellow oil. Purification on silicagel gave the title product as a yellow solid (4.05 g, 59%). ¹H NMR ($CDCl_3$, 300 MHz) δ 10.0 (s, 1H), 8.11 (d, 2H, J=8.3 Hz), 7.93 (d, 2H, J=8.6 Hz), 6.98 (s, 1H), 2.84 (t, 2H, J=7.2 Hz), 1.78-1.72 (m, 2H), 1.50-1.20 (m, 16H), 0.87 (t, 3H, J=6.8 Hz). M⁺(LC/MS(ESI)): 344.3

Step e) Formation of N-[4-(trifluoromethyl)benzyl]-N-[4-(4-undecyl-1,3-thiazol-2-yl)benzyl]amine The same procedure as employed in the preparation of Example 226 (step a) but using 4-(4-undecyl-1,3-thiazol-2-yl)benzaldehyde and 4-(trifluoromethyl)benzylamine gave the title compound as a colorless oil (90%). ¹H NMR ($CDCl_3$, 300 MHz) δ 7.78 (d, 2H, J=8.3 Hz), 7.45 (d, 2H, J=8.1 Hz), 7.35 (d, 2H, J=8.1 Hz), 7.25 (d, 2H, J=8.3 Hz), 6.72 (s, 1H), 3.689 (s, 2H, J=7.3 Hz), 3.74 (s, 2H), 2.67 (t, J=2H, 7.7 Hz), 1.95-1.72 (m, 1H), 1.62-1.55 (m, 2H), 1.37-1.05 (m, 16H), 0.74 (t, 3H, J=6.7 Hz). M⁺(LC/MS(ESI)): 503.4. HPLC (Condition A), Rt: 4.99 min (HPLC purity: 91.2%).

Step f) Formation of ethyloxo{[4-(trifluoromethyl)benzyl][4-(4-undecyl-1,3-thiazol-2-yl)benzyl]amino}acetate The same procedure as employed in the preparation of Example 15 (step b) but using 4-(4-undecyl-1,3-thiazol-2-yl)benzaldehyde gave the title compound as a colorless oil (93%). ¹H NMR ($CDCl_3$, 300 MHz) δ 7.98-7.88 (m, 2H), 7.65-7.56 (m, 2H), 7.40-7.23 (m, 4H), 6.89 (d, 1H, J=3.8 Hz), 4.54 (d, 2H, J=4.5 Hz), 4.41-4.29 (m, 4H), 2.82 (t, 2H, J=7.7 Hz), 1.81-1.70 (m, 2H), 1.40-1.21 (m, 19H), 0.87 (m, 3H). HPLC (Condition A), Rt: 6.52 min (HPLC purity: 98.9%).

Step g) Formation of oxo{[4-(trifluoromethyl)benzyl][4-(4-undecyl-1,3-thiazol-2-yl)benzyl]amino}acetic acid The same procedure as employed in the preparation of Example 1 (step e) but using ethyloxo{[4-(trifluoromethyl)benzyl][4-(4-undecyl-1,3-thiazol-2-yl)benzyl]amino}acetate gave the title compound as a colorless oil (95%). M⁻(LC/MS(ESI)): 573.3; M⁺(LC/MS(ESI)): 575.1. HPLC (Condition A), Rt: 5.98 min (HPLC purity: 98.6%).

Step h) Formation of oxo{[4-(trifluoromethyl)benzyl][4-(4-undecyl-1,3-thiazol-2-yl)benzyl]amino}acetic acid The same procedure as employed in the preparation of Example 1 (step e) but using oxo{[4-(trifluoromethyl)benzyl][4-(4-undecyl-1,3-thiazol-2-yl)benzyl]amino}acetic acid gave the title compound as a white powder (93%). M⁻(LC/MS(ESI)): 573.4; M⁺(LC/MS(ESI)): 575.3. HPLC (Condition A), Rt: 5.99 min (HPLC purity: 99.3%). Analysis calculated for $C_{31}H_{37}F_3N_2O_3S \cdot C_7H_{17}NO_5 \blacksquare 0.1H_2O$: C, 59.14; H, 7.08; N, 5.45%. Found: C, 58.87; H, 6.96; N, 5.38%.

Example 394

{(4-dec-1-ynylbenzyl [2-(2-fluorophenyl)ethyl]amino}(oxo)acetic acid

Step a) Formation of N-(4-dec-1-ynylbenzyl)-N-[2-(2-fluorophenyl)ethyl]amine

To a solution of 4-dec-1-ynylbenzaldehyde (24.2 mg, 0.1 mmol) in anhydrous THF (0.6 mL) was added the 2-(2-fluorophenyl)ethylamine (13.9 mg, 0.1 mmol) and anhydrous $MgSO_4$ (50 mg). The mixture was stirred overnight at RT. The reaction mixture was filtered and evaporated to give an oily residue. This crude product was taken up in MeOH (0.5 mL) then the sodium triacetoxyborohydride (53 mg, 0.25 mmol) was added and the reaction mixture was stirred overnight at rt. The solvents were evaporated under vacuum to give a solid. This solid was suspended in DCM (0.75 mL) and eluted through a SCX column (Isolute, 1 g) with DCM (6 mL), then $NH_3$ (2M in MeOH, 4 mL). The desired fractions (TLC monitoring) were concentrated under vacuum to afford the title product as a yellow oil. $M^+$(LC/MS(ESI)): 366.3. HPLC (Condition A), Rt: 4.64 min (HPLC purity: 80.5%).

Step b) Formation of ethyl{(4-dec-1-ynylbenzyl)[2-(2-fluorophenyl)ethyl]amino}-(oxo)acetate The same procedure as employed in the preparation of Example 357 (step b) but using N-(4-dec-1-ynylbenzyl)-N-[2-(2-fluorophenyl)ethyl]amine gave the title compound as an oil. HPLC (Condition A), Rt: 6.18 min (HPLC purity: 65.5%).

Step c) Formation of {(4-dec-1-ynylbenzyl)[2-(2-fluorophenyl)ethyl]amino}(oxo)acetic acid The same procedure as employed in the preparation of Example 1 (step e) but using ethyl{(4-dec-1-ynylbenzyl)[2-(2-fluorophenyl)ethyl]amino}(oxo)acetate gave the title compound as an orange oil (5% overall yield from step a)). $M^-$(LC/MS(ESI)): 436.3. HPLC (Condition A), Rt: 5.45 min (HPLC purity: 87.5%).

Example 395

{(4-dodec-1-ynylbenzyl)[2-(2-fluorophenyl)ethyl] amino}(oxo)acetic acid

Step a) Formation of N-(4-dodec-1-ynylbenzyl)-N-[2-(2-fluorophenyl)ethyl]amine

The same procedure as employed in the preparation of Example 394 (step b) but using 4-dodec-1-ynylbenzaldehyde and 2-(2-fluorophenyl)ethylamine gave the title compound as an oil. $M^+$(LC/MS(ESI)): 394.4. HPLC (Condition A), Rt: 5.00 min (HPLC purity: 93.6%).

Step b) Formation of ethyl{(4-dodec-1-ynylbenzyl) [2-(2-fluorophenyl)ethyl]amino}-(oxo)acetate The same procedure as employed in the preparation of Example 357 (step b) but using N-(4-dodec-1-ynylbenzyl)-N-[2-(2-fluorophenyl)ethyl]amine gave the title compound as an oil.

Step c) Formation of {(4-dodec-1-ynylbenzyl)[2-(2-fluorophenyl)ethyl]amino}(oxo)acetic acid The same procedure as employed in the preparation of Example 1 (step e) but using ethyl{(4-dodec-1-ynylbenzyl)[2-(2-fluorophenyl)ethyl]amino}(oxo)acetate gave the title compound as an orange oil (21% overall yield from step a)). HPLC (Condition A), Rt: 5.78 min (HPLC purity: 82.2%).

Example 396

{{[4-(dodecyloxy)-1-naphthyl]methyl}[2-(2-fluorophenyl)ethyl]amino}-(oxo)acetic acid Step a) Formation of N-{[4-(dodecyloxy)-1-naphthyl]methyl}-N-[2-(2-fluorophenyl)-ethyl]amine The same procedure as employed in the preparation of Example 394 (step b) but using 4-(dodecyloxy)-1-naphthaldehyde and 2-(2-fluorophenyl)ethylamine gave the title compound as an oil. HPLC (Condition A), Rt: 5.48 min (HPLC purity: 86.4%).

Step b) Formation of ethyl{{[4-(dodecyloxy)-1-naphthyl]methyl}[2-(2-fluorophenyl)ethyl]-amino}(oxo)acetate The same procedure as employed in the preparation of Example 357 (step b) but using N-{[4-(dodecyloxy)-1-naphthyl]methyl}-N-[2-(2-fluorophenyl)ethyl]amine gave the title compound as an oil.

Step c) Formation of {{[4-(dodecyloxy)-1-naphthyl] methyl}[2-(2-fluorophenyl)ethyl]-amino}(oxo)acetic acid The same procedure as employed in the preparation of Example 1 (step e) but using ethyl{{[4-(dodecyloxy)-1-naphthyl]methyl}[2-(2-fluorophenyl)ethyl]amino}(oxo)acetate gave the title compound as an orange oil (7% overall yield from step a)). $M^-$(LC/MS(ESI)): 534.3. HPLC (Condition A), Rt: 6.25 min (HPLC purity: 92.8%).

Example 397

{[2-(2-fluorophenyl)ethyl][4-(octyloxy)benzyl] amino}(oxo)acetic acid

Step a) Formation of N-[2-(2-fluorophenyl)ethyl]-N-[4-(octyloxy)benzyl]amine

The same procedure as employed in the preparation of Example 394 (step b) but using 4-(octyloxy)benzaldehyde and 2-(2-fluorophenyl)ethylamine gave the title compound as an oil. HPLC (Condition A), Rt: 4.37 min (HPLC purity: 76.0%).

Step b) Formation of ethyl{[2-(2-fluorophenyl)ethyl] [4-(octyloxy)benzyl]amino}-(oxo)acetate The same procedure as employed in the preparation of Example 357 (step b) but using N-[2-(2-fluorophenyl)ethyl]-N-[4-(octyloxy)benzyl]amine gave the title compound as an oil.

Step c) Formation of {[2-(2-fluorophenyl)ethyl][4-(octyloxy)benzyl]amino}(oxo)acetic acid The same procedure as employed in the preparation of Example 1 (step e) but using ethyl{[2-(2-fluorophenyl)ethyl]

[4-(octyloxy)benzyl]amino}(oxo)acetate gave the title compound as a white solid (22% (overall yield from step a)). M⁻(LC/MS(ESI)): 428.3. HPLC (Condition A), Rt: 5.19 min (HPLC purity: 64.2%).

Example 398

{(4-dec-1-ynylbenzyl)[2-(trifluoromethyl)benzyl]amino}(oxo)acetic acid

Step a) Formation of N-(4-dec-1-ynylbenzyl)-N-[2-(trifluoromethyl)benzyl]amine

The same procedure as employed in the preparation of Example 394 (step b) but using 4-dec-1-ynylbenzaldehyde and 2-(trifluoromethyl)benzylamine gave the title compound as an oil. M⁺(LC/MS(ESI)): 402.3. HPLC (Condition A), Rt: 4.71 min (HPLC purity: 86.5%).

Step b) Formation of ethyl{(4-dec-1-ynylbenzyl)[2-(trifluoromethyl)benzyl]-amino}-(oxo)acetate The same procedure as employed in the preparation of Example 357 (step b) but using N-(4-dec-1-ynylbenzyl)-N-[2-(trifluoromethyl)benzyl]amine gave the title compound as an oil. HPLC (Condition A), Rt: 6.31 min (HPLC purity: 80.7%).

Step c) Formation of {(4-dec-1-ynylbenzyl)[2-(trifluoromethyl)benzyl]amino}(oxo)acetic acid The same procedure as employed in the preparation of Example 1 (step e) but using ethyl{(4-dec-1-ynylbenzyl)[2-(trifluoromethyl)benzyl]amino}(oxo)acetate gave the title compound as an orange oil (7% (overall yield from step a)). M⁻(LC/MS(ESI)): 472.1. HPLC (Condition A), Rt: 5.58 Min (HPLC purity: 94.0%).

Example 399

{(4-dodec-1-ynylbenzyl)[2-(trifluoromethyl)benzyl]amino}(oxo)acetic acid

Step a) Formation of N-(4-dodec-1-ynylbenzyl)-N-[2-(trifluoromethyl)benzyl]amine The same procedure as employed in the preparation of Example 394 (step b) but using 4-dodec-1-ynylbenzaldehyde and 2-(trifluoromethyl)benzylamine gave the title compound as an oil. M⁺(LC/MS(ESI)): 430.4. HPLC (Condition A), Rt: 5.05 min (HPLC purity: 96.9%).

Step b) Formation of ethyl{(4-dodec-1-ynylbenzyl)[2-(trifluoromethyl)benzyl]-amino}-(oxo)acetate The same procedure as employed in the preparation of Example 357 (step b) but using N-(4-dodec-1-ynylbenzyl)-N-[2-(trifluoromethyl)benzyl]amine gave the title compound as an oil.

Step c) Formation of {(4-dodec-1-ynylbenzyl)[2-(trifluoromethyl)benzyl]amino}(oxo)acetic acid The same procedure as employed in the preparation of Example 1 (step e) but using ethyl{(4-dodec-1-ynylbenzyl)[2-(trifluoromethyl)benzyl]amino}(oxo)acetate gave the title compound as an orange oil (17% (overall yield from step a)). M⁻(LC/MS(ESI)): 500.2. HPLC (Condition A), Rt: 5.92 min (HPLC purity: 82.5%).

Example 400

{{[4-(dodecyloxy)-1-naphthyl]methyl}[2-(trifluoromethyl)benzyl]amino}-(oxo)acetic acid Step a) Formation of N-{[4-(dodecyloxy)-1-naphthyl]methyl}-N-[2-(trifluoromethyl)-benzyl]amine The same procedure as employed in the preparation of Example 394 (step b) but using 4-(dodecyloxy)-1-naphthaldehyde and 2-(trifluoromethyl)benzylamine gave the title compound as an oil. HPLC (Condition A), Rt: 5.54 min (HPLC purity: 98.0%).

Step b) Formation of ethyl{{[4-(dodecyloxy)-1-naphthyl]methyl}[2-(trifluoromethyl)-benzyl]amino}(oxo)acetate The same procedure as employed in the preparation of Example 357 (step b) but using N-{[4-(dodecyloxy)-1-naphthyl]methyl}-N-[2-(trifluoromethyl)benzyl]amine gave the title compound as an oil.

Step c) Formation of {{[4-(dodecyloxy)-1-naphthyl]methyl}[2-(trifluoromethyl)benzyl-amino}(oxo)acetic acid The same procedure as employed in the preparation of Example 1 (step e) but using ethyl{{[4-(dodecyloxy)-1-naphthyl]methyl}[2-(trifluoromethyl)benzyl]amino}(oxo)acetate gave the title compound as an orange oil (8% (overall yield from step a)). M⁻(LC/MS(ESI)): 570.4. HPLC (Condition A), Rt: 6.30 min (HPLC purity: 79.2%).

Example 401

{[4-(octyloxy)benzyl][2-(trifluoromethyl)benzyl]amino}(oxo)acetic acid

Step a) Formation of N-[4-(octyloxy)benzyl]-N-[2-(trifluoromethyl)benzyl]amine

The same procedure as employed in the preparation of Example 394 (step b) but using 4-(octyloxy)benzaldehyde and 2-(trifluoromethyl)benzylamine gave the title compound as an oil. HPLC (Condition A), Rt: 4.24 min (HPLC purity: 91.0%).

Step b) Formation of ethyl{[4-(octyloxy)benzyl][2-(trifluoromethyl)benzyl]-amino}(oxo)acetate The same procedure as employed in the preparation of Example 357 (step b) but using N-[4-(octyloxy)benzyl]-N-[2-(trifluoromethyl)benzyl]amine gave the title compound as an oil.

Step c) Formation of {[4-(octyloxy)benzyl][2-(trifluoromethyl)benzyl]amino}(oxo)acetic acid The same procedure as employed in the preparation of Example 1 (step e) but using ethyl{[4-(octyloxy)benzyl][2-(trifluoromethyl)benzyl]amino}(oxo)acetate gave the title compound as a yellow oil (13% (overall yield from step a)). M⁻(LC/MS(ESI)): 464.3. HPLC (Condition A), Rt: 5.33 min (HPLC purity: 92.2%).

Example 402

{(4-dec-1-ynylbenzyl)[2-(3,4-dichlorophenyl)ethyl] amino}(oxo)acetic acid

Step a) Formation of N-(4-dec-1-ynylbenzyl)-N-[2-(3,4-dichlorophenyl)ethyl]amine The same procedure as employed in the preparation of Example 394 (step b) but using 4-dec-1-ynylbenzaldehyde and 2-(3,4-dichlorophenyl)ethylamine gave the title compound as an oil. M⁺(LC/MS(ESI)): 416.3. HPLC (Condition A), Rt: 4.91 min (HPLC purity: 72.4%).

Step b) Formation of ethyl{(4-dec-1-ynylbenzyl)[2-(3,4-dichlorophenyl)ethyl]amino}-(oxo)acetate The same procedure as employed in the preparation of Example 357 (step b) but using N-(4-dec-1-ynylbenzyl)-N-[2-(3,4-dichlorophenyl)ethyl]amine gave the title compound as an oil. HPLC (Condition A), Rt: 6.45 min (HPLC purity: 62.5%).

Step c) Formation of {(4-dec-1-ynylbenzyl)[2-(3,4-dichlorophenyl)ethyl]amino}(oxo)acetic acid The same procedure as employed in the preparation of Example 1 (step e) but using ethyl{(4-dec-1-ynylbenzyl)[2-(3,4-dichlorophenyl)ethyl]amino}(oxo)acetate gave the title compound as an orange oil (11% (overall yield from step a)). M⁻(LC/MS(ESI)): 486.1. HPLC (Condition A), Rt: 5.76 min (HPLC purity: 89.8%).

Example 403

[[2-(3,4-dichlorophenyl)ethyl](4-dodec-1-ynylbenzyl amino](oxo)acetic acid

Step a) Formation of N-[2-(3,4-dichlorophenyl)ethyl]-N-(4-dodec-1-ynylbenzyl)amine The same procedure as employed in the preparation of Example 394 (step b) but using 4-dodec-1-ynylbenzaldehyde and 2-(3,4-dichlorophenyl)ethylamine gave the title compound as an oil. M⁺(LC/MS(ESI)): 444.4. HPLC (Condition A), Rt: 5.27 min (HPLC purity: 83.9 %).

Step b) Formation of ethyl[[2-(3,4-dichlorophenyl)ethyl](4-dodec-1-ynylbenzyl)amino]-(oxo)acetate The same procedure as employed in the preparation of Example 357 (step b) but using N-[2-(3,4-dichlorophenyl)ethyl]-N-(4-dodec-1-ynylbenzyl)amine gave the title compound as an oil.

Step c) Formation of [[2-(3,4-dichlorophenyl)ethyl](4-dodec-1-ynylbenzyl)amino]-(oxo)acetic acid The same procedure as employed in the preparation of Example 1 (step e) but using ethyl[[2-(3,4-dichlorophenyl)ethyl](4-dodec-1-ynylbenzyl)amino](oxo)acetate gave the title compound as a yellow oil (4% (overall yield from step a)). M⁻(LC/MS(ESI)): 514.1. HPLC (Condition A), Rt: 6.08 min (HPLC purity: 96.1%).

Example 404

([2-(3,4-dichlorophenyl)ethyl]{[4-(dodecyloxy)-1-naphthyl]methyl}amino)-(oxo)acetic acid Step a) Formation of N-[2-(3,4-dichlorophenyl) ethyl]-N-{[4-(dodecyloxy)-1-naphthyl] methyl}amine The same procedure as employed in the preparation of Example 394 (step b) but using 4-(dodecyloxy)-1-naphthaldehyde and 2-(3,4-dichlorophenyl)ethylamine gave the title compound as an oil. HPLC (Condition A), Rt: 5.72 min (HPLC purity: 82.0%).

Step b) Formation of ethyl([2-(3,4-dichlorophenyl) ethyl]{[4-(dodecyloxy)-1-naphthyl]-methyl}amino) (oxo)acetate The same procedure as employed in the preparation of Example 357 (step b) but using N-[2-(3,4-dichlorophenyl) ethyl]-N-{[4-(dodecyloxy)-1-naphthyl]methyl}amine gave the title compound as an oil.

Step c) Formation of ([2-(3,4-dichlorophenyl)ethyl]{[4-(dodecyloxy)-1-naphthyl]methyl}amino)(oxo) acetic acid The same procedure as employed in the preparation of Example 1 (step e) but using ethyl ([2-(3,4-dichlorophenyl) ethyl]{[4-(dodecyloxy)-1-naphthyl]methyl}amino)(oxo)acetate gave the title compound as a yellow oil (6% (overall yield from step a)). M⁻(LC/MS(ESI)): 584.0. HPLC (Condition A), Rt: 6.50 min (HPLC purity: 63.7%).

Example 405

{[2-(3,4-dichlorophenyl)ethyl][4-(octyloxy)benzyl] amino}(oxo)acetic acid

Step a) Formation of N-[2-(3,4-dichlorophenyl) ethyl]-N-[4-(octyloxy)benzyl]amine The same procedure as employed in the preparation of Example 394 (step b) but using 4-(octyloxy)benzaldehyde and 2-(3,4-dichlorophenyl)ethylamine gave the title compound as an oil. HPLC (Condition A), Rt: 4.69 min (HPLC purity: 71.8%).

Step b) Formation of ethyl{[2-(3,4-dichlorophenyl) ethyl][4-(octyloxy)benzyl]amino}(oxo)acetate The same procedure as employed in the preparation of Example 357 (step b) but using N-[2-(3,4-dichlorophenyl) ethyl]-N-[4-(octyloxy)benzyl]amine gave the title compound as an oil.

Step c) Formation of {[2-(3,4-dichlorophenyl)ethyl] [4-(octyloxy)benzyl]amino}(oxo)acetic acid The same procedure as employed in the preparation of Example 1 (step e) but using ethyl{[2-(3,4-dichlorophenyl) ethyl][4-(octyloxy)benzyl]amino}(oxo)acetate gave the title compound as a yellow oil (6% (overall yield from step a)). M⁻(LC/MS(ESI)): 478.1. HPLC (Condition A), Rt: 5.47 min (HPLC purity: 65.4%).

Example 406

({4-[(4-hexylphenyl)ethynyl]benzyl}{1-methyl-1-[4-(trifluoromethyl)-phenyl]ethyl}amino)(oxo)acetic acid The same procedure as employed in the preparation of Example 392 but using 1-methyl-1-[4-(trifluoromethyl)phenyl]ethylamine and 4-[(4-hexylphenyl)ethynyl]benzaldehyde (in step a) gave the title compound as a white powder. M⁻(LC/MS(ESI)): 548.1. HPLC (Condition A), Rt: 5.89 min (HPLC purity: 98.7%).

Example 407

{4[(5-cyclohexylpent-1-ynyl)benzyl][4-(trifluoromethyl)benzyl]-amino}(oxo)acetic acid The same procedure as employed in the preparation of Example 226 (step c) but using pent-4-ynylcyclohexane gave the title compound as a yellow oil. M⁻(LC/MS(ESI)): 484.2. HPLC (Condition A), Rt: 5.53 min (HPLC purity: 98.8%).

Example 408

{{3-[(4-hexylphenyl)ethynyl]benzyl}[4-(trifluoromethyl)benzyl]-amino}(oxo)acetic acid The same procedure as employed in the preparation of Example 226 (step c) but using 1-ethynyl-4-hexylbenzene gave the title compound as a white powder. M⁻(LC/MS(ESI)): 520.0. HPLC (Condition A), Rt: 5.68 min (HPLC purity: 99.9%).

Example 409

{[4-(4-ethyl-3-hydroxyoct-1-ynyl)benzyl][4-(trifluoromethyl)benzyl]-amino}(oxo)acetic acid The same procedure as employed in the preparation of Example 226 (step c) but using 4-ethyloct-1-yn-3-ol gave the title compound as a yellow foam. M⁻(LC/MS(ESI)): 488.2. HPLC (Condition A), Rt: 4.79 min (HPLC purity: 98.9%).

Example 410

{(2-dec-1-ynylbenzyl)[4-(trifluoromethyl)benzyl]amino}(oxo)acetic acid

The same procedure as employed in the preparation of Example 226 (step c) but using ethyl{(2-bromobenzyl)[4-(trifluoromethyl)benzyl]amino}(oxo)acetate and dec-1-yne gave the title compound as a pale yellow oil. M⁻(LC/MS(ESI)): 472.0. HPLC (Condition A), Rt: 5.51 min (HPLC purity: 99.6%).

Example 411

{(4-dec-1-ynylbenzyl)[4-(trifluoromethyl)benzyl]amino}(oxo)acetic acid, L-lysine salt The same procedure as employed in the preparation of Example 2 but using {(4-dec-1-ynylbenzyl)[4-(trifluoromethyl)benzyl]amino}(oxo)acetic acid and L-lysine gave the title compound as a white powder. M⁻(LC/MS(ESI)): 472.3. HPLC (Condition A), Rt: 5.59 min (HPLC purity: 99.4%).

Example 412

{(4-dec-1-ynylbenzyl)[4-(trifluoromethyl)benzyl]amino}(oxo)acetic acid, tromethamine (i.e. (2-amino-2-hydroxymethyl)-1,3-propanediol) salt The same procedure as employed in the preparation of Example 2 but using {(4-dec-1-ynylbenzyl)[4-(trifluoromethyl)benzyl]amino}(oxo)acetic acid and tris (hydroxymethyl)amino methane gave the title compound as a white solid. M⁻(LC/MS(ESI)): 472.3. HPLC (Condition A), Rt: 5.58 min (HPLC purity: 99.5%).

Example 413

{(4-dec-1-ynylbenzyl)[4-(trifluoromethyl)benzyl]amino}(oxo)acetic acid L-arginine salt The same procedure as employed in the preparation of Example 2 but using {(4-dec-1-ynylbenzyl)[4-(trifluoromethyl)benzyl]amino}(oxo)acetic acid and L-arginine gave the title compound as a white powder. M⁻(LC/MS(ESI)): 472.4. HPLC (Condition A), Rt: 5.55 min (HPLC purity 99.6%).

Example 414 sodium {(4-dec-1-ynylbenzyl)[4-(trifluoromethyl)benzyl]-amino}-(oxo)acetate

The same procedure as employed in the preparation of Example 2 but using {(4-dec-1-ynylbenzyl)[4-(trifluoromethyl)benzyl]amino}(oxo)acetic acid and sodium hydroxide gave the title compound as a white solid. M⁻(LC/MS(ESI)): 472.2. HPLC (Condition A), Rt: 5.54 min (HPLC purity: 99.6%).

Example 415

Preparation of a pharmaceutical formulation
Pharmaceutical formulations using the compounds of formula (I) may be prepared according to standard procedures known to a person skilled in the art The following formulation examples illustrate representative pharmaceutical compositions using compounds of formula (I), while it is emphasised that the present invention is not to be construed as being limited to said the below formulations.

Formulation 1—Tablets

An substituted methylene amide derivative of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active substituted methylene amide derivative per tablet) in a tablet press.

Formulation 2—Capsules

Substituted methylene amide derivative of formula (I) is admixed as a dry powder with a starch diluent in an approximate 1:1 weight ratio. The mixture is filled into 250 mg capsules (125 mg of substituted methylene amide derivative per capsule).

Formulation 3—Liquid

Substituted methylene amide derivative of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added.

Formulation 4—Tablets

A substituted methylene amide derivative of formula (I), is admixed as a dry powder with a dry gelatin binder in an approximate 1:2 weight ratio. A minor amount of magnesium stearate is added as a lubricant. The mixture is formed into 300-600 mg tablets (150-300 mg of active substituted methylene amide derivative) in a tablet press.

Formulation 5—Injection

A substituted methylene amide derivative of formula (I), is dissolved in a buffered sterile saline injectable aqueous medium to a concentration of approximately 5 mg/ml.

Example 416

Biological Assays

The compounds of formula (I), may be subjected to the following assays:
(1) The PTP Enzyme Assay
(2) The in vivo assay in db/db mice (1) The PTP Enzyme Assay (In Vitro Assay)

Assays for the determination of the PTP inhibitory activity of test compounds are well known to a person skilled in the art. An example of such an assay is described below:

The PTP Enzyme Assay aims at determining the extent of inhibition of PTPs, e.g. of PTP1B, SHP-1, SHP-2 or GLEPP-1 in the presence of a test compound of formula (I). The inhibition is illustrated by $IC_{50}$ values which denote the concentration of test compound necessary to achieve an inhibition of 50% of said PTP's using the following concentration of the PTP substrate DiFMUP:

5 µM DiFMUP for PTP1B;
20 λM DiFMUP for SHP-1 and SHP-2;
30 µM DiFMUP for GLEPP-1.

a) PTPs Cloning

The cloning and expression of the catalytic domain of PTPIB, may be performed as described in *J. Biol. Chem.* 2000, 275(13), pp 9792-9796.

b) Materials and Methods

The DiFMUP assay allows to follow the dephosphorylation of DiFMUP (6,8-DiFluoro-4-MethylUmbelliferyl Phosphate)—which is the PTP substrate—mediated by PTP into its stable hyrolysis product, i.e. DiFMU (6,8-difluoro-7-hydroxy coumarin). Due to its rather low pKa and its high quantum yield, DiFMU allows to measure both acidic and alkaline phosphatase activities with a great sensitivity.

Assays were performed in a 96 well plate format, using the catalytic core of a human recombinant PTP as the enzyme and 6,8-DiFluoro-4-MethylUmbelliferyl Phosphate (DiFMUP, Molecular Probes, D-6567) as a substrate. Compounds to be tested were dissolved in 100% DMSO at a concentration of 2 mM. Subsequent dilutions of the test compounds (to yield a concentration of 100, 30, 10, 3, 1, 0.3, 0.1, 0.03, 0.01, 0.001 µM) were performed in 100% DMSO using a Tecan Stand Alone Workstation. 5 µl of diluted compound or vehicle (100% DMSO=control) was distributed to a black Costar 96 well plate. 25 µl of DiFMUP diluted in the assay buffer (20 mM Tris HCl pH 7.5, 0.01% IGEPAL CA-630, 0.1 mM ethylenediaminetetracetic acid, 1 mM DL-Dithiothreitol) were added, followed by 20 µl of human recombinant PTP enzyme diluted in assay buffer in order to start the enzymatic reaction. Alternatively, 20 µl of human recombinant PTP enzyme diluted in assay buffer can be added to the dilutions of compound or vehicle (distributed to a black Costar 96 well plate), followed by 251 µl of DiFMUP diluted in the assay buffer. The reaction ran for 30 minutes at room temperature before reading the fluorescence intensity (integral or intensity) on a Perkin-Elmer Victor 2 spectrofluorimeter (excitation of 6,8-difluoro-7-hydroxy coumarin is at 355 nm, the emission at 460 nm, for 0.1 s). The percentage of inhibition is determined by measuring the relative fluorescence ion absence of a test compound (PTP inhibitor), i.e. with the solvent alone (5% DMSO). The $IC_{50}$ values for inhibition were determined in triplicates.

The tested compounds according to formula (I) display an inhibition (illustrated by $IC_{50}$ values) with regard to PTP of preferably less than 10 µM, more preferred less than 5 µM.

For instance, the compound of example 10 displays an $IC_{50}$ value of 2.224 µM in respect of PTP1B, an $IC_{50}$ value of 1.40 in respect of GLEPP-1, an $IC_{50}$ value of 2.40 and 2.70 in respect of SHP-1 and SHP-2.

The compound of example 4 displays an $IC_{50}$ value of 0.916 M in respect of PTP1B and an $IC_{50}$ value of 0.50 in respect of GLEPP-1, an $IC_{50}$ value of 1 and 1.4 in respect of SHP-1 and SHP-2.

(2) In Vivo Assay in db/db Mice

The following assay aims at determining the anti-diabetic effect of the test compounds of formula (I) in a model of postprandial glycemia in db/db mice, in vivo.

The assay was performed as follows:

A total of 24 db/db mice (about 8-9 weeks; obtained from IFFACREDO, l'Arbreste, France) were fasted during 20 hours.

4 groups, each consisting of 6 animals were formed:

Group 1: The animals were administered (per os) a dose of 10 mg/kg of vehicle.

Group 2: The animals were administered (per os) a dose of 20 mg/kg of the test compound according to formula (I).

Group 3: The animals were administered (per os) a dose of 100 mg/kg of the test compound according to formula (I).

Group 4: The animals were administered (per os) a dose of 200 mg/kg of the test compound according to formula (I).

After oral administration of the compounds of formula (I) solubilized or suspended in CarboxyMethylCellulose (0.5%), Tween 20 (0.25%) and water as vehicle, the animals had access to commercial food (D04, UAR, Villemoisson/Orge, France) ad libitum. The diabetic state of the mice was verified by determining the blood glucose level before drug administration. Blood glucose and serum insulin levels were then determined 4 hrs after drug administration.

The determination of the blood glucose level was performed using a glucometer (Precision Q.I.D., Medisense, Abbot, ref. 212.62.31).

The determination of the Insulin level was performed using an ELISA kit (Crystal CHEM, Ref. INSK R020).

Changes in blood glucose and serum insulin of drug treated mice were expressed as a percentage of control (group 1: vehicle treated mice).

Treatment (er os) of the animals with substituted methylene amide compounds of formula (I), at a dosage of 50 mg/kg, decreased the blood glucose level induced by food intake by about 20-40%.

For instance, upon using the compound of example 10, i.e. {4-[(dodecylamino)carbonyl]-benzyl}[4-(trifluoromethyl) benzyl]amino}(oxo)acetic acid, the following decrease in blood glucose level as well as insulin level was determined:

| Animal Group | Decrease in blood glucose | ± SEM | Decrease in serum insulin | ± SEM |
|---|---|---|---|---|
| Group 2 | 17 | 6 | −2 | 7 |
| Group 3 | 42 | 6 | 66 | 8 |
| Group 4 | 48 | 4 | 89 | 2 |

= (SEM Standard Error of the Means)

LIST OF REFERENCES

*American Journal of Medicine,* 60, 80 (1976) by Reaven et al;
*Metabolism,* 34, 7 (1985) by Stout et al.;
*Diabetes/Metabolism Reviews,* 5, 547 (1989) by Pyorala et al;
*European Journal of Endocrinology* 138, 269-274 (1998) by A. Dunaif;
*Endocrine Reviews* 18(6), 774-800 (1997);
*Diabetes Care,* 14, 173 (1991) by DeFronzo and Ferranninni;
*J. Mol. Med.* 78, 473-482 (2000) by A. Cheng et al.;
*Current Opinion in Drug Discovery & Development* 3(5), 527-540 (2000);
*Molecular and Cellular Biology,* 5479-5489 (2000) by Lori Klaman et al.;
*Diabetes,* 40, 939 (1991) by McGuire et al.;
*J. Clinical Invest.,* 84, 976 (1989) by Meyerovitch et al;
*Metabolism,* 44, 1074, (1995) by Sredy et al.;
*Curr. Opin. Chem. Biol.,* 5(4), 416-23 (2001) by Zhang et al.;
*J. Biol. Chem.,* 275(52), 41439-46 (2000) by Bjorge J. D et al.;
*J. Neurosci. Res.,* 63(2), 143-150 (2001) by Pathre et al.;
*Mol. Brain. Res.,* 28(1), 110-16 (1995) by Shock L. P et al;
*Biochemical Pharmacology,* Vol. 60, 877-883, (2000) by Brian P. Kennedy et al.;
*Leptin. Annu. Rev. Physiol.* 62 p. 413-437 (2000) by Ahima R. S. et al;
*Developmental Cell.,* vol. 2, p. 497-503 (2002).

The invention claimed is:

1. A substituted methylene amide of Formula (I):
as well as its geometrical isomers, its optically active forms as enantiomers,

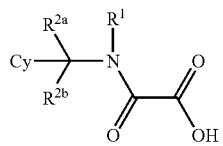

(I)

diastereomers and its racemate forms, as well as pharmaceutically acceptable salts thereof, wherein
(I)
$R^1$ is $CH_2$—$CH_2$-phenyl, $CH_2$—$CH_2$-napthyl, $CH_2$-phenyl, or $CH_2$-napthyl;
$R^{2a}$ and $R^{2b}$ are each independently are H or ($C^1$-$C^{12}$)alkyl;
Cy is a phenyl substituted by (1), (2) or (3):
(1) an oxadiazole group;
(2) 1 or 2 moieties selected from the group consisting of —NH—CO—$R^3$, —$SO_2$—$NR^3R^{3'}$ and —CO—$NR^3R^{3'}$ wherein $R^3$ and $R^{3'}$ are independently selected from H and ($C_1$-$C_{15}$)alkyl; or
(3) B-$R^4$ wherein B is an ethynyl group and $R^4$ is a ($C_1$-$C_{12}$)alkyl phenyl;
(II)
$R^{2a}$ and $R^{2b}$ are each H, $R^1$ is —$CH_2$-A with A being phenyl optionally substituted by cyano, halogen, methoxy, hydroxyl, phenoxy, —$NO_2$, or trifluoromethyl, and Cy is phenyl or biphenyl substituted by —$SO_2R^3$, or —CO—$NR^3R^{3'}$ where $R^{3'}$ is H and $R^3$ is ($C_7$-$C_{12}$)alkyl or ($C_7$-$C_{15}$)alkyl; or
(III)
$R^{2a}$ and $R^{2b}$ are each H, $R^1$ is selected from the group consisting of phenyl, benzyl, phenethyl, or 1-methylbenzyl which may be substituted by ($C_1$-$C_6$)alkyl or cycloalkyl, and Cy is phenyl or biphenyl substituted by —$SO_2R^3$, or —CO—$NR^3R^{3'}$ where $R^3$ is ($C_7$-$C_{15}$)alkyl.

2. The substituted methylene amide according to claim 1, wherein $R^{3'}$ is H and $R^3$ is selected from the group consisting of diphenyl-ethyl, dodecyl, octyl, 4-pentyl-benzyl, 4-phenoxy-phenethyl, ethyl-thiophen-2-yl, pentadecyl, tridecyl, hexyloxy-phenyl or (2-ethyl)-hexyl.

3. The substituted methylene amide according to claim 1 wherein:
$R^{2a}$ and $R^{2b}$ are each H.

4. A pharmaceutical composition comprising at least one substituted methylene amide according to claim 1 and a pharmaceutically acceptable carrier, diluent or excipient thereof.

5. The pharmaceutical composition according to claim 4 further comprising at least one supplementary drug.

6. A pharmaceutical composition comprising at least one substituted methylene amide according to claim 2 and a pharmaceutically acceptable carrier, diluent or excipient thereof.

7. A pharmaceutical composition comprising at least one substituted methylene amide according to claim 3 and a pharmaceutically acceptable carrier, diluent or excipient thereof.

8. A pharmaceutical composition comprising at least one substituted methylene amide according to claim 2 and a pharmaceutically acceptable carrier, diluent or excipient thereof.

9. A pharmaceutical composition comprising at least one substituted methylene amide according to claim 3 and a pharmaceutically acceptable carrier, diluent or excipient thereof.

10. {{4-[(4-hexylphenyl)ethynyl]benzyl}[4-(trifluoromethyl)benzyl]amino}-(oxo)acetic acid.

11. A pharmaceutical composition comprising at least one substituted methylene amide according to claim 10 and a pharmaceutically acceptable carrier, diluent or excipient thereof.

12. The substituted methylene amide of Formula (I) as well as its geometrical isomers, its optically active forms as enantiomers, diastereomers and its racemate forms, as well as pharmaceutically acceptable salts-thereof according to claim 1, $R^{2a}$ and $R^{2b}$ are each H, $R^1$ is —$CH_2$-A with A being phenyl optionally substituted by cyano, halogen, methoxy, hydroxyl, phenoxy, —$NO_2$, or trifluoromethyl, and Cy is phenyl or biphenyl substituted by —$SO_2R^3$, or —CO—$NR^3R^{3'}$ where $R^{3'}$ is H and $R^3$ is ($C_7$-$C_{12}$)alkyl or ($C_7$-$C_{15}$)alkyl.

13. A pharmaceutical composition comprising at least one substituted methylene amide according to claim 12 and a pharmaceutically acceptable carrier, diluent or excipient thereof.

14. The substituted methylene amide of Formula (I) as well as its geometrical isomers, its optically active forms as enantiomers, diastereomers and its racemate forms, as well as pharmaceutically acceptable salts-thereof according to claim 1, wherein $R^{2a}$ and $R^{2b}$ are each H, $R^1$ is selected from the group consisting of phenyl, benzyl, phenethyl, or 1-methylbenzyl which may be substituted by ($C_1$-$C_6$)alkyl or cycloalkyl, and Cy is phenyl or biphenyl substituted by —$SO^2R^3$, or —CO—$NR^3R^{3'}$ where $R^3$ is ($C_7$-$C_{15}$)alkyl.

15. A pharmaceutical composition comprising at least one substituted methylene amide according to claim 14 and a pharmaceutically acceptable carrier, diluent or excipient thereof.

* * * * *

UNITED STATES PATENT AND TRADEMARK OFFICE
CERTIFICATE OF CORRECTION

| | |
|---|---|
| PATENT NO. | : 7,592,477 B2 |
| APPLICATION NO. | : 10/501344 |
| DATED | : September 22, 2009 |
| INVENTOR(S) | : Swinnen et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 923 days.

Signed and Sealed this

Twenty-eighth Day of September, 2010

David J. Kappos
*Director of the United States Patent and Trademark Office*